(12) United States Patent
David et al.

(10) Patent No.: US 8,728,486 B2
(45) Date of Patent: May 20, 2014

(54) TOLL-LIKE RECEPTOR-7 AND -8 MODULATORY 1H IMIDAZOQUINOLINE DERIVED COMPOUNDS

(75) Inventors: Sunil A. David, Lawrence, KS (US); Nikunj M. Shukla, Lawrence, KS (US)

(73) Assignee: University of Kansas, Lawrence, KS (US)

( * ) Notice: Subject to any disclaimer, the term of this patent is extended or adjusted under 35 U.S.C. 154(b) by 0 days.

(21) Appl. No.: 13/475,284

(22) Filed: May 18, 2012

(65) Prior Publication Data

US 2012/0294885 A1 Nov. 22, 2012

Related U.S. Application Data

(60) Provisional application No. 61/487,320, filed on May 18, 2011.

(51) Int. Cl.
| | |
|---|---|
| C07D 471/04 | (2006.01) |
| A61K 39/385 | (2006.01) |
| A61K 39/39 | (2006.01) |
| A61P 31/00 | (2006.01) |
| C07D 519/00 | (2006.01) |
| C07F 5/02 | (2006.01) |
| C07K 17/02 | (2006.01) |
| C08B 37/00 | (2006.01) |
| G01N 21/64 | (2006.01) |
| G01N 33/53 | (2006.01) |

(52) U.S. Cl.
USPC ......... 424/193.1; 546/13; 546/82; 424/184.1; 435/29; 435/7.92; 530/331; 536/55.1; 544/261

(58) Field of Classification Search
None
See application file for complete search history.

(56) References Cited

U.S. PATENT DOCUMENTS

| | | | |
|---|---|---|---|
| 4,689,338 A | 8/1987 | Gerster | |
| 2004/0147543 A1* | 7/2004 | Hays et al. | 514/292 |
| 2009/0221556 A1* | 9/2009 | Kshirsagar et al. | 514/218 |

FOREIGN PATENT DOCUMENTS

| | | |
|---|---|---|
| EP | 145340 A2 | 6/1985 |
| WO | 9215582 A1 | 9/1992 |
| WO | 0134709 A1 | 5/2001 |
| WO | 0246188 A2 | 6/2002 |
| WO | 0246192 A2 | 6/2002 |
| WO | 2004058759 A1 | 7/2004 |
| WO | 2005018556 A2 | 3/2005 |
| WO | 2005020999 A1 | 3/2005 |
| WO | 2005032484 A2 | 4/2005 |
| WO | 2005048933 A2 | 6/2005 |
| WO | 2005051324 A2 | 6/2005 |
| WO | 2005123079 A2 | 12/2005 |
| WO | 2005123080 A2 | 12/2005 |
| WO | 2006009832 A1 | 1/2006 |
| WO | 2006086634 A2 | 8/2006 |
| WO | 2006091394 A2 | 8/2006 |
| WO | 2007006505 A1 | 1/2007 |
| WO | 2007006518 A2 | 1/2007 |
| WO | 2007006519 A1 | 1/2007 |
| WO | 2007079086 A1 | 7/2007 |
| WO | 2010048520 A1 | 4/2010 |
| WO | 2011068233 A1 | 6/2011 |

OTHER PUBLICATIONS

Shukla et al., 20(22) Bioorg. & Med. Chem. Letts 6384-6386 (2010).*

* cited by examiner

*Primary Examiner* — Janet L Andres
*Assistant Examiner* — Timothy R Rozof
(74) *Attorney, Agent, or Firm* — Thomas Horstemeyer, LLP

(57) ABSTRACT

The present disclosure provides novel imidazoquinoline derived compounds, derivatives thereof, analogues thereof, and pharmaceutically acceptable salts thereof, and methods of making and using such compounds. The present disclosure also provides TLR7 agonists and TLR7/TLR8 dual agonists, probes, tissue-specific molecules, adjuvants, immunogenic compositions, therapeutic compositions, and self-adjuvanting vaccines including the imidazoquinoline derived compounds, derivatives thereof, analogues thereof, and pharmaceutically acceptable salts thereof. Derivatives of the imidazoquinoline derived compounds also include dendrimers and dimers of the imidazoquinoline derived compounds, and methods of making and using the dendrimeic and dimeric imidazoquinoline derived compounds. The present disclosure also provides dual TLR2/TLR7 hybrid agonists that include imidazoquinoline derived compounds of the present disclosure.

39 Claims, 27 Drawing Sheets

TOLL-LIKE RECEPTOR-7 AND -8 MODULATORY 1H IMIDAZOQUINOLINE DERIVED COMPOUNDS

CROSS-REFERENCE TO RELATED APPLICATION

This application claims priority to U.S. provisional application entitled "TOLL-LIKE RECEPTOR-7 AND -8 MODULATORY 1H IMIDAZOQUINOLINE DERIVATIVES," having Ser. No. 61/487,320, filed on May 18, 2011, which is entirely incorporated herein by reference.

STATEMENT REGARDING FEDERALLY SPONSORED RESEARCH AND DEVELOPMENT

This invention was made with government support under Grant No. HHSN272200900033C awarded by the National Institue of Health (NIH) of the United States government. The government has certain rights in the invention.

BACKGROUND

Toll-like receptors (TLRs) recognize specific molecular patterns present in molecules that are broadly shared by pathogens, but are structurally distinct from host molecules.[1,2] The human genome includes 10 known TLRs.[2] The ligands for these receptors are highly conserved microbial molecules such as lipopolysaccharides (LPS) (recognized by TLR4), lipopeptides (TLR2 in combination with TLR1 or TLR6), flagellin (TLR5), single stranded RNA (TLR7 and TLR8), double stranded RNA (TLR3), CpG motif-containing DNA (recognized by TLR9), and profilin present on uropathogenic bacteria (TLR11).[3,4] TLR1, -2, -4, -5, and -6 respond to extracellular stimuli, while TLR3, -7, -8 and -9 respond to intracytoplasmic PAMPs.[2] The activation of TLRs by their cognate ligands leads to activation of innate immune effector mechanisms, including the production of pro-inflammatory cytokines, and up-regulation of MHC molecules and co-stimulatory signals in antigen-presenting cells as well as activating natural killer (NK) cells. The consequence of activation of the innate immune system mobilizes and amplifies specific adaptive immune responses involving both T- and B-cell effector functions.[5-7] Thus, TLR stimuli serve to link innate and adaptive immunity[5] by eliciting both primary and anamnestic immune responses.

TLR7 agonists stimulate virtually all subsets of lymphocytes without inducing dominant proinflammatory cytokine responses (unlike TLR4-5 or -8 agonists, which can be proinflammatory and therefore may exert systemic toxicity).[8] TLR7-active compounds therefore represent candidates as potential vaccine adjuvants and immune response modifiers.

In the 1970s and '80s a number of small molecules were synthesized and evaluated for antiviral activities owing to their pronounced Type I interferon (IFN-α and -β) inducing properties.[12-16] The 1H-imidazo[4,5-c]quinolines were found to be good Type I IFN inducers in human cell-derived assays.[17] Imiquimod is FDA approved for the treatment of basal cell carcinoma and actinic keratosis, and Gardiquimod is a another imidazoquinoline TLR7 agonist.[18] Several years later the mechanistic basis of IFN induction by the imidazoquinolines was found to be a consequence of TLR7 engagement and activation.[19] Certain imidazoquinoline compounds have been approved for use as antiviral agents as well as immune modulating compounds. However, the structure-activity relationship of the imidazoquinoline chemotype still remains largely unexplored and new, useful imidazoquinoline based compounds are still being developed.

SUMMARY

Embodiments of the present disclosure include imidazoquinoline derived compounds of Formula I, as well as derivatives and analogues, and pharmaceutically acceptable salts of the compounds, where Formula I is represented by the following structure.

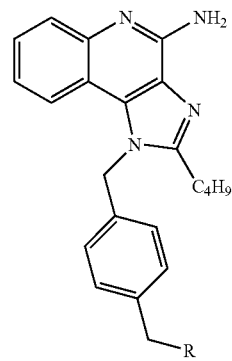

FORMULA I

In embodiments of the imidazoquinoline derived compounds of the present disclosure of Formula I, R is selected from the group consisting of: —NH(R$_5$) and isothiocyanate; R$_5$ is selected from the group consisting of hydrogen, acetyl, —CO-tert-Bu (-Boc), —CO—(CH$_2$)$_x$—R$_6$, C$_1$-C$_{16}$ alkyl, —CO-4-, —C(S)—NH—(CH$_2$)$_x$—NH—(CH$_2$)$_x$—NH—(CH$_2$)$_x$—NH$_2$,

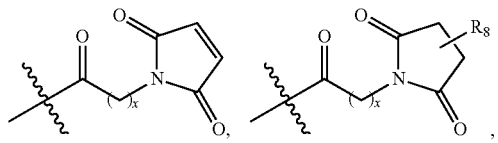

a reporter moiety, a tissue-specific moiety, a peptide antigen moiety, a protein antigen moiety, a polysaccharide antigen moiety, and a TLR$_2$ agonist moiety; R$_6$ is selected from the group consisting of hydrogen, alkyne, azido, carboxylic acid, and —CONH—(CH$_2$)$_x$—O—(CH$_2$)$_x$—O—(CH$_2$)$_x$—O—(CH$_2$)$_x$—R$_7$, R$_7$ is selected from the group consisting of amino, isothiocyanate, and —NH—CO—(CH$_2$)$_x$—CO$_2$H; R$_8$ is selected from a peptide antigen moiety or a protein antigen moiety; and x is any integer from 1 to 10.

The present disclosure also includes imidazoquinoline derived compounds having the structure of Formula II, below, and derivatives and analogues, and pharmaceutically acceptable salts of such compounds.

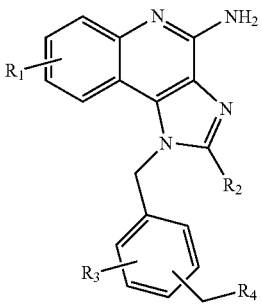

FORMULA II where, $R_1$ and $R_3$ are each independently selected from the group consisting of hydrogen, halogen, nitro, —$NH_2$, azido, hydroxyl, —$CF_3$, carboxylic acid, and —$CO_2R_2$; $R_2$ is a $C_2$-$C_5$ alkyl, and $R_4$ is selected from the group consisting of: —$NH(R_5)$ and isothiocyanate; $R_5$ is selected from the group consisting of hydrogen, acetyl, —CO-tert-Bu (-Boc), —CO—$(CH_2)_x$—$R_6$, $C_1$-$C_{16}$ alkyl, —CO-4-, —C(S)—NH—$(CH_2)_x$—NH—$(CH_2)_x$—NH—$(CH_2)_x$—$NH_2$,

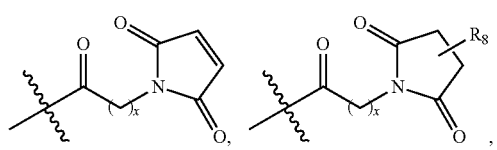

a reporter moiety, a tissue-specific moiety, a peptide antigen moiety, a protein antigen moiety, a polysaccharide antigen moiety, and a $TLR_2$ agonist moiety; $R_6$ is selected from the group consisting of hydrogen, alkyne (-, azido, carboxylic acid, and —CONH—$(CH_2)_x$—O—$(CH_2)_x$—O—$(CH_2)_x$—O—$(CH_2)_x$—$R_7$, $R_7$ is selected from the group consisting of amino, isothiocyanate and —NH—CO—$(CH_2)_x$—$CO_2H$; $R_8$ is selected from a peptide antigen moiety or a protein antigen moiety; and x is any integer from 1 to 10.

Embodiments of the present disclosure also include dendrimers and dimers of compounds of Formula I and Formula II as defined above, derivatives thereof, analogues thereof, and pharmaceutically acceptable salts thereof. Dendrimers of the compounds of Formulas I and II include, but are not limited to, trimers and hexamers of compounds of Formula I and II, as well as derivatives, analogues, and pharmaceutically acceptable salts of such dendrimers. The dimers of the present disclosure include dimers of compounds of Formulas I and II, as well as derivatives and analogues, and pharmaceutically acceptable salts of such dimers.

The present disclosure also provides TLR7 agonists including imidazoquinoline derived compounds chosen from compounds: 6c, 6d, 7c, 7d, 8, (12), 13, 14, (15), (16), 17, (18), 19, (21), (23), 25, 26-28, 30b, 31, 33, 35, 37, 39, 60, 61, 62, 64, and 65, as well as derivatives and analogues, and pharmaceutically acceptable salts of these compounds.

Embodiments of the present disclosure also include dual TLR7/TLR8 agonists including imidazoquinoline derived compounds chosen from compounds 7c, 7d, (19), 39, (35), 41, and 52c, and derivatives and analogues, and pharmaceutically acceptable salts of these compounds.

Embodiments of the present disclosure also include vaccine adjuvants and self-adjuvanting vaccines including the imidazoquinoline derived compounds of the present disclosure.

The present disclosure also includes methods of treatment of conditions such as, but not limited to, hepatitis, chronic myelogenous, and hairy cell leukemia by administering to a host in need of treatment for the condition an effective amount of an imidazoquinoline derived compound of the present disclosure coupled to a tissue-specific agent.

Embodiments of the present disclosure also include probes including imidazoquinoline derived compounds of the present disclosure that include a reporter moiety or are coupled to a reporter moiety that is capable of producing a detectible signal. The present disclosure also includes methods of imaging activation of TLR7 and/or TLR8 by contacting a sample including TLR7 and/or TLR8 with a probe of the present disclosure.

The present disclosure also includes TLR7 antagonists including imidazoquinoline derived dimeric compounds of Formula III, and derivatives, analogues and pharmaceutically acceptable salts of these compounds, where Formula III is represented by the following structure:

FORMULA III

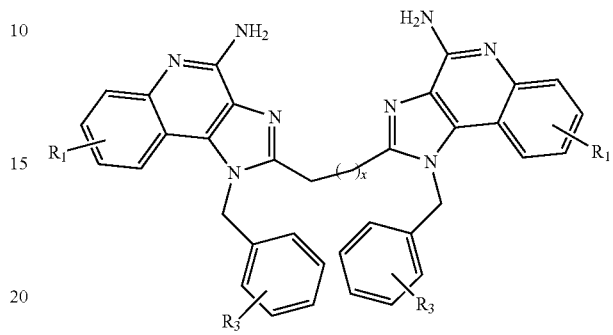

wherein $R_1$ is selected from the group consisting of hydrogen, halogen, nitro, —$NH_2$, azido, hydroxyl, and —$CF_3$,
$R_3$ is selected from the group consisting of hydrogen and —$(CH_2)_x$—$NH_2$, and
x is any integer form 1 to 10.

BRIEF DESCRIPTION OF THE DRAWINGS

Further aspects of the present disclosure will be more readily appreciated upon review of the detailed description of its various embodiments, described below, when taken in conjunction with the accompanying drawings.

DESCRIPTION

Figure 1:
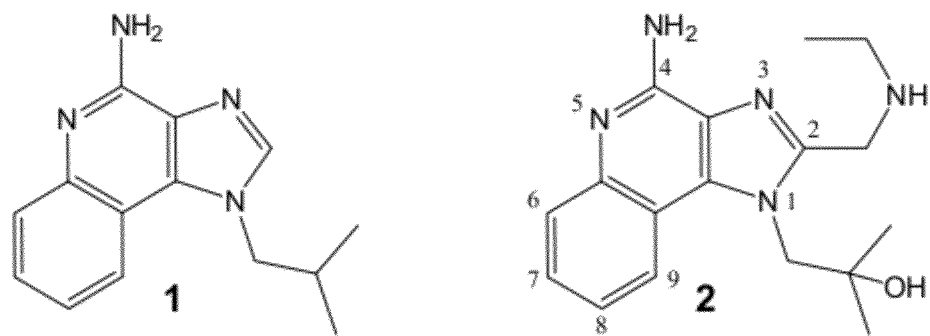
FIG. 1 illustrates the structures of Imiquimod (1) and Gardiquimod (2).

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification that are incorporated by reference are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Unless otherwise indicated, any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained in the literature.

It must be noted that, as used in the specification and the appended embodiments, the singular forms "a," "an," and "the" include plural referents unless the context clearly dictates otherwise. Thus, for example, reference to "a support" includes a plurality of supports. In this specification and in the embodiments that follow, reference will be made to a number of terms that shall be defined to have the following meanings unless a contrary intention is apparent.

As used herein, the following terms have the meanings ascribed to them unless specified otherwise. In this disclosure, "consisting essentially of" or "consists essentially" or the like, when applied to methods and compositions encompassed by the present disclosure refers to compositions like those disclosed herein, but which may contain additional structural groups, composition components or method steps. Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. Patent law, and the term is open-ended, allowing for the presence of more than that which is recited so long as basic or novel characteristics of that which is recited is not changed by the presence of more than that which is recited, but excludes prior art embodiments.

Prior to describing the various embodiments, the following definitions are provided and should be used unless otherwise indicated.

Definitions

In describing the disclosed subject matter, the following terminology will be used in accordance with the definitions set forth below.

The following abbreviations are used in the present disclosure and have the meanings ascribed below.

| | |
|---|---|
| AP-1 | activator protein-1 |
| APC | allophycocyanin |
| APCs | antigen presenting cells |
| CD | cluster of differentiation |
| CTL | cytotoxic T lymphocytes |
| DCs | dendritic cells |
| DMAP | 4-dimethylaminopyridine |
| DMF | N,N-dimethylformamide |
| DMSO | Dimethyl sulfoxide |
| $EC_{50}$ | half-maximal effective concentration |
| EDCl•HCl | 1-ethyl-3-(3-dimethylaminopropyl) carbodiimide hydrochloride |
| ELISA | enzyme linked immunosorbent assay |
| ESI-TOF | electrospray ionization-time of flight |
| FDA | Food and Drug Administration |
| FITC | fluorescein isothiocyanate |
| FSC | forward scatter |
| HATU | 2-(1H-7-azabenzotriazol-1-yl)-1,1,3,3-tetramethyl uronium hexafluorophosphate |
| HBTU | 2-(1H-benzotriazole-1-yl)-1,1,3,3-tetramethyl uronium hexafluorophosphate |
| HEK-293 | human embryonic kidney 293 |
| HSA | human serum albumin |
| IFN | interferon |
| Ig | immunoglobulin |
| IL | interleukin |
| LPS | lipopolysaccharide |
| m-CPBA | meta-chloroperoxy benzoic acid |
| MHC | major histocompatibility complex |
| N-Boc | N-tert-butyl carbamate |
| NF-κB | nuclear factor-kappa B |
| NK cells | natural killer cells |
| PAMP | pathogen associated molecular pattern |
| PBMCs | peripheral blood mononuclear cells |
| PE | phycoerythrin |
| RNA | ribonucleic acid |
| sAP | secreted alkaline phosphatase |
| SAR | structure activity relationship |
| $S_NAr$ | aromatic nucleophilic substitution |
| SSC | side scatter |
| ssRNA | single stranded RNA |
| Th1 | helper T-type 1 |
| THF | tetrahydrofuran |
| TLRs | toll like receptors |

The term "nucleic acid" as used herein refers to any natural and synthetic linear and sequential arrays of nucleotides and nucleosides, for example cDNA, genomic DNA, mRNA, tRNA, oligonucleotides, oligonucleosides and derivatives thereof. For ease of discussion, such nucleic acids may be collectively referred to herein as "constructs," "plasmids," or "vectors." Representative examples of the nucleic acids of the present disclosure include bacterial plasmid vectors including expression, cloning, cosmid and transformation vectors such as, but not limited to, pBR322, animal viral vectors such as, but not limited to, modified adenovirus, influenza virus, polio virus, pox virus, retrovirus, insect viruses (baculovirus), and the like, vectors derived from bacteriophage nucleic acid, and synthetic oligonucleotides like chemically synthesized DNA or RNA. The term "nucleic acid" further includes modified or derivatized nucleotides and nucleosides such as, but not limited to, halogenated nucleotides such as, but not only, 5-bromouracil, and derivatized nucleotides such as biotin-labeled nucleotides.

The term "isolated nucleic acid" as used herein refers to a nucleic acid with a structure (a) not identical to that of any naturally occurring nucleic acid or (b) not identical to that of any fragment of a naturally occurring genomic nucleic acid spanning more than three separate genes, and includes DNA, RNA, or derivatives or variants thereof. The term covers, for example, (a) a DNA which has the sequence of part of a naturally occurring genomic molecule but is not flanked by at least one of the coding sequences that flank that part of the molecule in the genome of the species in which it naturally occurs; (b) a nucleic acid incorporated into a vector or into the genomic nucleic acid of a prokaryote or eukaryote in a manner such that the resulting molecule is not identical to any vector or naturally occurring genomic DNA; (c) a separate molecule such as a cDNA, a genomic fragment, a fragment produced by polymerase chain reaction (PCR), ligase chain reaction (LCR) or chemical synthesis, or a restriction fragment; (d) a recombinant nucleotide sequence that is part of a hybrid gene, e.g., a gene encoding a fusion protein, and (e) a recombinant nucleotide sequence that is part of a hybrid sequence that is not naturally occurring. Isolated nucleic acid molecules of the present disclosure can include, for example, natural allelic variants as well as nucleic acid molecules modified by nucleotide deletions, insertions, inversions, or substitutions.

It is advantageous for some purposes that a nucleotide sequence is in purified form. The term "purified" in reference to nucleic acid represents that the sequence has increased purity relative to the natural environment.

The terms "polynucleotide," "oligonucleotide," and "nucleic acid sequence" are used interchangeably herein and include, but are not limited to, coding sequences (polynucleotide(s) or nucleic acid sequence(s) which are transcribed and translated into polypeptide in vitro or in vivo when placed under the control of appropriate regulatory or control sequences); control sequences (e.g., translational start and stop codons, promoter sequences, ribosome binding sites, polyadenylation signals, transcription factor binding sites, transcription termination sequences, upstream and downstream regulatory domains, enhancers, silencers, and the like); and regulatory sequences (DNA sequences to which a transcription factor(s) binds and alters the activity of a gene's promoter either positively (induction) or negatively (repression)). No limitation as to length or to synthetic origin is suggested by the terms described herein.

The term "peptide" or "polypeptide" as used herein refers to proteins and fragments thereof. Peptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

The term "variant" refers to a peptide or polynucleotide that differs from a reference peptide or polynucleotide, but retains essential properties. A typical variant of a peptide differs in amino acid sequence from another, reference peptide. Generally, differences are limited so that the sequences of the reference peptide and the variant are closely similar overall and, in many regions, identical. A variant and reference peptide may differ in amino acid sequence by one or more modifications (e.g., substitutions, additions, and/or deletions). A variant of a peptide includes conservatively modified variants (e.g., conservative variant of about 75, about 80, about 85, about 90, about 95, about 98, about 99% of the original sequence). A substituted or inserted amino acid residue may or may not be one encoded by the genetic code. A variant of a peptide may be naturally occurring, such as an allelic variant, or it may be a variant that is not known to occur naturally.

The present disclosure includes peptides which are derivable from the naturally occurring sequence of the peptide. A peptide is said to be "derivable from a naturally occurring amino acid sequence" if it can be obtained by fragmenting a naturally occurring sequence, or if it can be synthesized based upon knowledge of the sequence of the naturally occurring amino acid sequence or of the genetic material (DNA or RNA) that encodes this sequence. Included within the scope of the present disclosure are those molecules which are said to be "derivatives" of a peptide. Such a "derivative" or "variant" shares substantial similarity with the peptide or a similarly sized fragment of the peptide and is capable of functioning with the same biological activity as the peptide.

A derivative of a peptide is said to share "substantial similarity" with the peptide if the amino acid sequences of the derivative is at least 80%, at least 90%, at least 95%, or the same as that of either the peptide or a fragment of the peptide having the same number of amino acid residues as the derivative.

The protein or peptide derivatives of the present disclosure include fragments which, in addition to containing a sequence that is substantially similar to that of a naturally occurring peptide may contain one or more additional amino acids at their amino and/or their carboxy termini. Similarly, the invention includes peptide fragments which, although containing a sequence that is substantially similar to that of a naturally occurring peptide, may lack one or more additional amino acids at their amino and/or their carboxy termini that are naturally found on the peptide.

The disclosure also encompasses the obvious or trivial variants of the above-described fragments which have inconsequential amino acid substitutions (and thus have amino acid sequences which differ from that of the natural sequence) provided that such variants have an activity which is substantially identical to that of the above-described derivatives. Examples of obvious or trivial substitutions include the substitution of one basic residue for another (i.e. Arg for Lys), the substitution of one hydrophobic residue for another (i.e. Leu for Ile), or the substitution of one aromatic residue for another (i.e. Phe for Tyr), etc.

Modifications and changes can be made in the structure of the peptides of this disclosure and still obtain a molecule having similar characteristics as the peptide (e.g., a conservative amino acid substitution). For example, certain amino acids can be substituted for other amino acids in a sequence without appreciable loss of activity. Because it is the interactive capacity and nature of a peptide that defines that peptide's biological functional activity, certain amino acid sequence substitutions can be made in a peptide sequence and nevertheless obtain a peptide with like properties.

In making such changes, the hydropathic index of amino acids can be considered. The importance of the hydropathic amino acid index in conferring interactive biologic function on a peptide is generally understood in the art. It is known that certain amino acids can be substituted for other amino acids having a similar hydropathic index or score and still result in a peptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant peptide, which in turn defines the interaction of the peptide with other molecules, such as enzymes, substrates, receptors, antibodies, antigens, and the like. It is known in the art that an amino acid can be substituted by another amino acid having a similar hydropathic index and still obtain a functionally equivalent peptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly, where the biological functional equivalent peptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2);

glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent peptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu).

The term "fragment" as used herein to refer to a nucleic acid (e.g., cDNA) refers to an isolated portion of the subject nucleic acid constructed artificially (e.g., by chemical synthesis) or by cleaving a natural product into multiple pieces, using restriction endonucleases or mechanical shearing, or a portion of a nucleic acid synthesized by PCR, DNA polymerase or any other polymerizing technique well known in the art, or expressed in a host cell by recombinant nucleic acid technology well known to one of skill in the art. The term "fragment" as used herein may also refer to an isolated portion of a polypeptide, wherein the portion of the polypeptide is cleaved from a naturally occurring polypeptide by proteolytic cleavage by at least one protease, or is a portion of the naturally occurring polypeptide synthesized by chemical methods well known to one of skill in the art.

As used herein, the term "moiety" means a chemical group on a compound or capable of being coupled to a compound that includes a functional group/subunit. As used herein, a "moiety" may include a compound with a specific function that is a part of a larger compound or capable of being coupled to a different compound to form a larger compound. For instance, a "reporter moiety" is a chemical group that includes a reporter compound (e.g., a fluorescent dye molecule) that is coupled to or adapted to be coupled to another compound.

As used herein, the term "agonist" indicates a compound that induces a receptor molecule, for instance, a ligand that binds with and activates a receptor molecule. In embodiments of the present disclosure, imidazoquinoline derived compounds of the present disclosure are ligands that can activate certain receptors in a host immune system, such as TLR 7 and TLR8, thereby inducing the receptors to generate an immunological response. Thus, in embodiments, the imidazoquinoline derived compounds of the present disclosure can be TLR7 or dual TLR7/TLR8 agonists.

The term "reporter molecule" for use in the present disclosure includes any substance or group capable of being coupled to the imidazoquinoline derived compounds of the present disclosure (e.g., attached/bound to the imidazoquinoline derived compounds) and capable of producing a detectable signal, such as, but not limited to, molecules with particular optical, electrical, acoustic and magnetic properties that can generate a distinguishable signals different from the detecting target, such as, for instance, fluorescent molecules, fluorescent dyes, fluorescent quantum dots, MRI agents, and the like. Such reporter molecules may have the inherent ability to produce a detectable signal, or may produce a detectable signal in the presence of an activator. In embodiments, the reporter molecule produces a signal that is distinguishable from background signals. In embodiments the reporter molecule is "covalently coupled" to the imidazoquinoline derived compounds, meaning it is attached to the imidazoquinoline derived compound by a covalent bond. As used herein, a "reporter moiety" includes a reporter molecule as described above that is coupled to or capable of being coupled to imidazoquinoline derived compounds of the present disclosure.

In some exemplary embodiments, a fluorophor or a fluorescent dye is used as the reporter molecule to label the host and reference samples. Suitable dye molecules include, but are not limited to, Alexa 350, Alexa 430, Alexa 488, Alexa 532, Alexa 546, Alexa 568, and Alexa 594 dyes, AMCA, Lucifer Yellow, fluorescein, luciferins, aequorins, rhodamine 6G, tetramethylrhodamine or Cy3, Cy5, lissamine rhodamine B, amine-bearing fluorophores, such as the bora-diazaindacene dye, BODIPY-TR-cadaverine, and Texas Red, (the numbers in the Alexa names indicate the approximate excitation wavelength maximum in nm).

A "probe" according to the present disclosure, refers to a compound used for detecting a target, such as by binding or otherwise interacting with a target in such a way that interaction between the probe and the target can be detected. Probes may be used to detect a target either in vivo (e.g, in host, living cell, or tissue sample) or in vitro (e.g., in a sample, culture, composition). In embodiments a probe may include a portion that interacts with the target (e.g., by binding the target) and another portion that produces a detectable signal to allow detection (e.g., by imaging) of the target/probe complex. In embodiments of the present disclosure, a probe may include an imidazoquinoline derived compound of the present disclosure coupled to a reporter molecule.

The terms "treat", "treating", and "treatment" are an approach for obtaining beneficial or desired clinical results. Specifically, beneficial or desired clinical results include, but are not limited to, alleviation of symptoms, diminishment of extent of disease, stabilization (e.g., not worsening) of disease, delaying or slowing of disease progression, substantially preventing spread of disease, amelioration or palliation of the disease state, and remission (partial or total) whether detectable or undetectable. In addition, "treat", "treating", and "treatment" can also mean prolonging survival as compared to expected survival if not receiving treatment and/or can be therapeutic in terms of a partial or complete cure for a disease and/or adverse effect attributable to the disease. As used herein, the terms "prophylactically treat" or "prophylactically treating" refers completely, substantially, or partially preventing a disease/condition or one or more symptoms thereof in a host. Similarly, "delaying the onset of a condition" can also be included in "prophylactically treating", and refers to the act of increasing the time before the actual onset of a condition in a patient that is predisposed to the condition.

The term "host" or "organism" as used herein includes humans, mammals (e.g., cats, dogs, horses, etc.), insects, living cells, and other living organisms. A living organism can be as simple as, for example, a single eukaryotic cell or as complex as a mammal. Typical hosts to which embodiments of the present disclosure relate will be insects (e.g., *Drosophila melanogaster*) mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For some applications, hosts may also include plants. For diagnostic or research applications, a wide variety of mammals will be suitable subjects, including rodents (e.g., mice, rats, hamsters), rabbits, primates, and swine such as inbred pigs and the like. Additionally, for in vitro applications, such as in vitro diagnostic and research applications, body fluids and cell samples of the above subjects will be suitable for use, such as mammalian (particularly primate such as human) blood, urine, or tissue samples, or blood, urine, or tissue samples of the animals mentioned for veterinary applications. Hosts that are "predisposed to" condition(s) can be defined as hosts that do not exhibit overt symptoms of one or more of these conditions but that are genetically, physiologically, or otherwise at risk of developing one or more of these conditions.

By "administration" is meant introducing a compound of the present disclosure into a subject; it may also refer to the act of providing a composition of the present disclosure to a subject (e.g., by prescribing). The term "therapeutically effective amount" as used herein refers to that amount of the compound being administered which will relieve or prevent to some extent one or more of the symptoms of the condition to be treated. In reference to conditions/diseases that can be directly treated with a composition of the disclosure, a therapeutically effective amount refers to that amount which has the effect of preventing the condition/disease from occurring in an animal that may be predisposed to the disease but does not yet experience or exhibit symptoms of the condition/disease (prophylactic treatment), alleviation of symptoms of the condition/disease, diminishment of extent of the condition/disease, stabilization (e.g., not worsening) of the condition/disease, preventing the spread of condition/disease, delaying or slowing of the condition/disease progression, amelioration or palliation of the condition/disease state, and combinations thereof. The term "effective amount" refers to that amount of the compound being administered which will produce a reaction that is distinct from a reaction that would occur in the absence of the compound. In reference to embodiments of the disclosure including the imidazoquinoline derived compounds of the disclosure as adjuvants or self-adjuvanting vaccines, an "effective amount" is that amount which increases the immunological response in the recipient over the response that would be expected without administration of the compound. In reference to probes, an "effective amount" or "detectably effective amount" would be that amount which produces a detectable signal that is distinguishable from background signal.

Compositions and immunogenic preparations of the present disclosure, including vaccine compositions, (including the imidazoquinoline derived compounds of the present disclosure, with or without an additional antigen) and capable of inducing protective immunity in a suitably treated host and a suitable carrier therefor are provided. "Immunogenic compositions" are those which result in specific antibody production or in cellular immunity when injected into a host. Such immunogenic compositions or vaccines are useful, for example, in immunizing hosts against infection and/or damage caused by viruses and/or bacteria.

By "immunogenic amount" or "immunogenic effective amount" is meant an amount capable of eliciting the production of antibodies directed against the virus and/or bacteria, in the host to which the vaccine has been administered.

As used herein, the term "adjuvant" indicates a compound that induces and/or enhances an immunological response in a host. The adjuvants of the present disclosure induce immunological responses by activating toll-like receptor (TLR) 7 or by activating TLR7 and TLR8. Some of the adjuvants of the present disclosure may also induce other immunological responses in the host in addition to the activation of TLR7 and/or 8, such as by stimulating interferons (IFN). In general, an "immunological response" refers to a response by the host's immune system to a stimuli, in this case, and adjuvant. Adjuvants that "enhance" an immunological response in a host induce a stronger immunological response to an antigen or other immunological stimulus in the host than would be seen by the administration of an antigen and/or stimulus alone.

The term "self-adjuvant" or "self-adjuvanting vaccine" indicates a compound and/or vaccine (e.g., an antigen that induces an immune response) where the adjuvant effect is induced by the compound itself without the need for a separate adjuvant compound. In embodiments of a self-adjuvant of the present disclosure, an adjuvant molecule is covalently coupled to an antigen. This is in contrast to an antigen and an adjuvant molecule that are physically separate from each other (e.g., not coupled), even though they may be co-administered.

As used herein, the term "tissue-specific" or "tissue-specific moiety" or "tissue-specific agent" refers to compounds or moieties of compounds that have a specific affinity for a certain tissue and/or location in a host system. As such, "tissue-specific" agents can be used to direct a compound to a desired tissue or location in a host sample or system. In embodiments of the present disclosure, a tissue-specific moiety including a tissue-specific compound can be coupled to an imidazoquinoline derived compound of the present disclosure to assist in directing and locating the imidazoquinoline derived compound to a desired tissue and/or location in a host sample or system.

As used herein in reference to the imidazoquinoline derived compounds of the present disclosure, the term "derivative" refers to a new chemical entity that is derived from A (Gardiquimod, in the example illustrated immediately below) by means of chemical transformation. Derivatives are distinguished from "analogues" of the compounds of the present disclosure, which refers to a new chemical entity that is structurally related to A, but which cannot be obtained from A, but has to be synthesized using other precursors. Below, the top row represents Gardiquimod and two of its derivatives, and the bottom row depicts Gardiquimod and two of its analogues.

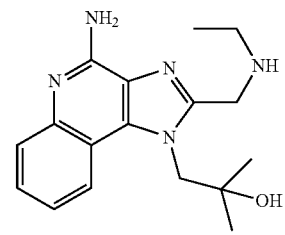

Gardiquimod

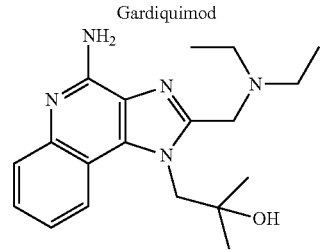

N-ethyl derivative

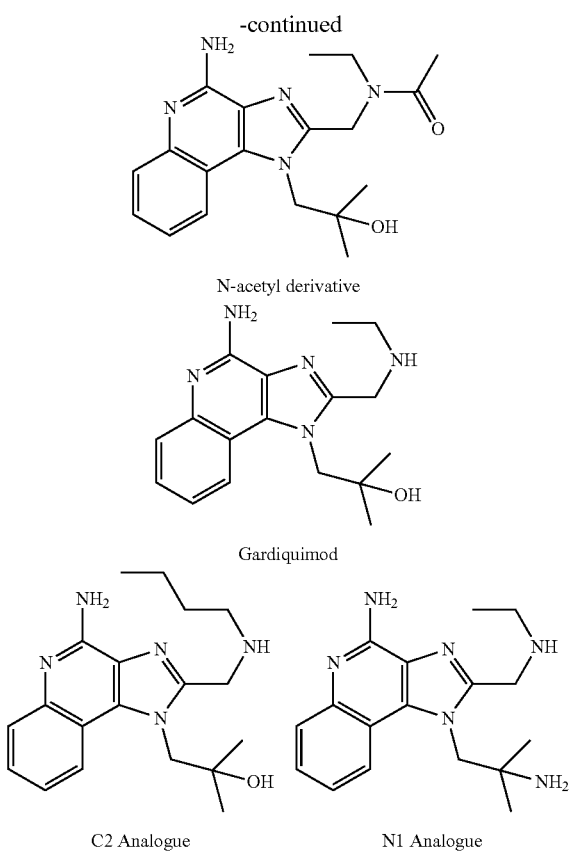

N-acetyl derivative

Gardiquimod

C2 Analogue

N1 Analogue

The term "imidazoquinoline derived compounds" refers to the imidazoquinoline derivatives and imidazoquinoline analogues of the present disclosure, as well as intermediates of such compounds.

"Dendrimers", as used herein, refers to branched compounds made of two or more, typically identical, sub-units or moieties. Typically, and as used in the present disclosure, the sub-units are covalently bound to each other. In the compounds of the present disclosure, dendrimers include two more identical imidazoquinoline derived compounds of the present disclosure that are covalently linked. In embodiments, dendrimers of the present disclosure include, but are not limited to, "dimmers" (two sub-units), "trimers" (three sub-units), and "hexamers" (six sub-units) of the imidazoquinoline derived compounds of the present disclosure.

"Pharmaceutically acceptable salt" refers to those salts which retain the biological effectiveness and properties of the free bases and which are obtained by reaction with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid, malic acid, maleic acid, succinic acid, tartaric acid, citric acid, and the like.

A "pharmaceutical composition" refers to a mixture of one or more of the compounds described herein, derivatives thereof, or pharmaceutically acceptable salts thereof, with other chemical components, such as pharmaceutically acceptable carriers and excipients. One purpose of a pharmaceutical composition is to facilitate administration of a compound to the organism.

As used herein, a "pharmaceutically acceptable carrier" refers to a carrier or diluent that does not cause significant irritation to an organism and does not abrogate the biological activity and properties of the administered compound.

As used herein, "alkyl" or "alkyl group" refers to a saturated aliphatic hydrocarbon radical which can be straight or branched, having 1 to 20 carbon atoms or the stated range of carbon atoms, where the stated range of carbon atoms includes each intervening integer individually, as well as sub-ranges. Examples of alkyl include, but are not limited to methyl, ethyl, n-propyl, i-propyl, n-butyl, s-butyl, t-butyl, n-pentyl, and s-pentyl.

As used herein, "alkenyl" or "alkenyl group" refers to an aliphatic hydrocarbon radical which can be straight or branched, containing at least one carbon-carbon double bond, having 2 to 20 carbon atoms or the stated range of carbon atoms, where the stated range of carbon atoms includes each intervening integer individually, as well as sub-ranges. Examples of alkenyl groups include, but are not limited to, ethenyl, propenyl, n-butenyl, i-butenyl, 3-methylbut-2-enyl, n-pentenyl, heptenyl, octenyl, decenyl, and the like.

Discussion:

Embodiments of the present disclosure include novel imidazoquinoline derived compounds, including derivatives and analogues of imiquimod and gardiquimod. In embodiments, the imidazoquinoline derived compounds are capable of activating TLR7 or dual activation of TLR7/TLR8. Embodiments of the present disclosure also include compositions including the imidazoquinoline derived compounds, methods of using the imidazoquinoline derived compounds, and methods of synthesis of the imidazoquinoline derived compounds. The imidazoquinoline derived compounds may be useful as adjuvants, probes, immunogenic compositions, and/or therapeutic compositions. The imidazoquinoline derived compounds may be coupled to reporter molecules, antigens, and/or other molecules for use as probes, vaccine adjuvants, and/or self-adjuvanting vaccines. Further embodiments of the disclosure include dendrimers (e.g., dimmers, trimers, hexamers, etc.) of the imidazoquinoline derived compounds, and use of the dendrimers for activation of TLR7 or TLR7/TLR8. Embodiments of the present disclosure also include dual TLR2/TLR7 hybrid agonists that include imidazoquinoline derived compounds of the present disclosure conjugated to PMM2CS TLR2 agonists. In embodiments, some of the imidazoquinoline derived compounds of the present disclosure may be used to treat certain disease conditions. These and other embodiments of the present disclosure will be described in greater detail below.

Novel Imidazoquinoline Derived Compounds

Although the imidazoquinoline compounds Imiquimod and Gardiquimod and many of their derivatives are known, the present disclosure provides novel derivatives and analogues of these compounds. Embodiments of the present disclosure include imidazoquinoline derived compounds having the following formula, as well as derivatives, analogues, and pharmaceutically acceptable salts of such compounds.

FORMULA I

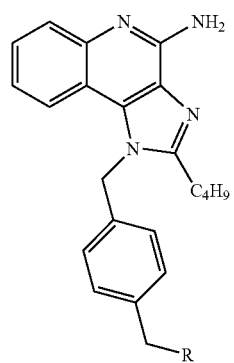

In embodiments of the imidazoquinoline derived compounds of the present disclosure of Formula I, R is selected from the group consisting of: —NH($R_5$) and isothiocyanate (—NCS);

$R_5$ is selected from the group consisting of hydrogen (—H), acetyl (e.g., a group that includes —COCH$_3$), —CO-tert-Bu (-Boc), —CO—(CH$_2$)$_x$—R$_6$, C$_1$-C$_{16}$ alkyl, —CO-4-(phenylboronic acid), —C(S)—NH—(CH$_2$)$_x$—NH—(CH$_2$)$_x$—NH—(CH$_2$)$_x$—NH$_2$,

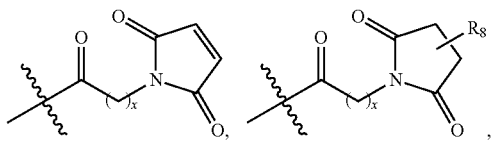

a reporter moiety, a tissue-specific moiety, a peptide antigen moiety, a protein antigen moiety, a polysaccharide antigen moiety, and a TLR$_2$ agonist moiety;

$R_6$ is selected from the group consisting of hydrogen (—H), alkyne (e.g., a group that includes a carbon-carbon triple bond such as —C≡CH), azido (e.g., a group that includes a —N$_3$), carboxylic acid (e.g., a group that includes a —CO$_2$H), and —CONH—(CH$_2$)$_x$—O—(CH$_2$)$_x$—O—(CH$_2$)$_x$—O—(CH$_2$)$_x$—R$_7$;

$R_7$ is selected from the group consisting of amino (e.g., a group that includes a —NH$_2$), isothiocyanate (e.g., a group that includes a —NCS) and —NH—CO—(CH$_2$)$_x$—CO$_2$H, $R_8$ is selected from a peptide antigen moiety or a protein antigen moiety; and x is any integer from 1 to 10.

In embodiments of the imidazoquinoline derived compounds of Formula I of the present disclosure where R is a reporter moiety, the reporter moiety includes a reporter molecule, such as, but not limited to, a fluorescent molecule or an MRI agent. In embodiments, the reporter molecule is selected from fluorescein, rhodamine B, bora-diazaindacene dye, and BODIPY-TR-cadaverine, and biotin. In embodiments the reporter moiety includes an isothiocyanate modified reporter molecule.

In embodiments of the imidazoquinoline derived compounds of Formula I of the present disclosure where R is a tissue-specific moiety, the tissue-specific moiety includes a tissue specific molecule. In embodiments, the tissue-specific molecule includes tissue-specific agents such as, but not limited to, galactosyl and vitamins such as folic acid, biotin, and pyridoxal.

In embodiments of the imidazoquinoline derived compounds of Formula I of the present disclosure where R is a peptide or protein antigen moiety or a polysaccharide antigen moiety, the moiety includes a peptide or protein antigen or a polysaccharide antigen, respectively. In embodiments, the protein antigen is α-lactalbumin. In embodiments where the antigen moiety is a peptide antigen, the peptide antigen can be, but is not limited to, tri-glycine methyl ester model peptide, and glutathione peptide. In embodiments, the polysaccharide antigen is maltoheptaose.

In embodiments of the imidazoquinoline derived compounds of Formula I of the present disclosure where R is a TLR2 agonist moiety, the TLR2 agonist moiety includes a TLR2 agonist, such as, but not limited to, S[2,3-bis(palmitoyloxy)-(2RS)-propyl]-R-cysteinyl-5-serine (PAM(2)CS) and derivatives of PAM(2)CS.

Embodiments of the present disclosure also include dimers and dendrimers of compounds of Formula I, including, but not limited to, dimers, trimers, and hexamers of compounds of Formula I, as well as derivatives, analogues, and pharmaceutically acceptable salts of such dendrimers.

Additional details regarding the compounds and methods of making compounds of Formula I, its precursors and derivatives can be found in Examples 1 and 2 below, as well as the other Examples. Embodiments of compounds of Formula I include, but are not limited to, compounds 6d, 7d, 8, 12, 13, 14, 15, 16, 17, 18, 19, 21, 23, 25, 26, 27, 28, 29, 30a, 30b, 31, 33, 35, 37, 39, 60, 61, 62, 63, 64, and 65, and derivatives and analogues of these compounds or pharmaceutically acceptable salts thereof, which are described in detail in the Examples below.

In embodiments of the imidazoquinoline derived compounds of the present disclosure of Formula I, R is selected from the group consisting of: —NH($R_5$) and isothiocyanate (—NCS), where $R_5$ is selected from the group consisting of hydrogen (—H), acetyl (e.g., a group that includes —COCH$_3$), —CO-tert-Bu (-Boc), —CO—(CH$_2$)$_x$—R$_6$, C$_1$-C$_{16}$ alkyl, —CO-4-(phenylboronic acid), —C(S)—NH—(CH$_2$)$_x$—NH—(CH$_2$)$_x$—NH—(CH$_2$)$_x$—NH$_2$,

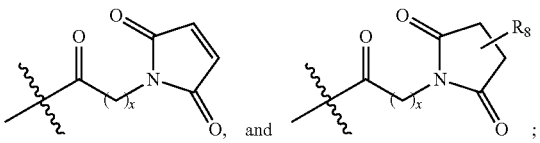

$R_6$ is selected from the group consisting of hydrogen (—H), alkyne (e.g., a group that includes —C≡CH), azido (—N$_3$), carboxylic acid (e.g., a group that includes —CO$_2$H), and —CONH—(CH$_2$)$_x$—O—(CH$_2$)$_x$—O—(CH$_2$)$_x$—O—(CH$_2$)$_x$—R$_7$; $R_7$ is selected from the group consisting of amino (e.g., a group including —NH$_2$), isothiocyanate (e.g., a group including —NCS) and —NH—CO—(CH$_2$)$_x$—CO$_2$H; $R_8$ is selected from a peptide antigen moiety or a protein antigen moiety, and x is any integer from 1 to 10. In such embodiments, the imidazoquinoline derived compounds of the present disclosure of Formula I can also include a moiety coupled to the R group, where the moiety is selected from a reporter moiety, a tissue-specific moiety, a peptide antigen moiety, a protein antigen moiety, a polysaccharide antigen moiety, and a TLR2 agonist moiety, as described in greater detail below.

The present disclosure also includes imidazoquinoline derived compounds having the structure of Formula II, below, and derivatives, analogues, and pharmaceutically acceptable salts of such compounds. The substituents shown on the N1-benzyl unit can be independently at the ortho, meta, or para positions, and $R_1$-$R_4$ are as defined below.

FORMULA II

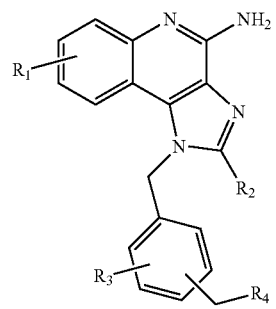

Where, $R_1$ and $R_3$ are each independently selected from the group consisting of hydrogen, halogen (e.g., a group that includes —Cl, —Br, —F), nitro (e.g., a group that includes —$NO_2$), —$NH_2$, azido (e.g., a group that includes —$N_3$), hydroxyl (e.g., a group that includes —OH), —$CF_3$, carboxylic acid (e.g., a group that includes —$CO_2H$) and —$CO_2R_2$;

$R_2$ is a $C_2$-$C_5$ alkyl, and $R_4$ selected from the group consisting of: —NH($R_5$) and isothiocyanate (e.g., a group that includes —NCS);

$R_5$ is selected from the group consisting of hydrogen (—H), acetyl (e.g., a group that includes —$COCH_3$), —CO-tert-Bu (-Boc), —CO—$(CH_2)_x$—$R_6$, $C_1$-$C_{16}$ alkyl, —CO-4-(phenylboronic acid), —C(S)—NH—$(CH_2)_x$—NH—$(CH_2)_x$—NH—$(CH_2)_x$—$NH_2$,

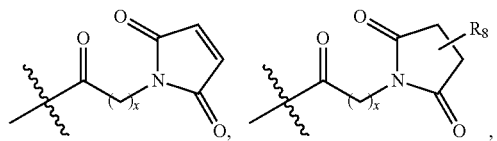

a reporter moiety, a tissue-specific moiety, a peptide antigen moiety, a protein antigen moiety, a polysaccharide antigen moiety, and a $TLR_2$ agonist moiety;

$R_6$ is selected from the group consisting of hydrogen (—H), alkyne (e.g., a group that includes a carbon-carbon triple bond such as —C≡CH), azido (e.g., a group including —$N_3$), carboxylic acid (e.g., a group that includes a —$CO_2H$), and —CONH—$(CH_2)_x$—O—$(CH_2)_x$—O—$(CH_2)_x$—O—$(CH_2)_x$—$R_7$;

$R_7$ is selected from the group consisting of amino (e.g., a group that includes a —$NH_2$), isothiocyanate (e.g., a group that includes a —NCS) and —NH—CO—$(CH_2)_x$—$CO_2H$;

$R_8$ is selected from a peptide antigen moiety or a protein antigen moiety; and x is any integer from 1 to 10.

In embodiments of the imidazoquinoline derived compounds of Formula II of the present disclosure $R_4$ is any of the substituents described above for R of Formula I. In embodiments of the imidazoquinoline derived compounds of the present disclosure of Formula II, $R_4$ is selected from the group consisting of: —NH($R_5$) and isothiocyanate (e.g., a group that includes —NCS), where $R_5$ is selected from the group consisting of hydrogen (—H), acetyl (e.g., a group that includes —$COCH_3$), —CO-tert-Bu (-Boc), —CO—$(CH_2)_x$—$R_6$, $C_1$-$C_{16}$ alkyl, —CO-4-(phenylboronic acid), —C(S)—NH—$(CH_2)_x$—NH—$(CH_2)_x$—NH—$(CH_2)_x$—$NH_2$,

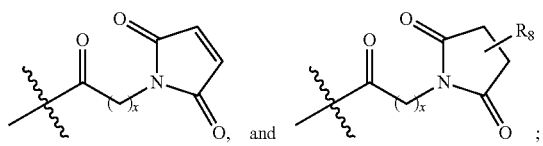

$R_6$ is selected from the group consisting of hydrogen (—H), alkyne (e.g., a group that includes —C≡CH), azido (—$N_3$), carboxylic acid (e.g., a group that includes —$CO_2H$), and —CONH—$(CH_2)_x$—O—$(CH_2)_x$—O—$(CH_2)_x$—O—$(CH_2)_x$—$R_7$, $R_7$ is selected from the group consisting of amino (e.g., a group including —$NH_2$), isothiocyanate (e.g., a group including —NCS) and —NH—CO—$(CH_2)_x$—$CO_2H$; $R_8$ is selected from a peptide antigen moiety or a protein antigen moiety, and x is any integer from 1 to 10. In such embodiments, the imidazoquinoline derived compounds of the present disclosure of Formula II can also include a moiety coupled to the $R_4$ group, where the moiety is selected from a reporter moiety, a tissue-specific moiety, a peptide antigen moiety, a protein antigen moiety, a polysaccharide antigen moiety, and a TLR2 agonist moiety, as described in greater detail below.

Some examples of compounds of the present disclosure having Formula II include, but are not limited to: 6c, and 7c, and derivatives and analogues thereof or pharmaceutically acceptable salts thereof, as well as the compounds of Formula I set forth above.

Many of the imidazoquinoline derived compounds of Formula I and II above and their various derivatives, and analogues thereof are described in greater detail in the discussion and examples below.

Embodiments of the present disclosure also include derivatives and analogues of the compounds of Formula I and Formula II above, including, but not limited to, dendrimers and dimers of the compounds of Formula I and Formula II. These and other dendrimers and dimers will be discussed in greater detail below.

Structure-activity Relationships in Human TLR7-active and TLR7/8 Dual Active Imidazoquinoline Analogues Toll-like receptors (TLR)-7/-8 are innate immune receptors present in the endosomal compartment that are activated by single-stranded RNA (ssRNA) molecules of viral as well as nonviral origin, inducing the production of inflammatory cytokines necessary for the development of adaptive immunity. Molecules that induce (TLR)-7/-8 (e.g., agonists) represent potential vaccine adjuvants. Synthetic small molecule agonists of TLR7 include the imidazoquinoline class of compounds such as Gardiquimod [1-(4-amino-2-((ethylamino)methyl)-1H-imidazo[4,5-c]quinolin-1-yl)-2-methylpropan-2-ol]. With the goal of developing more potent TLR7 agonists as adjuvants, various derivatives and analogues of gardiquimod were synthesized and a detailed SAR study on the imidazoquinoline chemotype was performed, which led to the discovery of highly potent, lipophilic, human TLR7 agonists. Details regarding the imidazoquinoline derived compounds with TLR7 and/or TLR7/8 agonistic activity, methods of synthesizing the imidazoquinoline derived compounds, and methods of using such compounds are described in greater detail in the Examples below.

The present disclosure provides adjuvants including imidazoquinoline derived compounds chosen from compounds of Formulas I and II and derivatives and analogues thereof and pharmaceutically acceptable salts thereof, where the compound is capable of activating TLR7. In embodiments of the present disclosure, imidazoquinoline derived compounds include compounds of Formula I and/or Formula II, including, but not limited to, compound 7d and derivatives and analogues of compound 7d. In embodiments, these imidazoquinoline derived compounds have been demonstrated to activate TLR7, as discussed in more detail in the Examples. In embodiments some of the compounds capable of inducing TLR7 activity include, but are not limited to, compounds 6c, 6d, 7c, 7d, 8, 12, 13, 14, 15), 16, 17, 18, 19, 21, 23, 25, 26-28, 30b, 31, 33, 35, 37, 39, 41, 43, 51a-d, 52a-c, 55a-c, 60, 61, 62, 64, 65, and derivatives, analogs, and pharmaceutically acceptable salts of those compounds.

In some embodiments, the imidazoquinoline derived compounds of the present disclosure are capable of dual activation of both TLR7 and TLR8. While traditionally it had been thought that activation of TLR8 might be undesirable due to potential systemic proinflammatory responses, it has now been discovered that in some instances dual activation of both TLR7 and TLR8 provides advantages and is desirable. It has been found that in some cases, induction of immunological responses from TLR7 alone may not produce as much reactivity as dual induction, and in such cases, dual induction of TLR7/8 provides additional immunological response. For instance, in the case of infants and very young babies, the induction of TLR7 may not produce a sufficient response to generate an effective immune response. However, in some embodiments, dual induction of TLR7 and TLR8 together can produce an effective response. The dual induction also induces the production of IL12 and IL18, which also play a role in inducing immunity. In embodiments, some of the compounds capable of inducing both TLR7 and TLR8 activity include imidazoquinoline derived compounds 7c, 7d, 19 and derivatives or analogs of those compounds.

Embodiments of the present disclosure also include TLR7 agonists including, but not limited to, the following imidazoquinoline derived compounds: 6c, 6d, 7c, 7d, 8, 12, 13, 14, 15, 16, 17, 18, 19, 21, 23, 25, 26-28, 30b, 31, 33, 35, 37, 39, 41, 43, 51a-d, 52a-c, 55a-c, 60, 61, 62, 64, 65, and derivatives and/or analogs of those compounds. The present disclosure also provides compositions including a TLR7 agonist or a dual TLR7/8 agonist of the present disclosure. In embodiments, the TLR7/8 agonists include, but are not limited to, compounds 7c, 7d, 19, 39, 35, 41, 52c, or derivatives of each of those or analogues thereof.

Further embodiments of the present disclosure include vaccine adjuvants including the imidazoquinoline derived compounds of the present disclosure. In representative embodiments, the imidazoquinoline derived compounds that can be used as vaccine adjuvants include, but are not limited to, the compounds listed above as representative TLR7 and/or TLR7/TLR8 agonists and derivatives or analogues of those compounds.

In other embodiments, the present disclosure provides methods of inducing an immunological response in a host by administering to the host an effective amount of an imidazoquinoline derived compound of the present disclosure, where the compound is capable of activating TLR7 or capable of dual activation of TLR7 and TLR8. Methods of the present disclosure also include methods of activating TLR7 by introducing a composition including an imidazoquinoline derived compound of the present disclosure, such as a compound of Formula I and/or II to one or more TLR7 receptors. In some embodiments the imidazoquinoline derived compound used to activate TLR7 is one or more of the imidazoquinoline derived compounds of Formula I and/or II described above or derivatives or analogues of each.

The present disclosure also provides methods of immunizing a host by administering a vaccine including an antigen to the host, and also administering to the host an adjuvant, where the adjuvant is an imidazoquinoline derived compound of the present disclosure that is capable of activating TLR7 or is capable of activating TLR7 and TLR8. The adjuvant may be administered in the same composition as the antigen, or they may be administered separately but at a similar time. In embodiments of the methods of immunizing a host, the adjuvant compound may be chosen from, but is not limited to, any of the compounds listed above as having TLR7 and/or TLR7/TLR8 agonist activity. The adjuvant compound may be capable of activating TLR7 and TLR8, for instance, compounds 7c, 7d, 19, 39, 35, 41, 52c, and derivatives and analogues of each of these.

Thus, embodiments of the disclosure also include, a TLR7 agonist comprising an imidazoquinoline derived compound chosen from compounds 6c, 6d, 7c, 7d, 8, 12, 13, 14, 15, 16, 17, 18, 19, 21, 23, 25, 26-28, 30b, 31, 33, 35, 37, 39, 60, 61, 62, 64, 65, derivatives thereof, analogues thereof, or pharmaceutically acceptable salts thereof. Embodiments of the present disclosure also include dual a TLR7/TLR8 agonist comprising an imidazoquinoline derived compound chosen from compounds 7c, 7d, 19, 39, 35, 41, 52c, derivatives thereof, analogues thereof, or pharmaceutically acceptable salts thereof. These agonists can be used as vaccine adjuvants (alone, or as self-adjuvanting vaccines when coupled to an antigen), as probes (when coupled to or including a reporter moiety), and the like, as described below.

Syntheses of Fluorescent Imidazoquinoline Conjugates as Probes of TLR7 or TLR7/8

Further exploration on the imidazoquinoline chemotype led to discovery of a highly active TLR7 and/or TLR7/8 dual agonistic molecule bearing a free primary amine on the $N^1$ substituent (e.g., compound 7d). In embodiments, this compound was modified with a fluorescent reporter moiety to synthesize fluorescent imidazoquinoline analogues that retained TLR7 and/or TLR7/8-agonistic activity, and were used to study the distribution of TLR7 and also to examine its differential uptake in lymphocytic subsets. Details regarding the fluorescent imidazoquinoline derived compounds of the present disclosure and methods of making and using such molecules are described in greater detail in Example 3 below.

The present disclosure thus describes probes for imaging activation of TLR7, TLR8 or dual activation of TLR7 and 8. In embodiments, probes of the present disclosure include a TLR7 ligand or a dual TLR7/TLR8 ligand chosen from imidazoquinoline derived compounds of the present disclosure having a reporter moiety. The reporter moiety includes a reporter molecule capable of producing a detectable signal. In embodiments the TLR7 or dual TLR7/TLR8 ligand is chosen from compounds 7c, 7d, and derivatives and analogues of these compounds. In embodiments, compound 7d was converted to an isothiocyanate derivative, compound 8, which allows for coupling to amine-bearing fluorophors (such as but not limited to bora-diazaindacene dye, and BODIPY-TR-cadaverine) to produce a fluorescent imidazoquinoline analogue, such as compound 28. In embodiments, the free primary amine on the $N^1$ substituent of 7d was covalently coupled directly to commercially-available fluorescein isothiocyanate and rhodamine B isothiocyanate, to produce fluorescent imidazoquinoline derived compounds 26 and 27. Compounds 26, 27, and 28 were shown to retain TLR7 agonistic activity.

In embodiments, the reporter moiety for the probes of the present disclosure may include any reporter molecule capable of producing a detectable signal (e.g., optical, acoustic, magnetic, electrical, etc.), including, but not limited to, fluorescent molecules (e.g., fluorophores, fluorescent dye, etc. as described above), MRI agents, and the like. In embodiments the reporter molecule is a fluorescent compound, such as in compounds 26, 27, and 28 as discussed in Example 3; in other embodiments the reporter molecule is biotin, such as in compound 37, discussed further in Example 6.

The present disclosure also provides methods of imaging activation of TLR7, TLR8, or both TLR7 and TLR8 using the probes of the present disclosure. In embodiments of the methods of imaging activation of TLR7, TLR8 or TLR7/8, a sample including the receptors to be activated is contacted with a probe of the present disclosure, and then the detectable signal produced by the reporter molecule can be imaged by imaging methods and technology known to those of skill in the art.

Self-adjuvanting Model Peptide, Protein and Polysaccharide Antigens with Covalently Bound TLR-7/8 Agonistic Imidazoquinolines Embodiments of the present disclosure also include self-adjuvanting antigen/imidazoquinoline derived compounds. Such embodiments include imidazoquinoline derived compounds of the present disclosure including a peptide or protein antigen moiety and/or a polysaccharide antigen moiety. In embodiments, the imidazoquinoline derived compounds of the present disclosure, such as the TLR7 and TLR7/8 dual agonistic compounds described above, are used as a convenient precursor for the synthesis of isothiocyanate derivatives (e.g., compound 8) and maleimide derivatives (e.g., compound 21), enabling direct conjugation to protein and polysaccharide antigens to make self-adjuvanting vaccine constructs. In an embodiment, the isothiocyanate derivative, 8, can be reacted with tri-glycine methyl ester model peptide to produce the adduct 29. In an embodiment, an isothiocyanate derivative (8) can be covalently coupled to a protein antigen, such as, but not limited to, α-lactalbumin, to produce an embodiment of a self-adjuvanting α-lactalbumin construct. This compound induced robust, high-affinity immunoglobulin titers in murine models of vaccination.

Additional embodiments of the present disclosure include maleimide derivatives of the imidazoquinoline derived compounds of the present disclosure, such as, but not limited to, compound 21. In embodiments, the maleimide derivative compound 21 can be coupled to glutathione to produce the derivative compounds 30a and 30b. In an embodiment, the maleimide derivative, 21, can be covalently coupled to a peptide or protein antigen moiety including an antigen, such as, but not limited to, α-lactalbumin, to produce an embodiment of a self-adjuvanting α-lactalbumin construct. Additional details regarding the self-adjuvanting antigens with covalently bound TLR7/8 dual agonistic molecules, and methods of making and using such self-adjuvanting antigens are described in greater detail in Example 4 below. While α-lactalbumin represents one example of a protein or peptide antigen moiety that can be coupled to the imidazoquinoline derived compounds of the present disclosure to produce self-adjuvanting peptide antigen imidazoquinoline derived compounds, other protein and peptide antigens can be used within the scope of the present disclosure.

Polysaccharide antigens can also be covalently coupled to imidazoquinoline derived compounds of the present disclosure to provide imidazoquinoline derived compounds having a polysaccharide antigen moiety, as described in greater detail in Example 5 below. In embodiments imidazoquinoline derived compounds of the present disclosure of Formula I or II, such as compound 7d can be coupled with a polysaccharide antigen, such as, but not limited to, maltoheptaose, which is used in a polysaccharide vaccine for *N. meningitidis*. In an embodiment compound 7d can be coupled with maltoheptaose to produce compound 31, which retained TLR7 activity. Embodiments of self-adjuvanting polysaccharide antigens of the present disclosure include, but are not limited to, compound 31, described below.

The present disclosure also provides self-adjuvanting vaccines. In embodiments, the self-adjuvanting vaccines include an antigen covalently coupled to an adjuvant compound of the present disclosure as described above. In embodiments the adjuvant compound can be a TLR7 agonist or a dual TLR7/8 agonist, such as the imidazoquinoline derived compounds as described above. In embodiments, the adjuvant compounds are imidazoquinoline derived compounds that include an antigen moiety and/or a functionality for covalently coupling the antigen moiety, such as a protein or peptide antigen (e.g., viral peptide) or a polysaccharide antigen (e.g., bacterial polysaccharide). For instance, the adjuvant compound can be isothiocyanate derivatives and maleimide derivatives of the dual TLR7/8 agonists of the present disclosure. In embodiments the adjuvant compound can be isothiocyanate derivatives and maleimide derivatives of a compound of Formula I or Formula II. In embodiments, the adjuvant compounds of the present disclosure include isothiocyanate derivatives and maleimide derivatives of compound 7d or derivatives or analogues of 7d. In embodiments such compounds include but are not limited to, compound 8 and compound 21. The isothiocyanate derivatives and maleimide derivatives of the adjuvant compounds of the present disclosure can be useful for covalently coupling peptide and protein antigens.

The present disclosure also includes methods of immunizing a host by administering a self-adjuvanting vaccine of the present disclosure to the host. The self-adjuvanting vaccines may be useful in inducing an enhanced immune response from the host.

Tissue-specific Imidazoquinoline Derived Compounds and Therapeutic Methods of Use Embodiments of the present disclosure also include imidazoquinoline derived compounds modified with tissue-specific moieties to target the imidazoquinoline derived compounds to a specific location in a host. In embodiments, the compounds of the present disclosure include a compound of Formula I including a tissue-specific moiety that includes a tissue-specific molecule/agent. In this manner, such tissue-specific imidazoquinoline derived compounds can also be used in methods of treating certain conditions where targeted delivery to a specific region in the host is useful. For instance, in an embodiment galactosyl-terminating molecules can be used to target delivery of compounds to the liver of a host. Embodiments of the present disclosure include a derivatives and analogues of a compound of Formula I or II, such as 7d, modified with galactose to produce a liver-specific imidazoquinoline compound 33. Vitamins, such as, but not limited to, folic acid, biotin, and pyridoxal can be used to target compounds to certain tumors. Thus, embodiments of the present disclosure include imidazoquinoline derived compounds of the present disclosure modified with vitamins, such as, but not limited to, folic acid, biotin and pyridoxal to produce tumor-specific compounds, such as folic acid derivative 35, biotin derivative 37, and pyridoxal derivative 39.

Embodiments of the present disclosure also include compositions for treatment of a condition such as, but not limited to, hepatitis, chronic myelogenous and hairy cell leukemias. In embodiments, such compositions include an imidazoquinoline derived compound of the present disclosure in an amount effective to treat the condition. Interferon alpha is the composition of choice for treating conditions such as hepatitis; however, many patients do not tolerate oral administration of the compound. Embodiments of the compounds of the present disclosure induce the production of interferon alpha. When targeted to the host's liver, compounds of the present disclosure can induce production of interferon alpha by the patient's own liver, thus bypassing the need for oral administration of interferon alpha. In an embodiment, imidazoquinoline derived compounds of the present disclosure, such as, but not limited to, compounds of Formulas I and II, and derivatives and analogues of such compounds can be modified by a tissue-specific agent to target the compound to the host's liver. In an embodiment, the tissue-specific agent is galactose, which directs the compound to the liver of the host. Embodiments of such tissue-specific imidazoquinoline derived compounds include, but are not limited to, compounds 33. Additional details regarding embodiments of tissue-specific imidazoquinoline derived compounds of the present disclosure are presented in Example 6, below.

In embodiments, imidazoquinoline derived compounds, such as, but not limited to, compounds 33, 35, 37, and 39 and derivatives of each of the foregoing compounds or analogues thereof can be used to treat conditions such as hepatitis, chronic myelogenous and hairy cell leukemias. In embodiments, compound 33, which directs the molecule to the liver of the host, can be used to treat Hepatitis C. This targeted delivery helps to reduce side effects. The present disclosure also provides methods of treatment of conditions such as, but not limited to, hepatitis, chronic myelogenous and hairy cell leukemias, including administering to a host in need of treatment for the condition an effective amount of an imidazoquinoline derived compound described immediately above. Thus, in embodiments the present disclosure includes a method of treatment of a condition chosen from hepatitis, chronic myelogenous and hairy cell leukemia comprising administering to a host in need of treatment for the condition an effective amount of an imidazoquinoline derived compound of Formula I or II, above, coupled to a tissue-specific agent selected from galactose, folic acid, biotin, or pyridoxal.

Additional methods of the present disclosure include methods of inducing production of interferon alpha in a host by administering to the host an effective amount of an imidazoquinoline derived compound of the present disclosure. In embodiments, the imidazoquinoline derived compound can be chosen from, but is not limited to, compound 33 and derivatives or analogues thereof.

The embodiments of tissue-specific imidazoquinoline derived compounds described above are merely representative examples, and the imidazoquinoline derived compounds of the present disclosure may be modified with many other tissue-specific compounds to achieve targeted delivery to various tissues and/or locations in a host.

Dendrimers and Dimers of Imidazoquinoline Derived Compounds

The present disclosure also includes dendrimers of the imidazoquinoline derived compounds of the present disclosure, and methods of making and using the dendrimers, including, but not limited to, trimers and hexamers of the imidazoquinoline derived compounds of the present disclosure. In embodiments, the present disclosure includes dendrimers (e.g., trimers and/or hexamers) of the imidazoquinoline derived compounds of Formula I or Formula II. The larger size of dendrimers bearing three or six units of an imidazoquinoline derived compound of the present disclosure may extend activity of the compounds by slowing diffusion of the compounds. Embodiments of the present disclosure include dendrimers of imidazoquinoline derived compounds of Formula I and/or Formula II. Embodiments include dendrimers of compound 7d, such as, but not limited to, the trimeric imidazoquinoline dendrimer 41 and the hexameric imidazoquinoline dendrimer 43.

In embodiments, trimers of the imidazoquinoline derived compounds of the present disclosure can be made and retain TLR7 and/or TLR7/8 agonistic activity. Embodiments including trimers and hexamers of compound 7d are described in greater detail in Example 7 below. In embodiments, trimers of imidazoquinoline derived compounds of the present disclosure include compound 41. In embodiments, hexamers of imidazoquinoline derived compounds of the present disclosure include compound 43, which retains TLR7 activity.

The present disclosure also includes dimeric imidazoquinoline variants of the imidazoquinoline derived compounds of the present disclosure. Embodiments of the disclosure include, but are not limited to, dimers of the imidazoquinoline derived compounds of Formulas I and/or II with the units linked at different positions, such as, but not limited to, the $N^1$-(4-aminomethylene)benzyl-linked dimers 52a-c, and the C8-$NH_2$ linked dimers 55a-c. In embodiments, the present disclosure includes dimers of variants of compound 7d, with the units linked at different positions, such as compounds 52a-c. Dimeric compounds 51a-d, 52a-c, and 55-a-c demonstrated TLR7 agonistic activity, and 55c demonstrated dual TLR7/TLR8 activity. Thus, the present disclosure includes TLR7 and/or dual TLR7/TLR8 agonists including dimeric compound derivatives of Formulas I and II, such as, but not limited to, the compounds 52a-c, and 55-a-c.

Embodiments of dimeric imidazoquinoline derived compounds of the present disclosure also include, but are not limited to, C2-linked compounds 47a-b, 49a-b, and the C4-$NH_2$ linked dimers 51a-d. Dimeric compounds 47a-b, 49a-b can be represented by the generic structure of Formula III, below.

FORMULA III

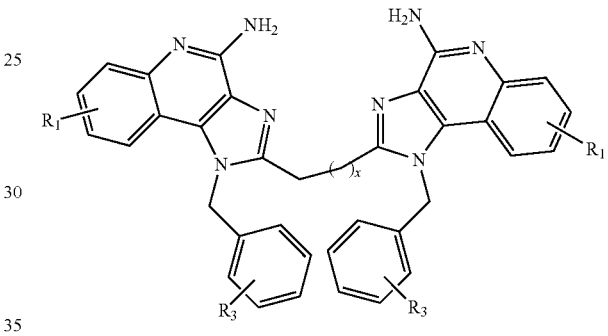

where, $R_1$ is independently selected from the group consisting of hydrogen, halogen (e.g., a group including —Cl, —Br, —F), nitro (e.g., a group including —$NO_2$), —$NH_2$, azido (e.g., a group including —$N_3$), hydroxyl (e.g., a group including —OH), —$CF_3$; $R_3$ is independently selected from the group consisting of hydrogen or —$(CH_2)_x$—$NH_2$, and x is any integer form 1 to 10. The dimeric imidazoquinoline derived compounds of Formula III, such as, but not limited to, 47a-b, and 49a-b demonstrated unexpected TLR7 antagonistic behavior, in contrast to the agonistic activity of the dimers based on the compounds of Formulas I and II, such as dimeric compounds 52a-c and 55a-c. Thus, in embodiments, the present disclosure includes TLR7 antagonists including compounds of Formula III, derivatives thereof, analogues thereof, and pharmaceutically acceptable salts thereof.

Additional details regarding embodiments of the dimers of the imidazoquinoline derived compounds of the present disclosure are described below in Example 8.

Dual TLR2/TLR7 Adjuvants

Embodiments of the present disclosure also include imidazoquinoline derived compounds with TLR7 agonistic activity including a TLR2 agonist moiety to provide dual TLR2/TLR7 adjuvant compounds. In embodiments, TLR7 activating imidazoquinoline derived compounds of the present disclosure described above, such as those of Formula I or II (e.g., compounds 7d, 8, 12, 13, 14, 15, etc.) or their derivatives and analogues are coupled to a TLR2 agonist moiety that includes a TLR2 agonist compound, such as, but not limited to, S-[2,3-bis(palmitoyloxy)-(2RS)-propyl]-R-cysteinyl-5-serine (PAM(2)CS) compounds and derivatives of PAM(2) CS compounds. Embodiments of dual TLR2/

TLR7 adjuvant compounds include, but are not limited to, thiourea-linked hybrid compounds 60-65, and derivatives and analogues of these compounds. Additional details regarding the dual TLR2/TLR7 adjuvant compounds of the present disclosure are described in Example 9 below.

Additional details regarding the imidazoquinoline derived compounds of the present disclosure, probes and adjuvants comprising the imidazoquinoline derived compounds, compositions comprising the imidazoquinoline derived compounds, methods of making the imidazoquinoline derived compounds of the present disclosure, and methods of using the imidazoquinoline derived compounds of the present disclosure can be found in the following Examples.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and protected by the following embodiments.

The following examples are put forth so as to provide those of ordinary skill in the art with a complete disclosure and description of how to perform the methods and use the compositions and compounds disclosed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value.

EXAMPLES

Now having described the embodiments of the present disclosure, in general, the following Examples describe some additional embodiments of the present disclosure. While embodiments of present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure Toll-like receptors (TLRs), of which 10 are known in the human genome, are pattern recognition receptors.[1,2] The ligands for these receptors are highly conserved microbial molecules. The activation of TLRs by their cognate ligands leads to activation of innate immune effector mechanisms, including the production of pro-inflammatory cytokines, and up-regulation of MHC molecules and co-stimulatory signals in antigen-presenting cells as well as activating natural killer (NK) cells. The consequence of activation of the innate immune system mobilizes and amplifies specific adaptive immune responses involving both T- and B-cell effector functions.[5-7] Thus, TLR stimuli serve to link innate and adaptive immunity[5] and can therefore be exploited as powerful adjuvants in eliciting both primary and anamnestic immune responses.

Representative members of virtually the entire compendium of known TLR agonists have been examined in a series of hierarchical assays including primary TLR-reporter assays, secondary indices of immune activation such as cytokine induction and activation of lymphocytic subsets in whole human blood, and tertiary screens characterizing transcriptomal activation patterns with a view to identifying optimal immunostimulatory chemotypes.[8] Of all the innate immune stimuli examined, TLR7 agonists were found to be extraordinarily immunostimulatory, stimulating virtually all subsets of lymphocytes, and yet without inducing dominant proinflammatory cytokine responses (unlike TLR4-5 or -8 agonists, which were proinflammatory and therefore may exert systemic toxicity).[8] TLR7-active compounds therefore represent candidates as potential vaccine adjuvants and immune response modifiers. In some embodiments is also desirable to identify compounds capable of dual activation of TLR7 and TLR8, as discussed in greater detail below.

Long before endosomal TLR7 was discovered to serve as the primary sensor for short, single-stranded, GU-rich RNA sequences (ssRNA), mainly of viral origin,[9-11] a number of small molecules were synthesized and evaluated in the 1970s and '80s for antiviral activities owing to their pronounced Type I interferon (IFN-$\alpha$ and -$\beta$) inducing properties.[12-16] The 1H-imidazo[4,5-c]quinolines were found to be good Type I IFN inducers in human cell-derived assays,[17] and FDA approval was obtained in 1997 for Imiquimod (1, FIG. 1) for the treatment of basal cell carcinoma and actinic keratosis, and Gardiquimod, 2 (FIG. 1), is a known imidazoquinoline TLR7 agonist.[18]

It was not until 2002, however, that the mechanistic basis of IFN induction by the imidazoquinolines was found to be a consequence of TLR7 engagement and activation.[19] Other than the original studies, performed by investigators at 3M Pharmaceuticals,[17] structure-activity relationships of the imidazoquinoline chemotype remains poorly explored, perhaps attributable in part to recent interest in the 8-hydroxy-adenine compounds as alternate TLR7-agonists,[20-23] which appear to lack emetic side-effects observed in ferrets upon oral administration.[22] A positive factor related to imidazoquinolines is that imiquimod is already approved for topical use. The present example describes the discovery of a novel and unique compound, 7d (Scheme 1), and its derivatives and analogues, which have not been described hitherto in the literature. This compound has served as a core structure for the syntheses of several imidazoquinoline derived compounds described herein.

Materials and Methods:

All of the solvents and reagents used were obtained commercially and used as such unless noted otherwise. Moisture- or air-sensitive reactions were conducted under nitrogen atmosphere in oven-dried (120° C.) glass apparatus. The solvents were removed under reduced pressure using standard rotary evaporators. Flash column chromatography was carried out using RediSep Rf 'Gold' high performance silica columns on CombiFlash Rf instruments unless otherwise mentioned, while thin-layer chromatography was carried out on silica gel CCM pre-coated aluminum sheets. Purity for all final compounds was confirmed to be greater than 97% by LC-MS using a Zorbax Eclipse Plus 4.6 mm×150 mm, 5 μm analytical reverse phase $C_{18}$ column with $H_2O$-isopropanol or $H_2O$—$CH_3CN$ gradients and an Agilent ESI-TOF mass spectrometer (mass accuracy of 3 ppm) operating in the positive ion acquisition mode. All the compounds synthesized were obtained as solids.

NF-κB Induction: The induction of NF-κB was quantified using HEK-Blue-7 cells and HEK-Blue-8 cells as previously described by us.[8,24] HEK293 cells were stably transfected with human TLR7 (or human TLR8), MD2, and secreted alkaline phosphatase (sAP), and were maintained in HEK-Blue™ Selection medium containing zeocin and normocin. Stable expression of secreted alkaline phosphatase (sAP) under control of NF-κB/AP-1 promoters is inducible by the TLR7 (or TLR8) agonists, and extracellular sAP in the supernatant is proportional to NF-κB induction. HEK-Blue cells were incubated at a density of ~$10^5$ cells/ml in a volume of 80 μL/well, in 384-well, flat-bottomed, cell culture-treated microtiter plates until confluency was achieved, and subsequently graded concentrations of stimuli. sAP was assayed spectrophotometrically using an alkaline phosphatase-specific chromogen (present in HEK-detection medium as supplied by the vendor) at 620 nm.

Example 1

Synthesis and Activity of $N^1$-Substituted Imidazoquinolines

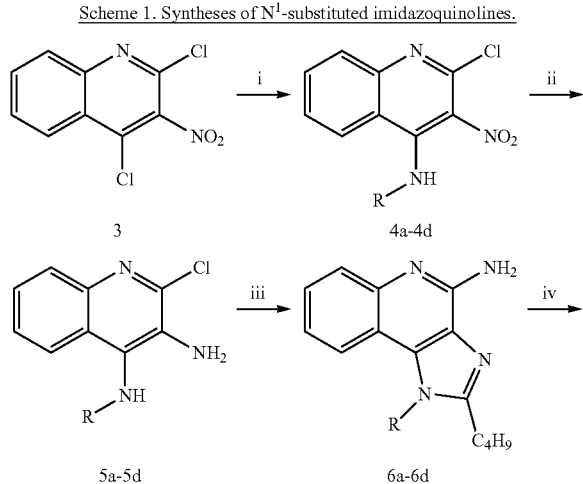

Scheme 1. Syntheses of $N^1$-substituted imidazoquinolines.

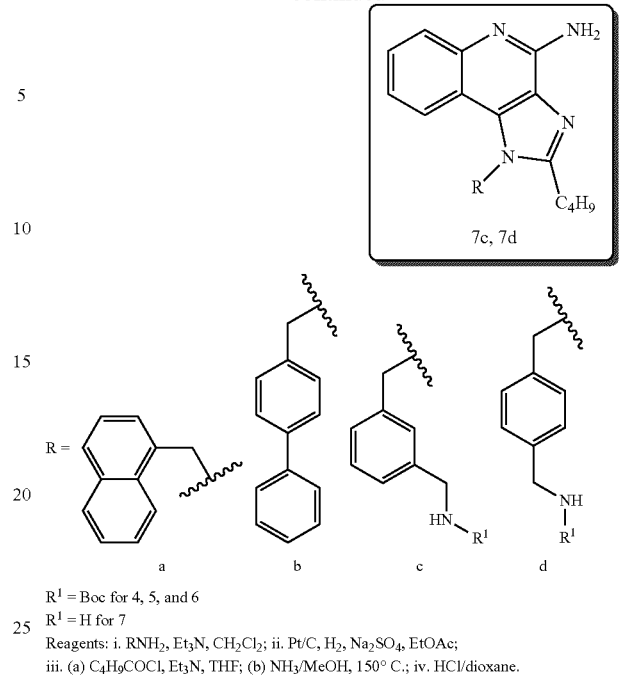

$R^1$ = Boc for 4, 5, and 6
$R^1$ = H for 7
Reagents: i. $RNH_2$, $Et_3N$, $CH_2Cl_2$; ii. Pt/C, $H_2$, $Na_2SO_4$, EtOAc;
iii. (a) $C_4H_9COCl$, $Et_3N$, THF; (b) $NH_3$/MeOH, 150° C.; iv. HCl/dioxane.

Synthesis of Compound 6a: 2-Butyl-1-(naphthalen-1-ylmethyl)-1H-imidazo[4,5-c]quinolin-4-amine

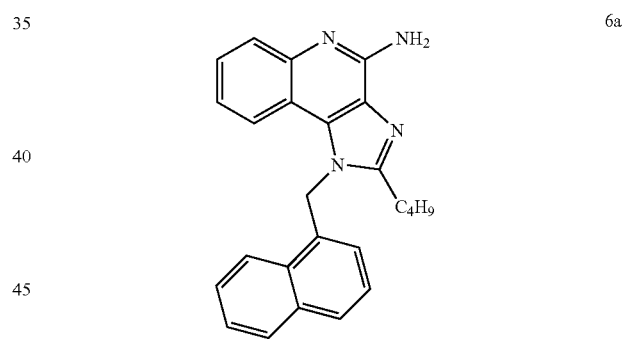

To a solution of 3 (100 mg, 0.41 mmol) in 5 mL of anhydrous dichloromethane, were added triethylamine (54 mg, 0.53 mmol) and naphthalen-1-ylmethanamine (71 mg, 0.45 mmol). The reaction mixture was refluxed at 45° C. for 30 minutes. The solvent was then evaporated under vacuum and product was isolated using column chromatography to obtain the intermediate compound 4a. To a solution of 4a in 10 mL of EtOAc, were added a catalytic amount of Pt/C and $Na_2SO_4$. The reaction mixture was subjected to hydrogenation at 55 psi hydrogen pressure for 4 hours. The reaction mixture was then filtered through celite and the filtrate was evaporated under vacuum to obtain compound 5a (90 mg). To a solution of 5a (90 mg, 0.27 mmol) in anhydrous THF, were added triethylamine (41 mg, 0.41 mmol) and valeryl chloride (39 mg, 0.32 mmol). The reaction mixture was stirred at room temperature for 6 hours. The solvent was then removed under vacuum, and the residue was dissolved in ethyl acetate and washed with water. The ethyl acetate fraction was then dried using $Na_2SO_4$ and evaporated under vacuum to obtain the intermediate amide compound, which was then dissolved in 2 mL of 2M solution of ammonia in MeOH. The sealed reaction vessel was heated 150° C. for 24 hours. The solvent was then removed under vacuum and the residue was purified using column chromatography (7% MeOH/dichloromethane) to obtain compound 6a (62 mg; 40%). $^1$H NMR (500 MHz, DMSO) δ 8.40 (d, J=8.3 Hz, 1H), 8.05 (d, J=8.1 Hz, 1H), 7.86 (d, J=8.2 Hz, 1H), 7.77 (t, J=7.2 Hz, 1H), 7.69 (t, J=7.5 Hz, 1H), 7.62 (d, J=8.2 Hz, 1H), 7.47 (d, J=8.2 Hz, 1H), 7.33 (t, J=7.5 Hz, 1H), 7.27 (t, J=7.7 Hz, 1H), 7.08 (s, 2H), 6.90 (t, J=7.5 Hz, 1H), 6.39 (d, J=7.1 Hz, 1H), 6.35 (s, 2H), 2.92 (t, J=7.6 Hz, 2H), 1.69 (dt, J=15.2, 7.6 Hz, 2H), 1.32 (dt, J=14.6, 7.4 Hz, 2H), 0.80 (t, J=7.3 Hz, 3H). $^{13}$C NMR (126 MHz, DMSO) δ 154.39, 151.16, 133.62, 133.25, 131.77, 129.64, 128.74, 127.88, 126.91, 126.80, 126.48, 126.15, 125.58, 123.07, 121.57, 121.42, 119.87, 114.11, 46.60, 29.45, 26.08, 21.70, 13.61. MS (ESI) calculated for $C_{25}H_{24}N_4$, m/z 380.20. found 381.21 (M+H)$^+$.

Compound 6b was Synthesized Similarly as Described for Compound 6a

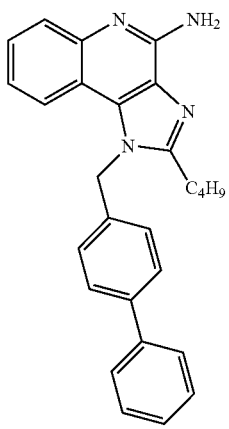

6b: 1-(Biphenyl-4-ylmethyl)-2-butyl-1H-imidazo[4,5-c]quinolin-4-amine $^1$H NMR (500 MHz, CDCl$_3$) δ 7.88 (d, J=7.9 Hz, 1H), 7.78-7.73 (m, 1H), 7.60-7.56 (m, 2H), 7.55-7.52 (m, 2H), 7.51-7.47 (m, 1H), 7.45-7.40 (m, 2H), 7.35 (ddt, J=8.5, 6.5, 1.4 Hz, 1H), 7.30-7.25 (m, 1H), 7.10 (d, J=8.3 Hz, 2H), 5.81 (s, 2H), 2.94-2.91 (m, 2H), 1.84 (dt, J=15.4, 7.6 Hz, 2H), 1.51-1.41 (m, 2H), 0.95 (t, J=7.4 Hz, 3H). $^{13}$C NMR (126 MHz, CDCl$_3$) δ 156.27, 149.52, 141.25, 139.59, 135.17, 132.65, 129.02, 128.64, 127.93, 127.52, 126.72, 125.52, 124.77, 124.58, 120.31, 120.23, 112.54, 48.72, 29.17, 26.80, 22.15, 13.47. MS (ESI) calculated for $C_{27}H_{26}N_4$, m/z 406.22. found 407.22 (M+H)$^+$.

Synthesis of Compound 7c: 1-(3-(Aminomethyl) benzyl)-2-butyl-1H-imidazo[4,5-c]quinolin-4-amine

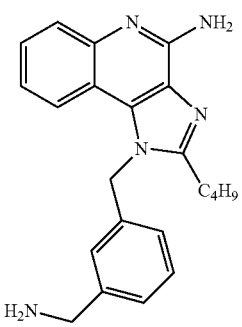

To a solution of 3 (200 mg, 0.83 mmol) in 5 mL of anhydrous dichloromethane, were added triethylamine (92 mg, 0.91 mmol) and tert-butyl 3-(aminomethyl)benzylcarbamate (215 mg, 1.06 mmol) dissolved in 2 mL of anhydrous MeOH. The reaction mixture was refluxed at 45° C. for 30 minutes. The solvent was then evaporated under vacuum and product was isolated using column chromatography to obtain the intermediate compound 4c. To a solution of 4c in 10 mL of EtOAc, were added a catalytic amount of Pt/C and Na$_2$SO$_4$. The reaction mixture was subjected to hydrogenation at 55 psi hydrogen pressure for 4 hours. The reaction mixture was then filtered through celite and the filtrate was evaporated under vacuum to obtain compound 5c (202 mg). To a solution of 5c (202 mg, 0.49 mmol) in anhydrous THF, were added triethylamine (64 mg, 0.64 mmol) and valeryl chloride (73 mg, 0.54 mmol). The reaction mixture was stirred at room temperature for 6 hours. The solvent was then removed under vacuum, and the residue was dissolved in ethyl acetate and washed with water. The ethyl acetate fraction was then dried using Na$_2$SO$_4$ and evaporated under vacuum to obtain the intermediate amide compound, which was then dissolved in 2 mL of 2M solution of ammonia in MeOH. The sealed reaction vessel was heated 150° C. for 24 hours. The solvent was then removed under vacuum and the residue was purified using column chromatography (9% MeOH/dichloromethane) to obtain compound 6c (44 mg; 12%). This was then dissolved in 10 mL of HCl/dioxane solution and stirred for 12 hours. The solvent was then removed to obtain compound 7c (52 mg, 15%). $^1$H NMR (500 MHz, MeOD) δ 7.85 (s, 1H), 7.67 (d, J=7.0 Hz, 1H), 7.52 (s, 1H), 7.39-7.18 (m, 4H), 7.02 (s, 1H), 5.92 (s, 2H), 4.01 (s, 2H), 2.94 (s, 2H), 1.80 (s, 2H), 1.41 (d, J=4.4 Hz, 2H), 0.88 (t, J=6.1 Hz, 3H). $^{13}$C NMR (126 MHz, MeOD) δ 159.02, 150.28, 137.51, 135.84, 135.26, 131.34, 131.06, 129.95, 127.66, 127.46, 126.67, 125.73, 123.01, 119.66, 114.08, 50.24, 44.18, 30.32, 27.98, 23.45, 14.25. MS (ESI) calculated for $C_{22}H_{25}N_5$, m/z 359.21. found 360.22 (M+H)$^+$.

Compound 7d was Synthesized Similarly as Described for Compound 7c

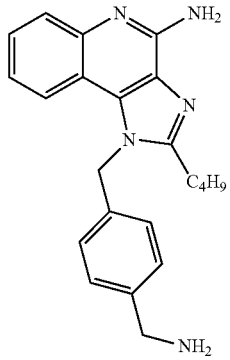

7d: 1-(4-(Aminomethyl)benzyl)-2-butyl-1H-imidazo[4,5-c]quinolin-4-amine $^1$H NMR (500 MHz, MeOD) δ 7.85 (d, J=8.2 Hz, 1H), 7.69 (d, J=8.3 Hz, 1H), 7.54 (t, J=7.7 Hz, 1H), 7.40 (d, J=7.7 Hz, 2H), 7.26 (t, J=7.6 Hz, 1H), 7.10 (d, J=7.8 Hz, 2H), 5.93 (s, 2H), 4.01 (s, 2H), 2.94 (t, J=7.6 Hz, 2H), 1.83-1.71 (m, 2H), 1.43-1.32 (m, 2H), 0.86 (t, J=7.3 Hz, 3H). $^{13}$C NMR (126 MHz, MeOD) δ 159.02, 150.27, 137.51, 137.47, 135.33, 134.59, 131.17, 131.11, 127.54, 126.51, 125.53, 122.95, 119.66, 114.03, 49.93, 43.81, 30.31, 27.78, 23.35, 14.12. MS (ESI) calculated for $C_{22}H_{25}N_5$, m/z 359.21. found 360.22 (M+H)$^+$.

Figure 2:
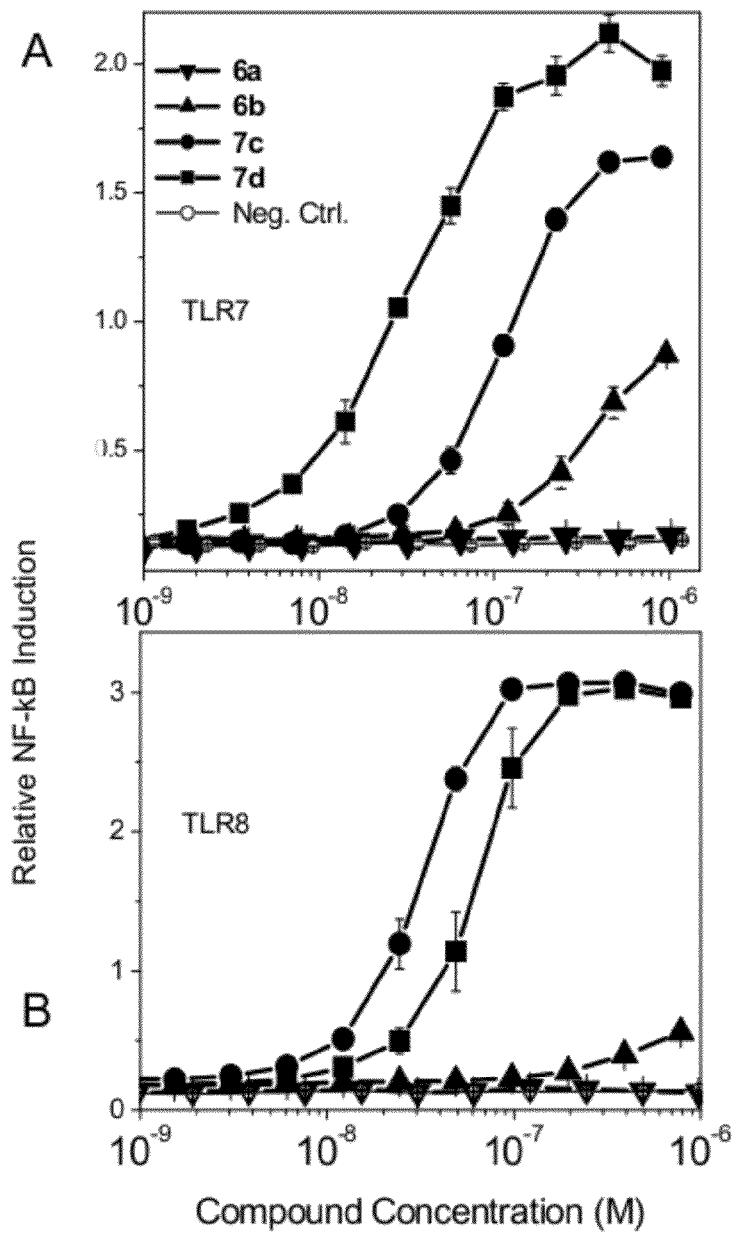
FIGS. 2A and 2B are graphs of TLR-7 and TLR-8 agonistic activities of compounds 6a-b and 7c-d.

TLR7 and TLR8 agonistic activity of compound 6a, 6b, 7c, and 7d were tested, and results are shown in FIGS. 2A (TLR7 activity) and 2B (TLR8 activity). The N$^1$-naphthylenemethyl-substituted compound 6a was inactive, and the N$^1$-biphenyl-4-methyl compound 6b was weakly active (EC$_{50}$: 396 nM); the N$^1$-(4-aminomethyl)benzyl substituted analogue 7d was the most active compound and served as a core structure for the syntheses of many other imidazoquinoline derived compounds described below. (EC$_{50}$: 20 nM, FIGS. 2A and 2B). 7d was more active than its N$^1$-(3-aminomethyl)benzyl regioisomer 7c (EC$_{50}$: 110 nM, FIGS. 2A-2B).

Imidazoquinoline Derived Compounds

From compound 7d, a variety of imidazoquinoline derived compounds of the present disclosure, represented by FORMULA I, below, were synthesized as described in greater detail below.

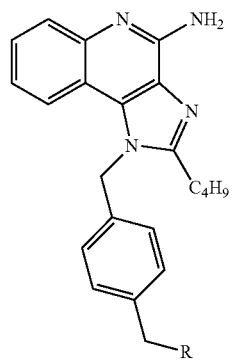

FORMULA I

In embodiments of the imidazoquinoline derived compounds of the present disclosure of Formula I, R is selected from the group consisting of: —NH(R$_5$) or isothiocyanate (—NCS);

R$_5$ is selected from the group consisting of hydrogen (—H), acetyl (e.g., a group that includes —COCH$_3$), —CO-tert-Bu (-Boc), —CO—(CH$_2$)$_x$—R$_6$, C$_1$-C$_{16}$ alkyl, —CO-4-(phenylboronic acid), —C(S)—NH—(CH$_2$)$_x$—NH—(CH$_2$)$_x$—NH—(CH$_2$)$_x$—NH$_2$,

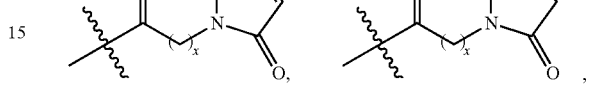

a reporter moiety, a tissue-specific moiety, a peptide antigen moiety, a protein antigen moiety, a polysaccharide antigen moiety, and a TLR$_2$ agonist moiety;

R$_6$ is selected from the group consisting of hydrogen (—H), alkyne (e.g., a group that includes a carbon-carbon triple bond such as —C≡CH), azido (—N$_3$), carboxylic acid (e.g., a group that includes a —CO$_2$H), —CONH—(CH$_2$)$_x$O—(CH$_2$)$_x$—O—CH$_2$)$_x$—O—(CH$_2$)$_x$—R$_7$;

R$_7$ is selected from the group consisting of amino (e.g., a group that includes a —NH$_2$), isothiocyanate (e.g., a group that includes a —NCS) or —NH—CO—(CH$_2$)$_x$—CO$_2$H;

R$_8$ is selected from a peptide antigen moiety or a protein antigen moiety; and x is any integer from 1 to 10.

Embodiments of compounds of Formula I and derivatives of such compounds were synthesized and tested including, but not limited to, compounds 6d, 7d, 8, 12, 13, 14, 15, 16, 17, 18, 19, 21, 23, 25, 26, 27, 28, 29, 30a, 30b, 31, 33, 35, 37, 39, 60, 61, 62, 63, 64, and 65, which are described in detail in the Examples below.

Furthermore, as described in Scheme 1, and as shown by the exemplary compounds 7c and 7d, a variety of compounds can be synthesized as shown by the representative structure of Formula II, below, wherein substituents shown on the N1-benzyl unit could be independently at the ortho, meta, or para positions, and the R groups are as defined below.

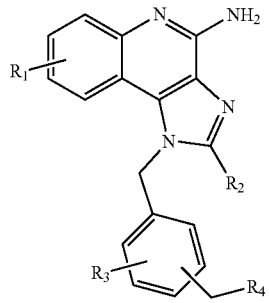

FORMULA II where,

R$_1$ and R$_3$ are each independently selected from the group consisting of hydrogen, halogen (e.g., a group that includes —Cl, —Br, —F), nitro (e.g., a group that includes —NO$_2$), —NH$_2$, azido (e.g., a group that includes —N$_3$), hydroxyl (e.g., a group that includes —OH), —CF$_3$, carboxylic acid (e.g., a group that includes —CO$_2$H) or —CO$_2$R$_2$;

$R_2$ is a $C_2$-$C_5$ alkyl, and $R_4$ selected from the group consisting of: —NH($R_5$) or isothiocyanate (—NCS);

$R_5$ is selected from the group consisting of hydrogen (—H), acetyl (e.g., a group that includes —COCH$_3$), —CO-tert-Bu (-Boc), —CO—(CH$_2$)$_x$—R$_6$, C$_1$-C$_{16}$ alkyl, —CO-4-(phenylboronic acid), —C(S)—NH—(CH$_2$)$_x$—NH—(CH$_2$)$_x$—NH—(CH$_2$)$_x$—NH$_2$,

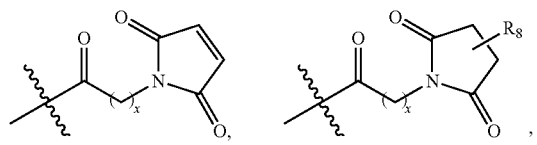

a reporter moiety, a tissue-specific moiety, a peptide antigen moiety, a protein antigen moiety, a polysaccharide antigen moiety, and a TLR2 agonist moiety;

$R_6$ is selected from the group consisting of hydrogen (—H), alkyne (e.g., a group that includes a carbon-carbon triple bond such as —C≡CH), azido (—N$_3$), carboxylic acid (e.g., a group that includes a —CO$_2$H), —CONH—(CH$_2$)$_x$—O—(CH$_2$)$_x$—O—(CH$_2$)$_x$—O—(CH$_2$)$_x$—R$_7$;

$R_7$ is selected from the group consisting of amino (e.g., a group that includes a —NH$_2$), isothiocyanate (e.g., a group that includes a —NCS) or —NH—CO—(CH$_2$)$_x$-CO$_2$H;

$R_8$ is selected from a peptide antigen moiety or a protein antigen moiety; and x is any integer from 1 to 10.

Embodiments of compounds of Formula II, and derivatives of such compounds were synthesized and tested as described in detail in these Examples.

Example 2

Derivatives of 1-(4-(Aminomethyl)benzyl)-2-butyl-1H-imidazo[4,5-c]quinolin-4-amine (7d)

Scheme 7. Syntheses of N$^1$-substituted imidazoquinolines.

Scheme 2. Syntheses of derivatives of 7d.

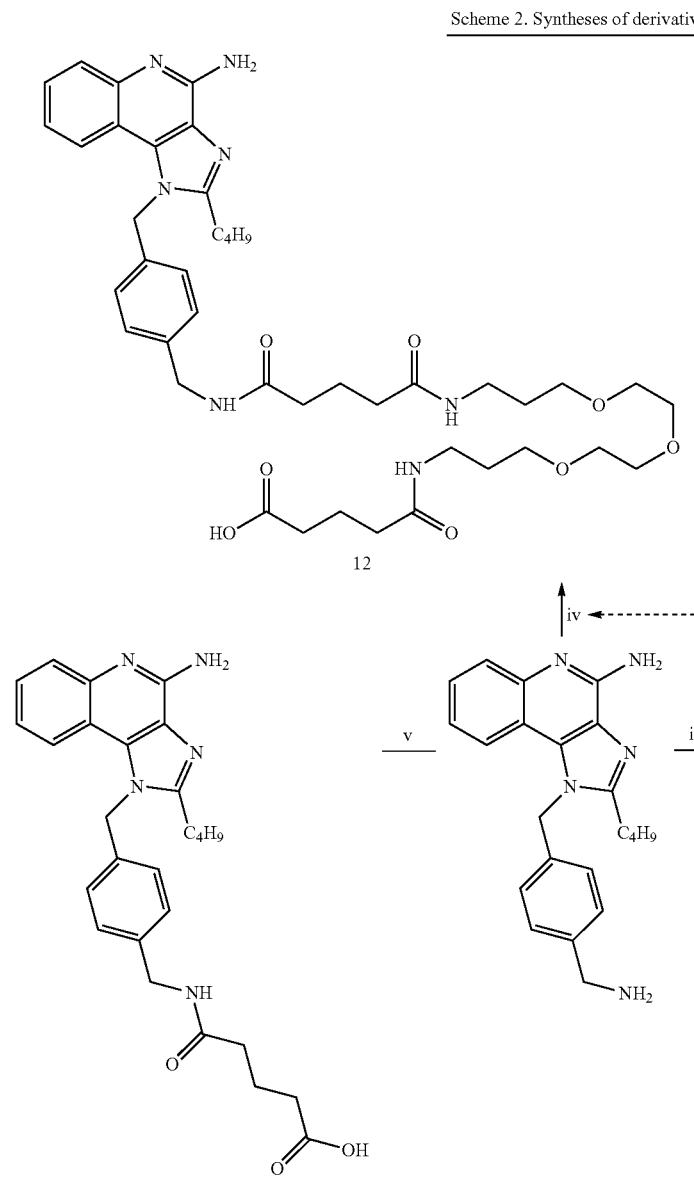

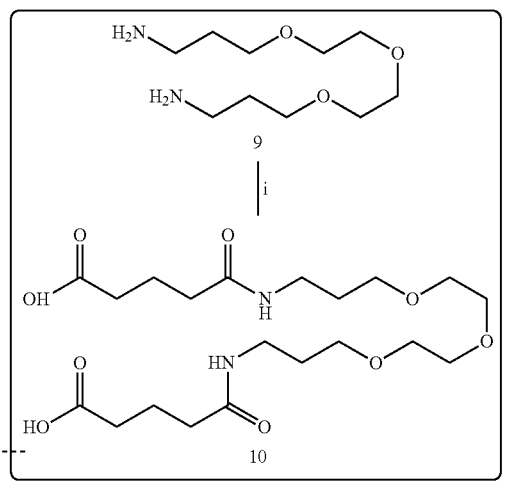

-continued
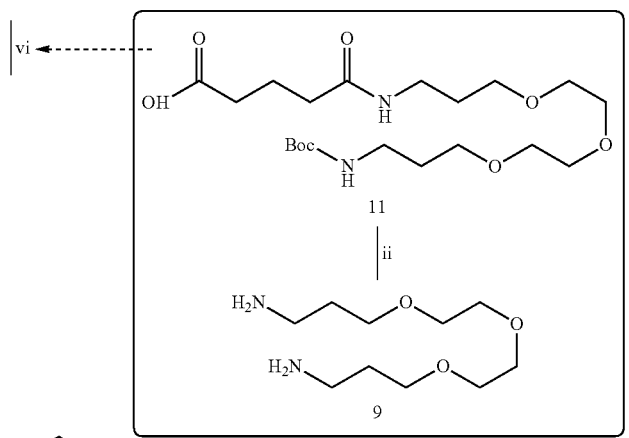
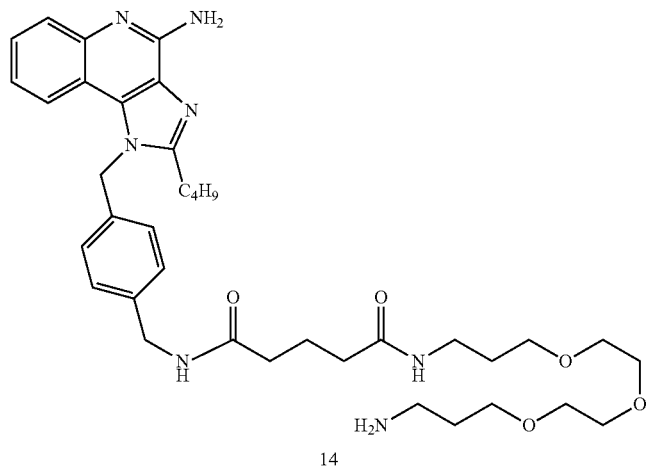
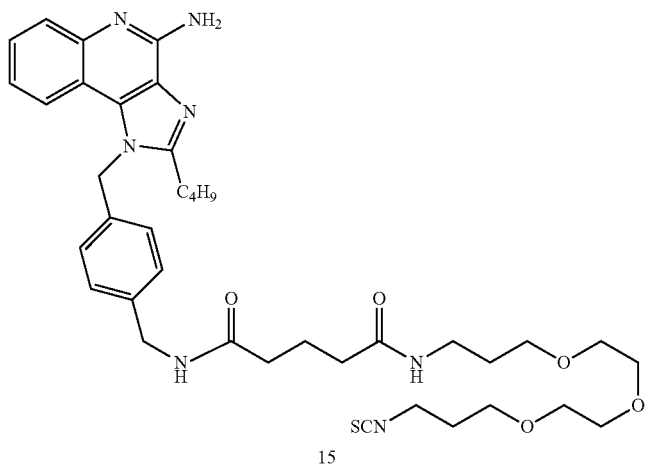
Reagents and conditions: i. Glutaric anhydride, Et₃N, THF; ii. (a) 0.9 equivalent (Boc)₂O, (b) glutaric anhydride, Et₃N, THF; iii. CS₂, Et₃N, (Boc)₂O, DMAP, CH₂Cl₂; iv. 10, Et₃N, HBTU, DMF; v. glutaric anhydride, Et₃N, THF; vi. (a) 11, Et₃N, HBTU, DMF, (b) 4M HCl/dioxane; vii. CS₂, Et₃N, (Boc)₂O, DMAP, CH₂Cl₂.
Scheme 3. Syntheses of derivatives of 7d.
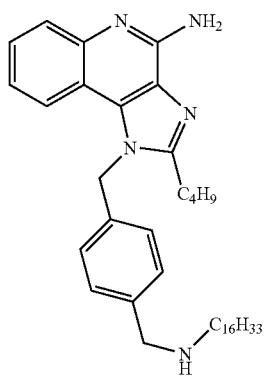

-continued
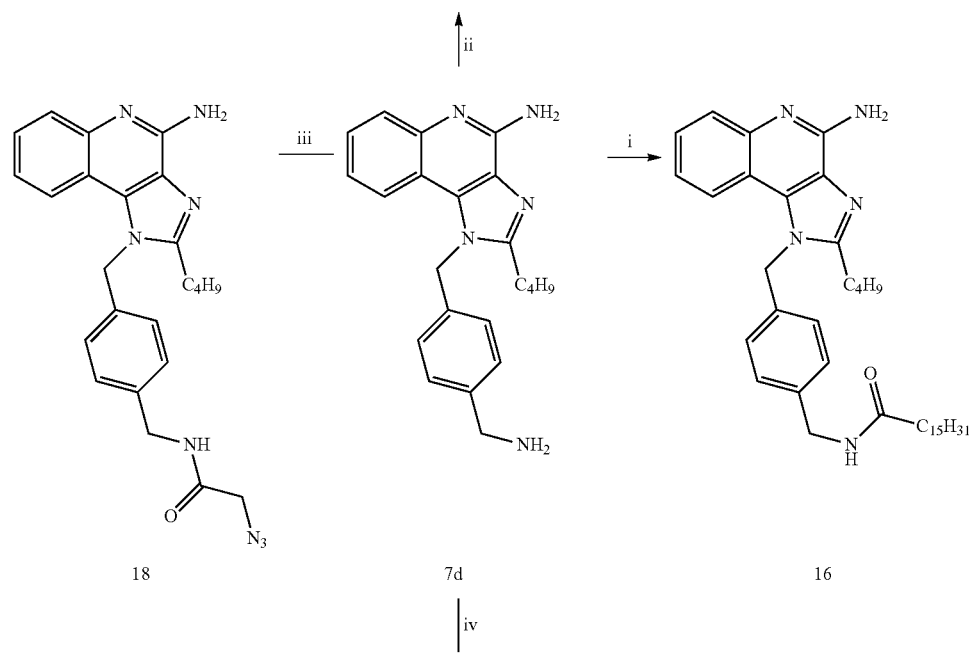
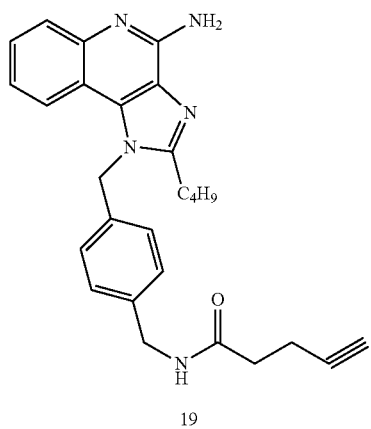
Reagents and conditions: i. Palmitoyl chloride, Et$_3$N, THF; ii. iodohexadecane, Et$_3$N, DMF; iii. (a) 2-bromoacetic acid, propylphosphonic anhydride (T3P ®), Et$_3$N, DMF (b) NaN$_3$, Et$_3$N, DMF, 60° C.; iv. pentynoic acid, Et$_3$N, HBTU, DMF.

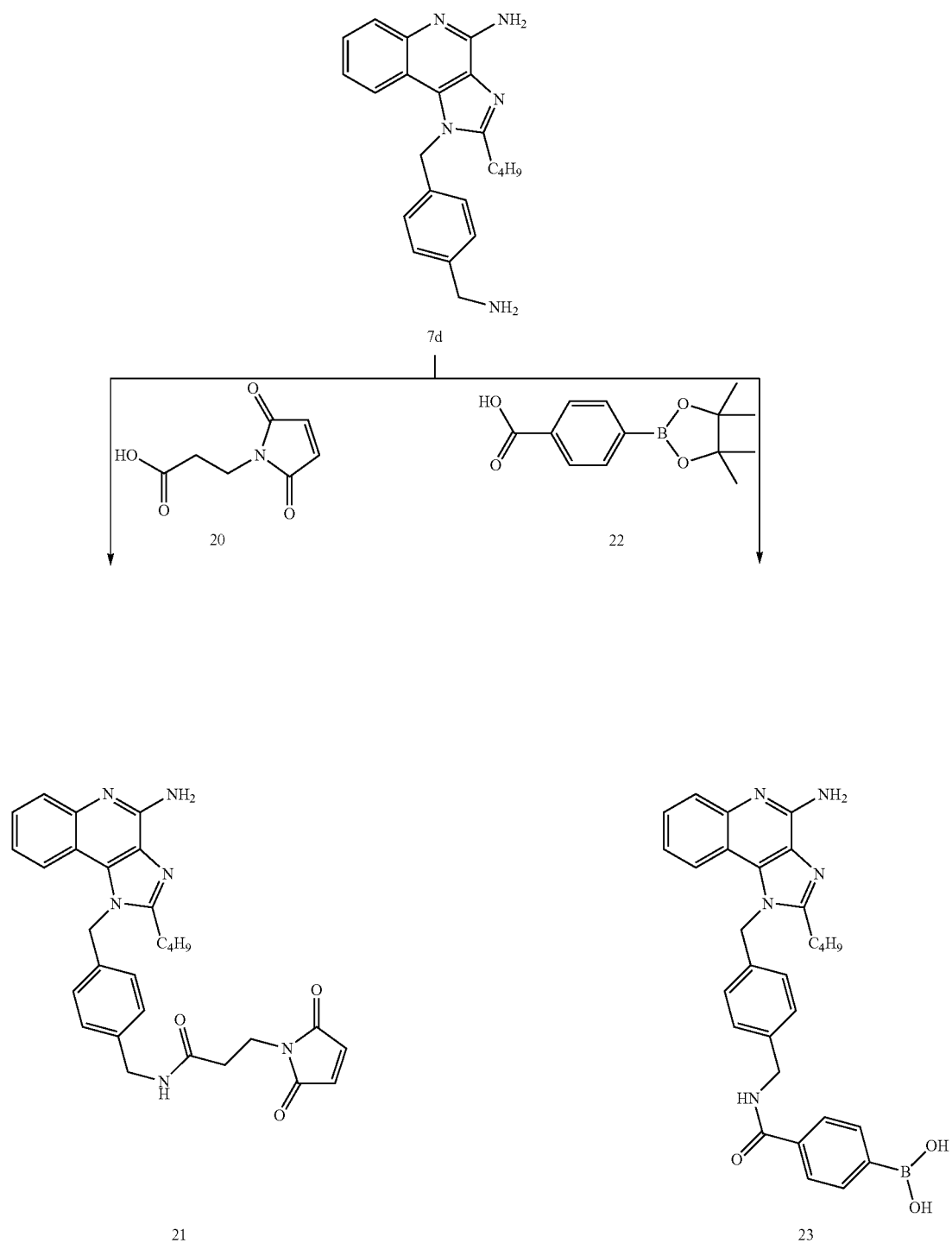
Reagents: i. HBTU, Et₃N, DMAP, DMF; ii. (a) HBTU, Et₃N, DMAP, DMF (b) Polymer-bound boronic acid, 1N·HCl, CH3CN.

Scheme 5. Syntheses of derivatives of 7d.

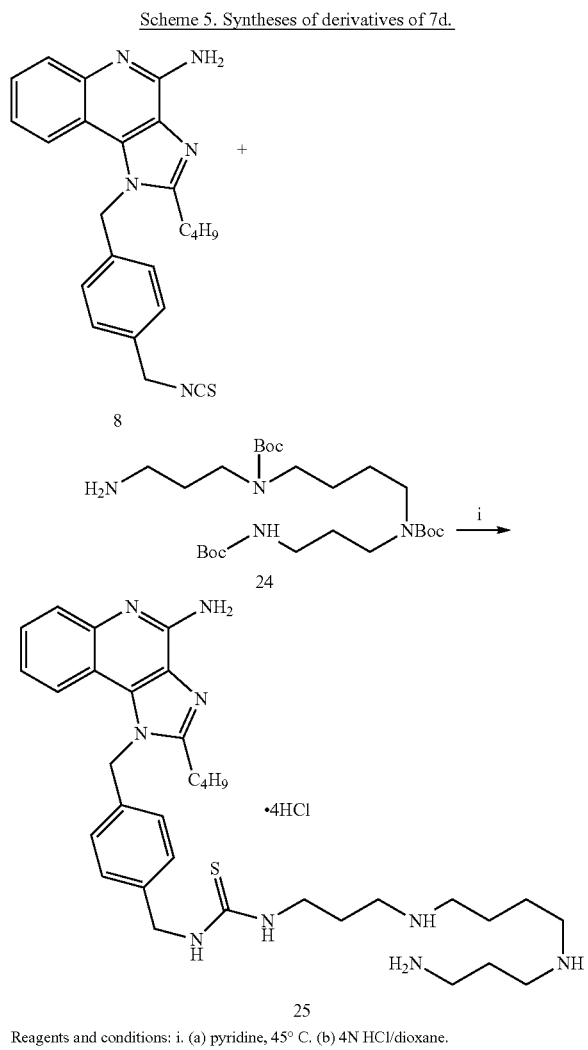

Reagents and conditions: i. (a) pyridine, 45° C. (b) 4N HCl/dioxane.

Synthesis of Compound 8: 2-Butyl-1-(4-(isothiocyanatomethyl)benzyl)-1H-imidazo[4,5-c]quinolin-4-amine

To a solution of 7d (150 mg, 0.35 mmol) in anhydrous dichloromethane, were added carbon disulfide (266 mg, 3.5 mmol) and triethylamine (106 mg, 1.05 mmol). The reaction mixture was stirred for an hour and then was cooled to 0° C. Di-tert-butyl dicarbonate (76 mg, 0.35 mmol) and a catalytic amount of DMAP were added to the reaction mixture. The reaction mixture was stirred for 18 hours and then the solvent was removed under vacuum. The residue was purified using column chromatography (7% MeOH/dichloromethane) to obtain compound 8 (105 mg, 75%). $^1$H NMR (400 MHz, CDCl$_3$) δ 7.87-7.83 (m, 1H), 7.68 (dd, J=8.3, 0.8 Hz, 1H), 7.51-7.45 (m, 1H), 7.32 (d, J=8.2 Hz, 2H), 7.23-7.17 (m, 1H), 7.10 (d, J=8.2 Hz, 2H), 6.52 (s, 2H), 5.78 (s, 2H), 4.71 (s, 2H), 2.94-2.86 (m, 2H), 1.82 (dt, J=15.5, 7.6 Hz, 2H), 1.52-1.41 (m, 2H), 0.95 (t, J=7.4 Hz, 3H). $^{13}$C NMR (101 MHz, CDCl$_3$) δ 155.19, 150.27, 135.10, 134.65, 134.57, 128.20, 127.95, 126.10, 125.92, 124.08, 123.59, 119.94, 113.99, 48.74, 48.21, 29.71, 27.12, 22.47, 13.76. MS (ESI) calculated for C$_{23}$H$_{23}$N$_5$S, m/z 401.17. found 402.18 (M+H)$^+$.

Synthesis of Compound 12: 1-(4-((4-amino-2-butyl-1H-imidazo[4,5-c]quinolin-1-yl)methyl)phenyl)-3,7,23-trioxo-12,15,18-trioxa-2,8,22-triazaheptacosan-27-oic acid

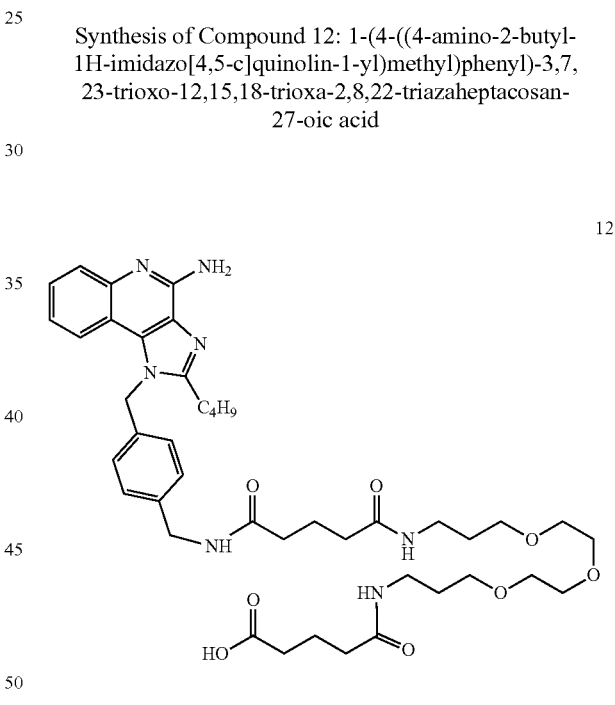

To a solution of compound 9 (200 mg, 0.91 mmol) in anhydrous THF, were added triethylamine (320 μL, 2.28 mmol) and glutaric anhydride (212 mg, 1.86 mmol) and the reaction mixture was stirred for 30 min. The solvent was then removed under vacuum to obtain the compound 10 in quantitative yields. To a solution of compound 10 (100 mg, 0.15 mmol) in anhydrous DMF, were added triethylamine (53 μL, 0.38 mmol), HBTU (64 mg, 0.17 mmol) and 7d (63 mg, 0.15 mmol). The reaction mixture was then stirred for 6 hours, followed by removal of the solvent under vacuum. The residue was then purified using column chromatography to obtain the compound 12 (37 mg, 32%). MS (ESI) calculated for C$_{42}$H$_{59}$N$_7$O$_8$, m/z 789.4425. found 790.4513 (M+H)$^+$.

Synthesis of Compound 13: 5-((4-((4-amino-2-butyl-1H-imidazo[4,5-c]quinolin-1-yl)methyl)benzyl)amino)-5-oxopentanoic acid

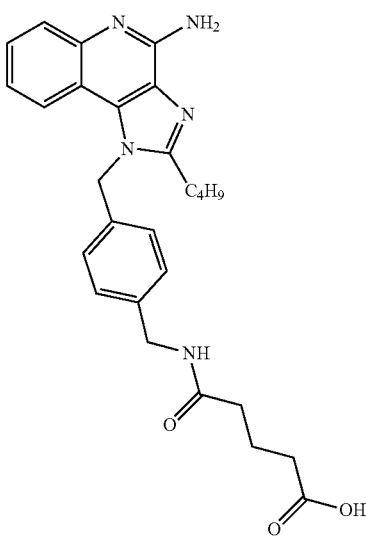

13

To a solution of compound 7d (50 mg, 0.12 mmol) in anhydrous THF, were added triethylamine (30 μL, 0.29 mmol) and glutaric anhydride (13 mg, 0.12 mmol) and the reaction mixture was stirred for 30 min. The solvent was then removed under vacuum to obtain the triethylammonium salt of compound 13 in quantitative yields. $^1$H NMR (400 MHz, DMSO) δ 7.91 (d, J=8.4 Hz, 1H), 7.73 (d, J=8.2 Hz, 1H), 7.54 (t, J=7.7 Hz, 1H), 7.27 (t, J=7.6 Hz, 1H), 7.20 (d, J=8.0 Hz, 2H), 7.01 (d, J=8.0 Hz, 2H), 5.91 (s, 2H), 5.75 (s, 1H), 4.20 (s, 2H), 4.12 (s, 1H), 3.07 (q, J=7.3 Hz, 12H), 2.94 (t, J=7.7 Hz, 2H), 2.30-2.09 (m, 4H), 1.78-1.64 (m, 4H), 1.38 (dd, J=14.9, 7.4 Hz, 2H), 1.20 (t, J=7.3 Hz, 17H), 0.87 (t, J=7.3 Hz, 3H). MS (ESI) calculated for $C_{27}H_{31}N_5O_3$, m/z 473.2427. found 474.2551 (M+H)$^+$.

Synthesis of compound 14: N$^1$-(4-((4-amino-2-butyl-1H-imidazo[4,5-c]quinolin-1-yl)methyl)benzyl)-N$^5$-(3-(2-(2-(3-aminopropoxy)ethoxy)ethoxy)propyl)glutaramide

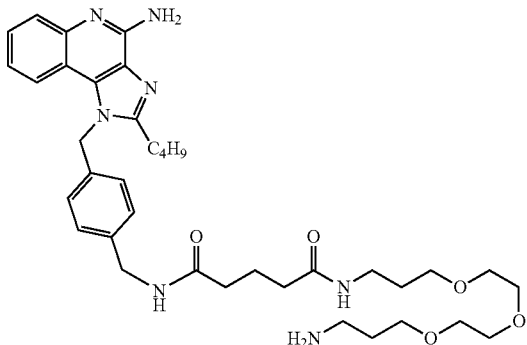

14

To the solution of compound 9 (500 mg, 2.3 mmol) in anhydrous dichloromethane was added, di-tert-butyl dicarbonate (454 mg, 2.08 mmol) and the reaction was stirred for 1 hour, followed by removal of the solvent under vacuum. To the residue dissolved in anhydrous THF were added, triethylamine (52 mg, 5.2 mmol) and glutaric anhydride (445 mg, 3.9 mmol). The reaction mixture was stirred for 2 hours followed by removal of the solvent under vacuum to obtain the crude residue which was purified using column chromatography (20% MeOH/dichloromethane) to yield compound 11 (400 mg, 41%). To a solution of 11 (125 mg, 0.23 mmol) in anhydrous DMF were added, triethylamine (60 mg, 0.59 mmol), HBTU (98 mg, 0.26 mmol), 7d (100 mg, 0.23 mmol) and a catalytic amount of DMAP sequentially. The reaction mixture was stirred for 12 hours followed by removal of the solvent under vacuum to obtain the residue which was purified using column chromatography (20% MeOH/$CH_2Cl_2$) to obtain the N-Boc protected intermediate which was N-Boc deprotected by stirring in 1 mL of 4M HCl/dioxane solution for 6 hours followed by removal of the solvent under vacuum to obtain hydrochloride salt of compound 14 (140 mg, 80%). $^1$H NMR (500 MHz, MeOD) δ 7.96 (dd, J=8.4, 0.7 Hz, 1H), 7.75 (dd, J=8.4, 0.8 Hz, 1H), 7.63 (ddd, J=8.4, 7.3, 1.2 Hz, 1H), 7.36 (ddd, J=8.4, 7.3, 1.1 Hz, 1H), 7.27 (d, J=8.3 Hz, 2H), 7.05 (d, J=8.2 Hz, 2H), 5.93 (s, 2H), 4.32 (s, 2H), 3.67-3.59 (m, 8H), 3.59-3.54 (m, 2H), 3.49 (t, J=6.1 Hz, 2H), 3.22 (t, J=7.0 Hz, 2H), 3.08 (t, J=6.4 Hz, 2H), 3.02-2.96 (m, 2H), 2.21 (dt, J=21.1, 7.6 Hz, 4H), 1.94-1.80 (m, 6H), 1.73 (dd, J=13.4, 6.5 Hz, 2H), 1.45 (dd, J=15.0, 7.5 Hz, 2H), 0.94 (t, J=7.4 Hz, 3H). $^{13}$C NMR (126 MHz, MeOD) δ 175.35, 175.26, 159.05, 150.46, 140.34, 137.61, 135.34, 135.23, 130.95, 129.50, 126.84, 126.42, 125.88, 122.97, 119.60, 114.22, 71.39, 71.09, 71.05, 71.00, 70.39, 69.65, 49.83, 43.54, 40.17, 37.66, 36.31, 36.20, 30.50, 30.34, 28.05, 27.76, 23.32, 23.28, 14.10. MS (ESI) calculated for $C_{37}H_{53}N_7O_5$, m/z 675.41. found 676.4270 (M+H)$^+$ and 338.7178 (M+2H)$^{+2}$.

Synthesis of Compound 15: N$^1$-(4-((4-amino-2-butyl-1H-imidazo[4,5-c]quinolin-1-yl)methyl)benzyl)-N$^5$-(3-(2-(2-(3-isothiocyanatopropoxy)ethoxy)ethoxy)propyl)glutaramide

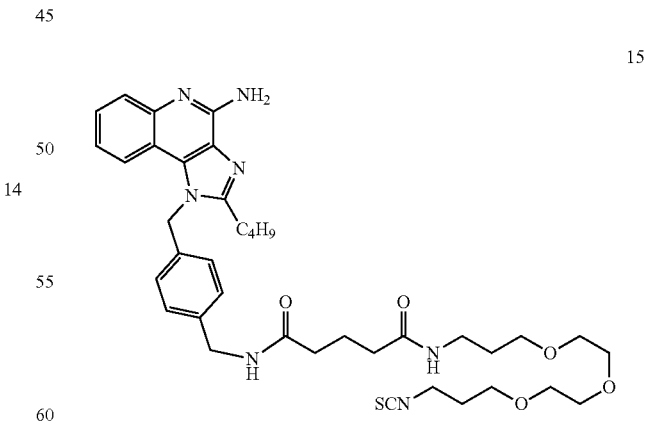

15

To a solution of 14 (140 mg, 0.19 mmol) in anhydrous dichloromethane, were added carbon disulfide (143 mg, 1.89 mmol) and triethylamine (47 mg, 0.469 mmol). The reaction mixture was stirred for an hour. Di-tert-butyl dicarbonate (41 mg, 0.19 mmol) and a catalytic amount of DMAP were added to the reaction mixture. The reaction mixture was stirred for 18 hours and then the solvent was removed under vacuum. The residue was purified using column chromatography (20% MeOH/CH$_2$Cl$_2$) to obtain the compound 15 (55 mg, 40%). MS (ESI) calculated for C$_{38}$H$_{51}$N$_7$O$_5$S, m/z 717.3672. found 718.3578. (M+H)$^+$.

Synthesis of compound 16: N-(4-((4-amino-2-butyl-1H-imidazo[4,5-c]quinolin-1-yl)methyl)benzyl)palmitamide

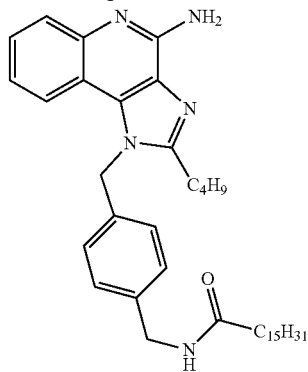

16

To a solution of compound 7d (50 mg, 0.116 mmol) in anhydrous THF, were added triethylamine (35 mg, 0.35 mmol) and palmitoyl chloride (35 mg, 0.13 mmol). The reaction mixture was stirred for 1 hour, followed by removal of the solvent under vacuum. The residue was then dissolved in ethylacetate and washed with water, brine, dried using sodium sulfate and concentrated under vacuum to obtain the residue which was purified using column chromatography (8% MeOH/dichloromethane) to obtain compound 16 (25 mg, 36%). $^1$H NMR (500 MHz, CDCl$_3$) δ 7.81 (dd, J=8.4, 0.7 Hz, 1H), 7.68 (dd, J=8.3, 0.9 Hz, 1H), 7.44 (ddd, J=8.4, 7.1, 1.3 Hz, 1H), 7.24 (d, J=8.2 Hz, 2H), 7.16 (ddd, J=8.3, 7.2, 1.2 Hz, 1H), 6.99 (d, J=8.2 Hz, 2H), 6.40 (s, 2H), 5.81 (t, J=5.7 Hz, 1H), 5.71 (s, 2H), 4.40 (d, J=5.9 Hz, 2H), 2.91-2.81 (m, 2H), 2.23-2.11 (m, 2H), 1.85-1.74 (m, 2H), 1.67-1.57 (m, 2H), 1.49-1.38 (m, 2H), 1.34-1.16 (m, 24H), 0.93 (t, J=7.4 Hz, 3H), 0.87 (t, J=7.0 Hz, 3H). $^{13}$C NMR (126 MHz, CDCl$_3$) δ 173.33, 155.29, 150.54, 139.05, 134.81, 134.10, 128.88, 128.22, 126.14, 125.95, 124.50, 123.58, 120.24, 114.35, 48.96, 43.12, 36.95, 32.12, 29.92, 29.90, 29.89, 29.88, 29.86, 29.84, 29.81, 29.68, 29.56, 29.53, 29.52, 27.30, 25.92, 22.89, 22.67, 14.33, 13.96. MS (ESI) calculated for C$_{38}$H$_{55}$N$_5$O, m/z 597.44. found 598.45 (M+H)$^+$.

Synthesis of compound 17: 2-butyl-1-(4-((hexadecylamino)methyl)benzyl)-1H-imidazo[4,5-c]quinolin-4-amine

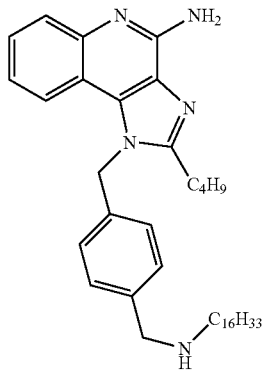

17

To a solution of compound 7d (50 mg, 0.116 mmol) in anhydrous DMF, were added triethylamine (35 mg, 0.35 mmol) and iodohexadecane (41 mg, 0.116 mmol). The reaction mixture was stirred for 18 hours followed by removal of the solvent under vacuum. The residue was then dissolved in ethylacetate and washed with saturated sodium bicarbonate solution, water, brine, dried using sodium sulfate and concentrated under vacuum to obtain the residue which was purified using column chromatography (15% MeOH/dichloromethane) to obtain compound 17 (11 mg, 16%). $^1$H NMR (500 MHz, MeOD) δ 7.94 (dd, J=8.4, 0.7 Hz, 1H), 7.76 (dd, J=8.4, 0.8 Hz, 1H), 7.63 (ddd, J=8.4, 7.3, 1.2 Hz, 1H), 7.52 (d, J=8.3 Hz, 2H), 7.34 (ddd, J=8.4, 7.3, 1.1 Hz, 1H), 7.20 (d, J=8.3 Hz, 2H), 6.01 (s, 2H), 4.17 (s, 2H), 3.03-2.95 (m, 4H), 1.87-1.81 (m, 2H), 1.70-1.63 (m, 2H), 1.47 (dd, J=15.0, 7.5 Hz, 2H), 1.37-1.24 (m, 26H), 0.94 (t, J=7.4 Hz, 3H), 0.89 (t, J=7.0 Hz, 3H). $^{13}$C NMR (126 MHz, MeOD) δ 159.19, 150.63, 138.26, 137.68, 135.47, 132.90, 132.19, 131.14, 127.71, 126.54, 126.14, 123.02, 119.77, 114.31, 51.86, 33.23, 30.95, 30.94, 30.92, 30.88, 30.77, 30.63, 30.62, 30.51, 30.31, 27.91, 27.73, 27.25, 23.89, 23.47, 14.59, 14.26. MS (ESI) calculated for C$_{38}$H$_{57}$N$_5$, m/z 583.46. found 584.47 (M+H)$^+$.

Synthesis of Compound 18: N-(4-((4-amino-2-butyl-1H-imidazo[4,5-c]quinolin-1-yl)methyl)benzyl)-2-azidoacetamide

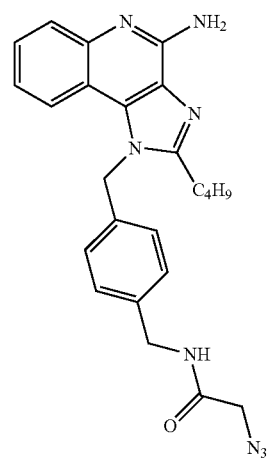

18

To a solution of 1-bromo acetic acid (52 mg, 0.37 mmol) in anhydrous DMF were added, triethylamine (130 μL, 0.93 mmol), 50 wt % propylphosphonic anhydride solution in ethylacetate (T3P®) (0.3 mL, 0.48 mmol) and compound 7d (160 mg, 0.37 mmol). The reaction mixture was stirred for 2 hours followed by removal of the solvent under vacuum. The residue was then dissolved in ethylacetate and washed thrice with water and brine. The ethylacetate was then removed under vacuum to obtain the crude intermediate bromo compound (95 mg) which was dissolved in anhydrous DMF and to it were added, triethylamine (33 μL, 0.24 mmol) and sodium azide (26 mg, 0.4 mmol). The reaction mixture was then heated at 60° C., followed by removal of the solvent under vacuum to obtain the residue which was purified using column chromatography to obtain the compound 18 (55 mg, 34%). $^1$H NMR (500 MHz, MeOD) δ 7.82 (d, J=8.3 Hz, 1H), 7.66 (d, J=8.4 Hz, 1H), 7.43 (dd, J=11.3, 4.1 Hz, 1H), 7.28 (d, J=8.1 Hz, 2H), 7.12 (t, J=7.7 Hz, 1H), 7.03 (d, J=8.1 Hz, 2H), 5.87 (s, 2H), 4.37 (s, 2H), 3.89 (s, 2H), 3.00-2.92 (m, 2H), 1.79 (dt, J=15.4, 7.6 Hz, 2H), 1.44 (dd, J=15.0, 7.5 Hz, 2H), 0.93 (t, J=7.4 Hz, 3H). $^{13}$C NMR (126 MHz, MeOD) δ 170.15, 156.38, 152.54, 144.50, 139.57, 136.25, 135.70, 129.50, 128.68, 126.92, 125.92, 123.60, 121.68, 115.71, 52.96, 49.62, 43.62, 30.88, 27.84, 23.43, 14.09. MS (ESI) calculated for $C_{24}H_{26}N_8O$, m/z 442.2230. found 443.2345 (M+H)$^+$.

Synthesis of Compound 19: N-(4-((4-amino-2-butyl-1H-imidazo[4,5-c]quinolin-1-yl)methyl)benzyl)pent-4-ynamide

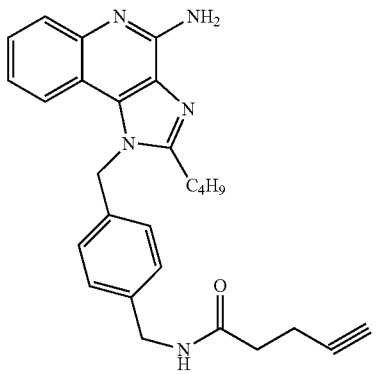

19

To a solution of pentynoic acid (13 mg, 0.13 mmol) in anhydrous DMF, were added triethylamine (35 mg, 0.35 mmol), HBTU (53 mg, 0.14 mmol), and 7d (50 mg, 0.116 mol). The reaction mixture was stirred for 1 hour, followed by removal of the solvent under vacuum. The residue was then dissolved in ethylacetate and washed with water, brine, dried using sodium sulfate and concentrated under vacuum to obtain the residue which was purified using column chromatography (6% MeOH/dichloromethane) to obtain compound 19 (37 mg, 73%). $^1$H NMR (500 MHz, MeOD) δ 7.96 (dd, J=8.4, 0.8 Hz, 1H), 7.73 (dd, J=8.3, 0.8 Hz, 1H), 7.63 (ddd, J=8.4, 7.3, 1.2 Hz, 1H), 7.36 (ddd, J=8.4, 7.3, 1.2 Hz, 1H), 7.30 (d, J=8.3 Hz, 2H), 7.05 (d, J=8.3 Hz, 2H), 5.92 (s, 2H), 4.35 (s, 2H), 3.02-2.97 (m, 2H), 2.49-2.43 (m, 2H), 2.43-2.38 (m, 2H), 2.23 (t, J=2.6 Hz, 1H), 1.85 (dt, J=21.1, 7.6 Hz, 2H), 1.46 (dd, J=15.0, 7.5 Hz, 2H), 0.95 (t, J=7.4 Hz, 3H). $^{13}$C NMR (126 MHz, MeOD) δ 174.12, 159.09, 150.66, 140.32, 137.69, 135.81, 135.32, 131.00, 129.65, 127.12, 126.92, 126.50, 126.47, 126.03, 123.07, 119.94, 118.82, 114.41, 112.00, 83.65, 70.50, 49.96, 43.73, 36.10, 30.48, 27.90, 23.45, 15.82, 14.23. MS (ESI) calculated for $C_{27}H_{29}N_5O$, m/z 439.24. found 440.25 (M+H)$^+$.

Synthesis of Compound 21: N-(4-((4-amino-2-butyl-1H-imidazo[4,5-c]quinolin-1-yl)methyl)benzyl)-3-(2,5-dioxo-2,5-dihydro-1H-pyrrol-1-yl)propanamide

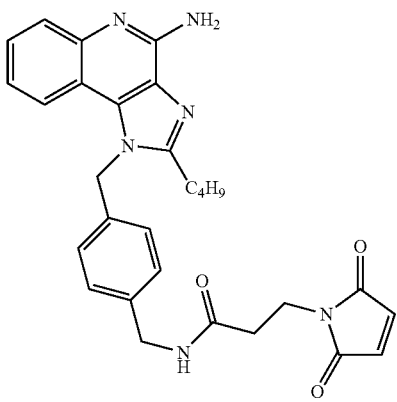

21

To a solution of 20 (30 mg, 0.18 mmol) in anhydrous DMF, were added triethylamine (50 mg, 0.49 mmol), HBTU (68 mg, 0.18 mmol), a catalytic amount of DMAP and 7d (70 mg, 0.16 mmol). The reaction mixture was stirred for 14 hours and then the solvent was removed under vacuum. The residue was dissolved in ethyl acetate and washed with water. The ethyl acetate fraction was then dried using Na$_2$SO$_4$ and evaporated under vacuum to obtain the residue, which was purified using column chromatography (5% MeOH/dichloromethane) to obtain compound 21 (65 mg, 80%). $^1$H NMR (500 MHz, MeOD) δ 7.97 (dd, J=8.4, 0.7 Hz, 1H), 7.74-7.71 (m, 1H), 7.64 (ddd, J=8.4, 7.2, 1.2 Hz, 1H), 7.38 (ddd, J=8.4, 7.2, 1.2 Hz, 1H), 7.26 (d, J=8.3 Hz, 2H), 7.04 (d, J=8.3 Hz, 2H), 6.73 (s, 2H), 5.93 (s, 2H), 4.27 (s, 2H), 3.75 (t, J=7.0 Hz, 2H), 3.02-2.97 (m, 2H), 2.47 (t, J=7.0 Hz, 2H), 1.85 (dt, J=21.1, 7.6 Hz, 2H), 1.46 (dq, J=14.8, 7.4 Hz, 2H), 0.94 (t, J=7.4 Hz, 3H). $^{13}$C NMR (126 MHz, MeOD) δ 172.88, 172.10, 159.09, 150.46, 140.15, 137.66, 135.44, 135.36, 135.21, 130.99, 129.71, 126.83, 126.50, 125.89, 123.02, 119.59, 114.25, 49.85, 43.65, 35.59, 35.40, 30.35, 27.78, 23.33, 14.12. MS (ESI) calculated for $C_{29}H_{30}N_6O_3$, m/z 510.24. found 511.25 (M+H)$^+$.

Synthesis of compound 23: (4-((4-((4-amino-2-butyl-1H-imidazo[4,5-c]quinolin-1-yl)methyl)benzyl)carbamoyl)phenyl)boronic acid

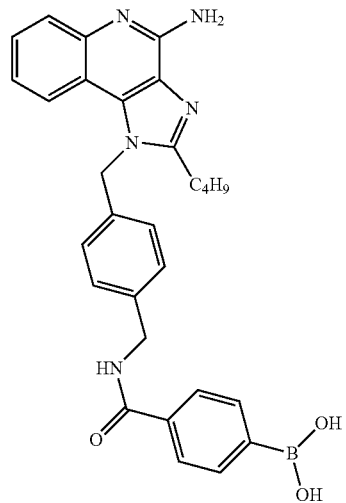

23

To a solution of 22 (63 mg, 0.26 mmol) in anhydrous DMF, were added triethylamine (58 mg, 0.58 mmol), HBTU (97 mg, 0.26 mmol), a catalytic amount of DMAP and 7d (100 mg, 0.23 mol). The reaction mixture was stirred for 1 hour, followed by removal of the solvent under vacuum. The residue was then dissolved in ethylacetate and washed with water, brine, dried using sodium sulfate and concentrated under vacuum to obtain the crude boronic acid pinacolester derivative. This was then dissolved in a solution of 9:1 acetonitrile:1N HCl and polymer-bound boronic acid (767 mg, 1.15 mmol) was added to the solution. The reaction was stirred for 12 hours. The beads were then filtered and the filtrate was concentrated under reduced pressure to obtain the residue which was purified using C$_{18}$ reverse-phase column chromatography (60% MeOH/H$_2$O) to obtain compound 23 (83 mg, 71%). $^1$H NMR (500 MHz, DMSO) δ 9.00 (t, J=6.0 Hz, 1H), 8.19 (s, 1H), 7.98 (dd, J=13.6, 5.5 Hz, 1H), 7.87-7.77 (m, 4H), 7.63 (d, J=8.8 Hz, 2H), 7.44-7.36 (m, 2H), 7.33-7.20 (m, 3H), 7.13 (d, J=7.6 Hz, 1H), 7.01 (t, J=6.3 Hz, 2H), 5.87 (d, J=5.6

Hz, 2H), 4.42 (d, J=5.9 Hz, 2H), 2.91 (dd, J=14.4, 6.8 Hz, 2H), 1.70 (dd, J=15.3, 7.8 Hz, 2H), 1.42-1.32 (m, 2H), 0.86 (t, J=7.4 Hz, 3H). $^{13}$C NMR (126 MHz, DMSO) δ 166.28, 150.81, 150.78, 150.60, 138.98, 135.47, 134.71, 133.90, 127.79, 127.72, 126.06, 125.47, 120.48, 114.73, 113.91, 113.77, 47.89, 42.12, 40.12, 40.06, 39.97, 39.89, 39.80, 39.73, 39.64, 39.56, 39.47, 39.30, 39.14, 38.97, 29.46, 26.18, 21.79, 13.66.

Synthesis of compound 25: 1-(4-((4-amino-2-butyl-1H-imidazo[4,5-c]quinolin-1-yl)methyl)benzyl)-3-(3-((4-((3-aminopropyl)amino)butyl)amino)propyl)thiourea

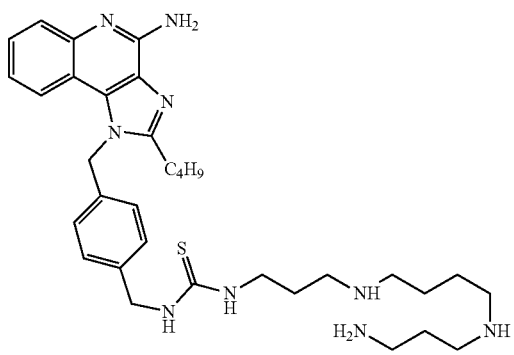

To solution of compound 24 (23 mg, 0.046 mmol) in pyridine was added compound 8 (18 mg, 0.046 mmol). The reaction mixture was then heated at 45° C. for 12 hours followed by removal of the solvent under vacuum. The residue was then purified using column chromatography to obtain the Boc-protected intermediate, which was then dissolved in 1 mL of 4N HCl solution in dioxane and stirred for 2 hours followed by removal of the solvent under vacuum to obtain compound 25 (32 mg, 89%). $^1$H NMR (500 MHz, MeOD) δ 7.96 (d, J=8.4 Hz, 1H), 7.76 (d, J=8.4 Hz, 1H), 7.64 (t, J=7.8 Hz, 1H), 7.37 (dd, J=8.3, 7.3 Hz, 1H), 7.32 (d, J=8.1 Hz, 2H), 7.06 (d, J=8.0 Hz, 2H), 5.94 (s, 2H), 4.74-4.60 (m, 2H), 3.67 (s, 2H), 3.12 (dd, J=16.0, 8.3 Hz, 2H), 3.09-2.96 (m, 10H), 2.08 (dd, J=9.0, 6.5 Hz, 2H), 1.99-1.88 (m, 2H), 1.88-1.71 (m, 6H), 1.47 (dd, J=15.0, 7.5 Hz, 2H), 0.95 (t, J=7.4 Hz, 3H). $^{13}$C NMR (126 MHz, MeOD) δ 162.69, 162.39, 159.00, 150.58, 137.58, 135.39, 135.33, 130.92, 129.46, 126.81, 126.36, 125.89, 122.93, 119.59, 114.20, 49.83, 48.26, 48.01, 45.95, 45.86, 41.58, 37.79, 30.34, 27.80, 27.76, 25.39, 24.36, 24.33, 24.21, 23.32, 14.09. MS (ESI) calculated for $C_{33}H_{49}N_9S$, m/z 603.38. found 604.39 (M+H)$^+$.

Figure 3:
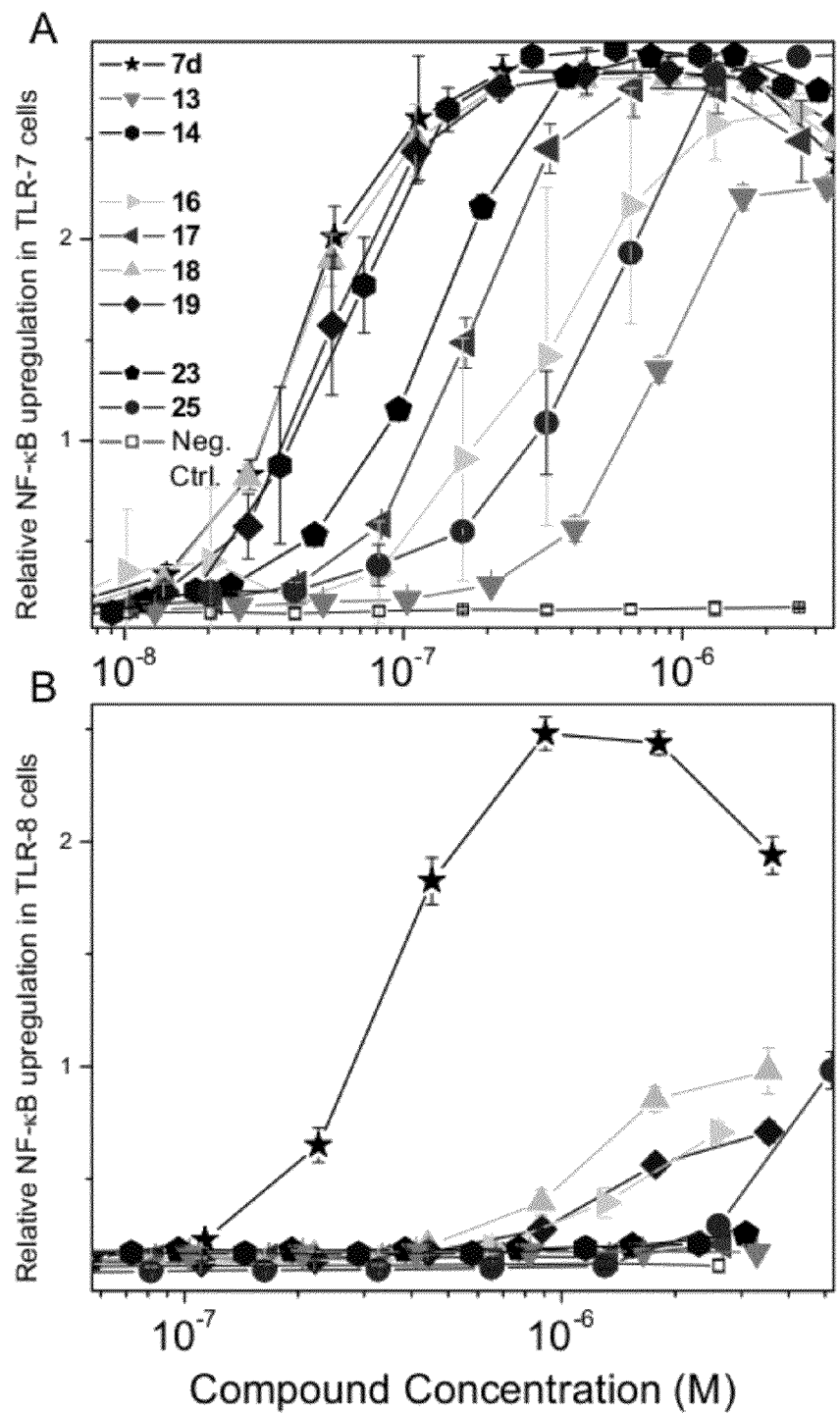
FIGS. 3A and 3B are graphs illustrating the TLR-7 and TLR-8 agonistic activities of derivatives of compound 7d.

As shown in FIGS. 3A and 3B, several imidazoquinoline derived compounds of the present disclosure show differential TLR7/TLR8 activities. The retention of TLR7-agonistic activity with attenuation of TLR8-agonistic activity may result in immune modifiers with low proinflammatory properties.

Example 3

Fluorescent Imidazoquinoline Derived Compounds

Compound 7d served as a convenient precursor for the covalent attachment of fluorophores without significant loss of activity. Fluorescence microscopy experiments show that the fluorescent analogues are internalized and distributed in the endosomal compartment. Flow cytometry experiments using whole human blood show differential partitioning into B, T, and natural killer (NK) lymphocytic subsets, which correlate with the degree of activation in these subsets. These fluorescently-labeled imidazoquinolines will likely be useful in examining in detail the trafficking of TLR7 in immunological synapses.

The free primary amine on the N$^1$ substituent of 7d was covalently coupled directly to commercially-available fluorescein isothiocyanate and rhodamine B isothiocyanate (Scheme 6). Conversely, the amine on 7d was converted first to the isothiocyanate 8, allowing the subsequent coupling of amine-bearing fluorophores, such as the bora-diazaindacene dye, BODIPY-TR-cadaverine (Scheme 6, overleaf).

Figure 4:
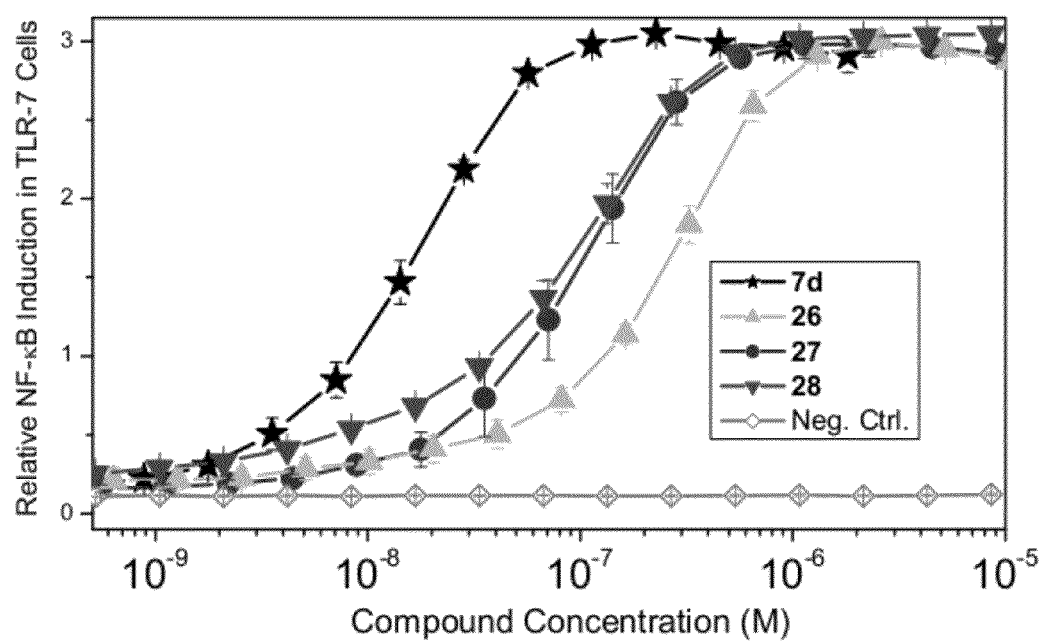
FIG. 4 is a graph of the activities of 7d, 26, 27, and 28 in reporter gene assays using human TLR7.

The syntheses of fluorescent imidazoquinoline analogues that retain TLR7-agonistic activity are expected to be useful probes in examining the anatomical basis of their potential immunostimulatory and adjuvantic properties. All three fluorescent conjugates retain TLR7-agonistic activity, although their potencies are slightly attenuated relative to the parent compound, 7d (FIG. 4).

Scheme 6. Syntheses of fluorescent analogues of 7d.

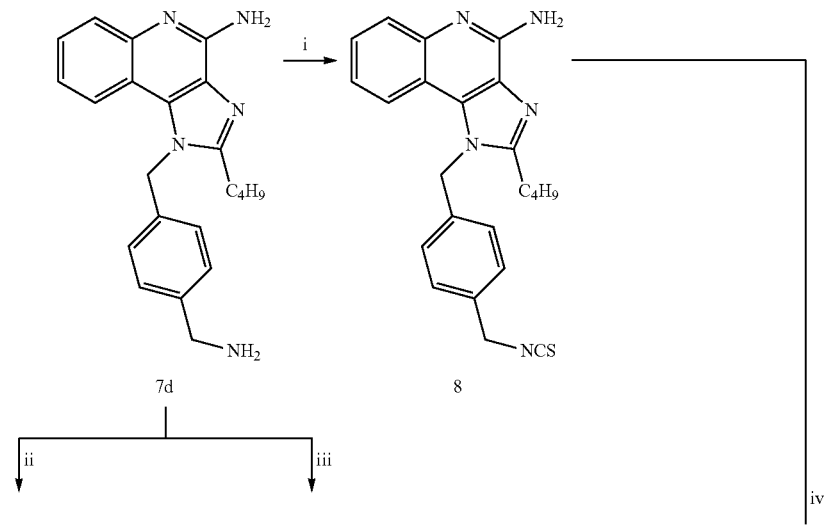

-continued
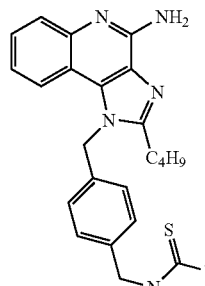
26
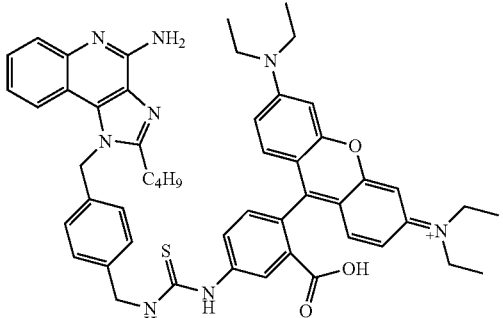
27
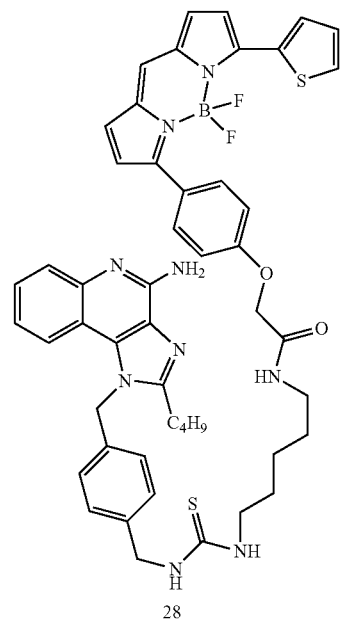
28
Reagents: i. CS₂, Et₃N, DMAP, (Boc)₂O, CH₂Cl₂; ii. Fluorescein isothiocyanate, Et₃N, MeOH;
iii. Rhodamine B isothiocyanate, Et₃N, CH₂Cl₂; iii. BODIPY® TR cadaverine, pyridine.

Synthesis of Compound 26: 2-(3-(4-((4-Amino-2-butyl-1H-imidazo[4,5-c]quinolin-1-yl)methyl)benzyl)thioureido)-6-(6-hydroxy-3-oxo-3H-xanthen-9-yl)benzoic acid

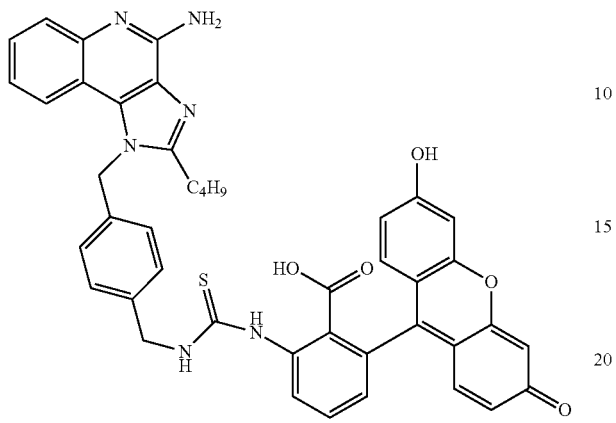

To a solution of fluorescein isothiocyanate (17 mg, 0.043 mmol) in anhydrous MeOH, were added triethylamine (13 mg, 0.13 mmol) and 7d (20 mg, 0.043 mmol). The reaction mixture was then heated at 45° C. for 18 hours and then the solvent was removed under vacuum. The residue was then purified using column chromatography (22% MeOH/dichloromethane) to obtain compound 26 (3 mg, 10%). $^1$H NMR (500 MHz, DMSO) δ 10.13 (s, 3H), 8.44 (s, 1H), 8.21 (s, 1H), 7.88-7.67 (m, 3H), 7.62-7.53 (m, 1H), 7.33 (t, J=8.1 Hz, 2H), 7.26-7.13 (m, 2H), 7.07-6.94 (m, 3H), 6.67 (d, J=2.1 Hz, 2H), 6.57 (tt, J=5.4, 4.0 Hz, 5H), 5.87 (s, 2H), 4.74 (s, 2H), 2.97-2.84 (m, 2H), 1.77-1.67 (m, 2H), 1.45-1.33 (m, 2H), 0.91-0.85 (m, 3H). MS (ESI) calculated for $C_{43}H_{36}N_6O_5S$, m/z 748.25. found 749.26 (M+H)$^+$.

Synthesis of Compound 27: N-(9-(4-(3-(4-((4-amino-2-butyl-1H-imidazo[4,5-c]quinolin-1-yl)methyl)benzyl)thioureido)-2-carboxyphenyl)-6-(diethylamino)-3H-xanthen-3-ylidene)-N-ethylethanaminium

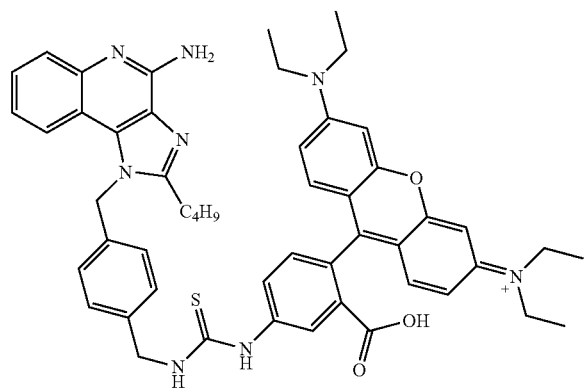

To a solution of rhodamine B isothiocyanate (50 mg, 0.12 mmol) in anhydrous dichloromethane, were added triethylamine (47 mg, 0.47 mmol) and 7d (64 mg, 0.12 mmol). The reaction mixture was then stirred for 14 hours and then the solvent was removed under vacuum. The residue was then purified using column chromatography (50% MeOH/dichloromethane) to obtain compound 27 (16 mg, 16%). $^1$H NMR (500 MHz, DMSO) δ 10.06 (s, 1H), 8.49 (s, 2H), 7.84 (d, J=8.4 Hz, 1H), 7.81-7.73 (m, 2H), 7.56 (dd, J=8.4, 1.0 Hz, 2H), 7.33-7.29 (m, 1H), 7.24 (d, J=8.1 Hz, 2H), 7.03-6.95 (m, 3H), 6.51 (dd, J=12.7, 8.4 Hz, 4H), 6.46-6.41 (m, 4H), 5.82 (s, 2H), 4.63 (s, 2H), 3.36 (dd, J=11.9, 4.8 Hz, 8H), 2.92-2.83 (m, 2H), 1.70 (dt, J=15.3, 7.6 Hz, 2H), 1.36 (dq, J=14.7, 7.4 Hz, 2H), 1.10 (t, J=7.0 Hz, 12H), 0.85 (t, J=7.4 Hz, 3H). MS (ESI) calculated for $C_{22}H_{23}N_3$, m/z 859.41. found 859.41 (M)$^+$.

Synthesis of Compound 28: BODIPY®-TR Cadaverine Conjugated to Compound 8

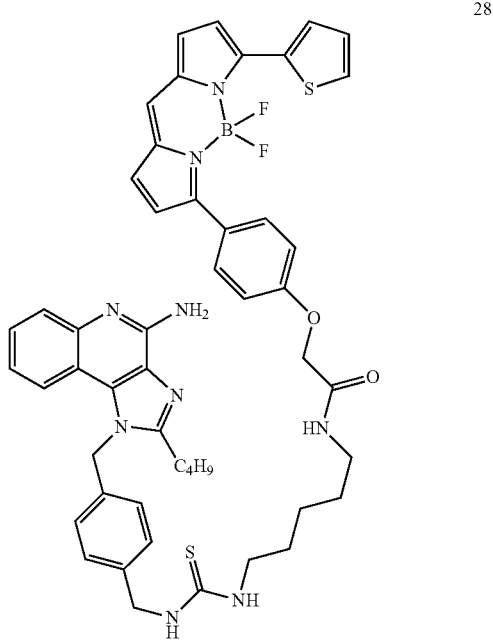

To a solution of BODIPY® TR cadaverine [5-(((4-(4,4-difluoro-5-(2-thienyl)-4-bora-3a,4a-diaza-s-indacene-3-yl)phenoxy)acetyl)amino)pentylamine]hydrochloride (Invitrogen, Inc., 10 mg, 0.02 mmol) in anhydrous pyridine, was added 8 (11 mg, 0.03 mmol). The reaction mixture was then heated at 45° C. for 18 hours and the solvent was then removed under vacuum. The residue was purified using column chromatography (8% MeOH/dichloromethane) to obtain compound 28 (2.34 mg, 15%). $^1$H NMR (400 MHz, MeOD) δ 7.99-7.93 (m, 3H), 7.82 (d, J=8.3 Hz, 1H), 7.66 (d, J=8.4 Hz, 1H), 7.56 (t, J=6.7 Hz, 2H), 7.42 (s, 1H), 7.26 (t, J=7.3 Hz, 3H), 7.17 (dd, J=8.5, 4.3 Hz, 2H), 7.06 (dd, J=8.9, 2.6 Hz, 3H), 6.95 (d, J=8.0 Hz, 2H), 6.83 (d, J=4.3 Hz, 1H), 6.74 (d, J=4.1 Hz, 1H), 5.73 (s, 2H), 4.57 (s, 2H), 3.22 (ddd, J=25.7, 16.1, 9.0 Hz, 4H), 2.88-2.83 (m, 2H), 1.76 (dt, J=15.3, 7.6 Hz, 3H), 1.51 (dt, J=18.8, 9.6 Hz, 4H), 1.39 (dd, J=15.1, 7.5 Hz, 2H), 1.36-1.24 (m, 3H), 0.90 (t, J=7.4 Hz, 3H). MS (ESI) calculated for $C_{49}H_{51}BF_2N_9O_2S_2^-$, m/z 910.37. found 910.37 (M$^+$).

Fluorescence Microscopy:

Murine macrophage J774.A1 cells were grown to confluency in optical-grade flat-bottomed 96 well plates as described earlier.[25,26] The cells were then exposed to graded concentrations of the fluorescently labeled compounds for 4 h at 37° C. Intravital epifluorescence and phase contrast images were obtained directly from the plated cells using an inverted Olympus IX-71 microscope equipped with long working-distance air objectives and temperature-controlled stage, using appropriate filter sets for the various fluorescent analogues. Images were processed on Image-J software.

Flow-cytometric Immunostimulation Experiments:

Methodology for flow-cytometirc immunostimulation is as described in Kawai et al., 2007.[1] Heparin-anticoagulated whole blood samples were obtained by venipuncture from healthy human volunteers with informed consent and as per guidelines approved by the University of Kansas Human Subjects Experimentation Committee. Two mL aliquots of whole human blood samples were stimulated with graded concentrations of 26 in a 6-well polystyrene plate and incubated at 37° C. in a rotary (100 rpm) incubator for 30 min. Negative (endotoxin free water) controls were included in each experiment. Following incubation, 200 µL aliquots of anticoagulated whole blood were stained with 20 µL of fluorochrome-conjugated antibodies (anti-CD3-PE, and anti-CD56-APC) at 37° C. in the dark for 30 min. Following staining, erythrocytes were lysed and leukocytes fixed in one step by mixing 200 µL of the samples in 4 mL pre-warmed Whole Blood Lyse/Fix Buffer (Becton-Dickinson Biosciences, San Jose, Calif.). After washing the cells twice at 200 g for 8 minutes in saline, the cells were transferred to a 96-well plate. Flow cytometry was performed using a BD FACSArray instrument in the tri-color mode. The primary gate for the lymphocytic population was obtained on FSC and SSC channels (100,000 gated events). Secondary gating included natural killer lymphocytes (NK cells: $CD3^-$ $CD56^+$), nominal B lymphocytes ($CD3^-CD56^-$), and nominal T lymphocytes ($CD3^+CD56^-$). Post-acquisition analyses were performed using FlowJo v 7.0 software (Treestar, Ashland, Oreg.). Compensation for spillover was computed for each experiment on singly-stained samples.

Figure 5:
FIG. 5 is a digital image of murine J774 cells treated with 10 nM of 28. An overlay of phase-contrast and epifluorescence images is depicted. An excitation filter at 562 nm and a long-pass emission filter (601-800) were used.

Incubation of murine macrophage J774.A1 cells with 27 and 28, followed by intravital epi- and confocal fluorescence microcopy showed prominent perinuclear localization, which is consistent with the expected endosomal distribution of TLR7.[27] Shown in FIG. 5 is a representative epifluorescence micrograph of J774 cells treated with 28 at 100 nM concentration.

Figure 6:
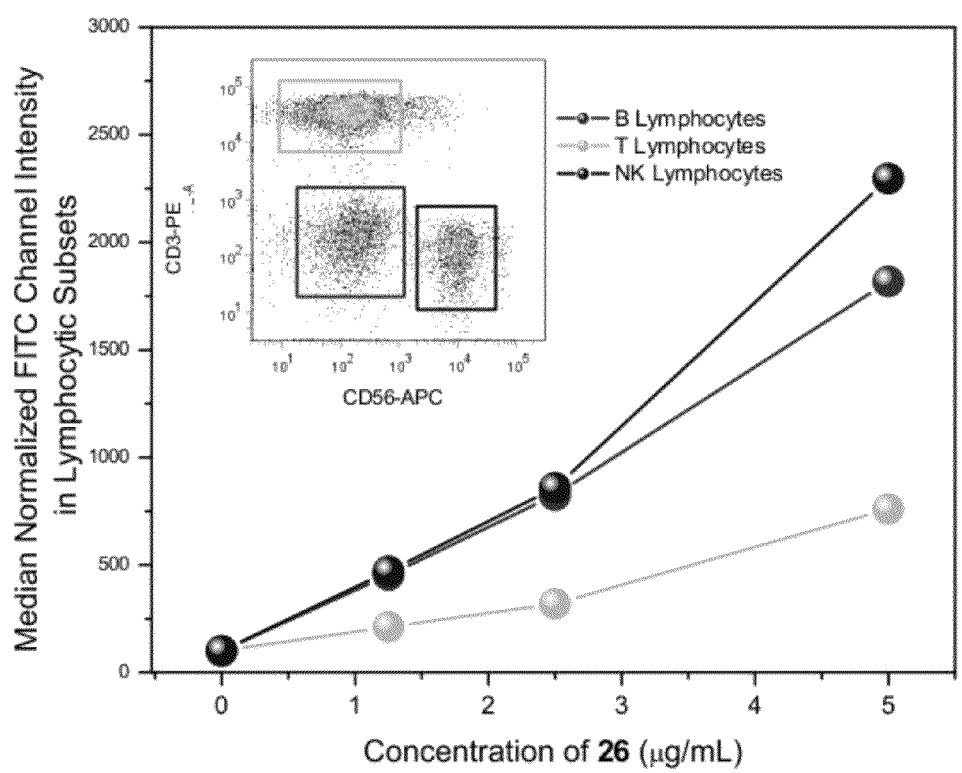
FIG. 6 illustrates the uptake of 26 in lymphacytic subsets as examined by flow cytometry. Whole human blood was incubated with graded concentrations of 26 for 30 min, lymphocytes stained with cell surface markers (anti-CD3-phycoerythrin [PE], and anti-CD56-PE-allophycocyanin). Erythrocytes were lysed, and 105 total events were acquired per sample.

Earlier immunoprofiling of the TLR7-agonistic imidazoquinolines had shown a very prominent activation of B- and NK-cells, but minimal activation of T cells,[8] which was believed to be potentially due to differential uptake of the TLR7 agonist in lymphocytic subsets. Flow cytometric analysis of the FITC-labeled 26 in experiments employing whole human blood indeed demonstrated a prominent uptake of 26 in $CD3^-CD56^+$ NK and $CD3^-CD56^-$ B lymphocytes as compared to $CD3^+CD56^-$ T lymphocytes (FIG. 6).

Example 4

Self-adjuvanting Imidazoquinoline Derived Compounds

One aspect of the present work in the area of evaluating TLR agonists as vaccine adjuvants[8,24,28] focuses on developing self-adjuvanting vaccine constructs, e.g., antigen covalently coupled to a suitable adjuvant. The premise of covalently decorating protein antigens with potential adjuvants offers the possibility of drastically reducing systemic exposure of the adjuvant, and yet maintaining relatively high local concentrations at the site of vaccination.[29] Most self-adjuvanting vaccine constructs to date have utilized TLR-2 agonistic 2,3-bis-(palmitoyloxy)propyl-cysteinyl peptides as the adjuvant.[30-35] The conjugation of the poorly soluble lipopeptide adjuvant to antigen has limited this approach to peptide[31-34,36] or glycopeptide[35] antigens, since native proteins are often irrevocably denatured under the coupling conditions employed, with potential loss of key epitopes. These limitations have recently been addressed by appending to the lipopeptide a long, water-solubilizing poly-lysine or polyethylene glycol moiety, and terminating in a free thiol.[37] However, in addition to the potential problem of oxidation of lipopeptide thiol to the disulfide, free exposed thiols in proteins are rare.[38] Furthermore, TLR2 ligation has been associated with Th2 and Th17 responses[39,40] which may, in many instances, be undesirable.

As describe above, the present disclosure provides potent TLR7 agonists, stimulating virtually all subsets of lymphocytes without inducing dominant proinflammatory cytokine responses.[8] A TLR7/8 dual-agonistic $N^1$-(4-aminomethyl) benzyl substituted imidazoquinoline 7d served as a convenient precursor for the syntheses of isothiocyanate and maleimide imidazoquinoline derived compounds for covalent attachment to free amine and thiol groups of peptides and proteins. Compound 7d was also amenable to direct reductive amination with maltoheptaose without significant loss of activity. Covalent conjugation of the isothiocyanate derivative 8 to α-lactalbumin could be achieved under mild, non-denaturing conditions, in a controlled manner and with full preservation of antigenicity. The self-adjuvanting α-lactalbumin construct induced robust, high-affinity immunoglobulin titers in murine models. The premise of covalently decorating protein antigens with adjuvants offers the possibility of drastically reducing systemic exposure of the adjuvant, and yet eliciting strong, Th1-biased immune responses.

Figure 7:
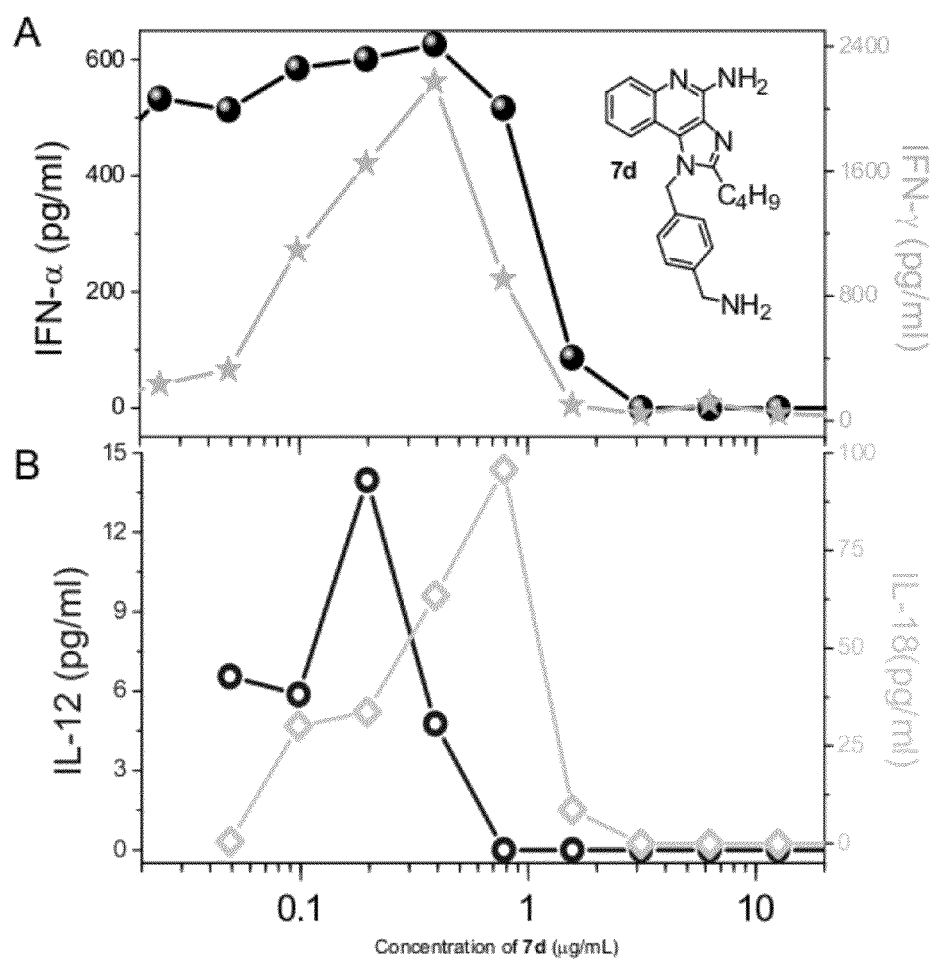
FIGS. 7A and 7B are graphs showing induction of IFN-α, IFN-γ (FIG. 7A) and IL-12 and IL-18 (FIG. 7B) by 7d in human PBMCs. IFN and cytokine levels were quantified by ELISA. Results of a representative experiment are shown.

Desirous of specifically identifying chemotypes with strong Th1-biased immunostimulatory signatures, additional screens were implemented that examine the induction of Type I[41-43] and Type II[44,45] interferons (IFN-α/β and IFN-γ, respectively), Interleukin-12 (IL-14[46,47] and Interleukin-18 (IL-18) using human PBMCs,[48-50] all of which are strongly associated with dominant Th1 outcomes. These experiments enabled determination that of all of the diverse chemotypes of the presently described and rapidly expanding libraries of TLR agonists,[24,28,51,52] an $N^1$-(4-aminomethyl)benzyl substituted imidazoquinoline 7d displayed a prominent Th1 bias (FIGS. 7A and 7B).

Figure 8:
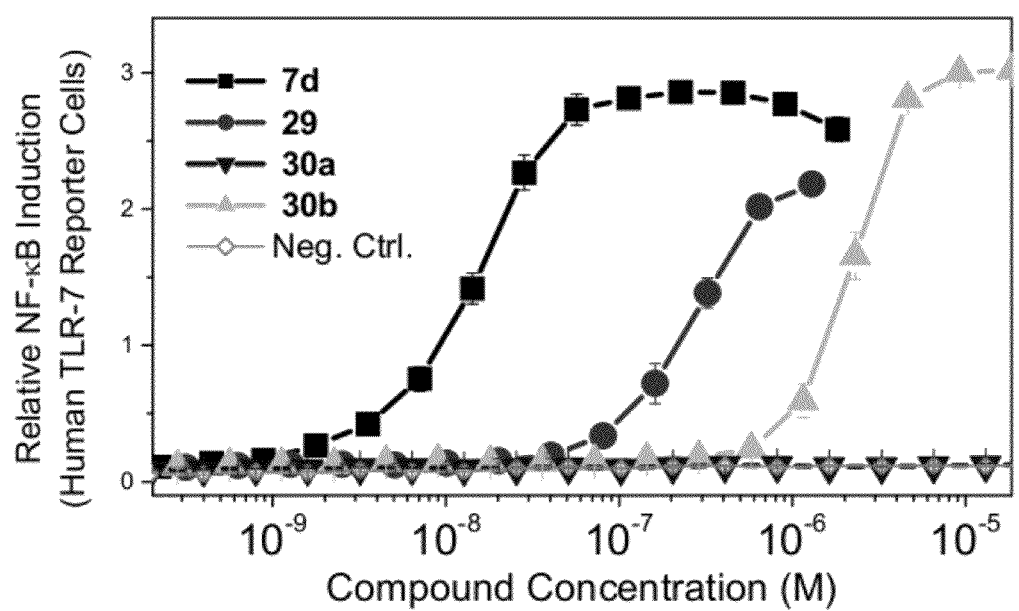
FIG. 8 is a graph illustrating TLR7-agonistic activities of imidazoquinoline analogues in a human TLR7-specific reporter gene assay.

Because the aqueous solubility of 7d and several of its congeners were excellent, direct covalent coupling to free amines and thiols on protein antigens via the introduction of conventional isothiocyanate and maleimide electrophilic handles on the imidazoquinoline scaffold was evaluated. The isothiocyanate derivative 8 (synthesis shown in Scheme 2) reacted well with a tri-glycine methyl ester model peptide, yielding the adduct 29 (Scheme 7), which was purified to homogeneity, and found to be active (FIG. 8). Facile adduction of the maleimide derivative 21 (synthesis shown in Scheme 4) with glutathione (reduced) also afforded the 30a in near-quantitative yields (Scheme 7).

Scheme 7. Syntheses of isothiocyanate and maleimide imidazoquinoline derived compounds of 7d, and their corresponding model peptide conjugates.

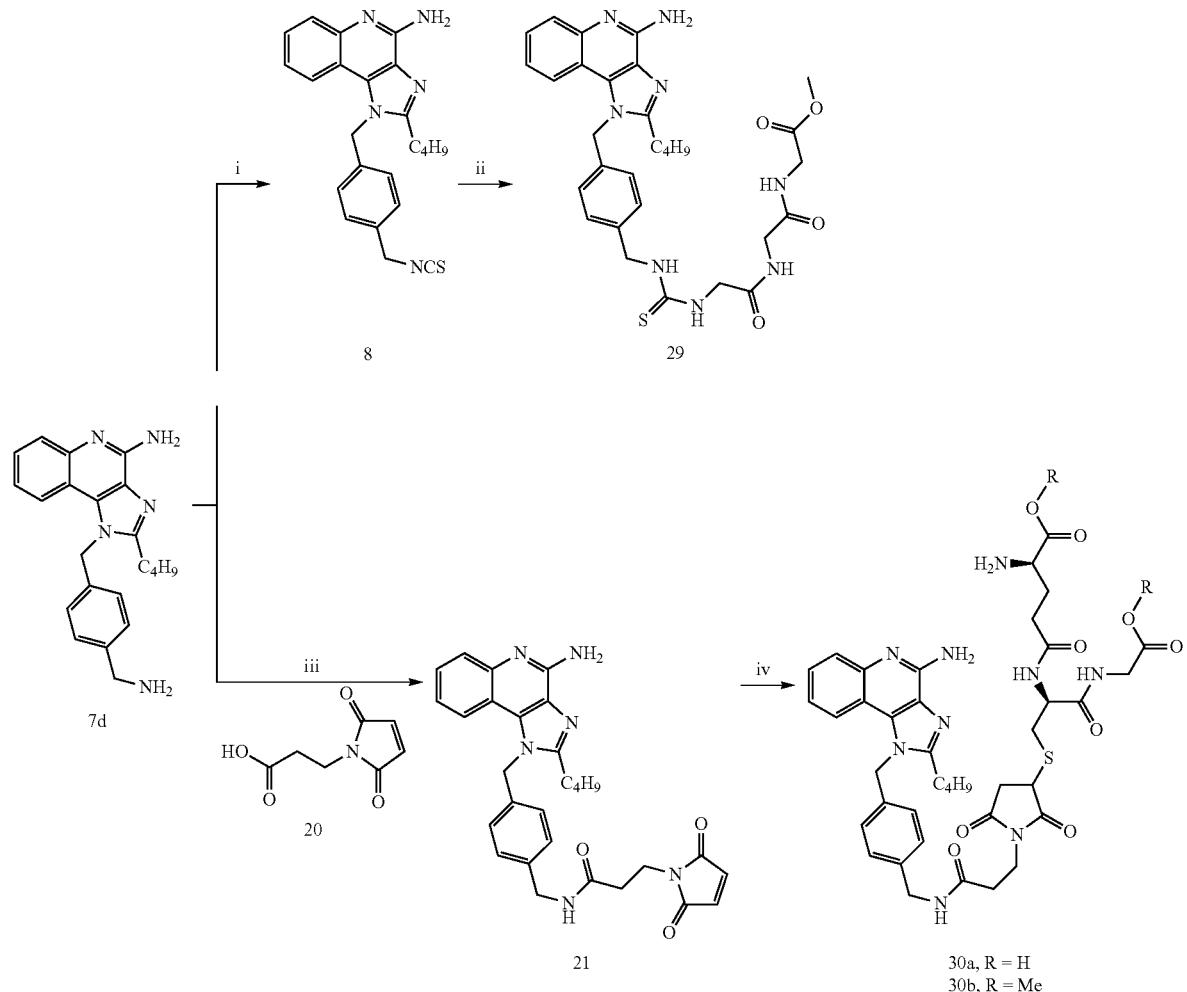

Reagents: i. CS$_2$, Et$_3$N, DMAP, (Boc)$_2$O, CH$_2$Cl$_2$; ii. Tri-glycine methyl ester, Et$_3$N, MeOH; iii. HBTU, Et$_3$N, DMAP, DMF; iv. glutathione-reduced (GSH) or GSH dimethyl ester, Et$_3$N, MeOH/CH$_2$Cl$_2$.

Synthesis of Compound 29: Methyl 1-(4-((4-amino-2-butyl-1H-imidazo[4,5-c]quinolin-1-yl)methyl)phenyl)-6,9-dioxo-3-thioxo-2,4,7,10-tetraazadodecan-12--oate

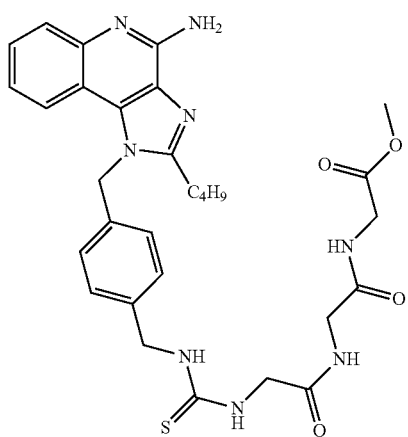

To a solution of 8 (15 mg, 0.037 mmol) in anhydrous MeOH, were added triethylamine (6 mg, 0.056 mmol) and methyl 2-(2-(2-aminoacetamido)acetamido)acetate hydrochloride (11 mg, 0.044 mmol). The reaction was heated at 45° C. for 4 hours. The solvent was then removed under vacuum and the residue was purified using column chromatography (14% MeOH/dichloromethane) to obtain compound 29 (5 mg, 22%). $^1$H NMR (400 MHz, DMSO) δ 8.36-8.14 (m, 3H), 7.79 (d, J=7.7 Hz, 1H), 7.58 (d, J=7.5 Hz, 2H), 7.33 (dd, J=11.2, 4.1 Hz, 1H), 7.25 (d, J=8.2 Hz, 2H), 7.05 (t, J=7.1 Hz, 1H), 7.00 (d, J=8.1 Hz, 2H), 6.59 (s, 2H), 5.85 (s, 2H), 4.61 (s, 2H), 4.11 (s, 2H), 3.83 (d, J=5.9 Hz, 2H), 3.75 (d, J=5.9 Hz, 2H), 3.62 (s, 3H), 2.96-2.86 (m, 2H), 1.72 (dt, J=15.3, 7.6 Hz, 2H), 1.45-1.31 (m, 2H), 0.88 (t, J=7.4 Hz, 3H). MS (ESI) calculated for C$_{30}$H$_{36}$N$_8$O$_4$S, m/z 604.26. found 605.27 (M+H)$^+$.

Synthesis of Compound 30b: (2R)-methyl 2-amino-5-((2S)-3-(1-(3-(4-((4-amino-2-butyl-1H-imidazo[4,5-c]quinolin-1-yl)methyl)benzylamino)-3-oxopropyl)-2,5-dioxopyrrolidin-3-ylthio)-1-(2-methoxy-2-oxoethylamino)-1-oxopropan-2-ylamino)-5-oxopentanoate

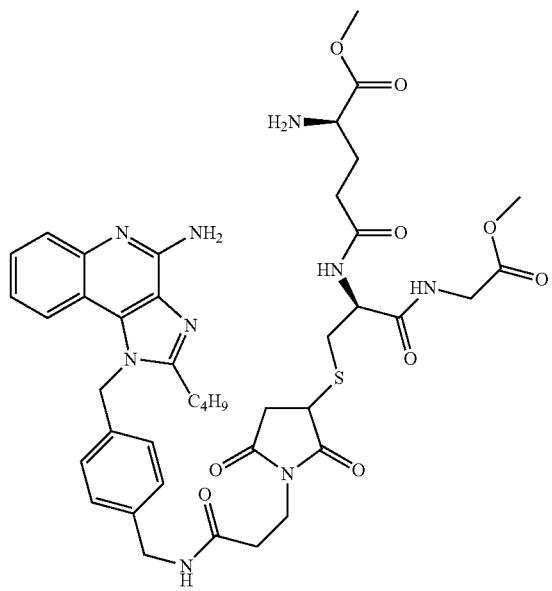

30b

To a solution of 21 (15 mg, 0.03 mmol) in anhydrous MeOH and a few drops of anhydrous dichloromethane, were added triethylamine (8 mg, 0.08 mmol) and glutathione reduced dimethyl ester (20 mg, 0.06 mmol). [Glutathione-reduced dimethyl ester was obtained from glutathione-reduced by stirring in mixture of methanol and 1 mL of HCl/dioxane solution for 30 hours, followed by removal of the solvent under vacuum]. The reaction mixture was stirred for 30 minutes, followed by removal of solvent under vacuum. The residue was then purified using column chromatography (20% MeOH/dichloromethane) to obtain compound 30b (5 mg, 60%). $^1$H NMR (500 MHz, MeOD) δ 7.75 (d, J=8.3 Hz, 1H), 7.57 (d, J=8.0 Hz, 1H), 7.36 (t, J=7.3 Hz, 1H), 7.17 (d, J=8.2 Hz, 2H), 7.06 (t, J=7.7 Hz, 1H), 6.94 (d, J=8.1 Hz, 2H), 5.79 (s, 2H), 4.19 (qd, J=15.2, 6.7 Hz, 2H), 3.84 (s, 2H), 3.68-3.61 (m, 5H), 3.58 (s, 3H), 3.54 (dt, J=10.7, 4.5 Hz, 1H), 3.14-2.93 (m, 3H), 2.93-2.82 (m, 2H), 2.39 (td, J=6.9, 2.4 Hz, 2H), 2.36-2.27 (m, 3H), 2.05-1.91 (m, 1H), 1.90-1.78 (m, 1H), 1.75-1.66 (m, 2H), 1.40-1.30 (m, 2H), 1.21 (t, J=7.3 Hz, 2H), 0.84 (t, J=7.4 Hz, 3H). MS (ESI) calculated for $C_{41}H_{51}N_9O_9S$, m/z 845.35. found 868.33 (M+Na$^+$).

Immunoassays for Interferon (IFN)-α, IFN-γ, Interleukin (IL)-12, and IL-18

Fresh human peripheral blood mononuclear cells (PBMC) were isolated from human blood obtained by venipuncture with informed consent and as per institutional guidelines on Ficoll-Hypaque gradients as described elsewhere.[53] Aliquots of PBMCs (10$^5$ cells in 100 µL/well) were stimulated for 12 h with graded concentrations of test compounds. Supernatants were isolated by centrifugation, diluted 1:20, and were assayed in triplicates using a high-sensitivity analyte-specific ELISA kits (PBL Interferon Source, Piscataway, N.J. and R&D Systems, Inc., Minneapolis, Minn.).

Protein Adduction and Mass Spectrometry Experiments:

Bovine α-lactalbumin (Sigma-Aldrich Chemical Co., St. Louis, Mo., and clinical grade human serum (Talecris Biotherapeutics, Research Triangle Park, N.C.) were incubated with 8 and 21, respectively at a molar ratio of 1:5 (protein:imidazoquinoline) in aqueous carbonate buffer at pH 8.0 overnight. The adducted proteins were analyzed by reverse-phase LC-ESI-MS performed on a Shimadzu LC system (LC-10AD binary pumps, SCL-10A diode array detector) using a Zorbax 3.0 mm×150 mm 3.5 µm stable-bond $C_{18}$ reverse-phase column with a forty-minute binary gradient (CH$_3$CN/water, 0.1% HCOOH) from 5% to 95% of CH$_3$CN. ESI-MS data was acquired on an Agilent LC/MSD-TOF instrument with a mass accuracy of 20 ppm and a range of 100-3500 Daltons. Calibration drift was minimized on a scan-by-scan basis by using internal standards corresponding to 922.0001 and 2721.0201 marker ions infused concurrently through a second nebulizer in the ionization chamber. Deconvolution was performed using on-board Agilent MassHunter software.

Animal Experiments:

All experiments were performed in accordance with animal care protocols approved by the University of Kansas IACUC Committee. Cohorts of 5 outbred CF-1 mice per group were immunized on Day 0 with vehicle (control 1), 50 µg/animal of bovine α-lactalbumin alone (control 2), or α-lactalbumin covalently coupled with 5 equivalents of 8, or α-lactalbumin mixed with 5 equivalents of 7d (control 3). All antigen preparations were in sterile, physiological saline (vehicle). A volume of 0.2 mL was injected intramuscularly into the flank region. Animals were boosted once on Day 14, and bled by terminal cardiac puncture (under isoflurane anesthesia) on Day 21. Sera were obtained from clotted blood by centrifugation at 3000 g×10 min, and stored at −80° C. until assayed.

Enzyme-linked Immunosorbent Assays (ELISA):

A precision 2000 liquid handler (Bio-Tek, Winooski, Vt.) was used for all serial dilution and reagent addition steps, and a Bio-Tek ELx405 384-well plate washer was employed for plate washes; 100 mM phosphate-buffered saline (PBS) pH 7.4, containing 0.1% Tween-20 was used as wash buffer. Nunc-Immuno MaxiSorp (384-well) plates were coated with 30 µL of α-lactalbumin in 100 mM carbonate buffer, pH 9.0 overnight at 4° C. After 3 washes, the plates were blocked with 3% bovine serum albumin (in PBS, pH 7.4) for 1 h at rt. Serum samples (in quadruplicate) were serially diluted in a separate 384-well plate using the liquid handler. After three additional washes of the assay plate, 30 µL of the serum dilutions were transferred using the liquid handler, and the plate incubated at 37° C. for 2 h. The assay plate was washed three times, and 30 µL of 1:10,000 diluted appropriate anti-mouse immunoglobulin (IgG [γ chain], IgM [µ chain], IgG1, IgG2a) conjugated with horseradish peroxidase was added to all wells. Following an incubation step at 37° C. for 1 h, and three washes, tetramethylbenzidine substrate was added at concentrations recommended by vendor (Sigma). The Chromogenic reaction was terminated at 30 min by the addition of 2M H$_2$SO$_4$. Plates were then read at 450 nm using a Spectra-Max M4 device (Molecular Devices, Sunnyvale, Calif.). Data visualization and statistics (Student's T test for significance) were performed using Origin 7.0 (Northampton, Mass.).

The imidazoquinolines themselves are small, non-polar, and basic, and therefore gain access to the endolysosomal compartment in which TLR7 is predominantly sequestered. The human embryonic kidney reporter cell lines stably transfected with TLR7 (and reporter secreted alkaline phosphatase genes) that were employed in our primary screen are not professional phagocytic cells. There was concern if the transmembrane permeability of the bulky, dianionic adduct 30a would be sufficient to trigger activation; thus, the conjugate of 21 with the dimethyl ester of reduced glutathione (30b) was also tested. The adducts 29 and 30b retained activity (EC$_{50}$:

269 nM and 2.2 µM), while 30a was inactive (FIG. 8), indicating that trans-cellular transport of the polar adduct with two net negative charges was insufficient.

The principle of electrophile-mediated conjugation was applied to bovine α-lactalbumin as a model antigen for self-adjuvanting vaccine constructs not only because it lent itself eminently well to rigorous characterization by electrospray ionization mass spectrometry (ESI-MS) methods (FIG. 9), but also because it is being evaluated as a potential antigen for breast cancer vaccines.[54]

Figure 9:
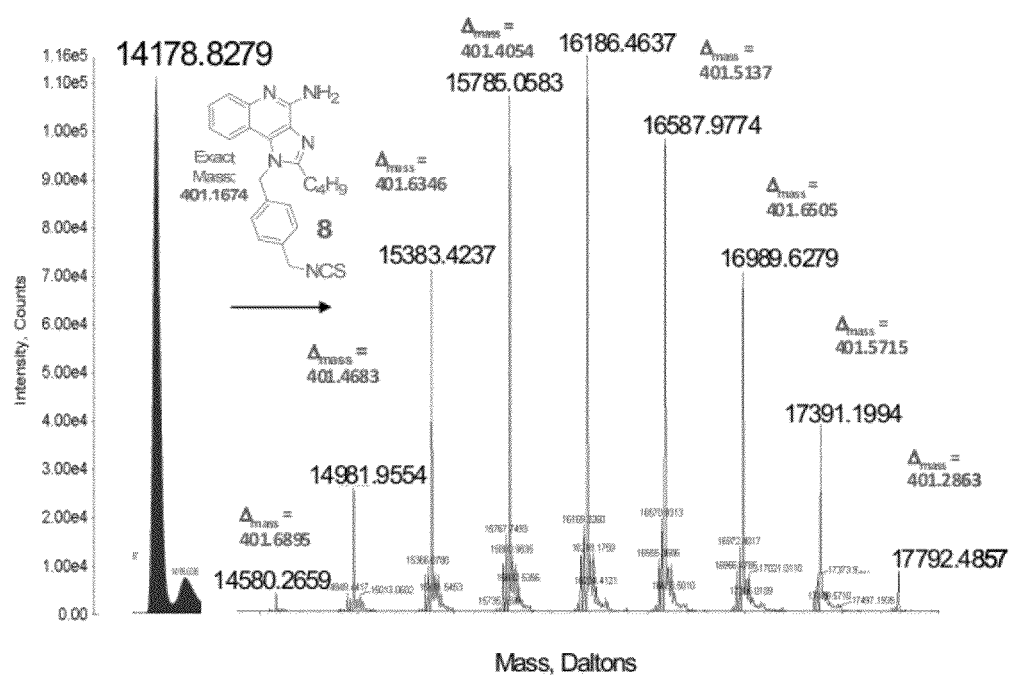
FIG. 9 illustrates a deconvoluted positive-mode ESI-MS spectra of native bovine α-lactalbumin (left) showing a mass of 14178.83 Da, and α-lactalbumin reacted with 5 eq. of 8, resulting in a stochastic coupling of the adjuvant with the centroid of the mass distribution corresponding to exactly 5 units of imidazoquinoline per protein molecule.
Figure 10:
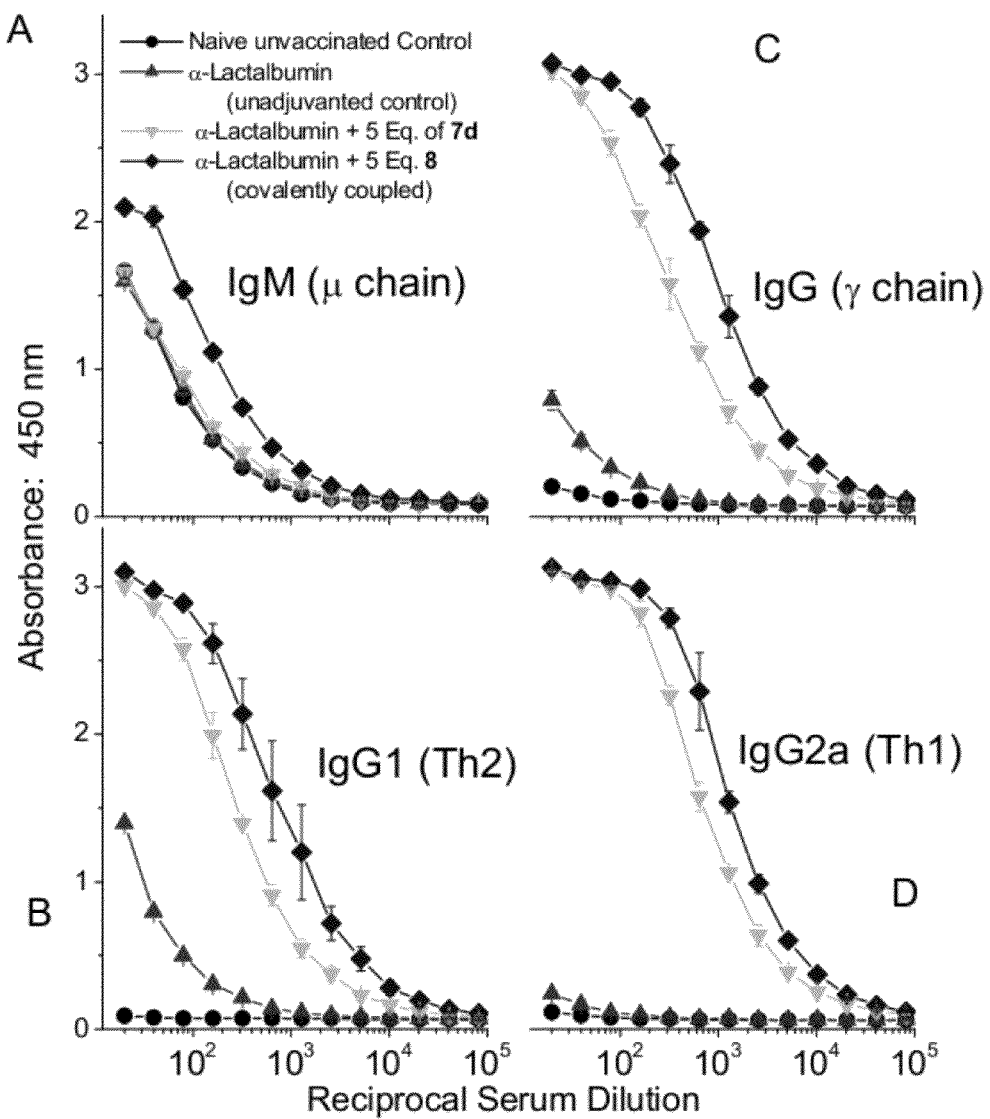
FIGS. 10A-10D are graphs illustrating immunoglobulin profiles in outbred CF-1 mice immunized on Day 0 with 50 μg/animal of α-lactalbumin, or α-lactalbumin covalently coupled with 5 equivalents of 8, or α-lactalbumin mixed with 5 equivalents of 7d. Animals (5 per cohort) were boosted once on Day 14 exactly as mentioned above, and bled on Day 21. α-lactalbumin-specific immunoglobulin levels were quantified by standard antibody-capture ELISA, performed in liquid handler-assisted 384-well format.

5 equivalents of 8 were reacted with bovine α-lactalbumin in isotonic aqueous buffer at pH 8.5. Direct LC-ESI-MS evidence was obtained for covalent adduction of 8 with the protein, indicating a remarkably beautiful and precise Gaussian distribution of adducted species, with the preponderant conjugate corresponding to a 1:5 molar ratio of protein:8 (FIG. 9).

Figure 11:
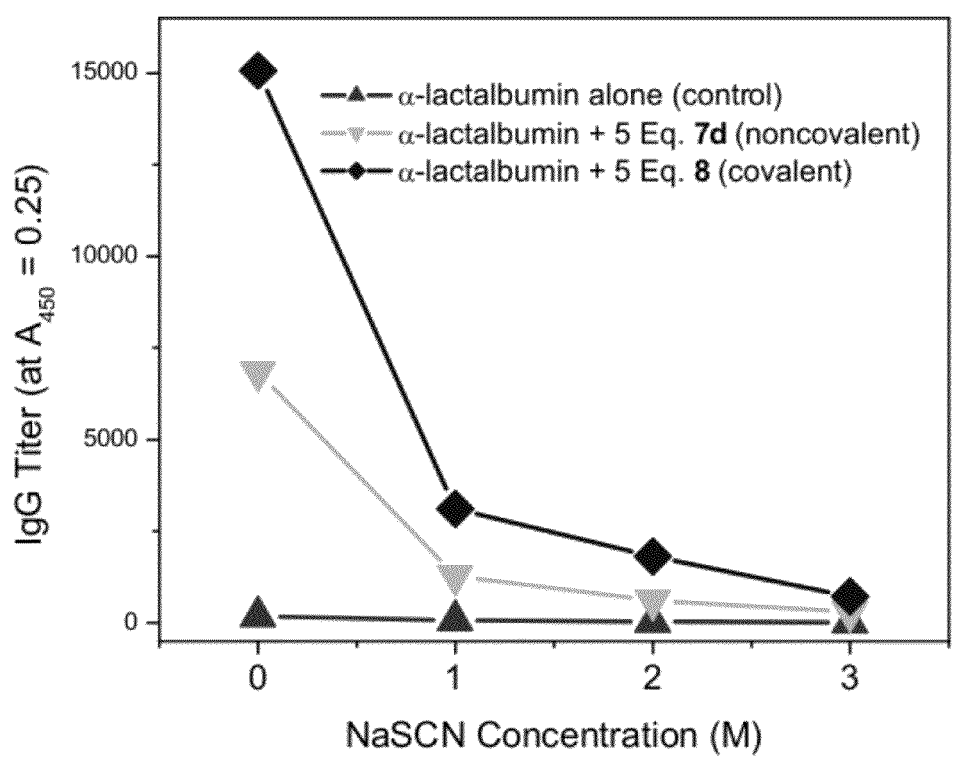
FIG. 11 is a graph illustrating affinity IgG ELISA showing antibody titer as a function of chaotrope (NaSCN) concentration. IgG titers on the ordinate axis were calculated from absorbance values at 0.25 (which corresponds to 36 above that of naïve controls).

It was of particular interest to evaluate this 8:α-lactalbumin conjugate (FIG. 9) as a self-adjuvanting subunit vaccine construct. It was of interest whether the conjugation procedure would preserve antigenicity of the protein, and whether the covalently-adducted construct would be superior to a physical mixture of α-lactalbumin and 7d. Cohorts (5 per group) of outbred CF-1 mice were immunized with 50 µg per animal of α-lactalbumin, or 50 µg of α-lactalbumin covalently conjugated with 5 equivalents of 8, or a mixture of 50 µg of α-lactalbumin and 5 equivalents of 7d. The animals were boosted once after two weeks following the priming dose, and bled after an additional week. α-lactalbumin-specific IgM, IgG, as well as IgG1 and IgG2a (isotypes characteristic of Th2 and Th1 responses,[55] respectively) were quantified by ELISA (FIGS. 10A-10D). As shown in FIGS. 10A-10D, dramatic enhancements in antibody titers were observed with both covalently- and non-covalently adjuvanted protein (relative to α-lactalbumin alone). Modest, but consistent, and statistically significant differences were also observed in titers between the covalently coupled self-adjuvanting construct, and mixture of antigen and adjuvant, indicating that self-adjuvanting subunit protein vaccines may indeed be generated with full preservation of antigenicity. Examination of the affinity of antigen-specific IgG using conventional chaotropic ELISA[56,57] also indicates higher quality IgG (FIG. 11) elicited by the self-adjuvanting construct.

Figure 12:
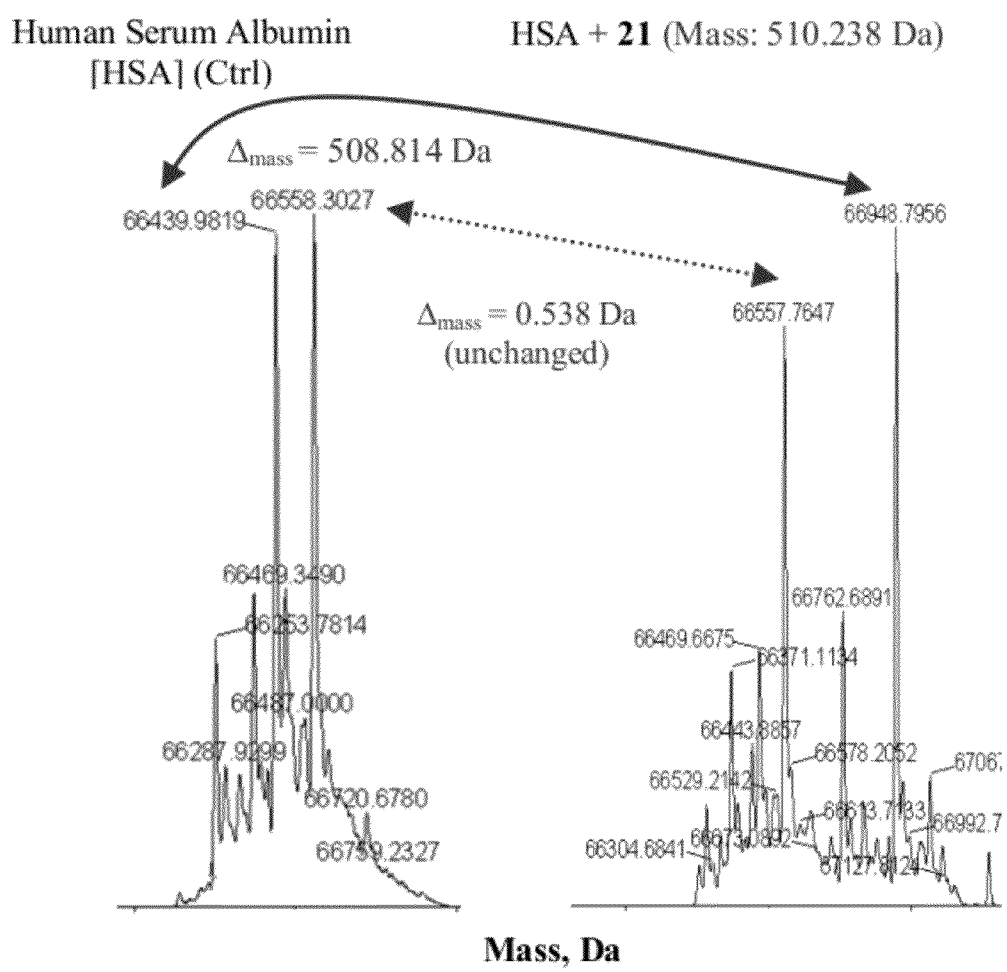
FIG. 12 illustrates covalent coupling of the thiol-specific maleimide derivative 21 with human serum albumin showing addition of a single equivalent of 21 to albumin, as examined by LC-ESI-TOF. An excess (5 equiv.) of 21 was used.

Encouraged by these results, conjugation of 21 with human serum albumin (HSA), a 66 kDa protein with a single free thiol was also performed. Clinical grade (meant for human parenteral use, formulated with amino acids) HSA was used, rather than the purer, 'essentially fatty acid free' protein available commercially. Furthermore, HSA is a carrier protein which binds promiscuously to a vast range of ligands including heavy metals, bilirubin, fatty acids, etc. For these reasons, it was anticipated that deconvoluted direct electrospray-time-of-flight mass (ESI-TOF) spectra would be polydisperse and microheterogeneous. In the HSA-alone control sample, two major peaks were found corresponding to 66439.9819 and 66558.3027 Da (FIG. 12). Reaction of HSA with 21 produced a shift in one of the peaks with a $\Delta_{mass}$ of 508.814 Da, which corresponds to the maleimide derivative 21 within instrument error (1.424 Da at 66 KDa=21.2 parts per million). The other peak at 66558 Da had remained unaltered upon addition of excess thiol-specific maleimide analogue 21, suggesting that the thiol was unreactive (FIG. 12). An examination of the difference between the species with the free, reactive thiol (66439 Da) and the unreactive thiol (66558 Da) in the control sample suggests that the 'blocking' group is cysteine (expected exact mass of cysteine−1 proton [disulfide]=118.02; observed $\Delta_{mass}$=118.321 Da).

Example 5

Self-adjuvanting Polysaccharide Vaccines

Figure 13:
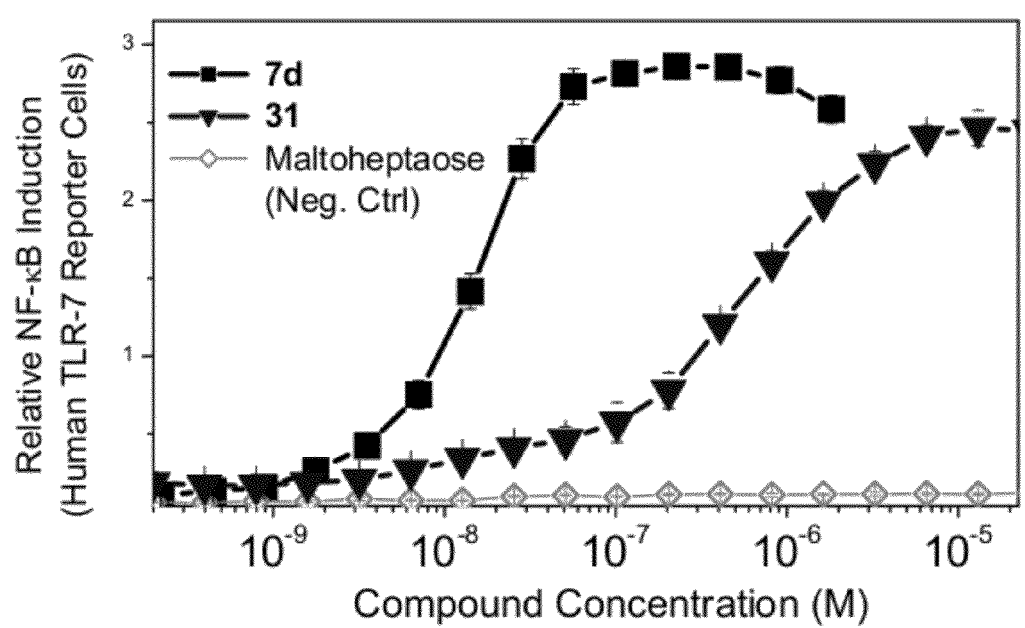
FIG. 13 is a graph of TLR7-agonistic activities of imidazoquinoline-maltoheptaose conjugate in a human TLR7-specific reporter gene assay.

Aside from engineering otherwise feebly immunogenic peptide and subunit protein vaccines for the induction of strong CTL responses, there is also interest in polysaccharide vaccines which have proved enormously useful in the prevention of infections by bacterial pathogens such as *N. meningitidis* and *H. influenzae*.[58-60] Bacterial polysaccharides, unlike conventional protein antigens, have been considered classic T cell-independent antigens that do not elicit cell-mediated immune responses but rather elicit non-anamnestic responses characterized by low-affinity IgM and restricted classes of IgG immunoglobulins without the recruitment of T cell help. Conversion to canonical, T lymphocyte-dependent responses require their covalent coupling to immunogenic 'carrier proteins' such as diphtheria toxoid.[61,62] This appears not to be the case for zwitterionic polysaccharides, however, which elicit potent CD4+ T cell responses.[63,64] The structural determinants of T-dependent and -independent humoral responses can be reexamined, especially in light of recent findings of intrinsic TLR2 activation by zwitterionic polysaccharides.[65,66] The free primary amine on the N¹ substituent of 7d lent itself well to direct reductive amination with maltoheptaose, a model oligosaccharide with a reducing terminal maltose unit (31, Scheme 8) which was found to be active in TLR7 assays (EC₅₀: 528 nM; FIG. 13). This method of direct coupling of 7d to oligosaccharides and polysaccharides will therefore be useful for constructing self-adjuvanting polysaccharide vaccines (such as against *N. meningitidis* Group C polysaccharide).[67]

Scheme 8. Syntheses of maltoheptaose conjugate.

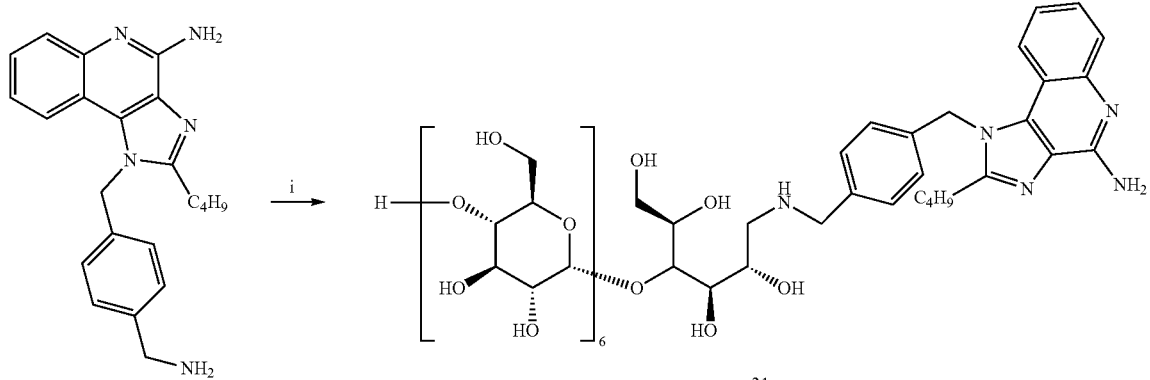

Reagents: i. Maltoheptaose, CH₃CO₂H, Macroporous resin-bound CNBH₃, 50° C., DMF.

Synthesis of Compound 31

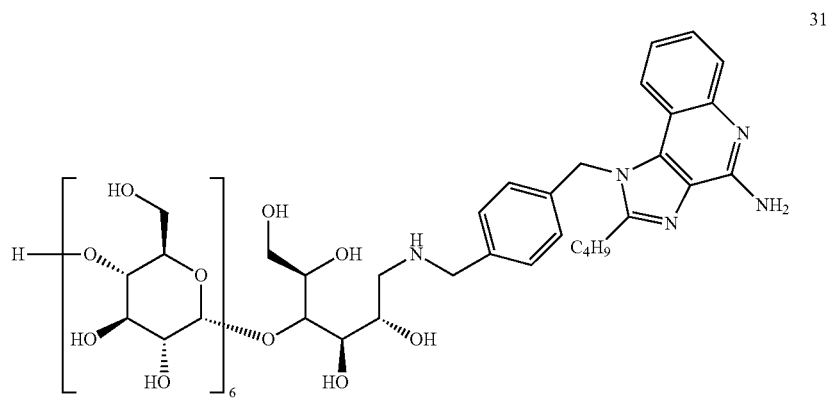

31

To a solution of compound 7d (8 mg, 0.019 mmol) in anhydrous DMF, were added 3-4 drops of acetic acid, maltoheptaose (20 mg, 0.018 mmol) and macroporous polystyrene-bound cyanoborohydride (15 mg, 0.033 mmol). The reaction mixture was heated at 50° C. for 24 hours. The solution was filtered to remove the solid resin and the filtrate was evaporated under vacuum to obtain the residue which was purified using $C_{18}$ reverse-phase column chromatography (40% MeOH/$H_2O$) to obtain compound 31 (12 mg, 45%). MS (ESI) calculated for $C_{64}H_{97}N_5O_{35}$, m/z 1495.60. found 1518.59 ($M+Na^+$) and 759.83 $(M+H+Na)^{2+}$.

Thus, 7d, with its free amine group, can be conveniently exploited in constructing covalent conjugates with peptides, proteins, as well as polysaccharides with preservation of immunostimulatory activity.

Example 6

Tissue-specific Imidazoquinoline Compounds

Figure 14:
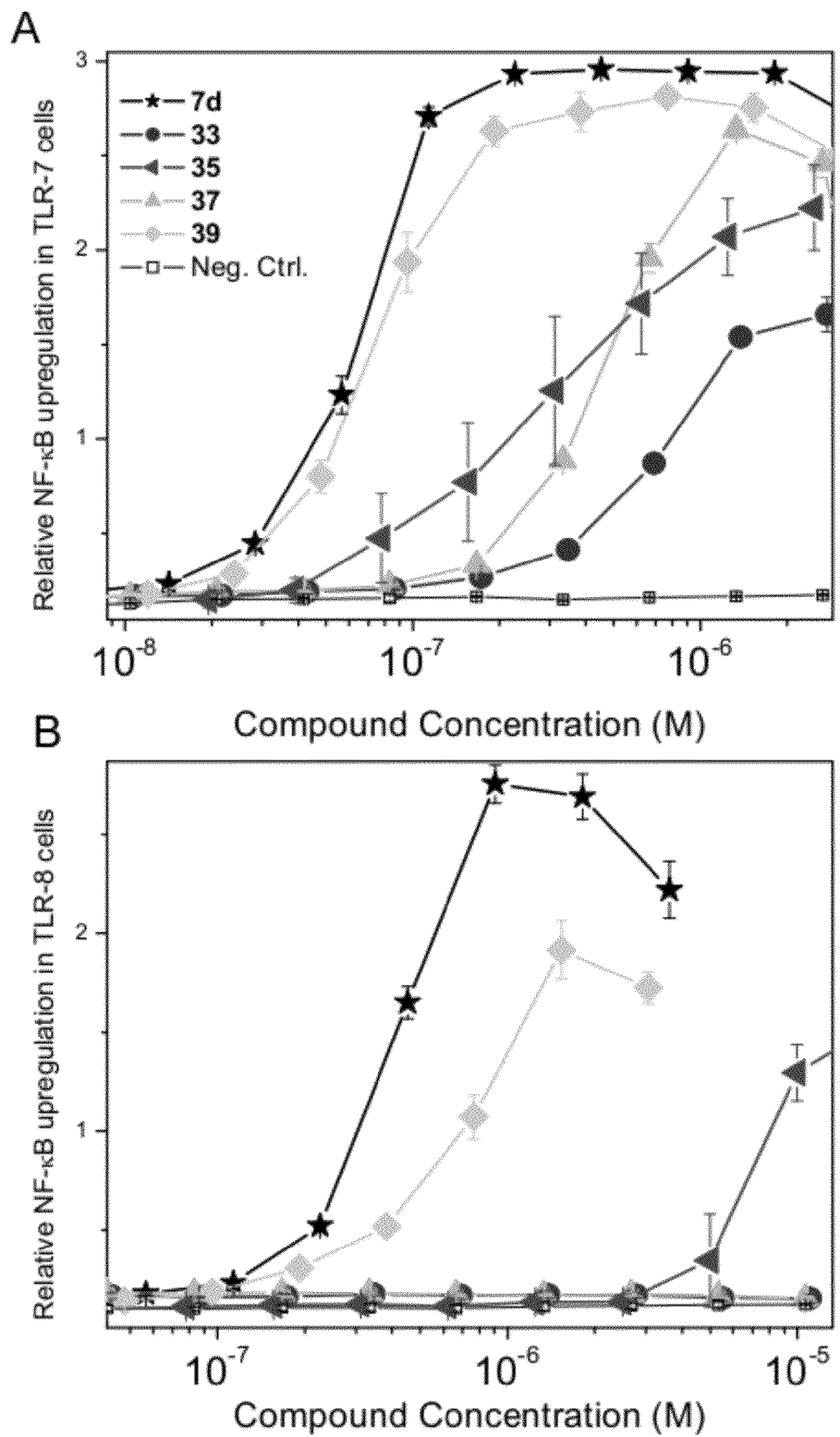
FIGS. 14A and 14B illustrate TLR-7 and TLR-8 agonistic activities of compounds 33, 35, 37 and 39.

Tissue-specific activity of 7d, can be enhanced by appending specific moieties that undergo selective uptake by particular cell-types. For instance, a selective delivery of drugs to liver can be obtained by conjugation with galactosyl-terminating molecules.[68] Selective targeting of tumors can be achieved by conjugation of drugs to vitamins such as folic acid.[68-71] Accordingly, the free amine group of 7d was coupled to galactose (Scheme 9) as well as a range of vitamins such as folic acid (vitamin $B_9$), biotin (vitamin $B_7$), and Pyridoxal (vitamin $B_6$) as shown in Schemes 10-12. Several analogues retain TLR7-stimulatory activity (FIGS. 14A (TLR7 activity) and 14B (TLR8 activity)).

Scheme 9. Synthesis of a galactose derivative 33.

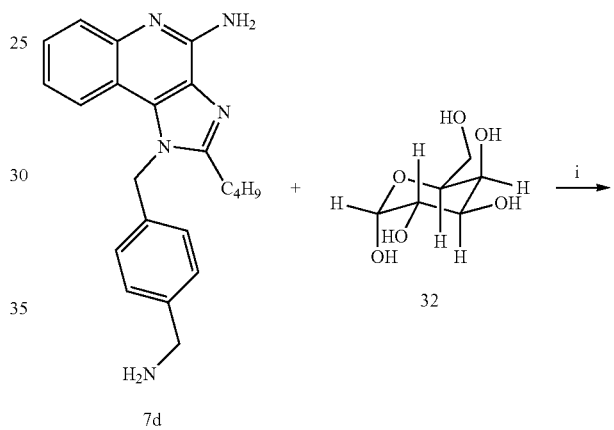

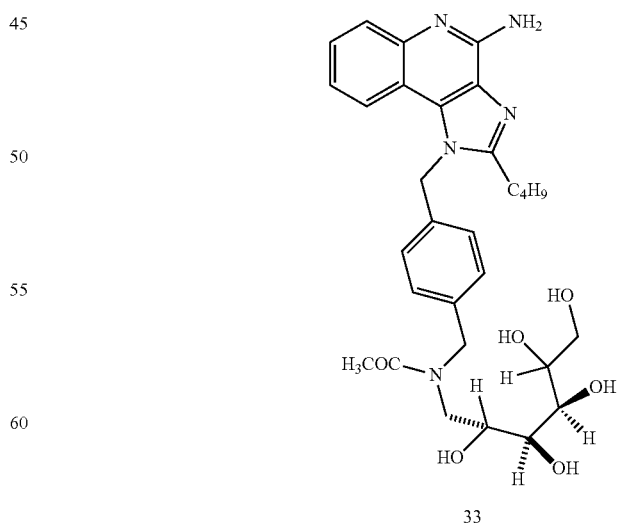

Reagents and conditions: i. (a) MP-CNBH₃, DMF, 50 °C. (b) acetic anhydride, Et₃N, DMF (c) NaOMe, MeOH.

Scheme 10. Synthesis of a folic acid derivative 35.
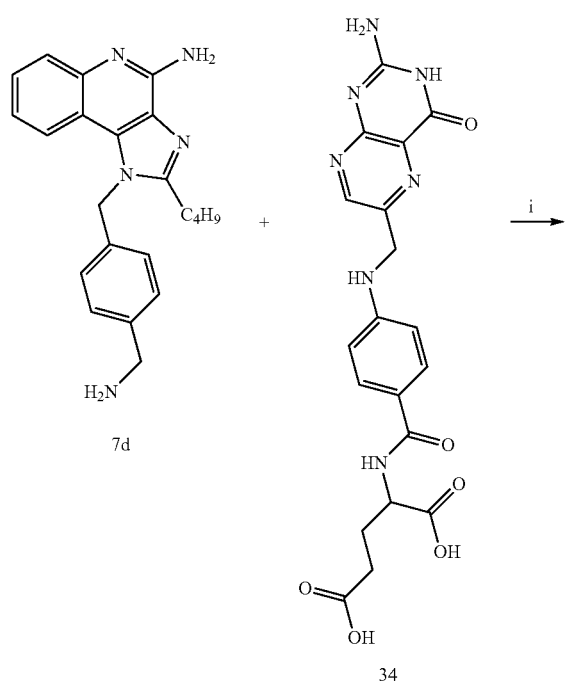
Reagents and conditions: i. HBTU, ET₃N, DMSO.
Scheme 11. Synthesis of a biotin derivative 37.
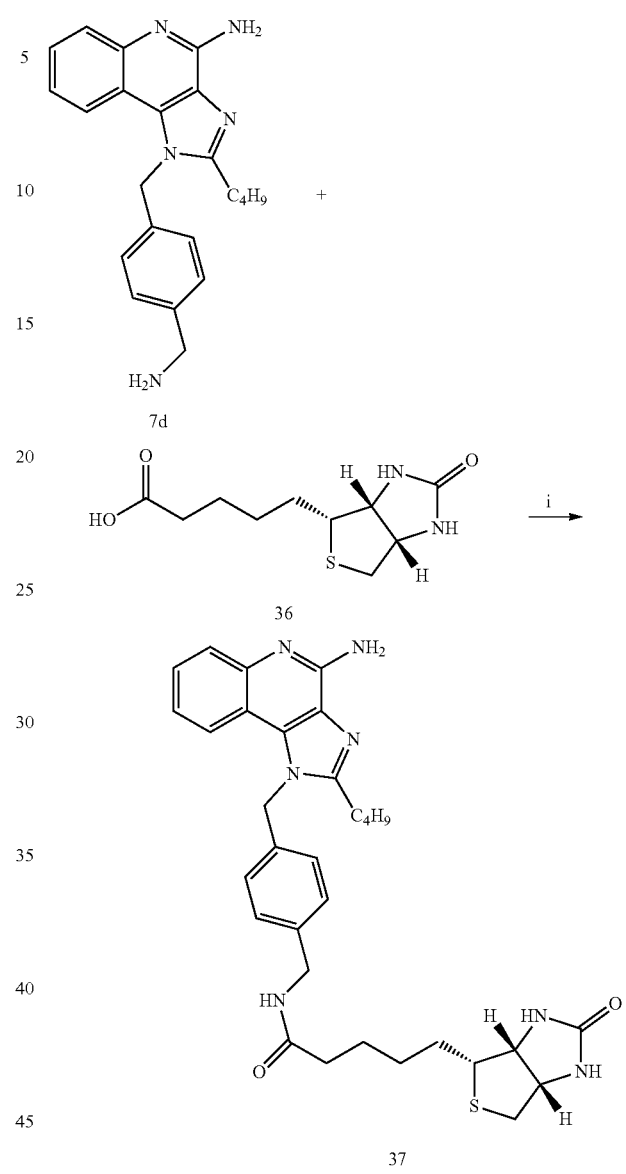
Reagents and conditions: i. Propylphosphonic anhydride, Et₃N, DMF.
Scheme 12. Synthesis of a pyridoxal derivative 39.
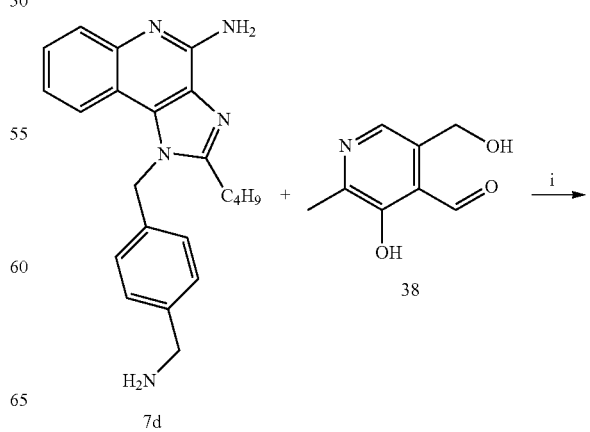

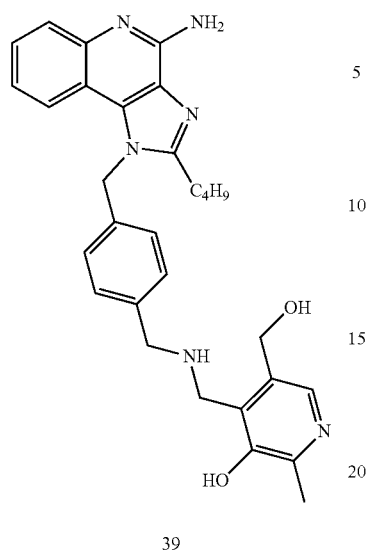

39

Reagents and conditions: i. sodium triacetoxyborohydride, MeOH.

Synthesis of compound 33: N-(4-((4-amino-2-butyl-1H-imidazo[4,5-c]quinolin-1-yl)methyl)benzyl)-N-((2R,3S,4R)-2,3,4,5,6-pentahydroxyhexyl)acetamide

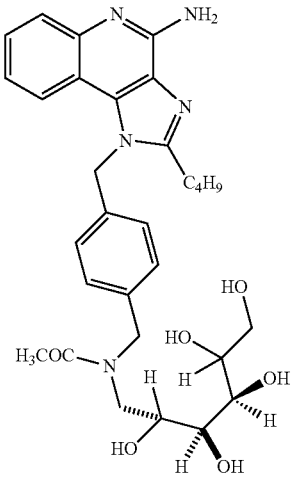

33

To a solution of 7d (30 mg, 0.076 mmol) in anhydrous DMF, were added galactose 32 (13 mg, 0.072 mmol), 4 drops of acetic acid and MP-CNBH$_3$ (50 mg, 0.114 mmol). The reaction mixture was heated at 50° C. for 2 hours and then filtered to obtain the filtrate. The filtrate was then concentrated under vacuum to obtain the residue to which anhydrous DMF was added, followed by the addition of triethylamine (10 eq.) and acetic anhydride (10 eq.) to acetylate the alcohols and the amines. The solvent was then removed and the residue was purified using column chromatography to obtain the per-acetylated product. The O-acetyl and C4-N-acetyl groups were then removed using sodium methoxide in methanol to obtain the compound 33 (9 mg, 21%).

Synthesis of compound 35: 5-((4-((4-amino-2-butyl-1H-imidazo[4,5-c]quinolin-1-yl)methyl)benzyl)amino)-2-(4-(((2-amino-4-oxo-3,4-dihydropteridin-6-yl)methyl)amino)benzamido)-5-oxopentanoic acid

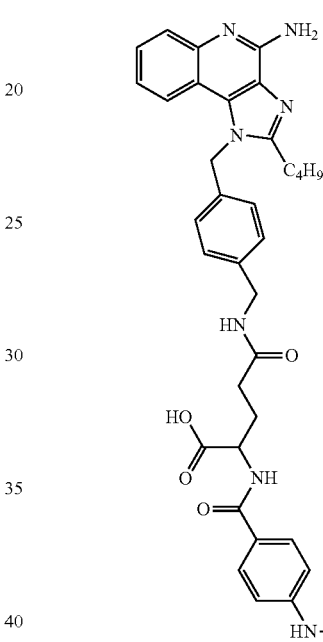

35

To a solution of folic acid, 34 (50 mg, 0.11 mmol) in anhydrous DMSO (1 mL), were added triethylamine (34 mg, 0.34 mmol), HBTU (50 mg, 0.13 mmol) and 7d (36 mg, 0.08 mmol). The reaction mixture was stirred for 14 hours followed by precipitating the solid using 50 mL of diethyl ether. The solid was thoroughly washed with diethyl ether 3 times and dried under vacuum to obtain the solid which was purified using semi preparative reverse phase column chromatography to obtain the compound 35 (3 mg, 5%). $^1$H NMR (500 MHz, DMSO) δ 8.62 (d, J=3.9 Hz, 1H), 8.31 (d, J=6.0 Hz, 3H), 7.74-7.67 (m, 1H), 7.64 (d, J=8.7 Hz, 1H), 7.56 (d, J=8.4 Hz, 2H), 7.36-7.26 (m, 2H), 7.23-7.14 (m, 2H), 7.05-6.90 (m, 4H), 6.62 (dd, J=8.7, 5.4 Hz, 4H), 5.83 (d, J=10.9 Hz, 2H), 4.47 (d, J=5.8 Hz, 1H), 4.38-4.29 (m, 1H), 4.25-4.15 (m, 2H), 2.92-2.86 (m, 2H), 2.27-2.18 (m, 1H), 1.96 (d, J=10.0 Hz, 1H), 1.86 (s, 1H), 1.75 (s, 2H), 1.77-1.66 (m, 2H), 1.40-1.34 (m, 2H), 1.23 (s, 2H), 0.85 (tt, J=4.8, 3.8 Hz, 3H). MS (ESI) calculated for C$_{41}$H$_{42}$N$_{12}$O$_5$, m/z 782.34. found 783.35 (M+H)$^+$.

Synthesis of compound 37: N-(4-((4-amino-2-butyl-1H-imidazo[4,5-c]quinolin-1-yl)methyl)benzyl)-5-(3aR,4R,6aS)-2-oxohexahydro-1H-thieno[3,4-d]imidazol-4-yl)pentanamide

Synthesis of compound 39: 4-(((4-((4-amino-2-butyl-1H-imidazo[4,5-c]quinolin-1-yl)methyl)benzyl)amino)methyl)-5-(hydroxymethyl)-2-methylpyridin-3-ol

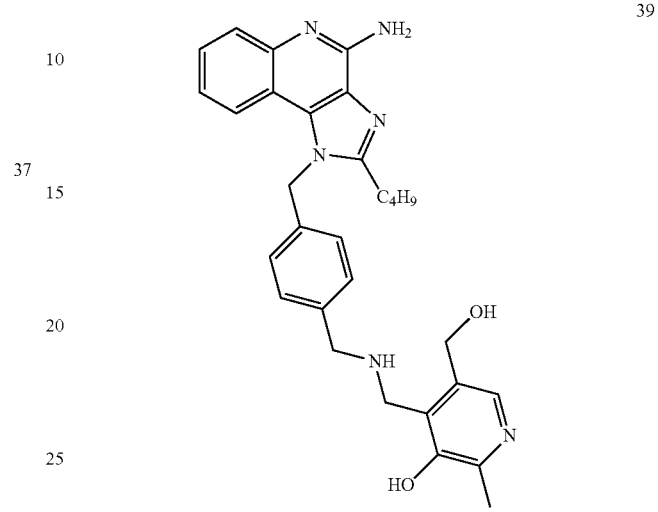

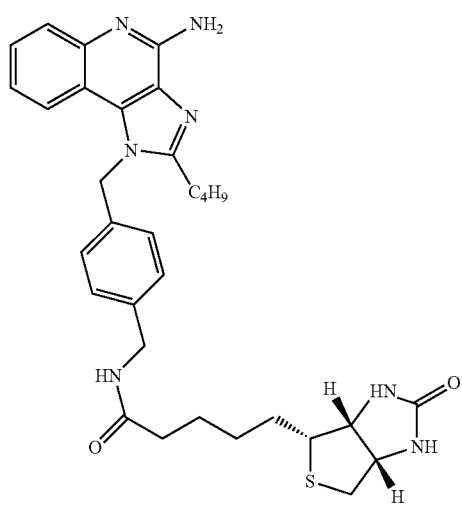

To a solution of compound 7d (50 mg, 0.116 mmol) in anhydrous methanol, were added pyridoxal hydrochloride (24 mg, 0.116 mmol) and sodium triacetoxyborohydride (77 mg, 0.35 mmol). The reaction mixture was stirred for 2 hours followed by removal of the solvent under vacuum. The residue was then dissolved in ethylacetate and washed with saturated sodium bicarbonate solution, water, brine, dried using sodium sulfate and concentrated under vacuum to obtain the residue which was purified using column chromatography (20% MeOH/dichloromethane) to obtain compound 39 (7 mg, 12%). $^1$H NMR (500 MHz, DMSO) δ 7.79 (d, J=7.5 Hz, 1H), 7.75 (s, 1H), 7.57 (dd, J=8.3, 0.9 Hz, 1H), 7.32 (s, 1H), 7.28 (d, J=8.2 Hz, 2H), 7.06-7.00 (m, 3H), 6.54 (s, 2H), 5.86 (s, 2H), 5.12-4.93 (m, 1H), 4.33 (s, 2H), 3.92 (s, 2H), 3.64 (s, 2H), 2.93-2.88 (m, 2H), 2.25 (s, 3H), 1.70 (d, J=7.6 Hz, 2H), 1.38 (d, J=7.5 Hz, 2H), 0.87 (t, J=7.4 Hz, 3H). $^{13}$C NMR (126 MHz, DMSO) δ 153.54, 152.49, 151.69, 145.14, 144.78, 137.96, 137.85, 135.58, 132.81, 132.71, 128.80, 127.36, 126.42, 126.27, 126.08, 125.57, 120.83, 120.04, 114.53, 99.49, 58.93, 51.22, 47.80, 45.97, 29.58, 26.20, 21.82, 18.69, 13.67. MS (ESI) calculated for $C_{30}H_{34}N_6O_2$, m/z 510.27. found 511.28 (M+H)$^+$.

To a solution of biotin 36 (30 mg, 0.069 mmol) in anhydrous DMF, were added triethylamine (17 mg, 0.076 mmol), propylphosphonic anhydride solution in ethylacetate (26 mg, 0.083 mmol) and 7d (30 mg, 0.069 mmol). The reaction mixture was stirred for 1 hour, followed by removal of the solvent under vacuum. The residue was then dissolved in ethylacetate and washed with water, brine, dried using sodium sulfate and concentrated under vacuum to obtain the residue which was purified using column chromatography (25% MeOH/dichloromethane) to obtain compound 36 (25 mg, 62%). $^1$H NMR (500 MHz, MeOD) δ 7.84 (d, J=8.3 Hz, 1H), 7.63 (d, J=8.3 Hz, 1H), 7.51 (t, J=7.8 Hz, 1H), 7.24 (t, J=7.8 Hz, 1H), 7.18 (d, J=8.1 Hz, 2H), 6.95 (d, J=8.0 Hz, 2H), 5.82 (s, 2H), 4.40-4.34 (m, 1H), 4.24-4.18 (m, 2H), 4.15 (dd, J=7.8, 4.4 Hz, 1H), 3.56 (s, 1H), 3.13-2.98 (m, 2H), 2.90 (t, J=7.6 Hz, 2H), 2.59 (t, J=13.3 Hz, 1H), 2.25 (t, J=7.4 Hz, 1H), 2.12 (t, J=7.3 Hz, 1H), 1.78-1.70 (m, 2H), 1.62-1.48 (m, 5H), 1.36 (dd, J=7.5, 5.6 Hz, 2H), 0.85 (t, J=7.4 Hz, 3H). $^{13}$C NMR (126 MHz, MeOD) δ 175.97, 166.10, 158.69, 150.75, 140.43, 137.36, 135.29, 130.65, 129.49, 129.14, 126.86, 126.04, 122.82, 120.51, 114.44, 63.39, 61.61, 57.03, 56.98, 52.03, 49.81, 49.64, 49.52, 49.47, 49.35, 49.30, 49.18, 49.01, 48.84, 48.67, 48.50, 43.54, 41.05, 36.70, 34.55, 30.77, 30.45, 29.75, 29.72, 29.50, 29.47, 27.79, 26.86, 25.92, 23.35, 14.11. MS (ESI) calculated for $C_{32}H_{39}N_7O_2S$, m/z 585.28. found 586.29 (M+H)$^+$.

Example 7

Imidazoquinoline Dendrimers

Figure 15:
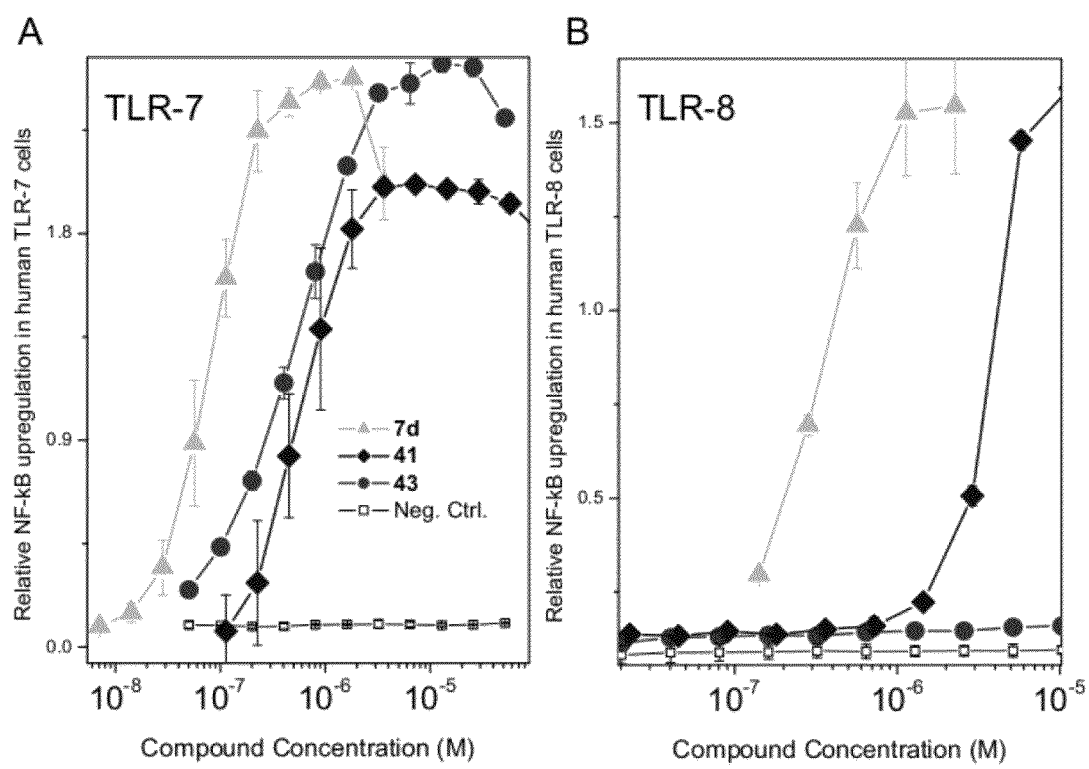
FIGS. 15A and 15B are graphs illustrating TLR-7 and -8 agonistic activity of 'Click reaction' derived imidazoquinoline dendrimer 43.
Figure 16:
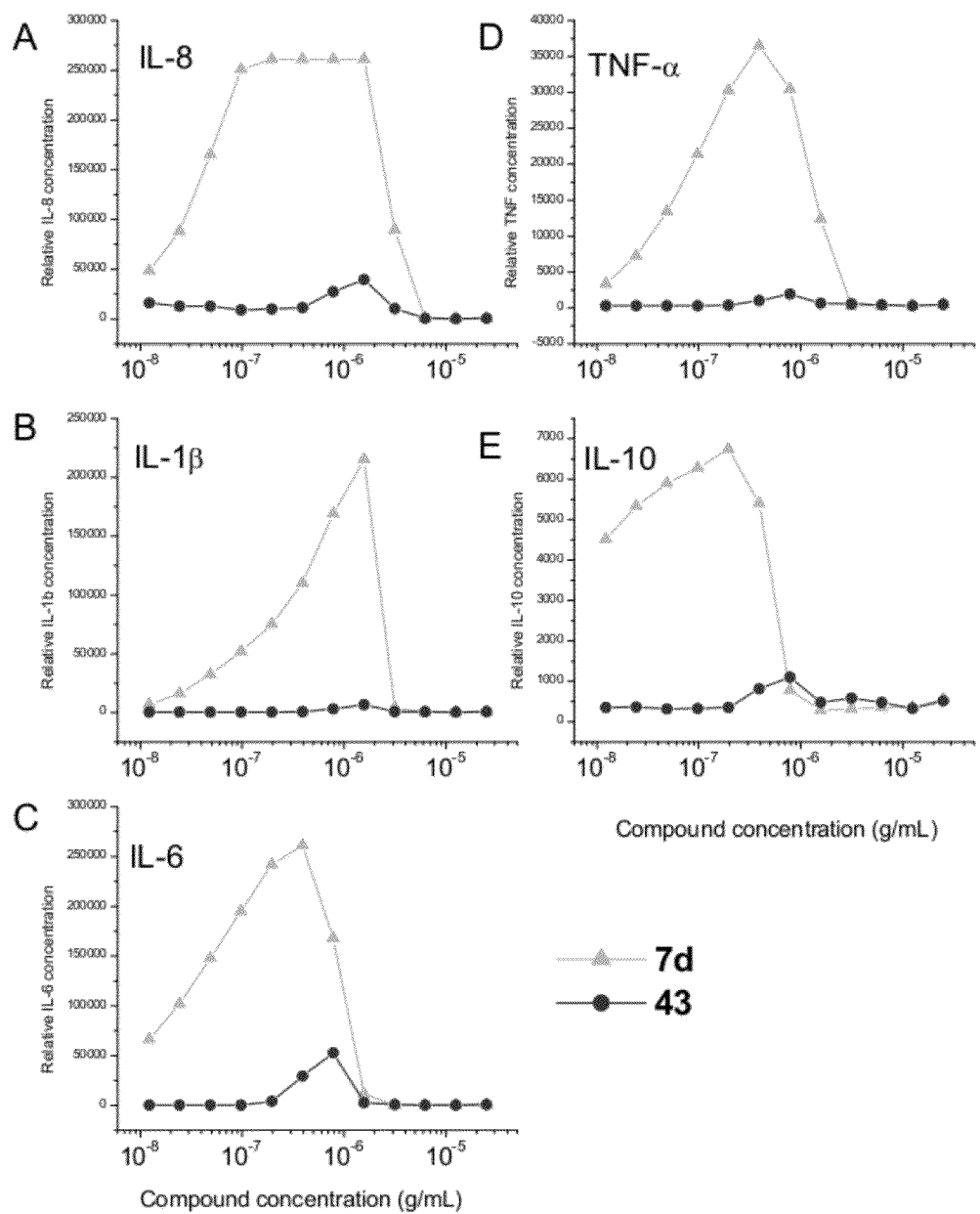
FIGS. 16A-16E illustrate proinflammatory cytokine induction in human PBMCs. Note selective and complete loss of TLR8-associated cytokine induction by the dendrimer 43.
Figure 17:
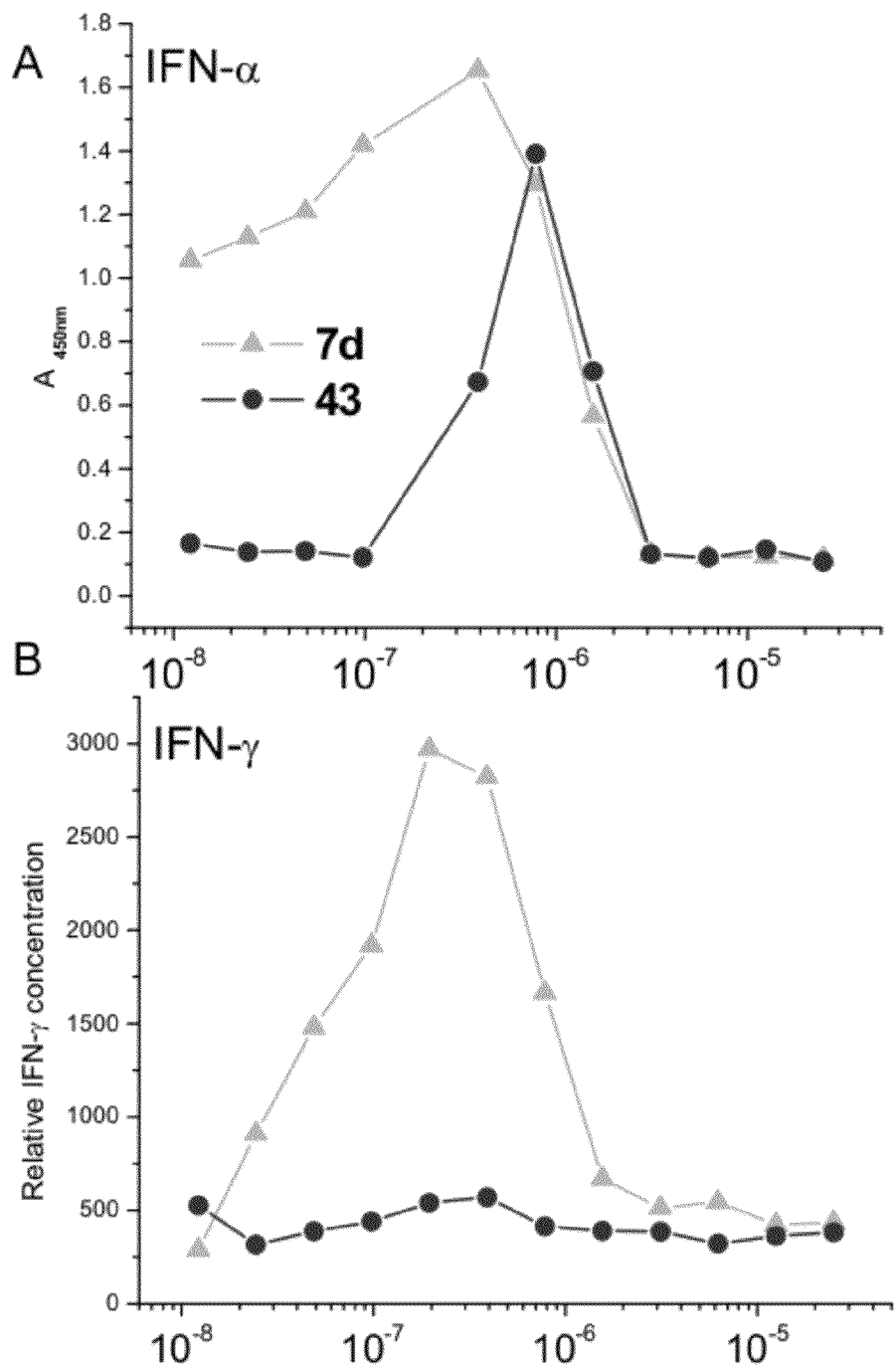
FIGS. 17A and 17B illustrate Type I and Type II Interferon induction in human PBMCs. Note selective and complete loss of TLR8-associated IFN-γ by the dendrimer 43.
Figure 18:
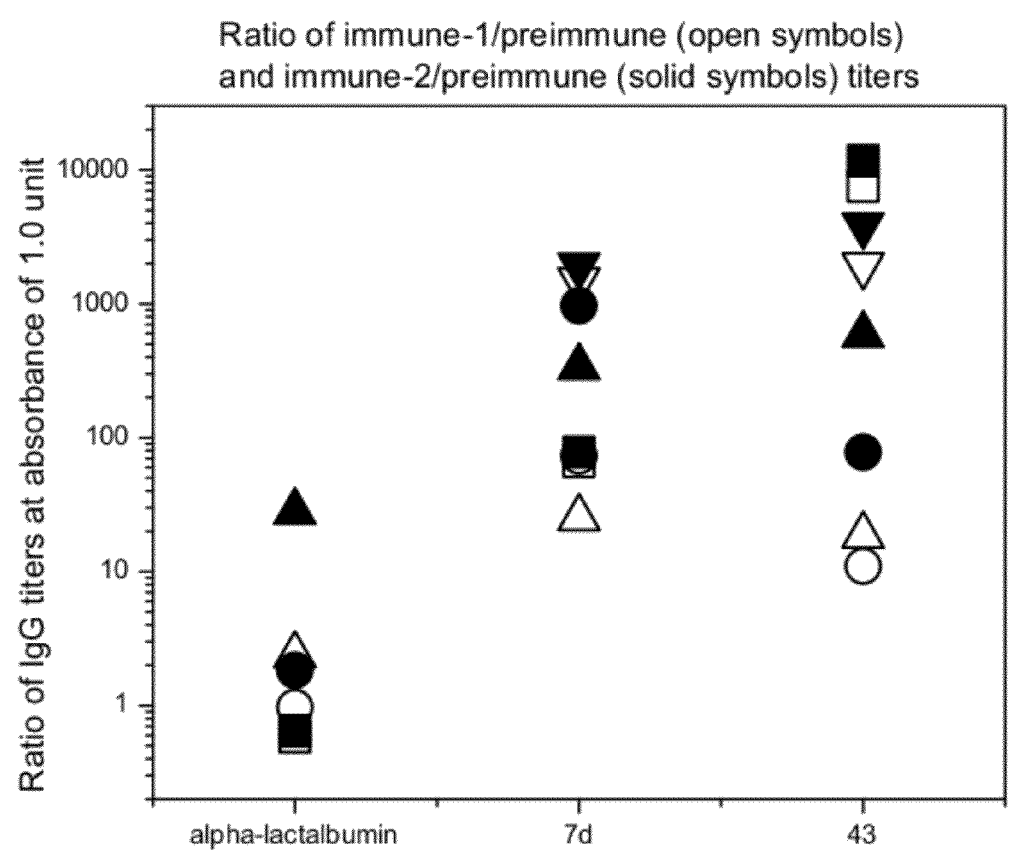
FIG. 18 illustrates ratios of Immune-1/pre-immune (after primary vaccination) and Immune-2/pre-immune (after Boost-1) anti-α-lactalbumin IgG titers in rabbits.

Being small, the imidazoquinolines may diffuse out quickly from the injection site. A dendrimeric molecule bearing three (41) or six units of 7d (43) were synthesized as shown in Schemes 13 and 14. In the case of 43, a loss of TLR8-stimulatory activity occurred (FIG. 15B), while retaining in large measure the TLR7-agonistic activity of its parent monomer (FIG. 15A). This is reflected by an absence of proinflammatory cytokine induction in human PBMCs as shown in FIGS. 16A-16E, which illustrates selective loss of TLR8-associated cytokine induction by the dendrimer 43. There was also dissociation between TLR7-driven IFN-α and TLR8-driven IFN-γ induction (FIGS. 17A and 17B, respectively). Based on current paradigms in innate immunity, it could be predicted that the dendrimer, by virtue of being a pure TLR7 agonist and consequently inducing IFN-α, and not proinflammatory cytokines, would manifest in lower reactogenicity (local and/or systemic inflammation). The dendrimer behaved better than 7d in rabbit immunization model using bovine α-lactalbumin as a model subunit vaccine (FIG. 18).

Scheme 13. Syntheses of the trimeric imidazoquinoline dendrimer.

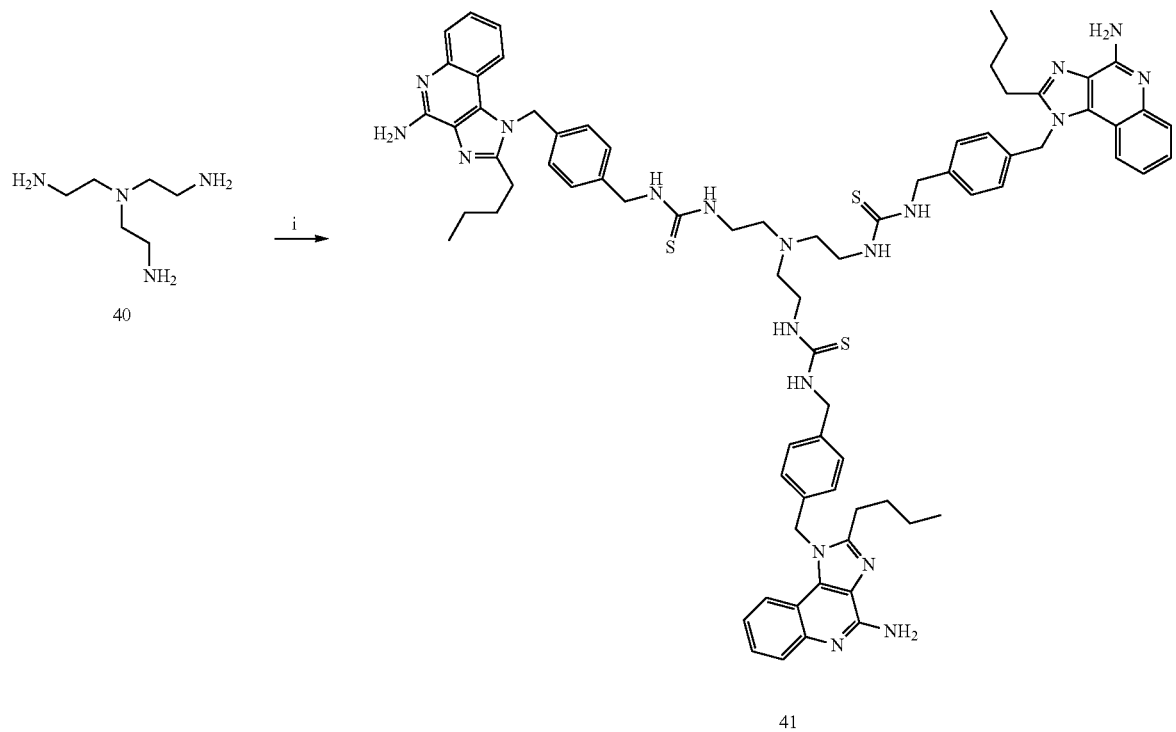

Reagents and conditions: i. 8, Pyridine, 45° C.

Scheme 14. Synthesis of a 'Click Reaction'-derived hexameric dendrimer.

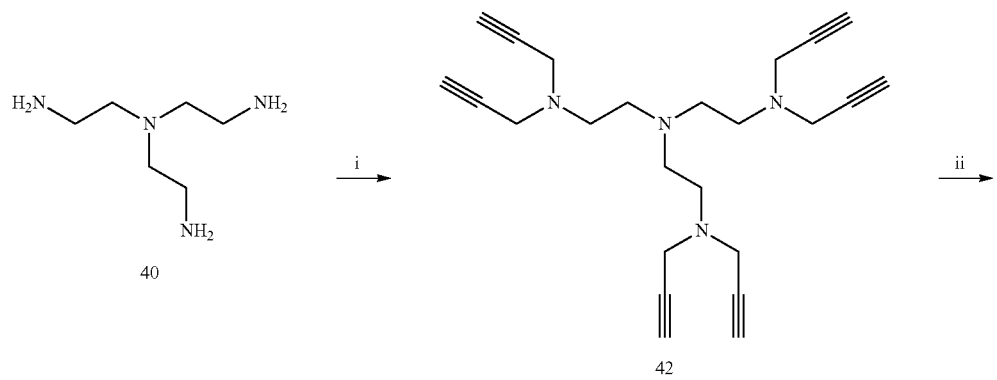

-continued
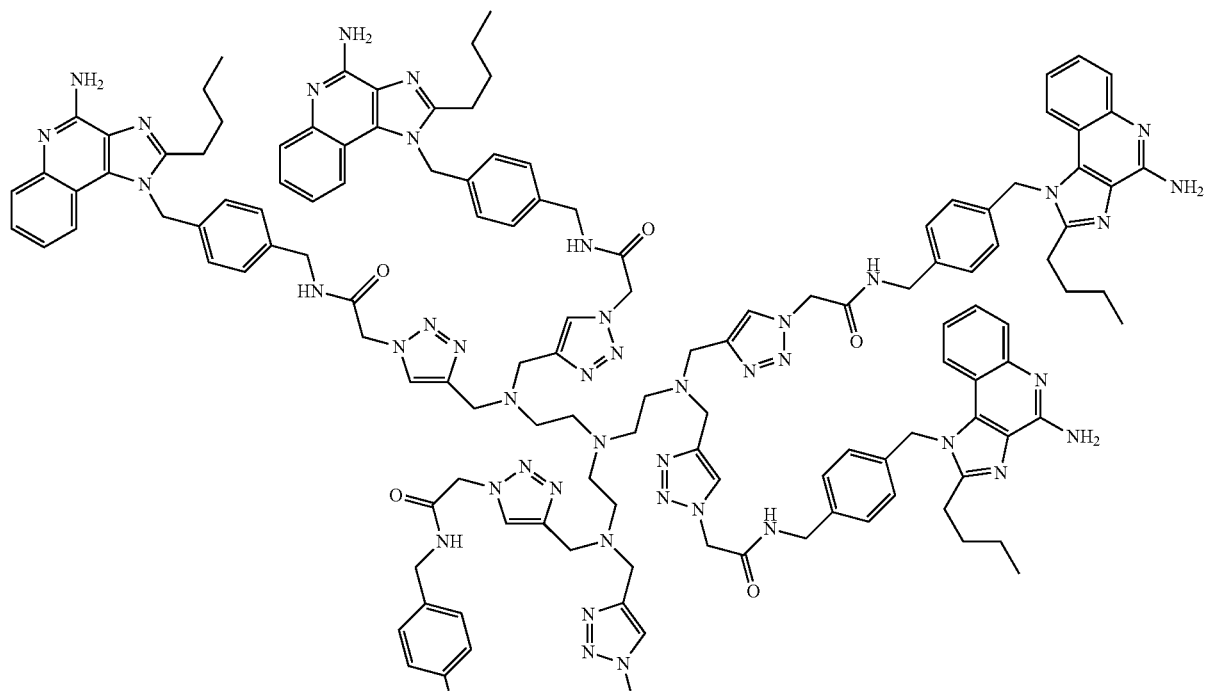
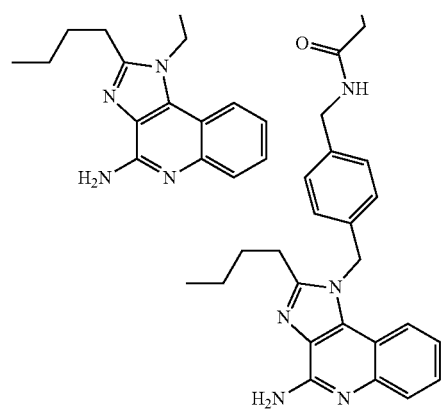
43
Reagents and conditions: i. propargyl bromide, Et₃N, CH₃CN; ii. 18, CuSO₄·5H₂O, sodium ascorbate, DMF.

Synthesis of Compound 41: 1,1',1''-(nitrilotris (ethane-2,1-diyl))tris(3-(4-((4-amino-2-butyl-1H-imidazo[4,5-c]quinolin-1-yl)methyl)benzyl)thiourea)

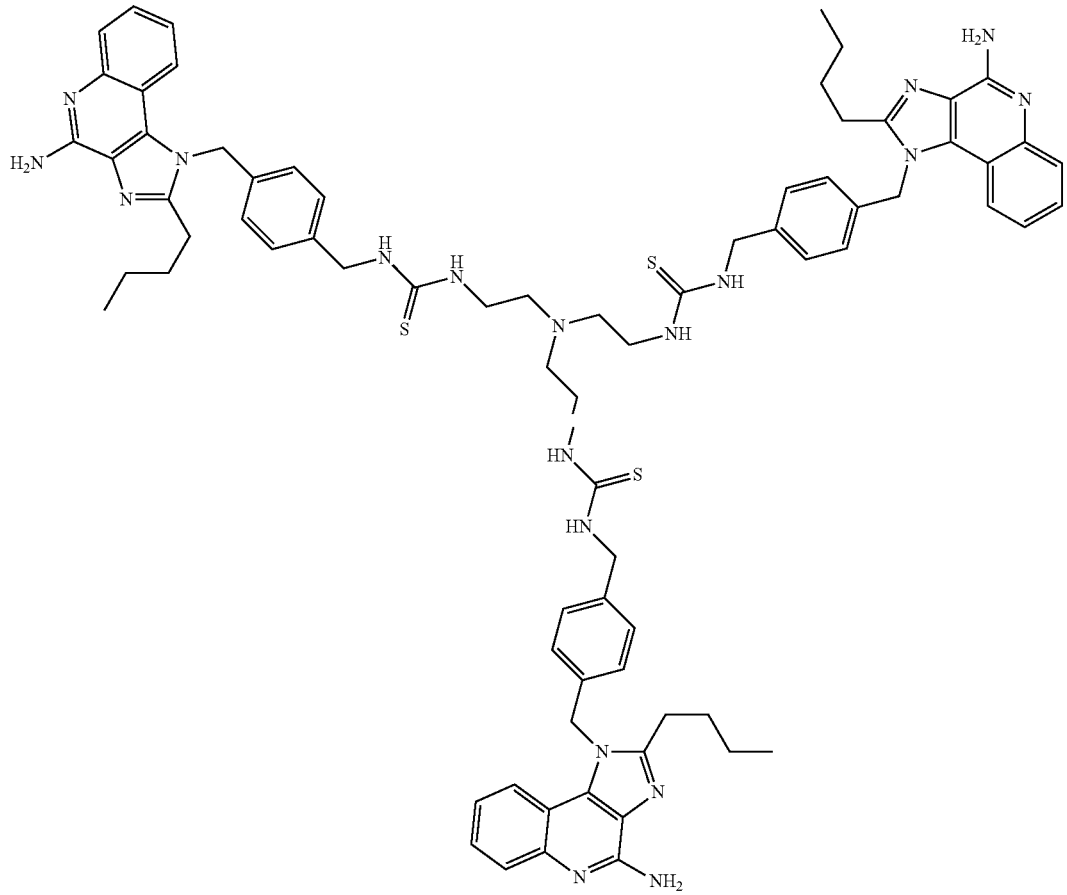

41

To a solution of compound 40 (4.2 mg, 0.29 mmol) in pyridine (1 mL) was added compound 8 (40 mg, 0.11 mmol). The reaction mixture was heated at 45° C. for 2 hours, followed by the addition of Polystyrene bound-NH$_2$ beads to quench the excess of compound 8. The reaction was stirred for another 30 minutes, followed by filtration of the beads. The filtrate thus obtained was concentrated under vacuum and the residue was washed several times with diethyl ether to afford compound 41 (22 mg, 56%). $^1$H NMR (500 MHz, MeOD) δ 7.70 (d, J=7.9 Hz, 3H), 7.59 (dd, J=8.4, 0.8 Hz, 3H), 7.36-7.32 (m, 3H), 7.05 (td, J=8.5, 4.4 Hz, 9H), 6.86 (d, J=6.9 Hz, 6H), 5.63 (s, 6H), 4.46 (s, 6H), 3.48-3.38 (m, 6H), 3.04-2.99 (m, 2H), 2.86-2.81 (m, 6H), 2.74-2.69 (m, 2H), 2.48 (s, 6H), 1.78-1.73 (m, 6H), 1.38 (dd, J=15.0, 7.5 Hz, 6H), 0.89 (t, J=7.4 Hz, 9H). $^{13}$C NMR (126 MHz, MeOD) δ 156.82, 151.91, 136.19, 135.05, 129.43, 129.30, 126.85, 126.71, 124.52, 121.92, 115.40, 67.09, 53.57, 38.74, 30.77, 30.68, 28.02, 23.54, 15.75, 14.52. MS (ESI) calculated for C$_{75}$H$_{87}$N$_{19}$S$_3$, m/z 1349.65. found 1350.66 (M+H)$^+$ and 675.83 (M+2H)$^{+2}$.

Synthesis of Compound 42: N$^1$,N$^1$-bis(2-(di(prop-2-yn-1-yl)amino)ethyl)-N$^2$,N$^2$-di(prop-2-yn-1-yl) ethane-1,2-diamine

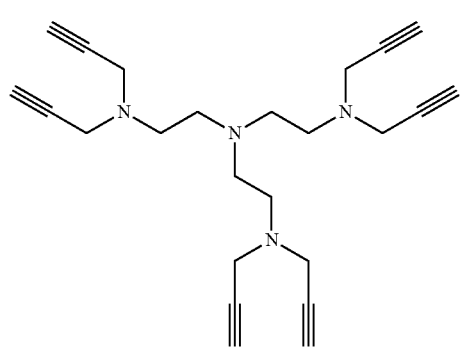

42

To a solution of compound 40 (299 μL, 2.0 mmol) in CH₃CN (20 mL) was added Et₃N (1.75 mL, 12.6 mmol). The reaction mixture was cooled to 0° C. and propargyl bromide (80% solution in toluene, 2 mL, 13.5 mmol) was added drop wise over a period of 10 min and the reaction mixture was kept stirring at room temperature for 6 hours. Water was added to the reaction mixture and the product was extracted in ethyl acetate. The organic layer was washed with water (2×20 mL), brine (2×20 mL) and dried over anhydrous sodium sulfate and evaporated. The crude residue was column purified to afford compound 42 as thick liquid (433 mg, 58%). $^1$H NMR (500 MHz, CDCl₃) δ 3.47 (d, J=2.4 Hz, 12H), 2.66 (s, 12H), 2.23 (t, J=2.4 Hz, 6H), 1.63 (s, 3H). $^{13}$C NMR (126 MHz, CDCl₃) δ 78.99, 73.23, 52.76, 50.65, 42.71. MS (ESI) calculated for $C_{24}H_{30}N_4$, m/z 374.25. found 375.25 (M+H)⁺.

Synthesis of Compound 43

To a stirred solution of compound 42 (5.0 mg, 0.013 mmol) and 3 (40 mg, 0.091 mmol) in DMF (2 mL), were added CuSO₄·5H₂O (23 mg, 0.091 mmol, in 0.5 mL water) and sodium ascorbate (36 mg, 0.18 mmol in 0.5 mL water) and the reaction mixture was stirred at room temperature for 1 h. The click dendrimer formed was purified by semipreparative reverse phase HPLC to afford solid compound 43 (25 mg, 63%). MS (ESI) calculated for $C_{168}H_{186}N_{52}O_6$, m/z 3027.5848. found 1514.8233 (M+2H)⁺² and 1010.8771 (M+3H)³⁺.

Example 8

Dimeric Imidazoquinoline Variants

The majority of TLRs signal via homo- or hetero-dimerization,[72] and it was therefore of interest to examine dimeric constructs with differing geometries. The first series of dimeric imidazoquinolines were linked at the C2 position and were synthesized via two different routes. Whereas the hexamethylene- and decamethylene-bridged compounds 49a and 49b could be conveniently obtained from 48 by a direct, one-step, bis-amidation using the corresponding dicarboxylic acid chlorides and cyclization (Scheme 15), the shorter chain

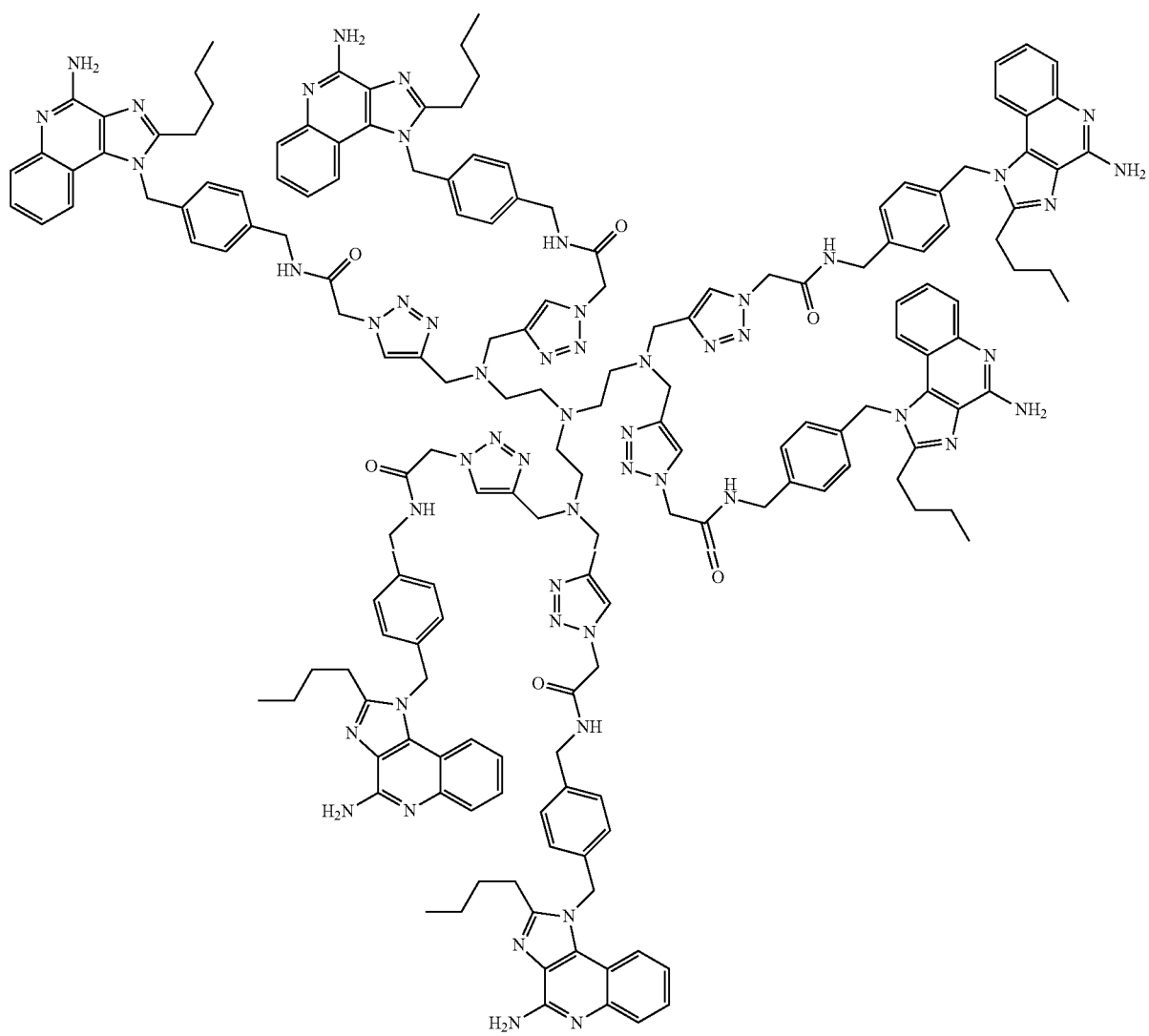

43 analogues were not amenable to this method because of intramolecular cyclization, giving rise to undesired quinolin-3-yl piperidinediones. This problem was circumvented by first reacting glutaric or adipic anhydride with 44, which yielded the monocarboxylic imidazoquinolines 45a and 45b, respectively; these intermediates were taken forward without purification and reacted again with 44 to afford the C4,C4'-des-amino precursors 46a and 46b (Scheme 15). Compounds 47a and 47b (with amines at C4 and C4', respectively) were obtained by sequential N-oxidation of the quinoline nitrogen, reaction with benzoyl isocyanate to afford the C4 and C4' N-benzoyl intermediate and, finally, cleavage of the N-benzoyl group using sodium methoxide as described by us earlier.[24,51] Next, the dimers linked via the C4-NH$_2$ (51a-d) were synthesized by direct S$_N$Ar on 50 using α,ω-bis-amino alkanes (Scheme 16). Similarly, dimers linked at the N$^1$ position on the 4-aminomethylene benzyl group (52a-c) were obtained using appropriate dicarboxylic acid chlorides (Scheme 17).

While the dimeric imidazoquinoline derivative compounds 52a-c and 55a-c are formed from dimerization of compounds of Formulas I and II of the present disclosure, the dimeric imidazoquinoline derivative compounds 47a-b and 49a-b are formed from dimerization of a slightly altered base compound. The dimeric structure of the 47 and 49 compounds can be represented by the following structure illustrated by Formula III.

FORMULA III

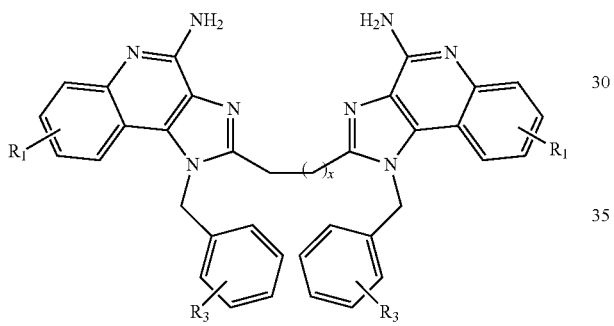

where R$_1$ is independently selected from the group consisting of hydrogen, halogen (—Cl, —Br, —F), nitro (—NO$_2$), —NH$_2$, azido (—N$_3$), hydroxyl (—OH), —CF$_3$; R$_3$ is selected from the group consisting of hydrogen or —(CH$_2$)$_x$—NH$_2$, and x is any integer form 1 to 10.

The dimeric imidazoquinoline derivative compounds 52a-c are formed from dimerization of a compound of Formula I of the present disclosure, specifically compounds 52a-c are dimers of compound 7d linked at the N$^1$ position on the 4-aminomethylene benzyl group. The dimeric imidazoquinoline derivative compounds 55a-c are formed from dimerization of a compound of Formula II of the present disclosure and can be represented by the general formula illustrated below.

FORMULA IV

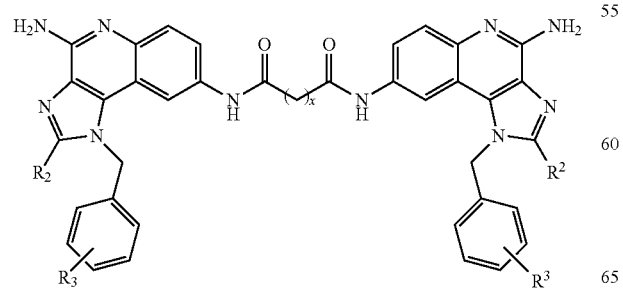

Where R$_2$ is a C$_2$-C$_5$ alkyl, R$_3$ is selected from the group consisting of hydrogen or —(CH$_2$)$_x$—NH$_2$, and x is any integer form 1 to 12.

Scheme 15. Syntheses of imidazoquinoline dimers linked at C2.

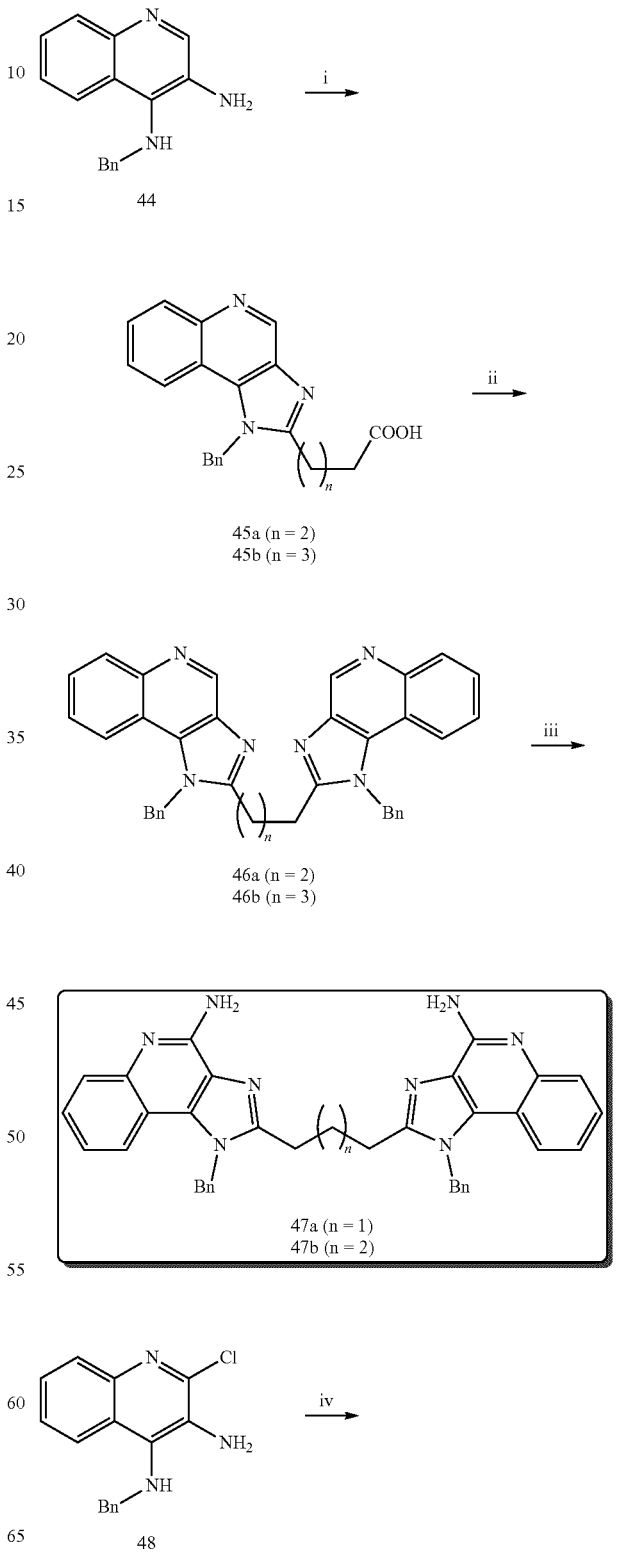

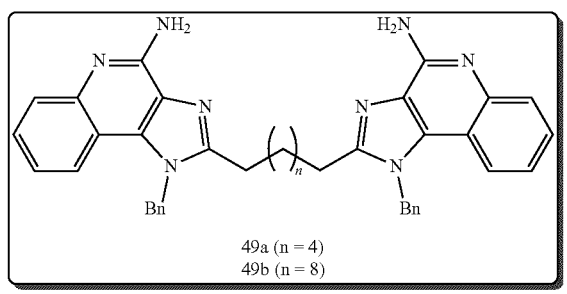

49a (n = 4)
49b (n = 8)

Reagents: i. Glutaric anhydride (n = 2) or adipic anhydride (n = 3), THF, 110° C.; ii. 44, HBTU, Et$_3$N, DMAP, DMF, 90° C.; iii. (a) 3-Chloroperoxybenzoic acid, CH$_2$Cl$_2$, CHCl$_3$, MeOH, 45° C.; (b) Benzoyl isocyanate, CH$_2$Cl$_2$, 45° C.; (c) NaOCH$_3$, MeOH, 80° C.; iv. (a) Suberoyl chloride (n = 4) or dodecanedioyl dichloride (n = 8), Et$_3$N, THF; (b) NH$_3$/MeOH, 150° C.

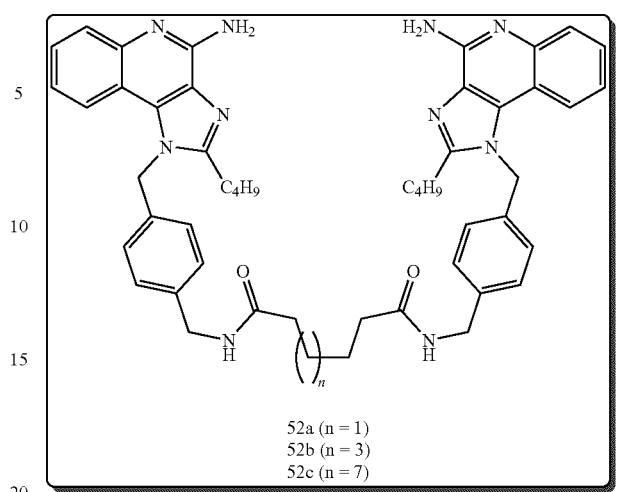

52a (n = 1)
52b (n = 3)
52c (n = 7)

Reagents: i. Adipoly chloride (n = 1) or suberoyl chloride (n = 3) or dodecanedioyl dichloride (n = 7), Et$_3$N, THF.

To link the 55 series of dimers via the quinoline ring an additional amine at position C8 was introduced. This was achieved via carefully controlled nitration of 7d using 1.2-1.3 equiv. of HNO$_3$, followed by N-Boc protection of the amine on the N$^1$ substituent, and subsequent reduction. Dimerization of the 4,8-diaminoimidazoquinoline 54 proceeded smoothly using dicarboxylic acid chlorides as described in the previous schemes (Scheme 18). It is to be noted that the mono-nitro and mono-amino precursors 53 and 54 were also N-Boc deprotected and tested for TLR-modulatory activities (Table 1).

Scheme 16. Syntheses of imidazoquinoline dimers linked at C4-NH$_2$.

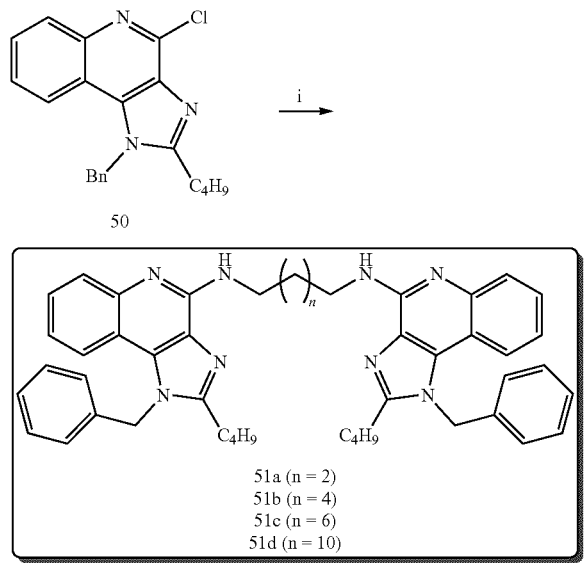

51a (n = 2)
51b (n = 4)
51c (n = 6)
51d (n = 10)

Reagents: i. 1,4-Diaminobutane (n = 2) or 1,8-diaminooctane (n = 4) or 1,10-diaminodecane (n = 6) or 1,12-diaminododecane (n = 10), MeOH, 140° C.;

Scheme 17. Syntheses of imidazoquinoline dimers linked at N$^1$-(4-aminomethylene)benzyl.

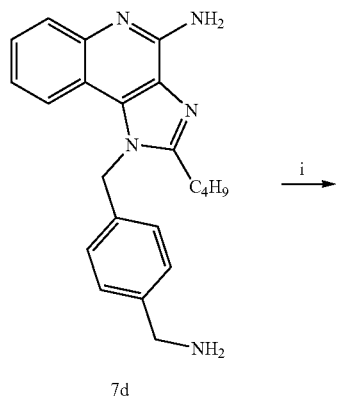

7d

Scheme 18. Syntheses of imidazoquinoline dimers linked at C8-NH$_2$

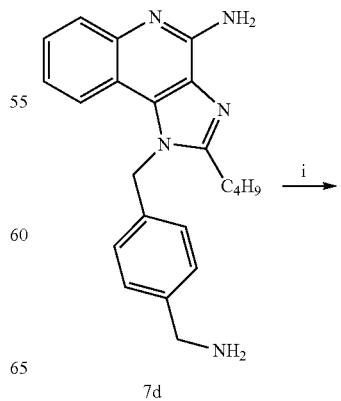

7d

-continued

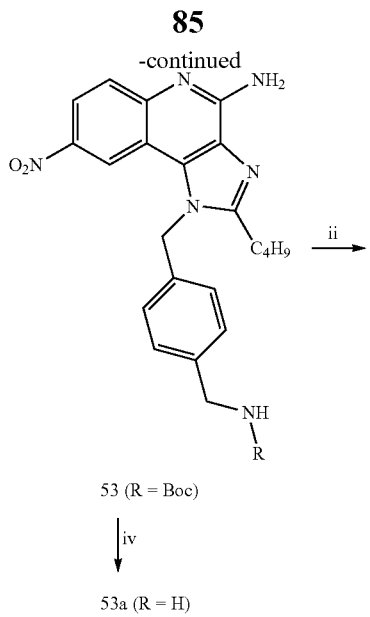

53 (R = Boc)

↓ iv 53a (R = H)

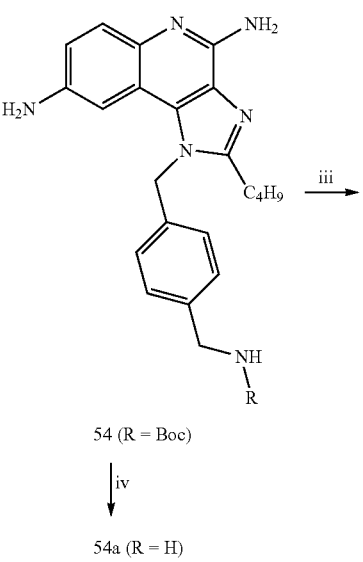

54 (R = Boc)

↓ iv 54a (R = H)

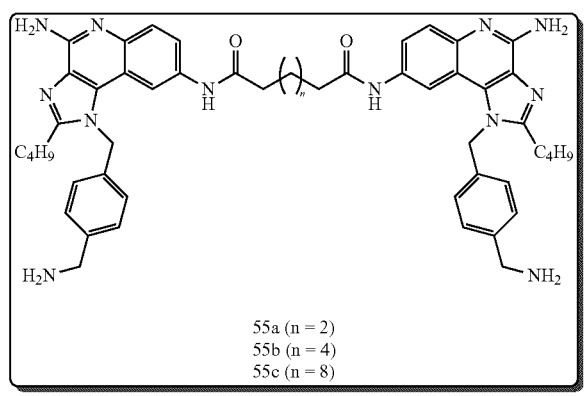

55a (n = 2)
55b (n = 4)
55c (n = 8)

Reagents: i. (a) HNO₃, H₂SO₄; (b) (Boc)₂O, Et₃N, MeOH; ii. H₂ Pt/C, MeOH, 60 psi, iii. (a) Adipoyl chloride (n = 2) or suberoyl chloride (n = 4) or dodecanedioyl dichloride (n = 8), Et₃N THF; (b) HCl/dioxane, iv. HCl/dioxane.

Synthesis of Compound 47a: 2,2'-(propane-1,3-diyl)bis(1-benzyl-1H-imidazo[4,5-c]quinolin-4-amine)

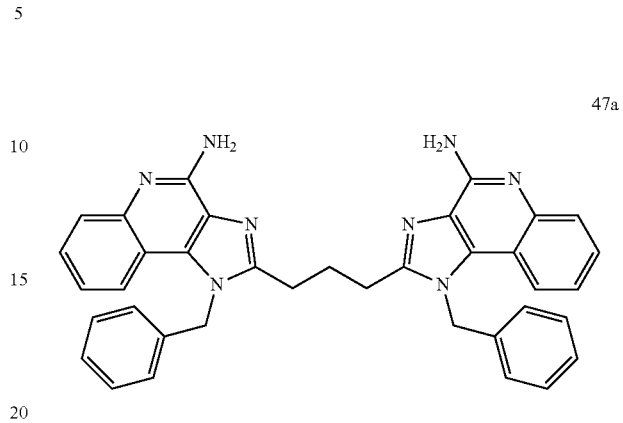

47a

To a solution of 44 (100 mg, 0.4 mmol) in anhydrous THF, were added triethylamine (53 mg, 0.52 mmol) and glutaric anhydride (60 mg, 0.52 mmol) and the reaction vessel was heated in a microwave for 2 hours at 110° C. The solvent was then removed under vacuum to obtain the crude product 45a, which was then dissolved in anhydrous DMF and to this solution, were added HBTU (167 mg, 0.44 mmol), triethylamine (53 mg, 0.52 mmol), 44 (100 mg, 0.4 mmol) and a catalytic amount of DMAP. The reaction mixture was stirred for 12 hours at 90° C. The solvent was then removed under vacuum and the residue was purified using column chromatography (12% MeOH/dichloromethane) to obtain the intermediate the compound 46a (157 mg). To a solution of 46a in solvent mixture of MeOH:dichloromethane:chloroform (0.1:1:1), was added 3-chloroperoxybenzoic acid (242 mg, 1.4 mmol) and the reaction mixture was refluxed at 45° C. for 40 minutes. The solvent was then removed and the residue was purified using column chromatography (35% MeOH/dichloromethane) to obtain the bis-N-oxide derivative (130 mg). bis-N-oxide derivative (110 mg, 0.19 mmol) was then dissolved in anhydrous dichloromethane, followed by the addition of benzoyl isocyanate (96 mg, 0.67 mmol) and heated at 45° C. for 15 minutes. The solvent was then removed under vacuum and the residue was dissolved in anhydrous MeOH, followed by addition of excess of sodium methoxide and heated at 80° C. for 2 hours. The solvent was then removed under vacuum and the residue was purified using column chromatography (50% MeOH/dichloromethane) to obtain the compound 47a (25 mg, 11%). $^1$H NMR (500 MHz, DMSO) δ 14.30 (s, 2H), 9.48-8.30 (bs, 4H), 7.93 (d, J=8.3 Hz, 2H), 7.77 (d, J=8.3 Hz, 2H), 7.65-7.60 (m, 2H), 7.38-7.34 (m, 2H), 7.26 (t, J=7.6 Hz, 4H), 7.17 (t, J=7.4 Hz, 2H), 7.03 (d, J=7.4 Hz, 4H), 5.94 (s, 4H), 3.16 (t, J=7.2 Hz, 4H), 2.44-2.35 (m, 2H). $^{13}$C NMR (126 MHz, DMSO) δ 156.22, 148.86, 135.32, 135.30, 133.48, 129.51, 128.93, 127.57, 125.47, 124.72, 124.54, 121.49, 118.31, 112.16, 48.35, 25.21, 24.43. MS (ESI) calculated for $C_{37}H_{32}N_8$, m/z 588.2750. found 589.2860 (M+H)$^+$.

Compound 47b was Synthesized Similarly as Described for Compound 47a

47b: 2,2'-(butane-1,4-diyl)bis(1-benzyl-1H-imidazo[4,5-c]quinolin-4-amine)

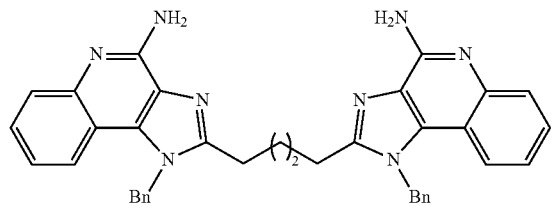

47b $^1$H NMR (500 MHz, DMSO) δ 13.86 (s, 2H), 8.88 (bs, 4H), 7.93 (d, J=8.2 Hz, 2H), 7.83-7.79 (m, 2H), 7.66-7.61 (m, 2H), 7.39-7.34 (m, 2H), 7.27 (t, J=7.6 Hz, 4H), 7.18 (t, J=7.4 Hz, 2H), 7.01 (d, J=7.4 Hz, 4H), 5.94 (s, 4H), 2.99 (s, 4H), 1.83 (s, 4H). $^{13}$C NMR (126 MHz, DMSO) δ 156.55, 148.75, 135.38, 133.62, 129.50, 128.95, 127.60, 125.42, 124.74, 124.54, 121.54, 118.48, 112.28, 48.34, 26.49, 26.14. MS (ESI) calculated for $C_{38}H_{34}$%, m/z 602.2906. found 603.3272 (M+H)$^+$ and 302.1705 (M+2H)$^{2+}$.

Synthesis of Compound 49a: 2,2'-(hexane-1,6-diyl)bis(1-benzyl-1H-imidazo[4,5-c]quinolin-4-amine)

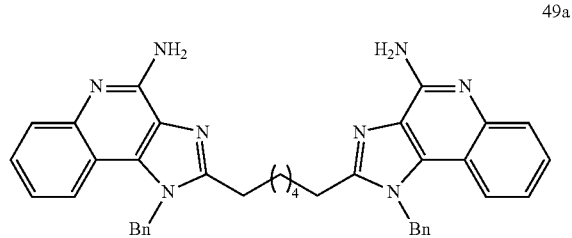

49a

To a solution of 48 (60 mg, 0.21 mmol) in anhydrous THF, were added triethylamine (54 mg, 0.53 mmol), and suberoyl chloride (23 mg, 0.11 mmol) and the reaction mixture was stirred for 6 hours. The solvent was then removed under vacuum and the residue was dissolved in EtOAc and washed with water/brine. The EtOAc fraction was then dried using sodium sulfate and evaporated under vacuum to obtain the intermediate amide compound, which was then dissolved in 1 mL solution of 2M ammonia in MeOH and heated at 150° C. for 15 hours. The solvent was then removed under vacuum and the residue was purified using column chromatography (20% MeOH/dichloromethane) to obtain the compound 49a (8 mg, 12%). $^1$H NMR (500 MHz, MeOD) δ 7.96 (d, J=8.3 Hz, 2H), 7.77 (d, J=8.4 Hz, 2H), 7.65 (dd, J=11.5, 4.2 Hz, 2H), 7.39 (t, J=7.8 Hz, 2H), 7.31 (t, J=7.4 Hz, 4H), 7.25 (t, J=7.3 Hz, 2H), 7.06 (d, J=7.4 Hz, 4H), 5.93 (s, 4H), 2.97 (t, J=7.5 Hz, 4H), 1.85 (d, J=7.0 Hz, 4H), 1.43 (s, 4H). $^{13}$C NMR (126 MHz, MeOD) δ 158.93, 137.73, 136.20, 135.30, 131.11, 130.47, 129.31, 126.65, 126.57, 125.81, 122.94, 119.65, 114.20, 50.13, 29.70, 27.92. MS (ESI) calculated for $C_{40}H_{38}N_8$, m/z 630.3219. found 631.3415 (M+H)$^+$.

Compound 49b was Synthesized Similarly as Described for Compound 49a

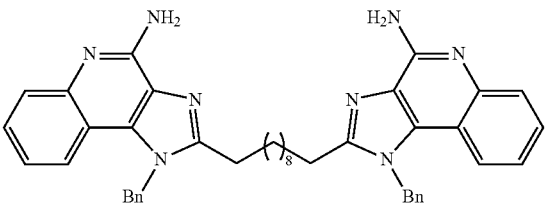

49b

49b: 2,2'-(decane-1,10-diyl)bis(1-benzyl-1H-imidazo[4,5-c]quinolin-4-amine)

$^1$H NMR (500 MHz, MeOD) δ 7.86 (d, J=8.3 Hz, 2H), 7.69 (d, J=8.4 Hz, 2H), 7.51 (t, J=7.7 Hz, 2H), 7.32 (t, J=7.3 Hz, 4H), 7.28 (d, J=7.2 Hz, 2H), 7.23 (t, J=7.7 Hz, 2H), 7.06 (d, J=7.4 Hz, 4H), 5.88 (s, 4H), 2.96 (t, J=7.6 Hz, 4H), 1.79 (dt, J=15.3, 7.7 Hz, 4H), 1.37 (dd, J=14.9, 7.4 Hz, 4H), 1.32-1.24 (m, J=11.6 Hz, 4H), 1.23 (d, J=10.1 Hz, 4H). $^{13}$C NMR (126 MHz, MeOD) δ 157.44, 151.60, 136.61, 130.41, 129.74, 129.22, 126.69, 126.46, 124.90, 123.38, 122.15, 115.12, 50.05, 30.32, 30.25, 30.17, 28.49, 28.17. MS (ESI) calculated for $C_{44}H_{46}N_8$, m/z 686.3845. found 687.3749 (M+H)$^+$ and 344.1949 (M+2H)$^{2+}$.

Synthesis of Compound 51b: $N^1$,$N^8$-bis(1-benzyl-2-butyl-1H-imidazo[4,5-c]quinolin-4-yl)octane-1,8-diamine

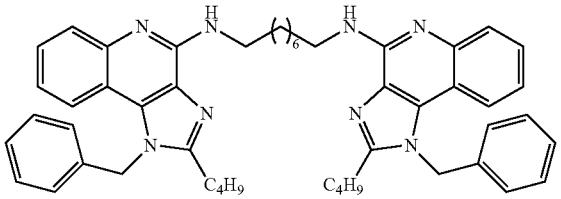

51b

To a solution of 50 (50 mg, 0.14 mmol) in 1 mL of anhydrous MeOH, was added 1,8-diaminooctane (10 mg, 0.07 mmol) and the reaction mixture was heated at 140° C. for 4 hours. The solvent was then removed under vacuum and the residue was purified using column chromatography (8% MeOH/dichloromethane) to obtain the compound 51b (12 mg, 22%). $^1$H NMR (400 MHz, CDCl$_3$) δ 7.87 (d, J=8.3 Hz, 2H), 7.68 (d, J=8.2 Hz, 2H), 7.41 (t, J=7.7 Hz, 2H), 7.36-7.26 (m, 6H), 7.09-7.01 (m, 6H), 5.78 (s, 2H), 5.72 (s, 4H), 3.77 (dd, J=12.8, 6.6 Hz, 4H), 2.92-2.83 (m, 4H), 1.87-1.74 (m, 8H), 1.58-1.50 (m, 4H), 1.45 (dt, J=15.1, 7.5 Hz, 8H), 0.93 (t, J=7.4 Hz, 6H). $^{13}$C NMR (101 MHz, CDCl$_3$) δ 153.34, 150.78, 145.51, 135.62, 129.20, 127.93, 127.41, 127.07, 126.68, 125.59, 121.34, 119.52, 114.87, 48.81, 40.76, 30.18, 29.98, 29.50, 27.21, 22.56, 13.77. MS (ESI) calculated for C$_{50}$H$_{58}$N$_8$, m/z 770.4784. found 771.4963 (M+H)$^+$ and 386.2570 (M+2H)$^{2+}$.

Compounds 51a, 51c and 51d were Synthesized Similarly as Described for Compound 51b

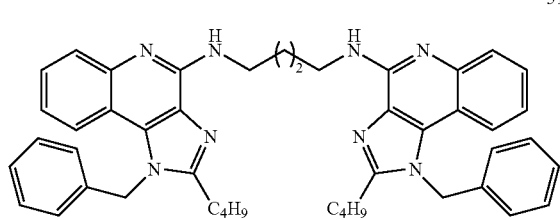

51a: N$^1$,N$^4$-bis(1-benzyl-2-butyl-1H-imidazo[4,5-c]quinolin-4-yl)butane-1,4-diamine $^1$H NMR (500 MHz, CDCl$_3$) δ 7.86 (d, J=8.2 Hz, 2H), 7.65 (dd, J=8.2, 1.0 Hz, 2H), 7.41-7.35 (m, 2H), 7.35-7.24 (m, 6H), 7.09-6.99 (m, 6H), 5.86 (s, 2H), 5.69 (s, 4H), 3.87 (s, 4H), 2.88-2.81 (m, 4H), 2.00 (s, 4H), 1.76 (ddd, J=13.0, 9.0, 7.7 Hz, 4H), 1.46-1.37 (m, 4H), 0.90 (t, J=7.4 Hz, 6H). $^{13}$C NMR (126 MHz, CDCl$_3$) δ 151.27, 148.66, 143.44, 133.52, 130.85, 128.77, 127.28, 127.13, 125.85, 125.38, 124.95, 124.60, 123.50, 123.40, 119.29, 117.45, 112.81, 46.71, 38.40, 28.01, 25.51, 25.10, 20.47, 11.68. MS (ESI) calculated for C$_{46}$H$_{50}$N$_8$, m/z 714.4158. found 715.4333 (M+H)$^+$ and 358.2263 (M+2H)$^{2+}$.

51c: N$^1$,N$^{10}$-bis(1-benzyl-2-butyl-1H-imidazo[4,5-c]quinolin-4-yl)decane-1,10-diamine

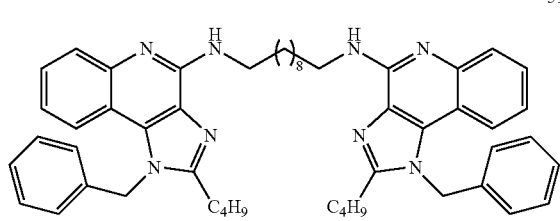

$^1$H NMR (500 MHz, CDCl$_3$) δ 7.84 (d, J=8.2 Hz, 2H), 7.66 (dd, J=8.2, 1.0 Hz, 2H), 7.40-7.36 (m, 2H), 7.33-7.26 (m, 6H), 7.07-7.01 (m, 6H), 5.73 (s, 2H), 5.70 (s, 4H), 3.74 (dd, J=12.7, 6.5 Hz, 4H), 2.88-2.83 (m, 4H), 1.80-1.72 (m, 8H), 1.53-1.24 (m, 16H), 0.91 (t, J=7.4 Hz, 6H). $^{13}$C NMR (126 MHz, CDCl$_3$) δ 151.76, 149.23, 143.97, 134.05, 131.32, 127.81, 127.63, 126.36, 125.85, 125.50, 125.10, 124.01, 123.84, 119.75, 117.95, 113.30, 47.23, 39.17, 28.62, 28.39, 28.06, 27.95, 25.65, 20.98, 12.20. MS (ESI) calculated for C$_{52}$H$_{62}$N$_8$, m/z 798.5097. found 799.5416 (M+H)$^+$ and 400.2799 (M+2H)$^{2+}$.

51d: N$^1$,N$^{12}$-bis(1-benzyl-2-butyl-1H-imidazo[4,5-c]quinolin-4-yl)dodecane-1,12-diamine

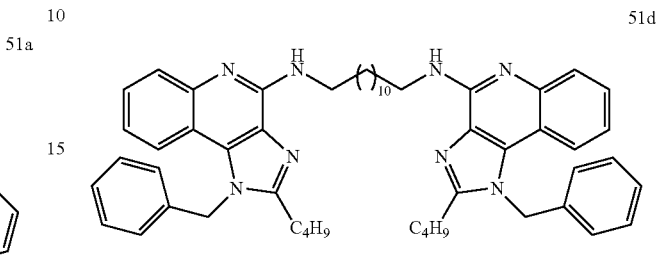

$^1$H NMR (500 MHz, CDCl$_3$) δ 7.84 (d, J=8.2 Hz, 2H), 7.65 (dd, J=8.2, 1.0 Hz, 2H), 7.38 (ddd, J=8.3, 7.1, 1.3 Hz, 2H), 7.34-7.24 (m, 6H), 7.06-7.00 (m, 6H), 5.74 (s, 2H), 5.69 (s, 4H), 3.74 (dd, J=12.6, 6.5 Hz, 4H), 2.86 (dd, J=17.4, 9.6 Hz, 4H), 1.83-1.69 (m, 8H), 1.56-1.30 (m, 20H), 0.91 (t, J=7.4 Hz, 6H). $^{13}$C NMR (126 MHz, CDCl$_3$) δ 151.81, 149.27, 144.02, 134.08, 131.36, 127.68, 126.41, 125.87, 125.53, 125.16, 124.05, 119.81, 118.00, 113.34, 47.27, 39.25, 28.65, 28.44, 28.15, 28.13, 28.01, 25.70, 25.68, 21.03, 12.24. MS (ESI) calculated for C$_{54}$H$_{66}$N$_8$, m/z 826.5410. found 827.5796 (M+H)$^+$ and 414.2977 (M+2H)$^{2+}$.

Synthesis of Compound 52b: N$^1$,N$^8$-bis(4-((4-amino-2-butyl-1H-imidazo[4,5-c]quinolin-1-yl)methyl)benzyl)octanediamide

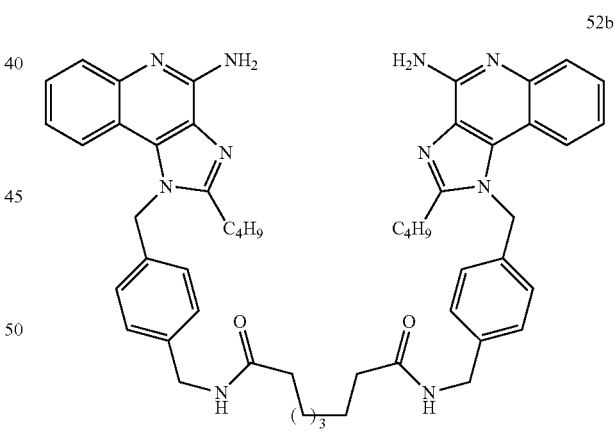

To a solution of 7d (25 mg, 0.058 mmol) in anhydrous THF, were added triethylamine (15 mg, 0.15 mmol) and suberoyl chloride (6 mg, 0.029 mmol). The reaction mixture was stirred for 1 hour and then the solvent was removed under vacuum. The residue was then purified using column chromatography (30% MeOH/dichloromethane) to obtain the compound 52b (8 mg, 32%) $^1$H NMR (500 MHz, MeOD) δ 7.65 (dd, J=8.3, 0.9 Hz, 2H), 7.55-7.51 (m, 2H), 7.27 (ddd, J=8.3, 7.1, 1.2 Hz, 2H), 7.12 (d, J=8.2 Hz, 4H), 6.95 (ddd, J=8.2, 7.2, 1.1 Hz, 2H), 6.88 (d, J=8.2 Hz, 4H), 5.69 (s, 4H), 4.18 (s, 4H), 2.84-2.78 (m, 4H), 2.03 (t, J=7.5 Hz, 4H), 1.64 (dt, J=15.4, 7.6 Hz, 4H), 1.47-1.37 (m, 4H), 1.30 (dq, J=14.8, 7.4 Hz, 4H), 1.16-1.10 (m, 4H), 0.80 (t, J=7.4 Hz, 6H). $^{13}$C NMR (126 MHz, MeOD) δ 176.03, 156.18, 152.62, 144.89, 140.08, 136.09, 135.55, 129.44, 128.54, 126.95, 126.86, 126.21, 123.42, 121.58, 115.75, 49.58, 43.58, 36.85, 30.85, 29.75, 27.82, 26.74, 23.43, 14.11. MS (ESI) calculated for $C_{52}H_{60}N_{10}O_2$, m/z 856.4901. found 879.4711 (M+Na$^+$) and 429.2430 (M+2H)$^{2+}$.

Compounds 52a and 52c were Synthesized Similarly as Described for Compound 52b

52a: $N^1,N^6$-bis(4-((4-amino-2-butyl-1H-imidazo[4,5-c]quinolin-1-yl)methyl)benzyl)adipamide

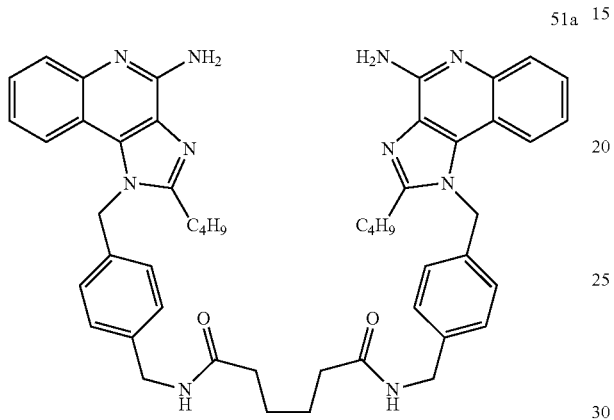

51a $^1$H NMR (400 MHz, MeOD) δ 7.85 (d, J=7.6 Hz, 2H), 7.68 (d, J=7.8 Hz, 2H), 7.52-7.45 (m, 2H), 7.26 (d, J=8.2 Hz, 4H), 7.23-7.16 (m, 2H), 7.02 (d, J=8.2 Hz, 4H), 5.85 (s, 4H), 4.30 (s, 4H), 2.99-2.93 (m, 4H), 2.19 (t, J=6.0 Hz, 4H), 1.80 (dd, J=15.3, 7.7 Hz, 4H), 1.58 (t, J=3.1 Hz, 4H), 1.45 (dd, J=15.0, 7.5 Hz, 4H), 0.94 (t, J=7.4 Hz, 6H). $^{13}$C NMR (101 MHz, MeOD) δ 174.28, 156.00, 150.28, 138.78, 135.01, 134.27, 128.13, 128.05, 125.44, 123.28, 121.97, 120.73, 113.67, 48.28, 42.15, 35.17, 29.21, 26.38, 25.03, 21.96, 12.68. MS (ESI) calculated for $C_{50}H_{56}N_{10}O_2$, m/z 828.4588. found 829.4440 (M+H)$^+$ and 415.2244 (M+2H)$^{2+}$.

52c: $N^1,N^{12}$-bis(4-((4-amino-2-butyl-1H-imidazo[4,5-c]quinolin-1-yl)methyl)benzyl)dodecane diamide

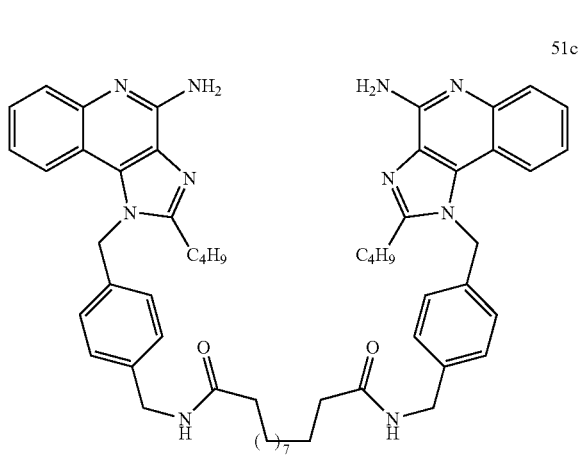

51c $^1$H NMR (500 MHz, MeOD) δ 7.69 (dd, J=8.3, 0.8 Hz, 2H), 7.54 (dd, J=8.4, 0.7 Hz, 2H), 7.31 (ddd, J=8.4, 7.2, 1.2 Hz, 2H), 7.14 (d, J=8.2 Hz, 4H), 7.00 (ddd, J=8.2, 7.2, 1.1 Hz, 2H), 6.90 (d, J=8.2 Hz, 4H), 5.73 (s, 4H), 4.20 (s, 4H), 2.85-2.81 (m, 4H), 2.06 (t, J=7.4 Hz, 4H), 1.66 (dt, J=15.4, 7.6 Hz, 4H), 1.44 (dt, J=14.4, 7.3 Hz, 4H), 1.31 (dq, J=14.8, 7.4 Hz, 4H), 1.10 (dd, J=29.4, 26.2 Hz, 12H), 0.81 (t, J=7.4 Hz, 6H). $^{13}$C NMR (126 MHz, MeOD) δ 176.17, 156.64, 152.26, 143.34, 140.20, 135.93, 135.90, 129.44, 128.92, 126.85, 126.77, 125.13, 123.90, 121.81, 115.51, 49.64, 43.55, 36.99, 30.78, 30.36, 30.23, 30.11, 27.82, 26.96, 23.41, 14.11. MS (ESI) calculated for $C_{56}H_{68}N_{10}O_2$, m/z 912.5527. found 913.5886 (M+H)$^+$ and 457.2974 (M+2H)$^{2+}$.

Synthesis of Compound 53: tert-butyl 4-((4-amino-2-butyl-8-nitro-1H-imidazo[4,5-c]quinolin-1-yl)methyl)benzylcarbamate

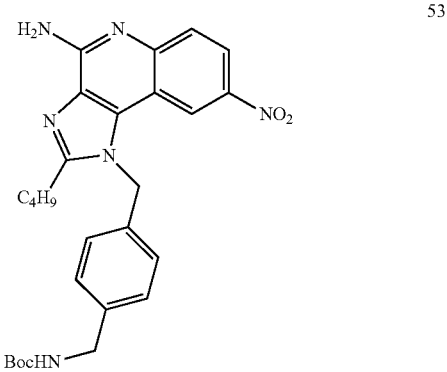

53

To a solution of 7d (500 mg, 1.16 mmol) in $H_2SO_4$, was added $HNO_3$ (95 mg, 1.511 mmol). The reaction mixture was stirred for 12 hours, followed by neutralization of sulfuric acid by slow addition of sodium carbonate solution. EtOAc was added to this solution to extract the compound, followed by washing with water/brine. The EtOAc fraction was then dried using sodium sulfate and evaporated under vacuum to obtain the residue. The residue as dissolved in MeOH and di-tert-butyl dicarbonate was added to it. The reaction was stirred for 30 minutes followed by removal of the solvent under vacuum to obtain the residue, which was purified using column chromatography (7% MeOH/dichloromethane) to obtain the compound 53 (200 mg, 34%). $^1$H NMR (400 MHz, CDCl$_3$) δ 8.67 (d, J=2.5 Hz, 1H), 8.24-8.18 (m, 1H), 7.76 (d, J=9.2 Hz, 1H), 7.28 (d, J=7.0 Hz, 2H), 7.08 (d, J=8.1 Hz, 2H), 5.95 (s, 2H), 5.76 (s, 2H), 4.87 (s, 1H), 4.29 (d, J=5.5 Hz, 2H), 3.05-2.95 (m, 2H), 1.88 (dt, J=15.5, 7.6 Hz, 2H), 1.51 (dd, J=14.9, 7.3 Hz, 2H), 1.45 (s, 9H), 0.99 (t, J=7.4 Hz, 3H). $^{13}$C NMR (101 MHz, CDCl$_3$) δ 155.18, 153.33, 148.68, 141.64, 139.53, 133.91, 133.29, 128.41, 127.42, 127.25, 125.92, 121.27, 117.28, 113.88, 48.81, 44.09, 30.00, 28.35, 27.20, 22.54, 13.78. MS (ESI) calculated for $C_{27}H_{32}N_6O_4$, m/z 504.2485. found 505.2541 (M+H)$^+$.

Synthesis of Compound 53a: 1-(4-(aminomethyl)benzyl)-2-butyl-8-nitro-1H-imidazo[4,5-c]quinolin-4-amine

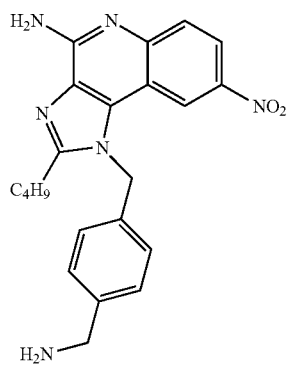

53a

Compound 53 (10 mg, 0.02 mmol) was dissolved in 1 mL solution of HCl/dioxane and stirred for 12 hours. The solvent was then removed under vacuum and the residue was washed with diethyl ether to afford the compound 53a in quantitative yields. $^1$H NMR (400 MHz, MeOD) δ 8.77 (d, J=1.7 Hz, 1H), 8.47-8.41 (m, 1H), 7.98 (d, J=9.1 Hz, 1H), 7.54 (d, J=7.7 Hz, 2H), 7.30 (d, J=7.7 Hz, 2H), 6.09 (s, 2H), 4.11 (s, 2H), 3.12 (t, J=7.5 Hz, 2H), 1.98-1.88 (m, 2H), 1.59-1.49 (m, 2H), 1.00 (t, J=7.3 Hz, 3H). $^{13}$C NMR (101 MHz, MeOD) δ 158.58, 150.14, 143.93, 137.46, 135.58, 135.36, 133.41, 129.86, 126.29, 125.89, 123.43, 119.40, 117.94, 112.44, 48.52, 42.36, 29.05, 26.44, 21.94, 12.71. MS (ESI) calculated for $C_{22}H_{24}N_6O_2$, m/z 404.1961. found 405.1993 (M+H)$^+$.

Synthesis of Compound 54: tert-butyl 4-((4,8-diamino-2-butyl-1H-imidazo[4,5-c]quinolin-1-yl)methyl)benzylcarbamate

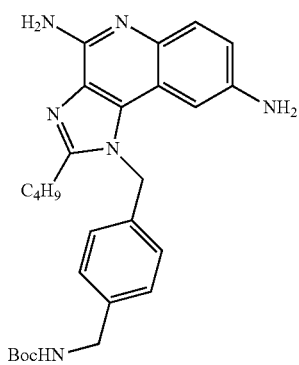

54

To a solution of 53 (190 mg, 0.377 mmol) in anhydrous MeOH, were added a catalytic amount of Pd/C and the reaction mixture was subjected to hydrogenation at 60 psi hydrogen pressure for 4 hours. The reaction mixture was then filtered through celite and the filtrate was evaporated under vacuum to obtain the compound 54 (160 mg, 90%). $^1$H NMR (400 MHz, MeOD) δ 7.49 (d, J=8.8 Hz, 1H), 7.25 (d, J=8.1 Hz, 2H), 7.14 (d, J=2.3 Hz, 1H), 7.02 (d, J=8.1 Hz, 2H), 6.97 (dd, J=8.9, 2.4 Hz, 1H), 5.75 (s, 2H), 4.19 (s, 2H), 2.92-2.86 (m, 2H), 1.73 (dt, J=15.4, 7.6 Hz, 2H), 1.43 (s, 9H), 0.92 (t, J=7.4 Hz, 3H). $^{13}$C NMR (101 MHz, MeOD) δ 154.56, 148.78, 142.89, 139.42, 136.71, 134.64, 133.60, 127.53, 125.80, 125.57, 118.16, 115.16, 103.42, 78.81, 43.18, 29.41, 27.33, 26.41, 22.01, 12.67. MS (ESI) calculated for $C_{27}H_{34}N_6O_2$, m/z 474.2743. found 475.2733 (M+H)$^+$.

Synthesis of Compound 54a: 1-(4-(aminomethyl)benzyl)-2-butyl-1H-imidazo[4,5-c]quinoline-4,8-diamine 54a Compound 54 (10 mg, 0.021 mmol) was dissolved in 1 mL of HCl/dioxane solution and stirred for 12 hours. The solvent was then removed under vacuum and the residue was washed with diethyl ether to obtain the compound 54a in quantitative yields. $^1$H NMR (500 MHz, MeOD) δ 8.10 (s, 1H), 7.97 (d, J=8.9 Hz, 1H), 7.67 (dd, J=8.9, 2.2 Hz, 1H), 7.51 (d, J=8.2 Hz, 2H), 7.23 (d, J=8.1 Hz, 2H), 6.04 (s, 2H), 4.12 (s, 2H), 3.03 (t, J=7.6 Hz, 2H), 1.92-1.84 (m, 2H), 1.53-1.43 (m, 2H), 0.96 (t, J=7.4 Hz, 3H). $^{13}$C NMR (126 MHz, DMSO) δ 156.84, 147.83, 135.56, 134.67, 133.58, 129.58, 129.54, 126.08, 125.63, 124.97, 119.52, 113.08, 48.08, 41.64, 29.09, 26.17, 21.75, 13.66. MS (ESI) calculated for $C_{22}H_{26}N_6$, m/z 374.2219. found 375.2508 (M+H)$^+$.

Synthesis of Compound 55b: N[1],N[8]-bis(4-amino-1-(4-(aminomethyl)benzyl)-2-butyl-1H-imidazo[4,5-c]quinolin-8-yl)octanediamide

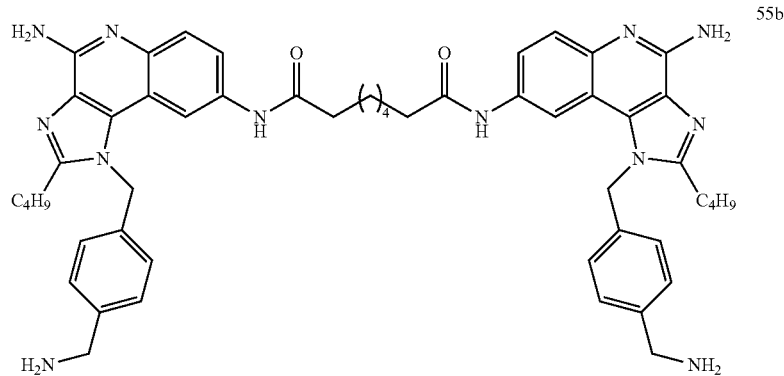

To a solution of 54 (74 mg, 0.156 mmol) in anhydrous THF, were added triethylamine (39 mg, 0.39 mmol) and suberoyl chloride (15 mg, 0.07 mmol), and the reaction mixture was stirred for 1 hour. The solvent was then removed under vacuum and the residue was purified using column chromatography (20% MeOH/dichloromethane) to obtain the bis-N-Boc protected compound which was then dissolved in 1 mL of HCl/dioxane solution and stirred for 14 hours. The solvent was then removed under vacuum and the residue was washed with diethyl ether to afford the compound 55b (12 mg, 19%; low yields were due to partial acylation of the C4-NH$_2$ which was found to be unstable). $^1$H NMR (500 MHz, MeOD) δ 8.62 (s, 2H), 7.70-7.65 (m, 2H), 7.61 (d, J=9.0 Hz, 2H), 7.44 (d, J=7.9 Hz, 4H), 7.18 (d, J=7.7 Hz, 4H), 5.93 (s, 4H), 4.07 (s, 4H), 2.98 (t, J=7.5 Hz, 4H), 2.37 (dd, J=16.6, 9.4 Hz, 4H), 1.85 (dt, J=15.0, 7.6 Hz, 4H), 1.71 (s, 4H), 1.52-1.40 (m, 8H), 0.94 (t, J=7.3 Hz, 6H). $^{13}$C NMR (126 MHz, MeOD) δ 174.75, 159.05, 149.75, 137.64, 137.34, 137.11, 134.51, 131.24, 130.93, 127.87, 126.22, 123.18, 119.97, 114.28, 111.99, 49.82, 43.82, 37.93, 30.27, 30.01, 27.81, 26.63, 23.36, 14.11. MS (ESI) calculated for $C_{52}H_{62}N_{12}O_2$, m/z 886.5119. found 909.5031 (M+Na$^+$) and 444.2632 (M+2H)$^{2+}$.

Compounds 55a and 55c were Synthesized Similarly as Described for Compound 55b

55a: N[1],N[6]-bis(4-amino-1-(4-(aminomethyl)benzyl)-2-butyl-1H-imidazo[4,5-c]quinolin-8-yl)adipamide $^1$H NMR (500 MHz, MeOD) δ 8.57 (s, 2H), 7.62-7.54 (m, 4H), 7.35 (d, J=8.1 Hz, 4H), 7.10 (d, J=8.0 Hz, 4H), 5.85 (s, 4H), 3.98 (s, 4H), 2.90 (t, J=7.6 Hz, 4H), 2.36 (s, 4H), 1.77

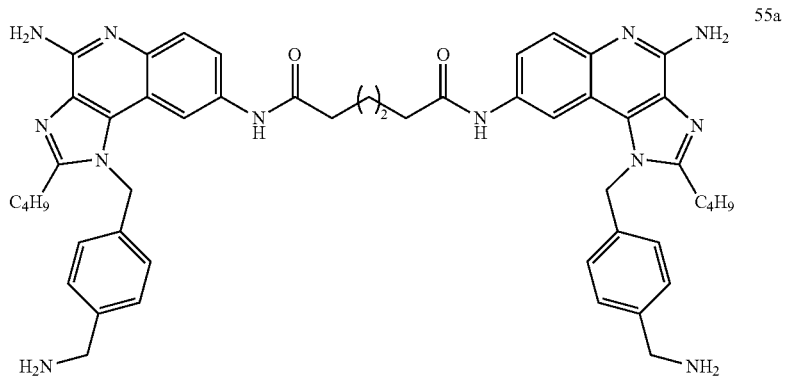

(dt, J=15.2, 7.6 Hz, 4H), 1.73-1.61 (m, 4H), 1.45-1.30 (m, 4H), 0.86 (t, J=7.4 Hz, 6H). $^{13}$C NMR (126 MHz, MeOD) δ 174.43, 159.11, 149.83, 137.66, 137.40, 137.16, 134.53, 131.33, 130.94, 127.89, 126.30, 123.18, 120.01, 114.38, 112.05, 49.82, 43.83, 37.65, 30.32, 27.81, 26.28, 23.37, 14.12. MS (ESI) calculated for $C_{50}H_{58}N_{12}O_2$, m/z 858.4806. found 859.4131 (M+H)$^+$ and 430.2113 (M+2H)$^{2+}$.

55c: $N^1,N^{12}$-bis(4-amino-1-(4-(aminomethyl)benzyl)-2-butyl-1H-imidazo[4,5-c]quinolin-8-yl)dodecanediamide

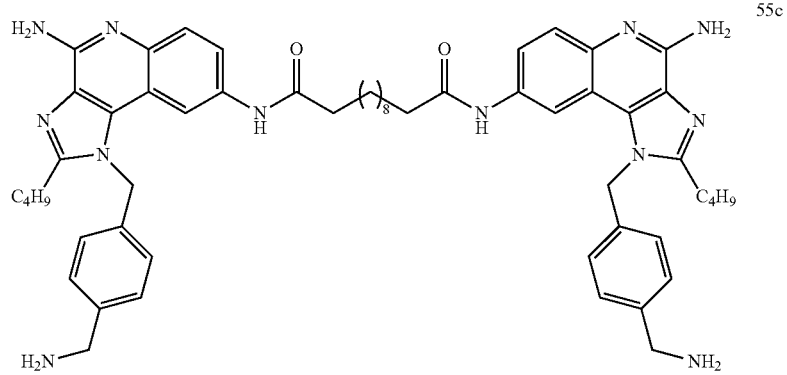

55c $^1$H NMR (500 MHz, MeOD) δ 8.63 (s, 2H), 7.66 (d, J=9.0 Hz, 2H), 7.58 (d, J=8.9 Hz, 2H), 7.41 (d, J=7.9 Hz, 4H), 7.15 (d, J=7.8 Hz, 4H), 5.91 (s, 4H), 4.04 (s, 4H), 2.96 (t, J=7.5 Hz, 4H), 2.33 (t, J=7.1 Hz, 4H), 1.83 (dt, J=15.2, 7.7 Hz, 4H), 1.65 (s, 4H), 1.44 (dq, J=14.7, 7.3 Hz, 4H), 1.38-1.21 (m, 12H), 0.92 (t, J=7.3 Hz, 6H). $^{13}$C NMR (126 MHz, MeOD) δ 174.82, 159.01, 149.63, 137.68, 137.27, 137.10, 134.50, 131.24, 130.93, 129.84, 127.86, 126.00, 123.16, 120.01, 114.24, 111.92, 49.87, 43.82, 43.75, 38.04, 30.45, 30.34, 30.29, 30.23, 27.78, 26.78, 23.35, 14.11. MS (ESI) calculated for $C_{56}H_{70}N_{12}O_2$, m/z 942.5745. found 943.5746 (M+H)$^+$ and 472.2987 (M+2H)$^{2+}$.

TLR3/7/8 Reporter Gene Assays (NF-κB Induction):

The induction of NF-κB was quantified using HEK-Blue-3, HEK-Blue-7 and HEK-Blue-8 cells as previously described by us.[8,24,51] HEK293 cells were stably transfected with human TLR3 (or human TLR7 or human TLR8), MD2, and secreted alkaline phosphatase (sAP), and were maintained in HEK-Blue™ Selection medium containing zeocin and normocin. Stable expression of secreted alkaline phosphatase (sAP) under control of NF-κB/AP-1 promoters is inducible by the TLR3 (or TLR7 or TLR8) agonists, and extracellular sAP in the supernatant is proportional to NF-κB induction. HEK-Blue cells were incubated at a density of ~105 cells/ml in a volume of 80 μl/well, in 384-well, flat-bottomed, cell culture-treated microtiter plates until confluency was achieved, and subsequently graded concentrations of stimuli. sAP was assayed spectrophotometrically using an alkaline phosphatase-specific chromogen (present in HEK-detection medium as supplied by the vendor) at 620 nm.

Antagonism assays were done as described by us earlier[73] using the following agonists at a constant concentration: TLR3 Poly(I:C) (10 ng/mL); TLR7: gardiquimod (1 μg/mL); TLR8: CL075 (1 μg/mL) mixed with graded concentrations of the test compounds.

IFN-α Induction in Human PBMCs:

Aliquots (10$^6$ cells in 100 μL) of hPBMCs isolated from blood obtained from healthy human donors after informed consent by conventional Ficoll-Hypaque gradient centrifugation were stimulated for 12 h with graded concentrations of test compounds. The supernatant was isolated by centrifugation, diluted 1:20, and IFN-α was assayed in triplicate using a high-sensitivity human IFN-α-specific ELISA kit (PBL Interferon Source, Piscataway, N.J.).

Cytokine and Chemokine in Human PBMCs:

Aliquots (10$^6$ cells in 100 μL) of hPBMCs isolated from blood obtained from healthy human donors after informed consent by conventional Ficoll-Hypaque gradient centrifugation were stimulated for 12 h with graded concentrations of test compounds. The supernatant was isolated by centrifugation, diluted 1:20, and cytokines and chemokines were assayed in triplicate using analyte-specific cytokine/chemokine bead array assays as reported by us previously.[74]

Figure 19:
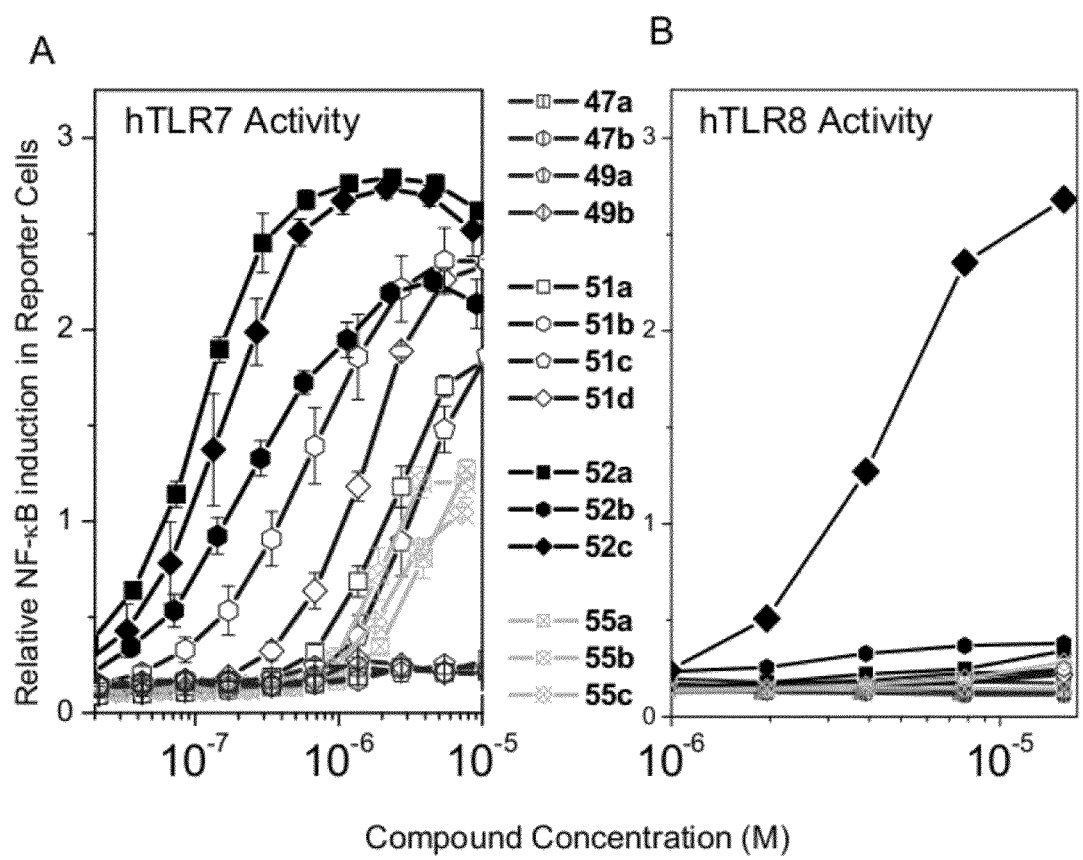
FIGS. 19A and 19B are graphs illustrating TLR7 and TLR8 agonistic activities of the imidazoquinoline dimers in human TLR-specific reporter gene assays.
Figure 20:
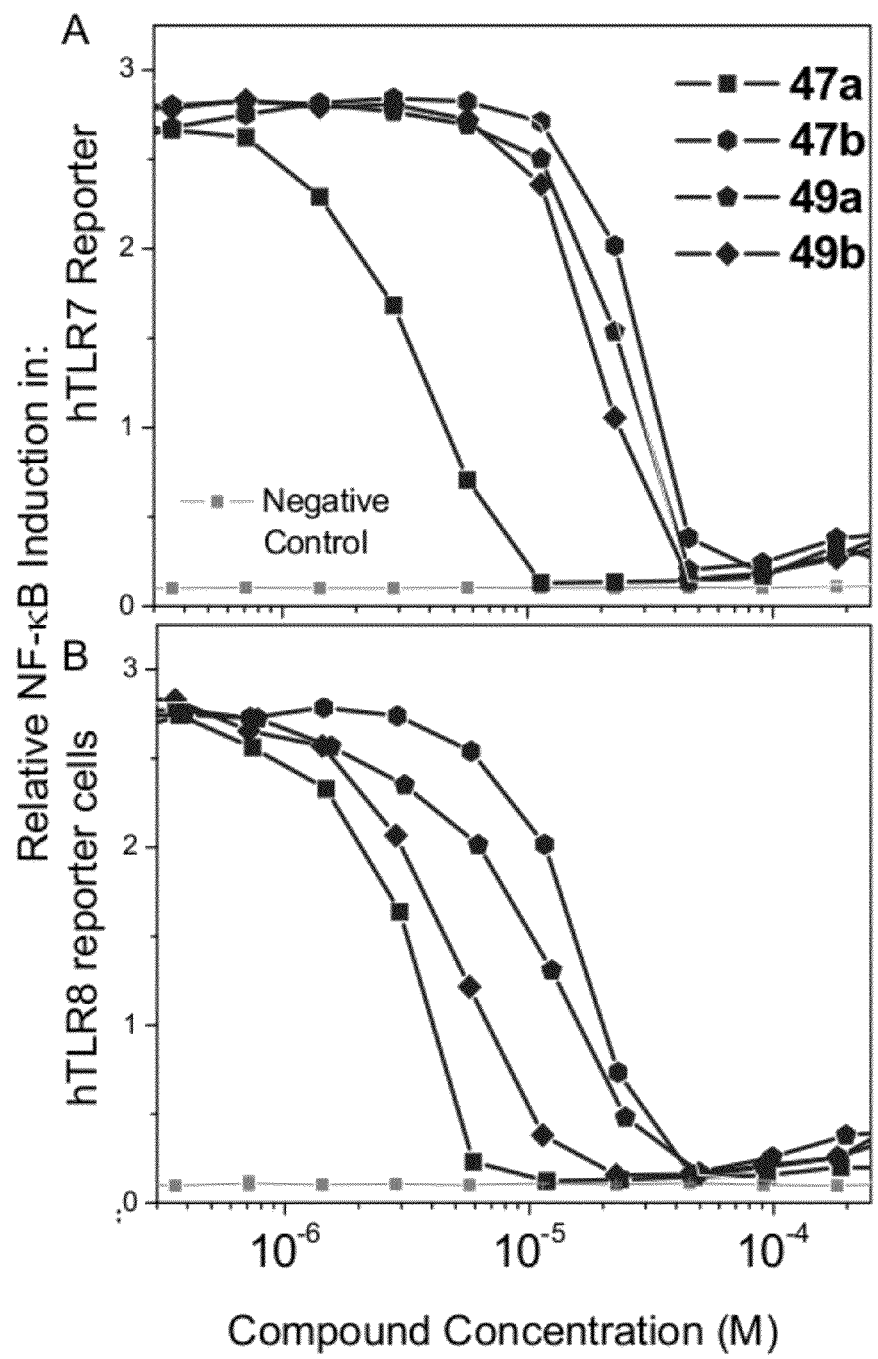
FIGS. 20A and 20B are graphs of TLR7 (20A) and TLR8 (20B) antagonistic activities of the imidazoquinoline dimers 47a-b and 49a-b in human TLR-specific reporter gene assays.

With the exception of the 47 and 49 series of compounds, all other dimers retained TLR7-agonistic properties, the 52 series being the most potent (FIG. 19A); interestingly, only 52c displayed both TLR7 and TLR8 agonism (FIGS. 19A and 19B, respectively, and Table 1), suggesting advantages of a long linker for dual agonism. The C2-linked dimeric compounds 47a, 47b, 49a, and 49b unexpectedly showed potent antagonistic activity in both TLR7 and TLR8 assays, with 47a being most potent (IC$_{50}$ values of 3.1 and 3.2 μM in TLR7 and TLR8 assays, FIGS. 20A and 20B, respectively; Table 1).

Figure 21:
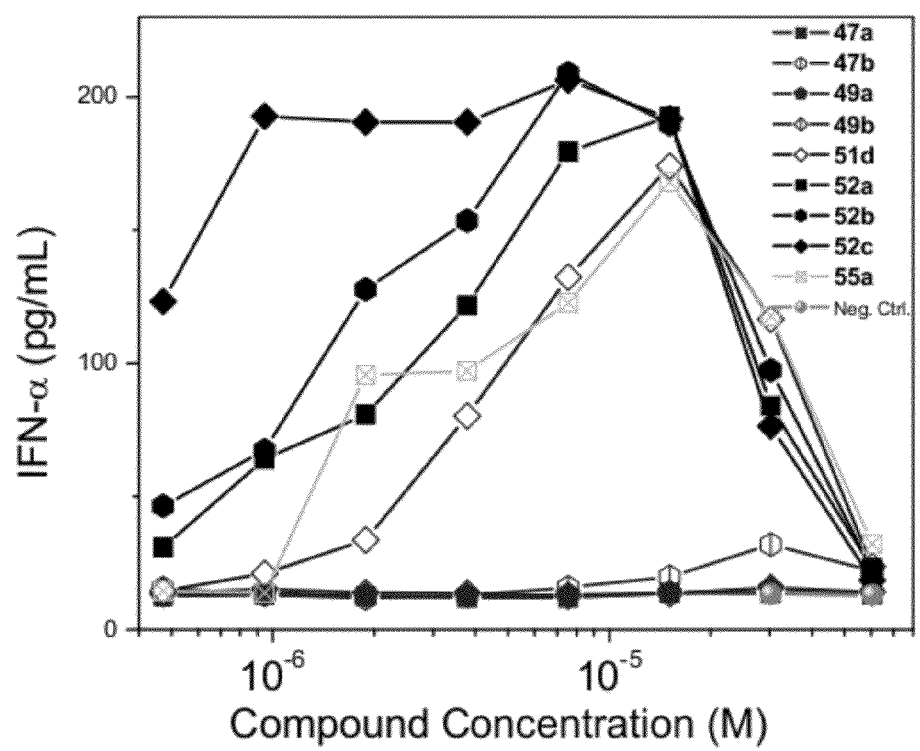
FIG. 21 is a graph illustrating IFN-α induction by select dimers in human peripheral blood mononuclear cells. IFN-α was assayed by analyte specific ELISA after incubation of hPBMCs with graded concentrations of the test compound for 12 h.

Both agonistic and antagonistic compounds were then tested in appropriate secondary screens employing ex vivo human blood-derived models. The ligation of TLR7 and TLR8 trigger inflammatory responses characterized by the elaboration of type I interferon (IFN-α/β) by virus-infected cells via activation of downstream NF-κB and IFN-β promoters.[75-80] IFN production is a hallmark response underlying cellular antiviral immune responses. It was desirable to verify that the TLR7 agonism observed (FIG. 19) manifested in IFN production in secondary screens. Using an ex vivo stimulation model using human peripheral blood mononuclear cells (hPBMC), it was demonstrated that IFN-α was indeed induced in a dose-dependent, bimodal manner as expected for innate immune responses (FIG. 21). Compound 52c was found to be the most potent.

Figure 22:
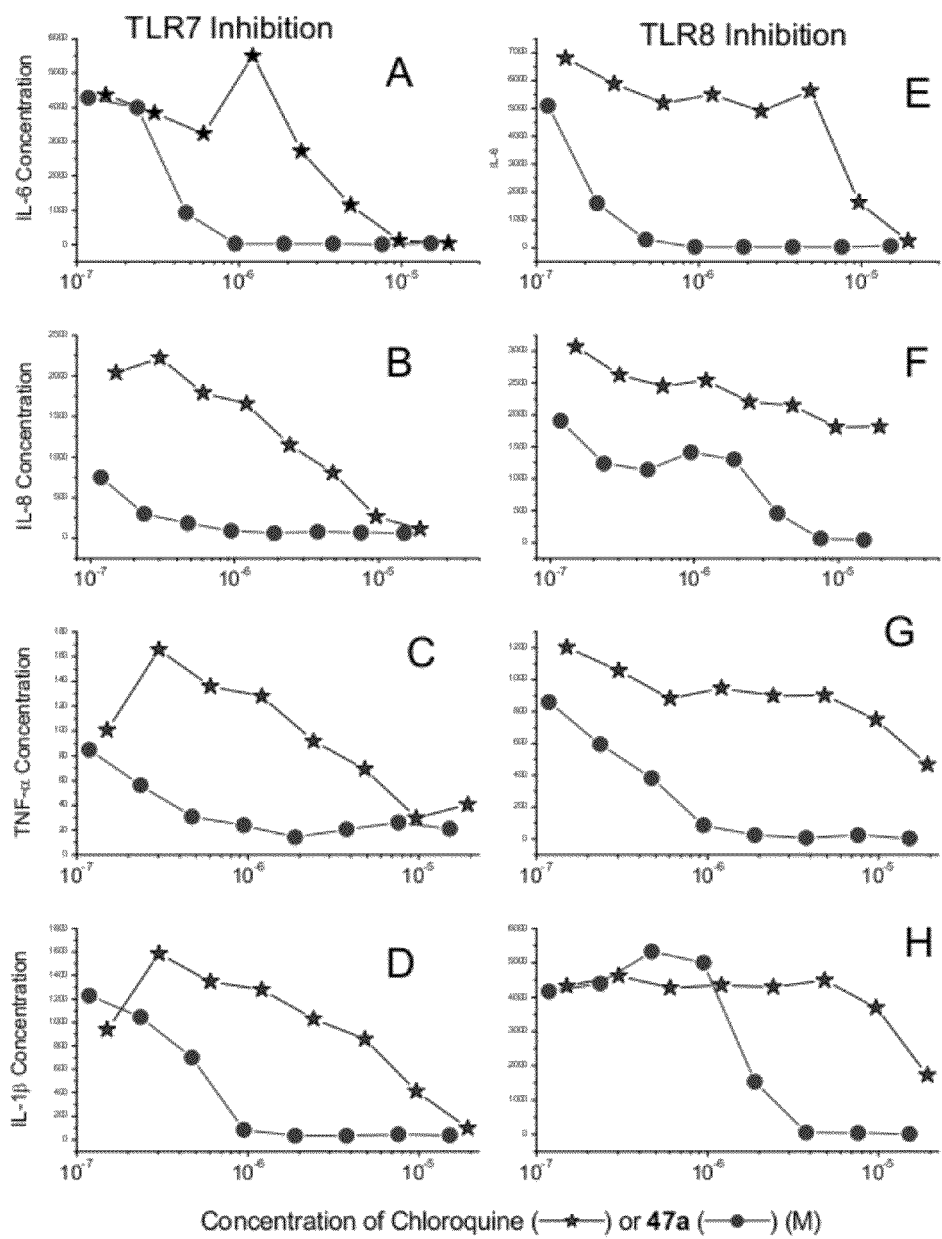
FIGS. 22A-22H illustrate inhibition of TLR7-mediated (FIGS. 22A-22D) and TLR8-mediated (FIGS. 22E-22H) proinflammatory cytokine production in human peripheral blood mononuclear cells by chloroquine or 47a. Proinflammatory cytokines were assayed by cytokine bead array methods after incubation of hPBMCs with graded concentrations of the test compound for 12 h in the presence of 10 μg/ml of either CL075 (TLR8 agonist) or gardiquimod (TLR7 agonist).
Figure 23:
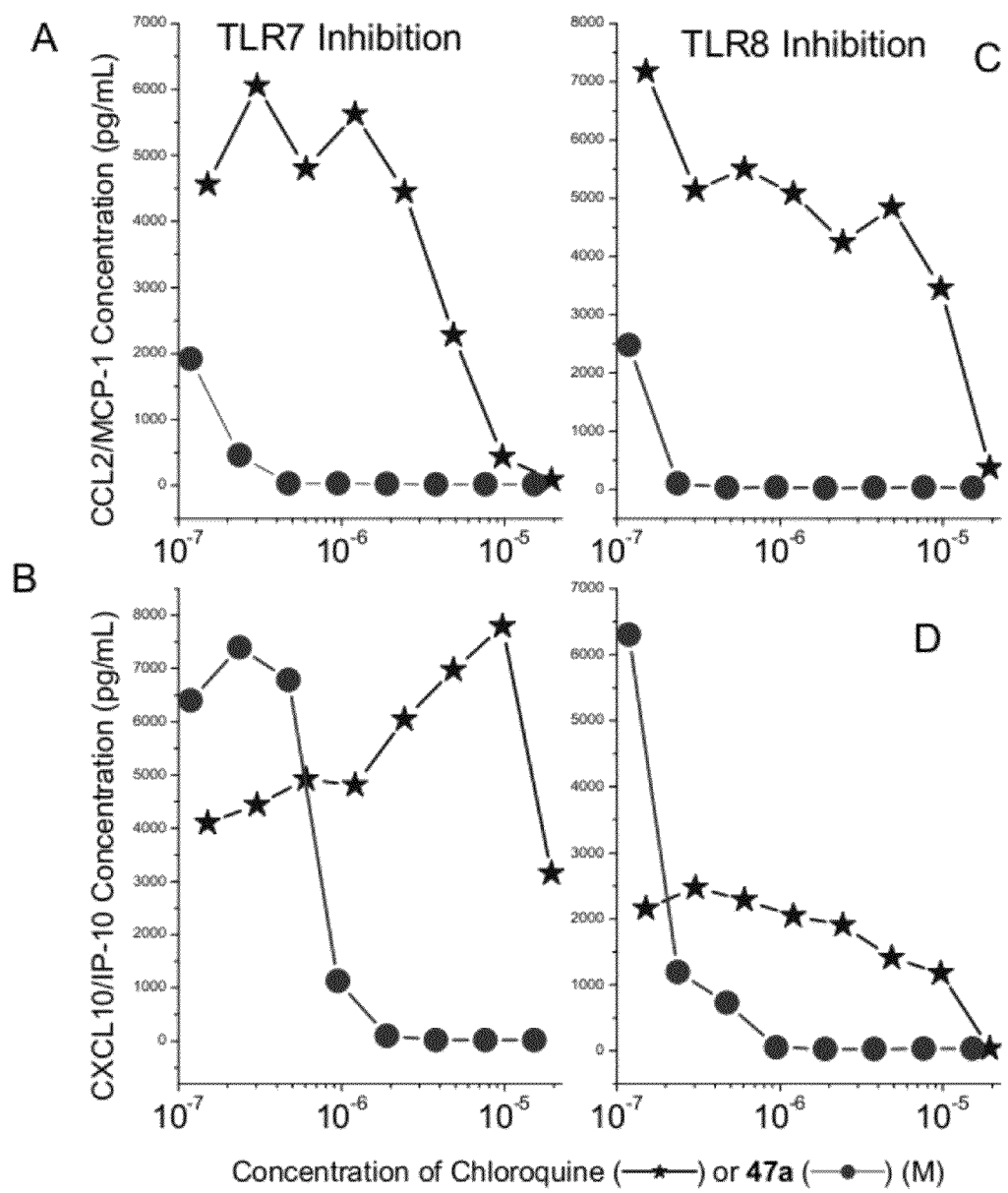
FIGS. 23A-23D illustrate inhibition of TLR7-mediated (FIGS. 23A-23B) and TLR8-mediated (FIGS. 23C-3D) chemokine production in human peripheral blood mononuclear cells by chloroquine or 47a. Chemokines were assayed by cytokine bead array methods after incubation of hPBMCs with graded concentrations of the test compound for 12 h in the presence of 10 μg/ml of either CL075 (TLR8 agonist) or gardiquimod (TLR7 agonist).
Figure 24:
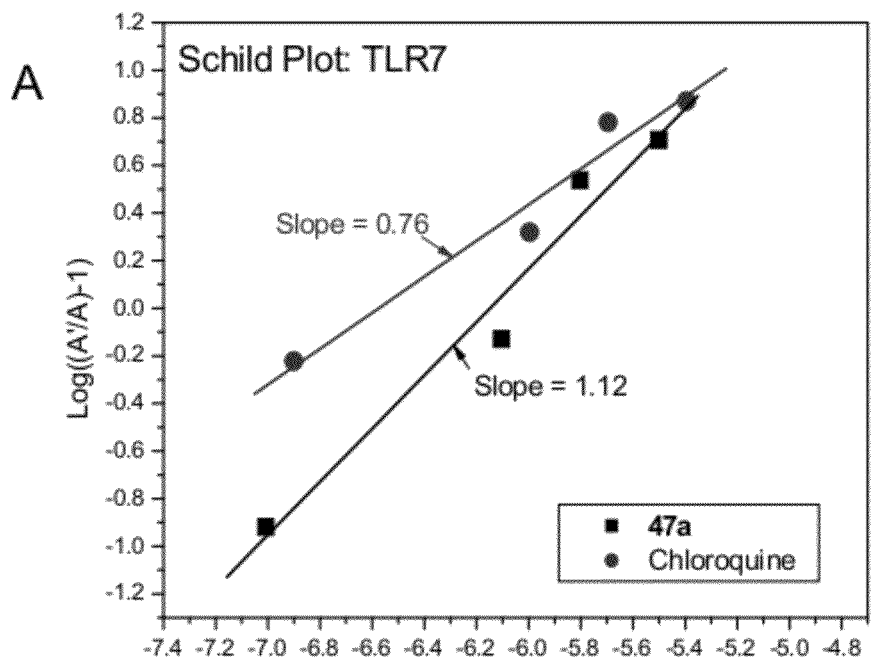
FIGS. 24A and 24B are graphs of the schild plot analyses of inhibition of TLR7- (24A) and TLR8-induced (24B) activation. Experiments were performed in checker-board format, using a liquid handler, in 384-well plates which permitted the concentrations of both agonist and antagonist to be varied simultaneously along the two axes of the plate. Either imidazoquinoline (TLR7-specific agonist) or CL075 (TLR8-specific agonist) was used at a starting concentration of 20 μg/mL, and were two-fold diluted serially (along the rows). Next, 47a or chloroquine was two-fold diluted serially in HEK detection medium (along columns). Reporter cells were then added, incubated, and NF-κB activation measured as described in the text. A and A' (Y-axis) are defined respectively as the $EC_{50}$ value in the absence of antagonist, and the $EC_{50}$ values in the presence of varying concentrations of antagonist.
Figure 24:
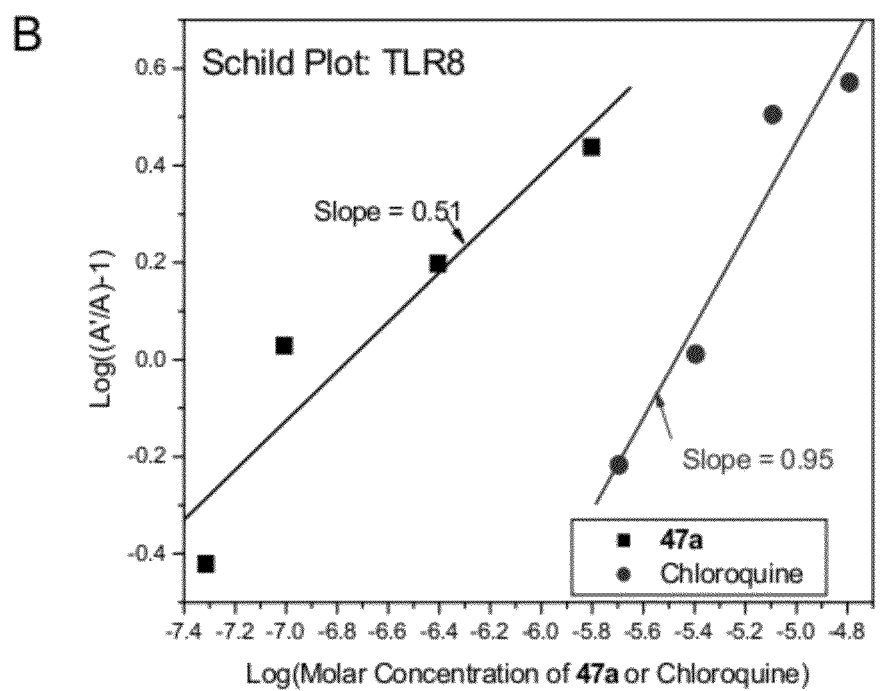

The antagonistic properties of 47a in inhibiting TLR7 and TLR8-mediated induction of various proinflammatory cytokines (FIGS. 22A-22H) and chemokines (FIGS. 23A-23D) were examined in detail in ex vivo models using human blood, since this compound was found to be the most potent antagonist in the series in primary screens (Table 1). The potency of 47a was compared alongside chloroquine, which is known to selectively suppress intracellular TLR7, but not TLR8 signaling via inhibition of endolysosomal acidification.[81,82] We found 47a to be a potent inhibitor of both TLR7 and TLR8-induced cytokine and chemokine release, with IC$_{50}$ values of about 0.05-0.3 μM (FIGS. 22, 23). TLR8 signaling manifests predominantly in the induction of pro-inflammatory cytokines such as TNF-α and IL-1β.[83,84] Chloroquine, a TLR7 antagonist, is a feeble inhibitor of TNF-α and IL-1β, while 47a, as would be expected for a TLR8 antagonist, potently inhibits the production of these proinflammatory cytokines (FIG. 23), as well as IL-6 and IL-8 which are typically induced secondarily, in an autocrine/paracrine manner. The relative specificity of chloroquine in inhibiting TLR7 as well as the dual TLR7/8-inhibitory activities of 47a are also evident in Schild plots (FIG. 24A-24B). Although the relationship between antagonist concentration and change in $EC_H$, for TLR7 inhibition by 47a is near-ideal (slope: 1.12, FIG. 24A), a distinct deviation from ideal competitive inhibition for TLR8 is observed (slope: 0.51, FIG. 24B), suggesting that additional mechanisms for TLR8 inhibition, possibly allosteric, may be operational.

TABLE 1

Agonistic and antagonistic activities of the dimers in TLR7 and TLR8 reporter gene assays.

| Compound number | Structure | TLR7 Agonism (μM) | TLR7 Antagonism (μM) | TLR8 Agonism (μM) | TLR8 Antagonism (μM) |
|---|---|---|---|---|---|
| 47a | 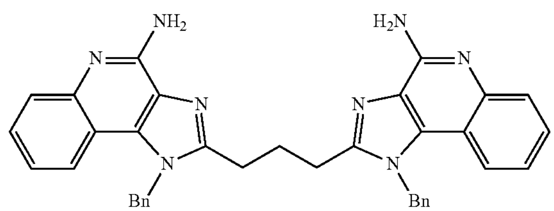 | ND | 3.1 | ND | 3.2 |
| 47b | 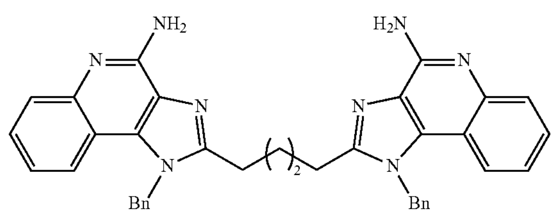 | ND | ND | ND | 15.63 |
| 49a | 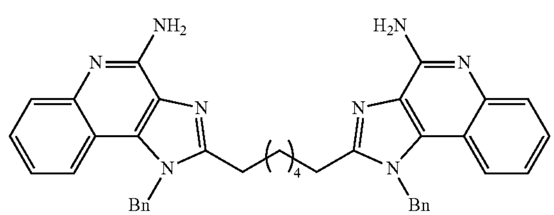 | ND | ND | ND | 10.92 |
| 49b | 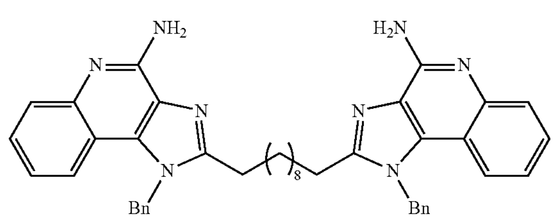 | ND | 17.88 | ND | 4.65 |
| 51a | 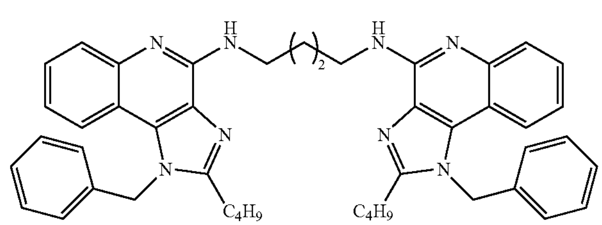 | 2.05 | ND | ND | ND |

TABLE 1-continued

Agonistic and antagonistic activities of the dimers in TLR7 and TLR8 reporter gene assays.

| Compound number | Structure | TLR7 Agonism (μM) | TLR7 Antagonism (μM) | TLR8 Agonism (μM) | TLR8 Antagonism (μM) |
|---|---|---|---|---|---|
| 51b | 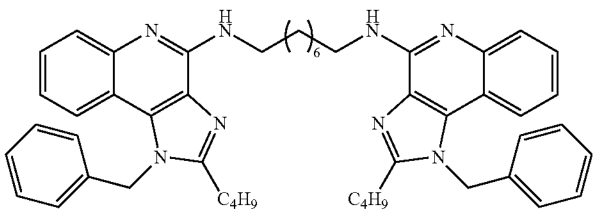 | 0.56 | ND | ND | ND |
| 51c | 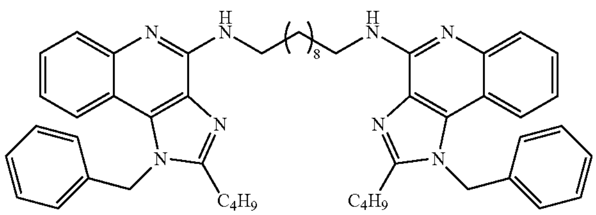 | 3.00 | ND | ND | ND |
| 51d | 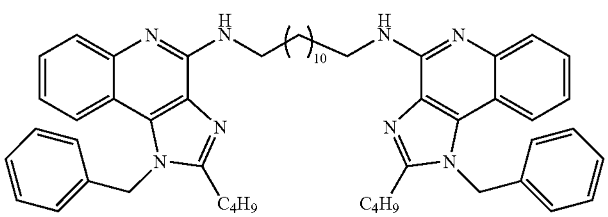 | 1.42 | ND | ND | ND |
| 52a | 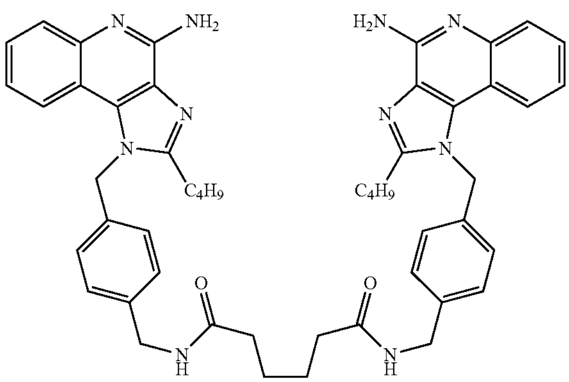 | 0.11 | ND | ND | ND |
| 52b | 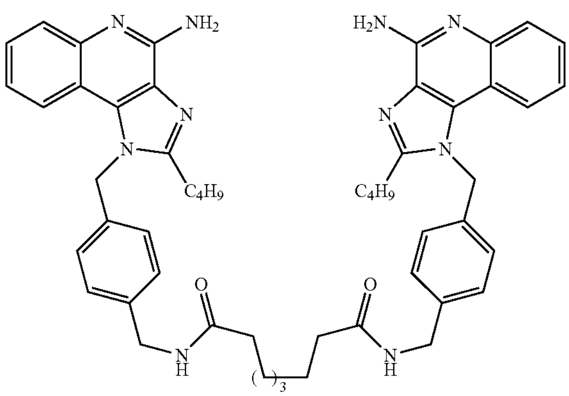 | 0.24 | ND | ND | ND |

TABLE 1-continued

*Agonistic and antagonistic activities of the dimers in TLR7 and TLR8 reporter gene assays.*

| Compound number | Structure | TLR7 Agonism (µM) | TLR7 Antagonism (µM) | TLR8 Agonism (µM) | TLR8 Antagonism (µM) |
|---|---|---|---|---|---|
| 52c | 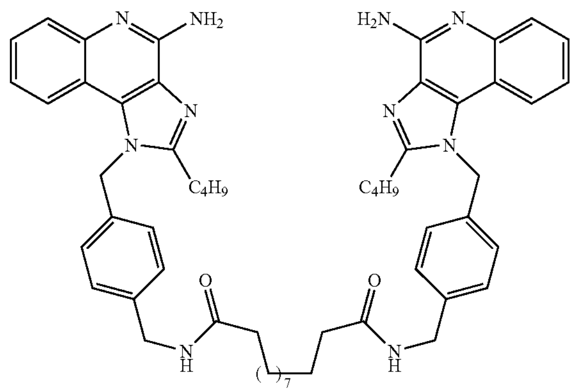 | 0.17 | ND | 4.78 | ND |
| 53a | 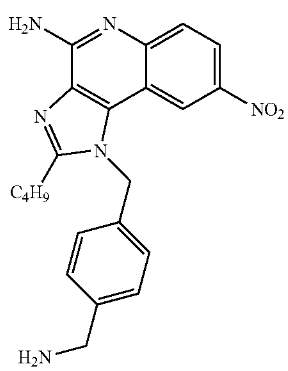 | 0.56 | ND | ND | ND |
| 54a | 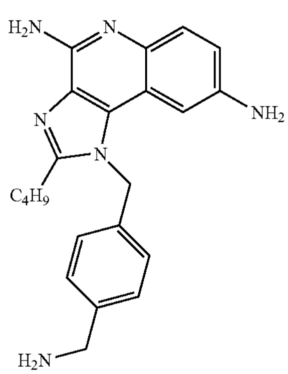 | 0.45 | ND | ND | ND |

TABLE 1-continued

Agonistic and antagonistic activities of the dimers in
TLR7 and TLR8 reporter gene assays.

| Compound number | Structure | TLR7 Agonism (μM) | TLR7 Antagonism (μM) | TLR8 Agonism (μM) | TLR8 Antagonism (μM) |
|---|---|---|---|---|---|
| 55a | [structure] | 7.24 | ND | ND | ND |
| 55b | [structure] | 4.02 | ND | ND | ND |
| 55c | [structure] | 5.4 | ND | ND | ND |

ND = not detected;
NT = not tested.

In conclusion, the present data demonstrate that the C4, C8, and N[1]-aryl-linked dimers are agonists, with the last being most potent. The N[1]-aryl-linked dimers are of interest as potential vaccine adjuvants are currently being evaluated in animal models. The C2-linked dimers were found to be potently antagonistic at both TLR7 and TLR8 and may be useful as small molecule probes for examining the effects of inhibiting endolysosomal TLR signaling in HIV and autoimmune states.

Example 9

Dual TLR2/TLR7 Adjuvants

Figure 25:
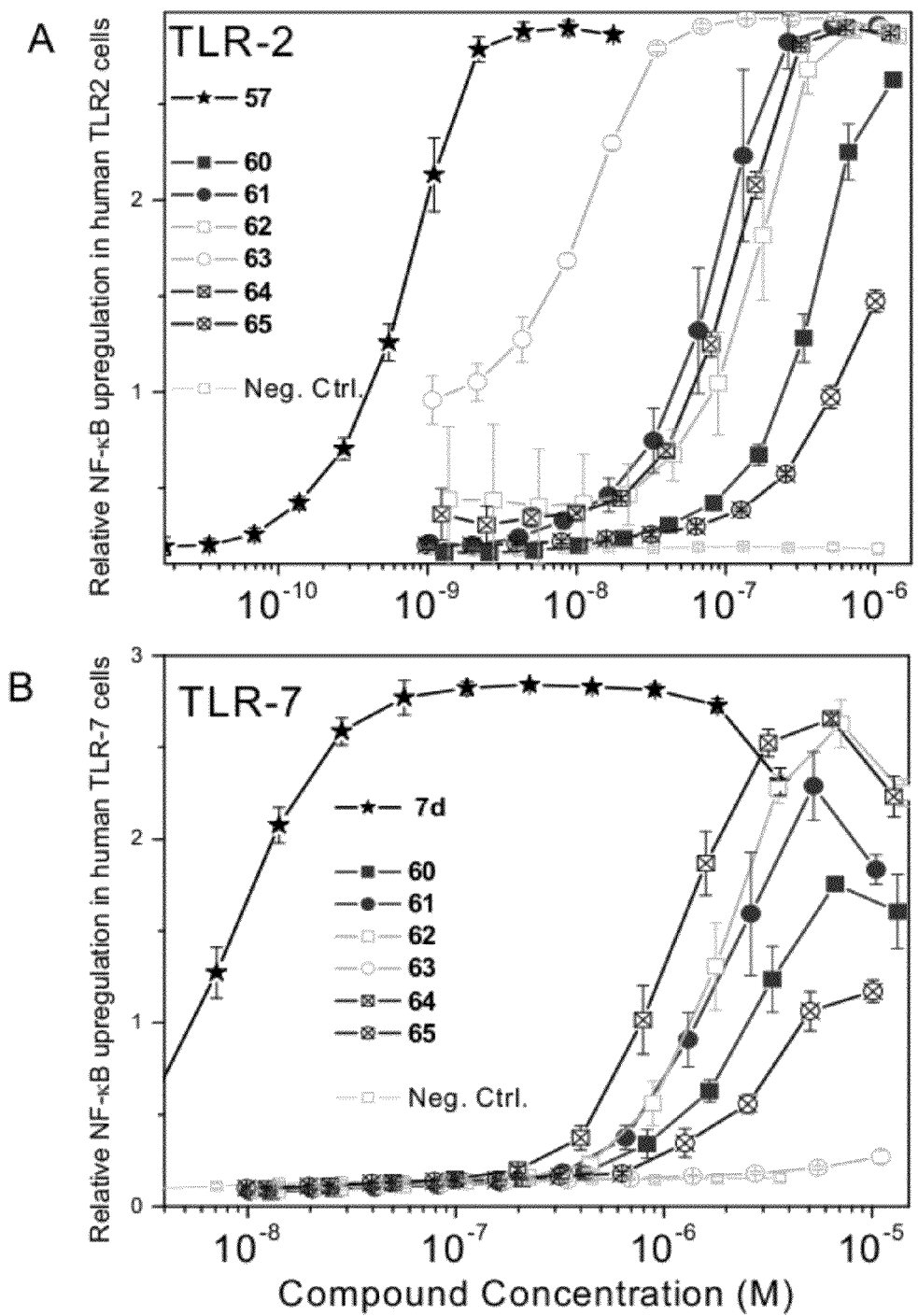
FIGS. 25A and 25B are graphs illustrating TLR-2 (25A) and -7 (25B) agonistic activities of compounds 60-65.
Figure 26:
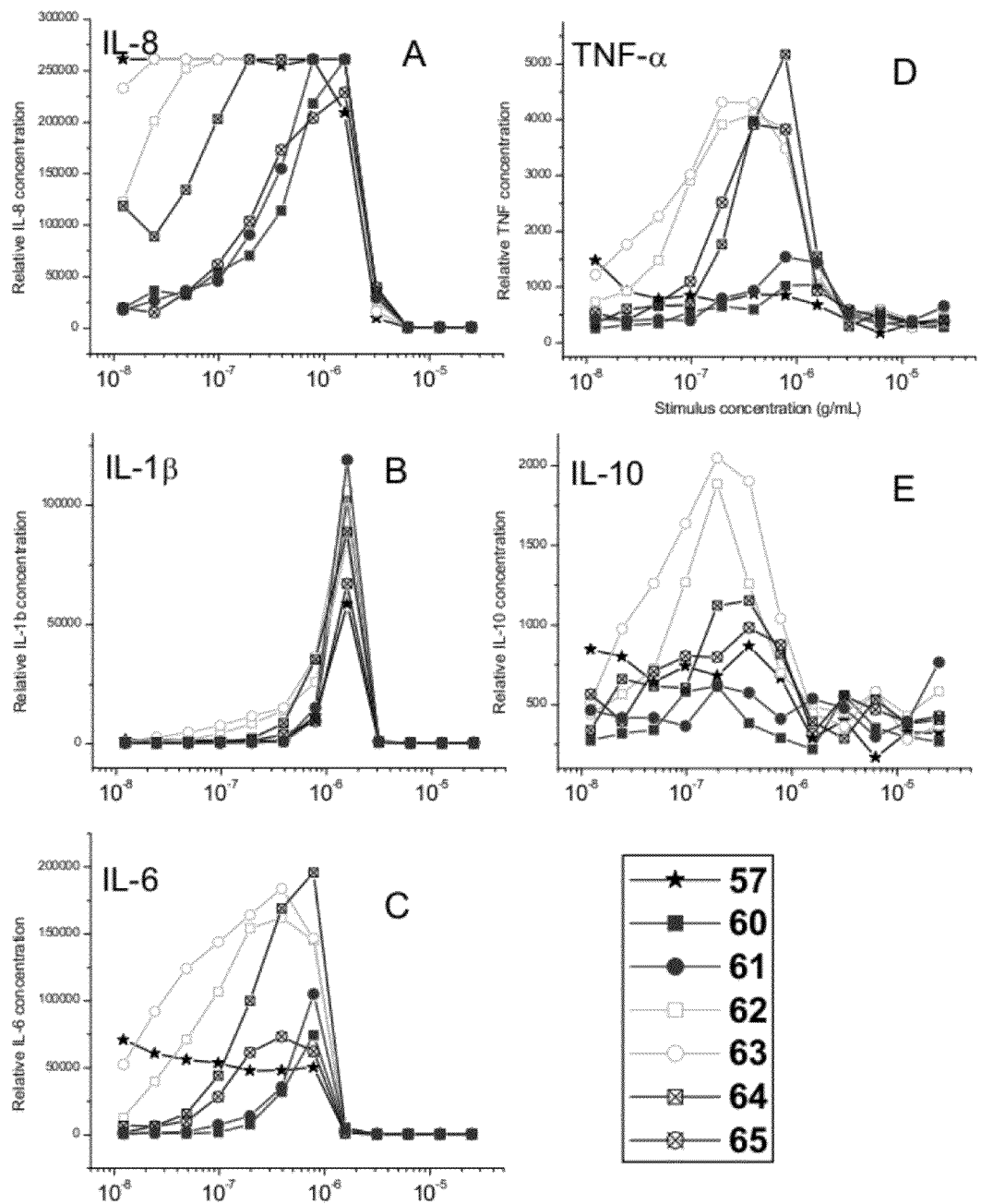
FIGS. 26A-26E are graphs illustrating cytokine induction in hPBMCS by the compounds 60-65.
Figure 27:
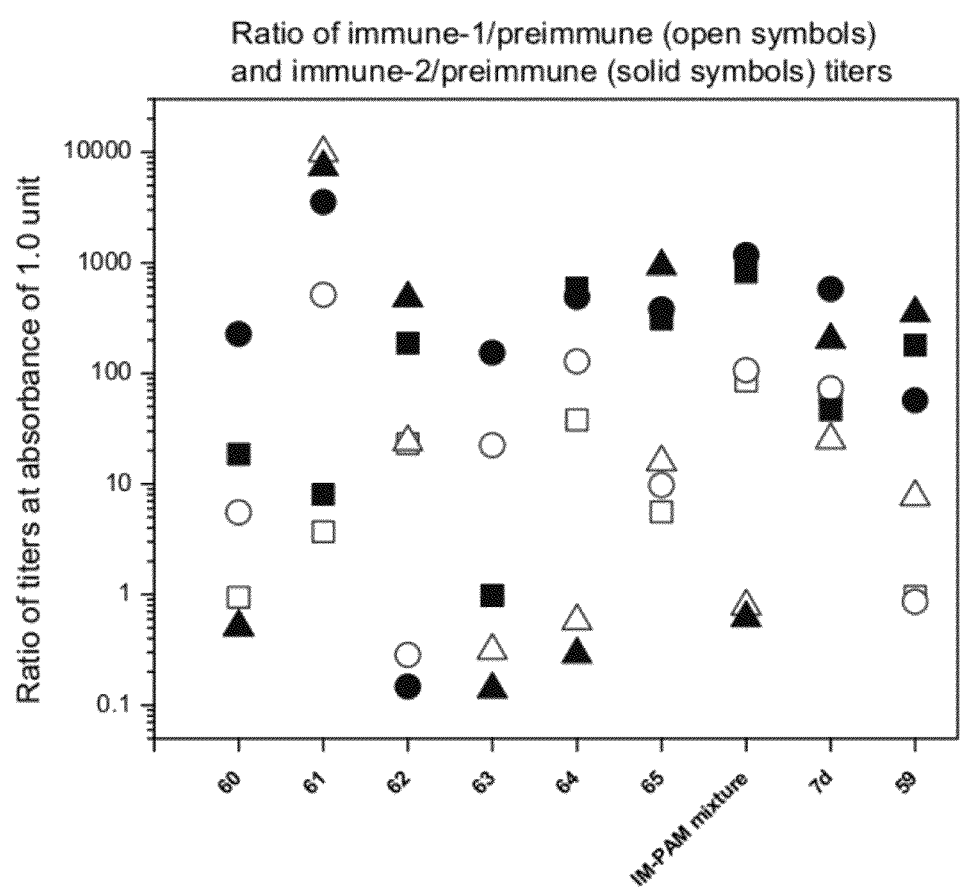
FIG. 27 illustrates ratios of immune-1/pre-immune (after primary vaccination) and Immune-2/pre-immune (after Boost-1) anti-α-lactalbumin IgG titers in rabbits using the hybrids as adjuvants. Also shown are the IMDQ (7d) and $PAM_2CS$, as well as IMDQ (7d)+PAM2CS mixture controls.

Toll-like receptor 2-agonistic lipopeptides typified by S-[2,3-bis(palmitoyloxy)-(2RS)-propyl]-R-cysteinyl-5-serine (PAM(2)CS) compounds are potential vaccine adjuvants.[52, 85, 86] Combining the individual TLR-agonistic activities of the PAM2CS (TLR2) and imidazoquinoline (TLR7) chemotypes may result in highly potent adjuvants. Six different hybrids in various configurations (60-65) were synthesized to examine how the TLR2 and TLR7 activities may be modulated in such compounds, and how such differences could manifest in adjuvantic activities in vivo. Imidazoquinoline derived compounds incorporating a free amine, carboxylic acid, or an isothiocyanate, with or without a triethylene glycol spacer were synthesized (Scheme 2), as were analogues of PAM2CS with a free carboxylate on the serine or a free amine on the cysteine fragment of the lipopeptide (Scheme 19). Coupling these synthons yielded six differently configured hybrids (Schemes 20-22). These analogues show divergent TLR2- and TLR7-specific activities in primary screens (FIGS. 25A and 25B, respectively), as well as in secondary cytokine induction screens (FIGS. 26A-26E). These hybrids are also adjuvantic in rabbit immunization studies (FIG. 27).

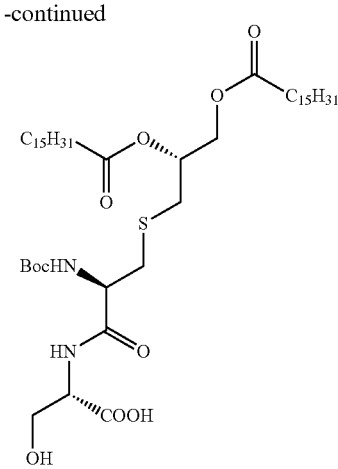

57

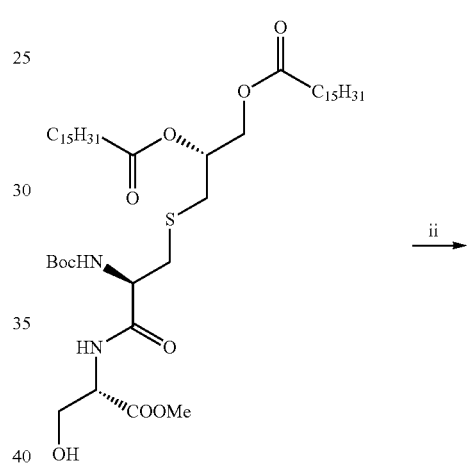

58

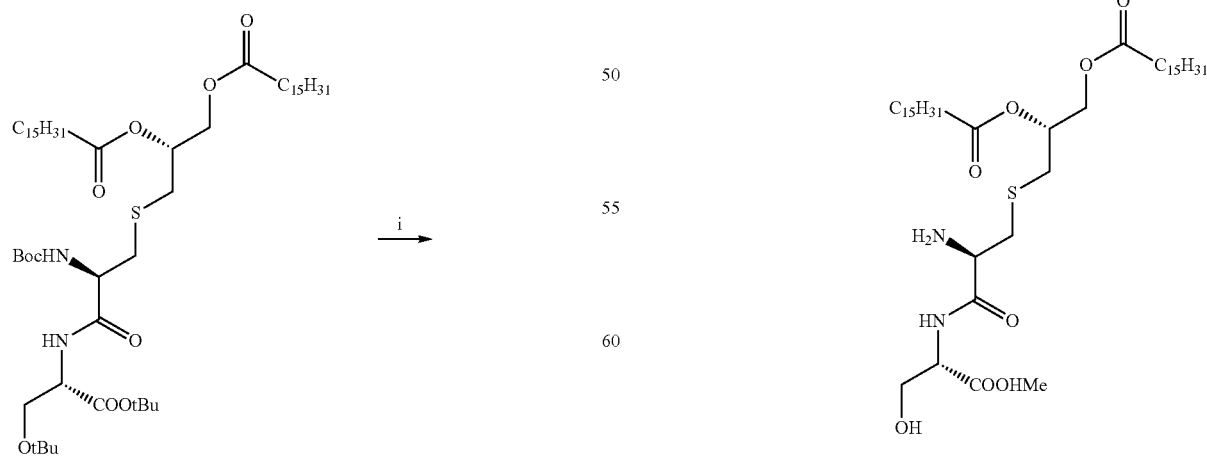

Reagents and conditions: i. (a) CF₃COOH, (b) (Boc)₂O, Et₃N, CH₂Cl₂; ii. CF₃COOH.

Scheme 20. Synthesis of thiourea-linked TLR-2/7 hybrid compounds 60 and 61.
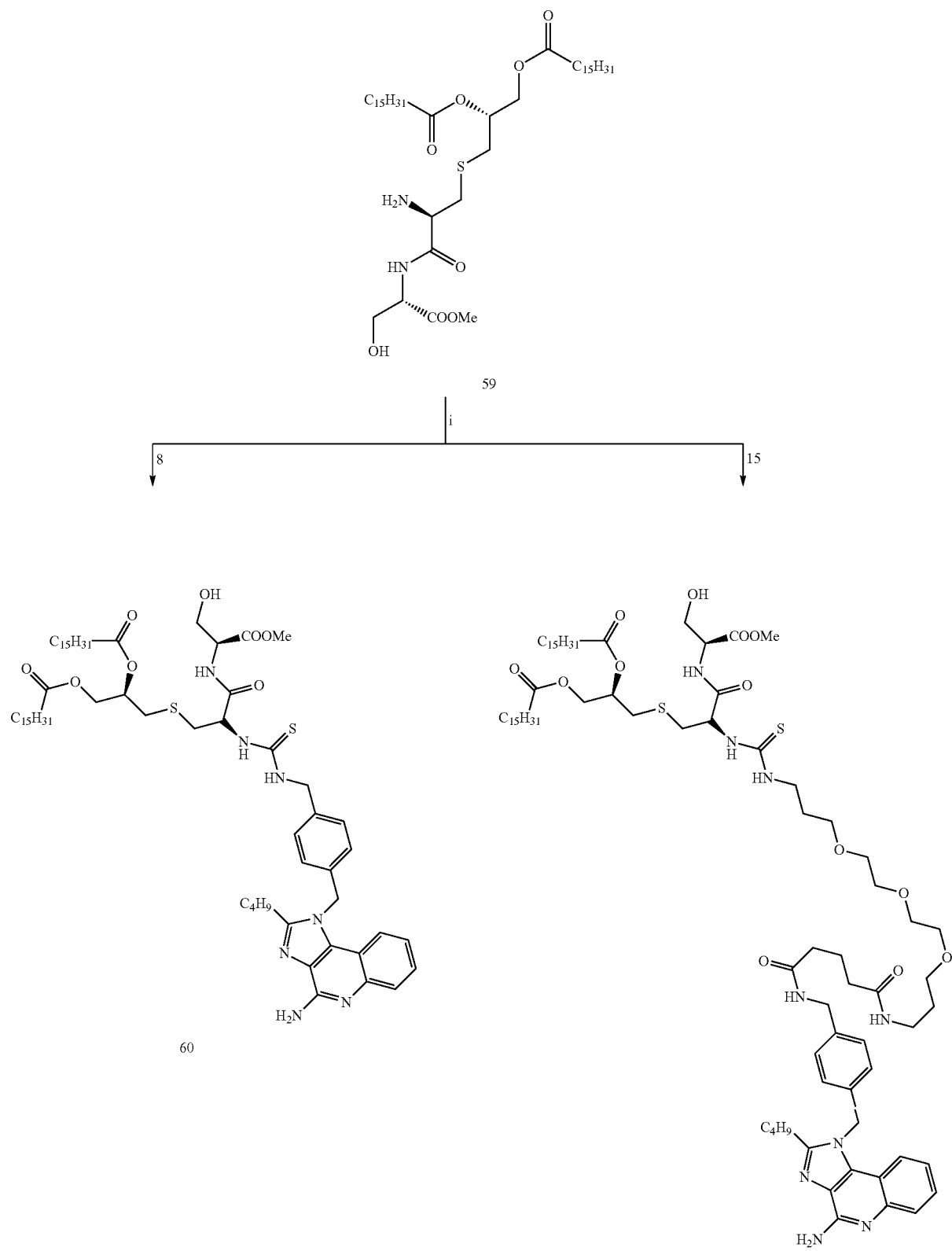
Reagents and conditions: i. Pyridine, 45° C.

Scheme 21. Synthesis of thiourea-linked TLR-2/7 hybrid compounds 62 and 63.
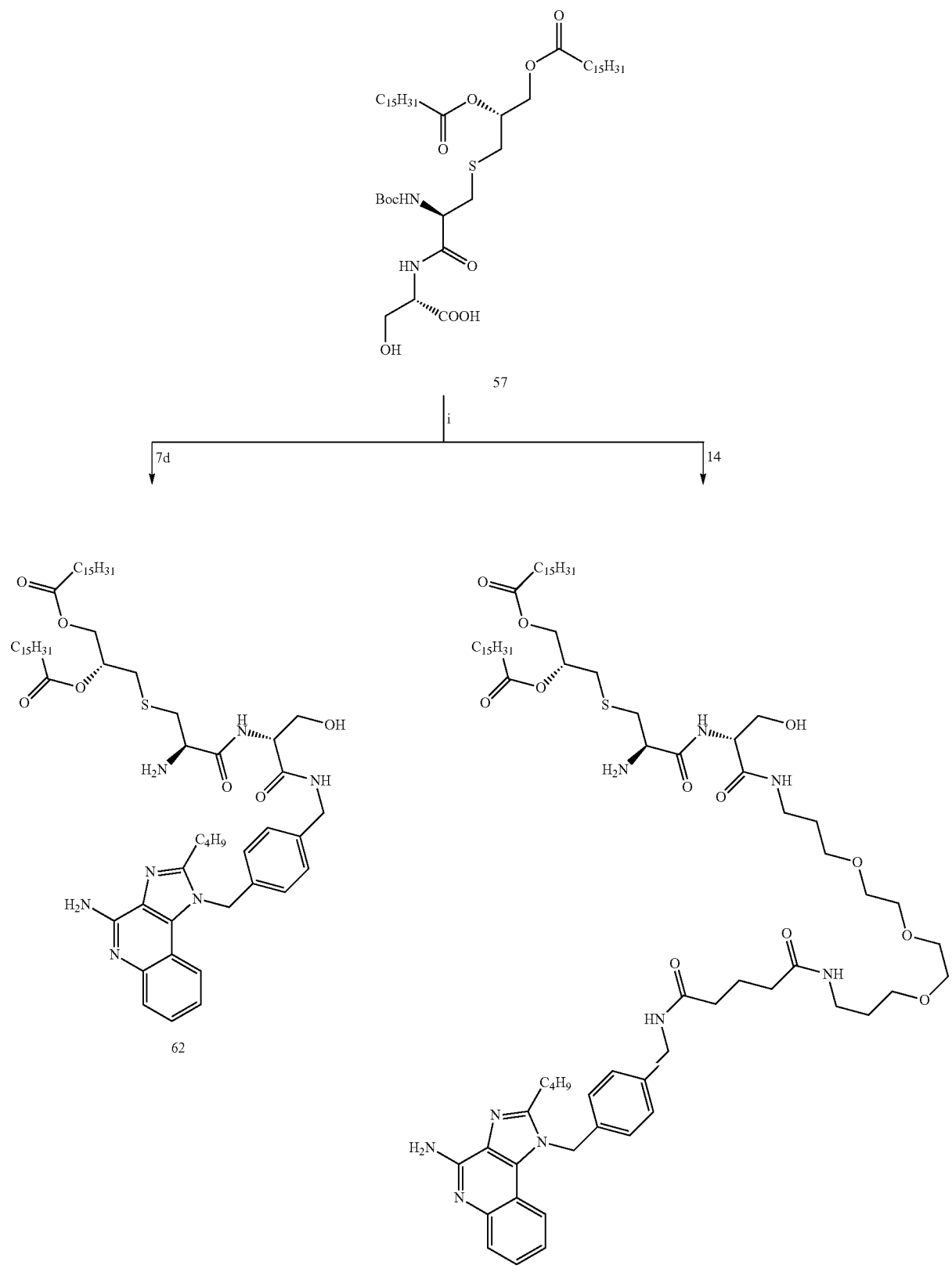
Reagents and conditions: i. HBTU, Et₃N, DMF.

Scheme 22. Synthesis of thiourea-linked TLR-2/7 hybrid compounds 64 and 65.
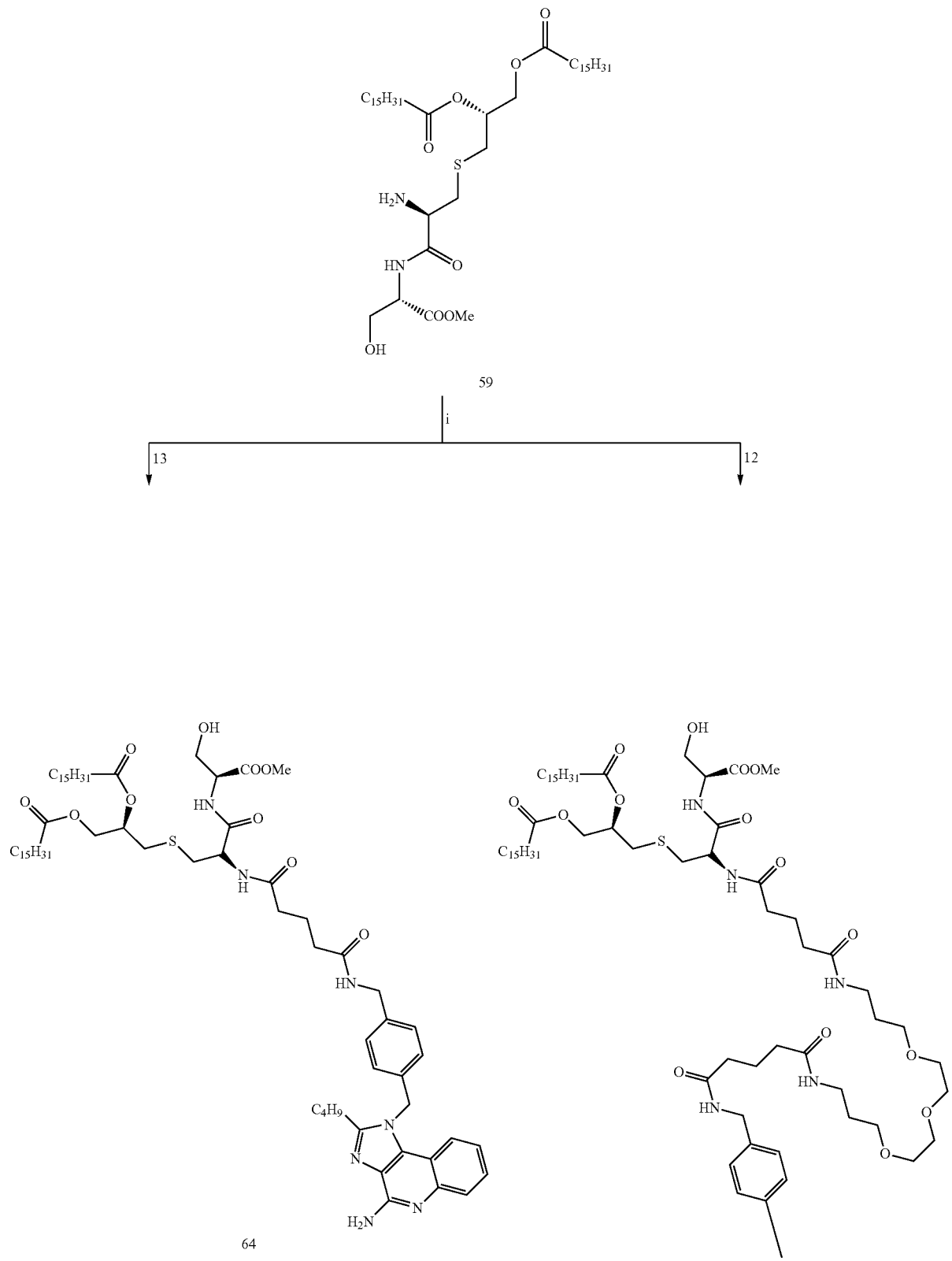

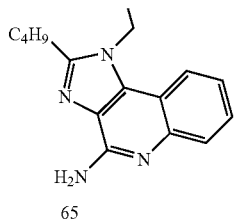

65

Reagents and conditions: i. HBTU, ET₃N, DMF.

Compounds 56, 58 and 59 were Synthesized as Described Earlier.[52,85,86]

Synthesis of Compound 57: (S)-2-((R)-3-(((R)-2,3-bis(palmitoyloxy)propyl)thio)-2-((tert-butoxycarbonyl)amino)propanamido)-3-hydroxypropanoic acid

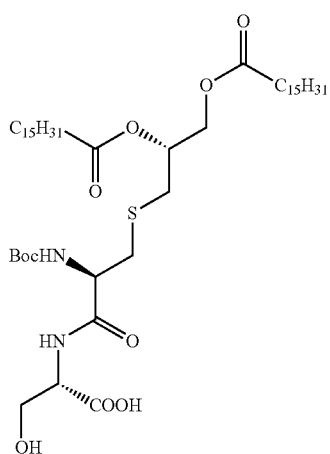

57

Compound 56 (200 mg, 0.21 mmol) was dissolved in trifluoroacetic acid and stirred for 40 min, followed by removal of the solvent under vacuum to obtain the free amine intermediate (170 mg), which was then dissolved in anhydrous CH₂Cl₂ followed by the addition of triethylamine (53 mL, 0.38 mmol) and di-tert-butyl dicarbonate (46 mg, 0.21 mmol). The reaction mixture was stirred for 2 hours followed by removal of the solvent under vacuum. The residue was purified using column chromatography (6% MeOH/CH₂Cl₂) to obtain the compound 57 (100 mg, 57%). MS (ESI) calculated for $C_{46}H_{86}N_2O_{10}S$, m/z 858.6003. found 859.6112 (M+H)⁺.

Synthesis of Compound 60

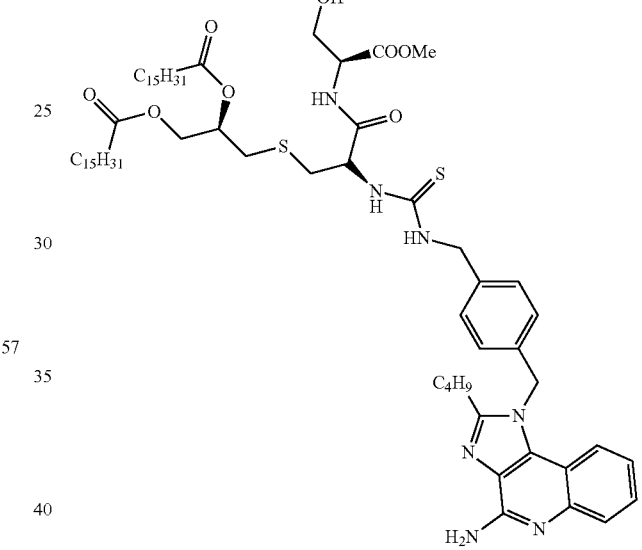

60

To the solution of compound 8 (50 mg, 0.12 mmol) in anhydrous pyridine was added compound 59 (166 mg, 0.19 mmol). The reaction mixture was heated at 45° C. for 24 hours, followed by removal of the solvent under vacuum. The residue was then purified using column chromatography to obtain the compound 60 (53 mg, 38%). ¹H NMR (500 MHz, CDCl₃) δ 15.40 (d, J=18.5 Hz, 1H), 10.56 (d, J=17.8 Hz, 1H), 7.81 (d, J=8.3 Hz, 1H), 7.68 (d, J=8.3 Hz, 1H), 7.47 (t, J=7.7 Hz, 1H), 7.35-7.28 (m, 3H), 7.28-7.23 (m, 1H), 6.98 (d, J=6.6 Hz, 2H), 5.72 (s, 2H), 5.37-5.07 (m, 2H), 4.83 (s, 1H), 4.71-4.53 (m, 2H), 4.33 (dd, J=11.7, 2.7 Hz, 1H), 4.08 (ddd, J=27.8, 11.9, 6.5 Hz, 1H), 4.00-3.88 (m, 2H), 3.71 (d, J=6.8 Hz, 3H), 3.26-3.01 (m, 4H), 2.91-2.77 (m, 4H), 2.73 (d, J=6.4 Hz, 1H), 2.34-2.25 (m, 4H), 1.84-1.76 (m, 2H), 1.56 (s, 4H), 1.49-1.39 (m, 2H), 1.33-1.19 (m, 48H), 0.94 (t, J=7.3 Hz, 3H), 0.87 (t, J=6.9 Hz, 6H). ¹³C NMR (126 MHz, CDCl₃) δ 174.58, 174.34, 173.83, 173.78, 170.50, 170.14, 156.77, 156.75, 149.65, 149.63, 135.60, 134.58, 132.97, 129.66, 128.68, 128.66, 125.63, 125.18, 124.72, 124.70, 120.56, 119.66, 112.45, 71.40, 70.26, 63.99, 63.81, 62.56, 62.40, 57.55, 57.35, 55.19, 55.02, 52.72, 52.69, 48.97, 47.80, 35.62, 34.47, 34.37, 34.23, 34.09, 33.91, 32.76, 31.93, 29.72, 29.69, 29.67, 29.52, 29.51, 29.37, 29.32, 29.29, 29.12, 29.09, 29.08, 26.93, 24.90, 24.88, 24.84, 24.83, 22.70, 22.38, 14.13, 13.72. MS (ESI) calculated for $C_{65}H_{103}N_7O_8S_2$, m/z 1173.7310. found 1174.7410 (M+H)⁺.

Synthesis of Compound 61

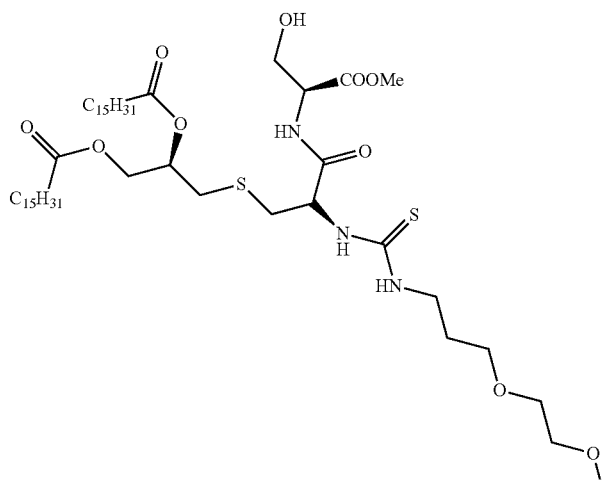

61

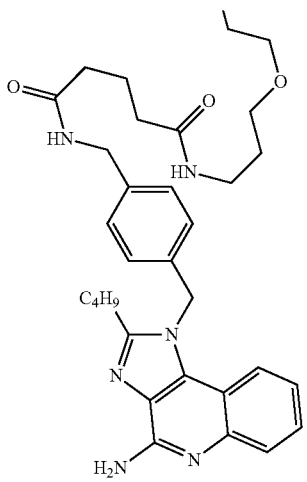

To the solution of compound 15 (50 mg, 0.07 mmol) in anhydrous pyridine was added compound 59 (54 mg, 0.07 mmol). The reaction mixture was heated at 45° C. for 24 hours, followed by removal of the solvent under vacuum. The residue was then purified using column chromatography (12% MeOH/CH$_2$Cl$_2$) to obtain the compound 61 (55 mg, 53%). $^1$H NMR (500 MHz, MeOD) δ 7.84 (d, J=8.2 Hz, 1H), 7.68 (d, J=8.0 Hz, 1H), 7.48-7.44 (m, 1H), 7.26 (d, J=8.2 Hz, 2H), 7.18-7.14 (m, 1H), 7.04 (d, J=8.2 Hz, 2H), 5.87 (s, 2H), 5.23 (bs, 2H), 4.53 (t, J=4.4 Hz, 1H), 4.38 (dd, J=11.9, 3.0 Hz, 1H), 4.33 (s, 2H), 4.14 (dd, J=12.0, 6.5 Hz, 1H), 3.91 (dd, J=11.3, 4.6 Hz, 1H), 3.80 (dd, J=11.3, 4.1 Hz, 1H), 3.73 (s, 3H), 3.61 (dd, J=5.9, 3.0 Hz, 4H), 3.56 (dd, J=5.7, 2.7 Hz, 4H), 3.53-3.47 (m, 4H), 3.22 (t, J=6.8 Hz, 2H), 3.14-3.07 (m, 1H), 3.04-2.92 (m, 3H), 2.88 (dd, J=14.1, 6.1 Hz, 1H), 2.80 (dd, J=14.2, 7.3 Hz, 1H), 2.35-2.28 (m, 4H), 2.21 (dt, J=21.8, 7.4 Hz, 4H), 1.91-1.76 (m, 6H), 1.72 (p, J=6.5 Hz, 2H), 1.64-1.53 (m, 4H), 1.44 (dt, J=14.7, 7.4 Hz, 2H), 1.27 (s, 50H), 0.94 (t, J=7.4 Hz, 3H), 0.89 (t, J=7.0 Hz, 6H). $^{13}$C NMR (126 MHz, MeOD) δ 175.24, 174.95, 174.76, 171.98, 156.76, 152.19, 140.07, 136.02, 135.90, 129.48, 129.10, 126.94, 126.79, 124.11, 121.90, 115.50, 79.56, 79.30, 79.04, 71.97, 71.54, 71.52, 71.20, 71.15, 69.97, 65.02, 62.83, 56.34, 56.29, 52.95, 49.72, 43.66, 37.92, 36.34, 36.21, 35.26, 35.02, 33.72, 33.13, 30.88, 30.84, 30.81, 30.73, 30.71, 30.55, 30.52, 30.33, 30.26, 30.24, 27.89, 26.12, 26.09, 23.80, 23.47, 23.28, 14.55, 14.21. MS (ESI) calculated for C$_{80}$H$_{131}$N$_9$O$_{13}$S$_2$, m/z 1489.9308. found 1490.9570 (M+H)$^+$.

Synthesis of Compound 62

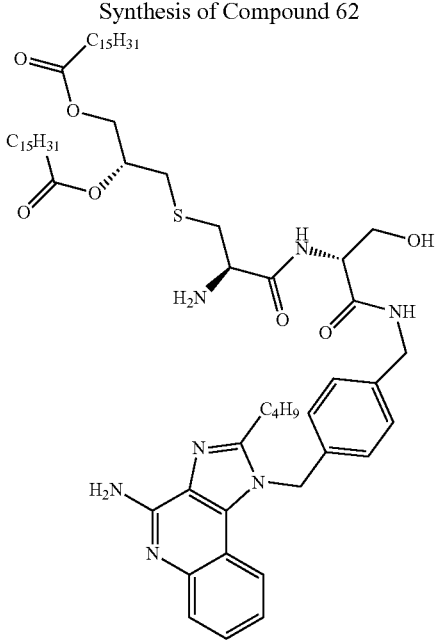

62

To a solution of compound 57 (60 mg, 0.07 mmol) in anhydrous DMF, were added triethylamine (24 µL, 0.18 mmol), HBTU (29 mg, 0.08 mmol) and 7d (30 mg, 0.07 mmol). The reaction mixture was stirred for 8 hours followed by removal of the solvent under vacuum to obtain the residue which was purified using column chromatography (8% MeOH/CH$_2$Cl$_2$) to obtain the compound 62 (26 mg, 34%). $^1$H NMR (500 MHz, CDCl$_3$) δ 10.79 (bs, 1H), 8.36 (d, J=37.2 Hz, 1H), 7.88 (t, 1H), 7.68 (t, 1H), 7.48 (t, J=5.7 Hz, 1H), 7.39 (s, 1H), 7.24 (d, J=6.7 Hz, 1H), 6.97 (d, J=7.0 Hz, 1H), 5.72 (s, 1H), 5.11 (s, 1H), 4.47-4.38 (m, 1H), 4.33 (d, J=9.5 Hz, 1H), 4.15-4.02 (m, 1H), 3.73-3.60 (m, 1H), 3.00 (s, 1H), 2.90-2.82 (m, 1H), 2.73-2.63 (m, 1H), 2.33-2.26 (m, 1H), 1.86-1.76 (m, 1H), 1.59 (s, 1H), 1.44 (dd, J=14.5, 7.3 Hz, 1H), 1.34-1.18 (m, 8H), 0.94 (t, J=7.2 Hz, 1H), 0.88 (t, J=6.9 Hz, 1H). $^{13}$C NMR (126 MHz, CDCl$_3$) δ 173.56, 173.45, 170.77, 156.66, 149.84, 138.59, 135.50, 134.73, 133.03, 129.56, 128.51, 125.64, 125.05, 124.96, 120.46, 119.84, 112.54, 70.25, 63.61, 62.30, 54.03, 48.89, 42.72, 34.29, 34.08, 32.77, 31.93, 29.72, 29.69, 29.67, 29.52, 29.37, 29.31, 29.14, 29.12, 26.96, 24.92, 24.86, 22.70, 22.38, 14.13, 13.72. MS (ESI) calculated for C$_{63}$H$_{101}$N$_7$O$_7$S, m/z 1099.7483. found 1100.7603 (M+H)$^+$.

Synthesis of Compound 63

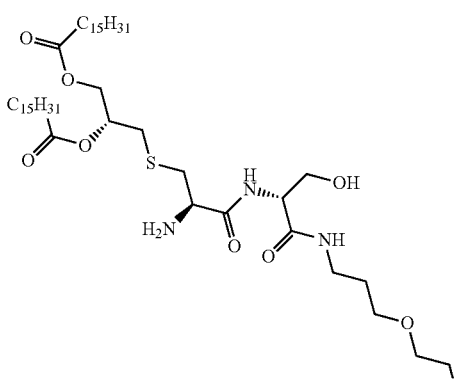

63

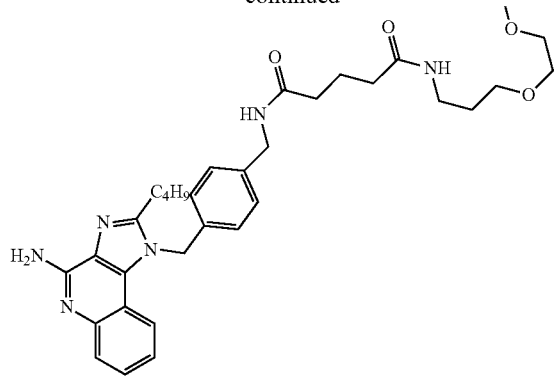

62 -continued

To a solution of compound 57 (40 mg, 0.05 mmol) in anhydrous DMF, were added triethylamine (16 µL, 0.12 mmol), HBTU (20 mg, 0.05 mmol) and 15 (37 mg, 0.05 mmol). The reaction mixture was stirred for 8 hours followed by removal of the solvent under vacuum to obtain the residue which was purified using column chromatography (10% MeOH/CH$_2$Cl$_2$) to obtain the compound 63 (16 mg, 24%). $^1$H NMR (500 MHz, CDCl$_3$) δ 15.18 (s, 1H), 10.33 (s, 1H), 9.05 (s, 1H), 7.89-7.58 (m, 3H), 7.58-7.33 (m, 2H), 7.34-7.15 (m, 2H), 7.03-6.82 (m, 2H), 5.98 (s, 1H), 5.71 (s, 2H), 5.14 (s, 1H), 4.45-4.25 (m, 5H), 4.06 (s, 2H), 3.90-3.35 (m, 18H), 3.30-2.64 (m, 12H), 2.37-2.10 (m, 7H), 2.03 (s, 3H), 1.86-1.50 (m, 11H), 1.41 (s, 2H), 1.24 (s, 44H), 0.95-0.83 (m, 9H). $^{13}$C NMR (126 MHz, CDCl$_3$) δ 173.68, 156.97, 149.61, 138.93, 135.59, 134.44, 132.80, 128.69, 125.55, 125.16, 120.70, 112.48, 69.88, 69.39, 63.72, 48.94, 35.14, 34.25, 34.03, 31.93, 29.73, 29.68, 29.56, 29.38, 29.16, 26.85, 24.90, 24.84, 22.69, 22.30, 14.13, 13.63. MS (ESI) calculated for C$_{78}$H$_{129}$N$_9$O$_{12}$S, m/z 1415.9481. found 1438.9406 (M+Na$^+$).

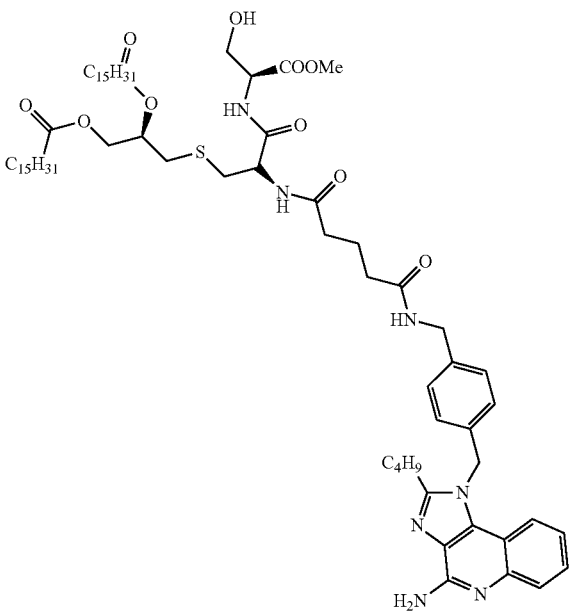

64

Synthesis of Compound 64

To a solution of compound 13 (50 mg, 0.09 mmol) in anhydrous DMF, were added triethylamine (30 μL, 0.22 mmol), HBTU (36 mg, 0.10 mmol) and 59 (77 mg, 0.09 mmol). The reaction mixture was stirred for 8 hours followed by removal of the solvent under vacuum to obtain the residue which was purified using column chromatography (6% MeOH/CH$_2$Cl$_2$) to obtain the compound 64 (40 mg, 33%). $^1$H NMR (500 MHz, CDCl$_3$) δ 7.92 (bs, 2H), 7.75 (d, J=8.1 Hz, 1H), 7.69 (t, J=8.3 Hz, 2H), 7.65-7.60 (m, 1H), 7.36 (dd, J=14.2, 7.0 Hz, 1H), 7.32-7.24 (m, 1H), 7.23-7.16 (m, 7H), 7.06-6.98 (m, 1H), 6.94 (dd, J=17.3, 6.3 Hz, 2H), 5.67 (s, 2H), 5.18-5.08 (m, 1H), 4.64-4.50 (m, 2H), 4.36-4.27 (m, 3H), 4.10 (dd, J=11.9, 6.3 Hz, 1H), 3.97-3.84 (m, 3H), 3.62 (d, J=8.7 Hz, 3H), 3.02-2.87 (m, 2H), 2.86-2.79 (m, 2H), 2.77-2.66 (m, 2H), 2.34-2.19 (m, 8H), 1.91 (s, 2H), 1.76 (dt, J=14.1, 7.1 Hz, 2H), 1.63-1.53 (m, 4H), 1.39 (dd, J=14.1, 6.7 Hz, 2H), 1.33-1.15 (m, 48H), 0.88 (dt, J=12.4, 4.4 Hz, 9H). $^{13}$C NMR (126 MHz, CDCl$_3$) δ 173.92, 173.86, 173.73, 173.69, 173.65, 173.54, 170.96, 170.80, 170.67, 157.21, 148.82, 142.53, 138.97, 135.91, 134.09, 132.80, 129.71, 128.66, 127.96, 125.64, 125.53, 125.46, 124.99, 124.61, 120.92, 119.35, 118.13, 112.70, 111.14, 70.35, 70.22, 63.72, 62.22, 55.04, 53.05, 52.66, 52.63, 52.44, 48.88, 42.83, 34.93, 34.75, 34.36, 34.21, 34.10, 33.57, 32.88, 32.02, 31.93, 29.72, 29.67, 29.55, 29.53, 29.37, 29.32, 29.16, 29.13, 26.85, 24.93, 24.89, 24.86, 22.70, 22.29, 21.55, 21.42, 14.14, 13.69. MS (ESI) calculated for C$_{69}$H$_{109}$N$_7$O$_{10}$S, m/z 1227.7957. found 1228.8095 (M+H)$^+$.

Synthesis of Compound 65

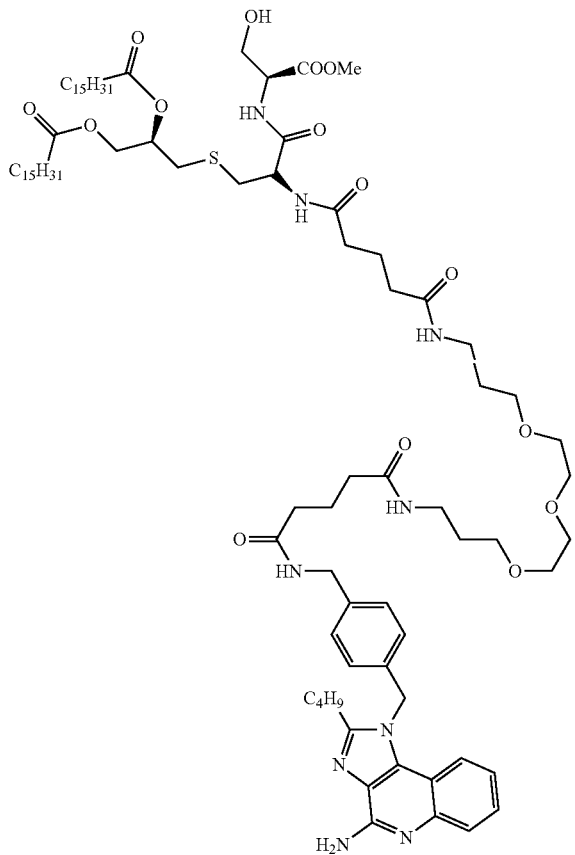

65

To a solution of compound 12 (37 mg, 0.05 mmol) in anhydrous DMF, were added triethylamine (16 μL, 0.12 mmol), HBTU (20 mg, 0.05 mmol) and 59 (42 mg, 0.05 mmol). The reaction mixture was stirred for 8 hours followed by removal of the solvent under vacuum to obtain the residue which was purified using column chromatography (18% MeOH/CH$_2$Cl$_2$) to obtain the compound 65 (20 mg, 28%). $^1$H NMR (500 MHz, CDCl$_3$) δ 7.82 (dd, J=15.3, 7.9 Hz, 1H), 7.70 (d, J=8.2 Hz, 1H), 7.45 (t, J=7.7 Hz, 1H), 7.24 (d, J=8.0 Hz, 1H), 7.15 (t, J=7.6 Hz, 1H), 6.98 (d, J=8.0 Hz, 1H), 6.70 (dd, J=11.6, 5.9 Hz, 1H), 5.71 (s, 1H), 5.15 (ddd, J=9.5, 6.3, 3.1 Hz, 1H), 4.75-4.67 (m, 1H), 4.58 (ddd, J=13.5, 7.2, 3.5 Hz, 1H), 4.38 (d, J=5.8 Hz, 1H), 4.32 (ddd, J=10.4, 7.2, 3.2 Hz, 1H), 4.15-4.09 (m, 1H), 4.05-3.94 (m, 1H), 3.90 (td, J=11.4, 2.8 Hz, 1H), 3.76-3.70 (m, 2H), 3.65-3.45 (m, 7H), 3.34-3.20 (m, 3H), 3.07 (dd, J=13.9, 6.9 Hz, 1H), 3.01-2.93 (m, 1H), 2.90-2.86 (m, 1H), 2.77-2.69 (m, 1H), 2.35-2.22 (m, 5H), 2.21-2.16 (m, 2H), 2.00-1.77 (m, 4H), 1.74-1.67 (m, 2H), 1.63-1.57 (m, 2H), 1.49-1.40 (m, 1H), 1.31-1.22 (m, 26H), 0.94 (t, J=7.4 Hz, 2H), 0.88 (t, J=6.9 Hz, 3H). $^{13}$C NMR (126 MHz, CDCl$_3$) δ 173.60, 173.54, 173.52, 173.32, 173.26, 173.13, 172.96, 172.86, 170.92, 170.68, 170.64, 170.56, 154.64, 150.89, 138.75, 134.26, 134.02, 128.55, 127.71, 126.28, 125.73, 122.92, 119.92, 114.54, 70.37, 70.30, 70.08, 69.87, 69.85, 69.83, 69.78, 69.51, 63.71, 62.46, 62.29, 55.27, 52.66, 52.54, 52.07, 48.68, 42.84, 37.74, 37.70, 37.56, 37.47, 35.47, 35.29, 35.05, 34.99, 34.75, 34.34, 34.10, 33.82, 33.11, 32.24, 31.93, 29.84, 29.72, 29.69, 29.67, 29.54, 29.52, 29.37, 29.32, 29.15, 29.13, 28.91, 28.89, 28.85, 27.10, 24.94, 24.91, 24.87, 22.70, 22.50, 22.02, 21.61, 21.48, 14.14, 13.79. MS (ESI) calculated for C$_{84}$H$_{137}$N$_9$O$_{15}$S, m/z 1543.9955. found 1545.0105 (M+H)$^+$.

REFERENCES

The following references are hereby incorporated herein in their entirety.

1. Kawai, T. and Akira, S. TLR signaling. *Semin. Immunol.* 2007, 19, 24-32.
2. Kumagai, Y.; Takeuchi, O.; and Akira, S. Pathogen recognition by innate receptors. *J. Infect. Chemother.* 2008, 14, 86-92.
3. Akira, S. Innate immunity to pathogens: diversity in receptors for microbial recognition. *Immunol. Rev.* 2009, 227, 5-8.
4. Akira, S.; Uematsu, S.; and Takeuchi, O. Pathogen recognition and innate immunity. *Cell* 2006, 124, 783-801.
5. Akira, S.; Takeda, K.; and Kaisho, T. Toll-like receptors: critical proteins linking innate and acquired immunity. *Nature Immunol.* 2001, 2, 675-680.
6. Cottalorda, A.; Verschelde, C.; Marcais, A.; Tomkowiak, M.; Musette, P.; Uematsu, S.; Akira, S.; Marvel, J.; and Bonnefoy-Berard, N. TLR2 engagement on CD8 T cells lowers the threshold for optimal antigen-induced T cell activation. *Eur. J. Immunol.* 2006, 36, 1684-1693.
7. Kaisho, T. and Akira, S. Toll-like receptors as adjuvant receptors. *Biochim. Biophys. Acta* 2002, 1589, 1-13.
8. Hood, J. D.; Warshakoon, H. J.; Kimbrell, M. R.; Shukla, N. M.; Malladi, S.; Wang, X.; and David, S. A. Immunoprofiling toll-like receptor ligands: Comparison of immunostimulatory and proinflammatory profiles in ex vivo human blood models. *Hum. Vaccin.* 2010, 6, 1-14.
9. Lee, J.; Chuang, T. H.; Redecke, V.; She, L.; Pitha, P. M.; Carson, D. A.; Raz, E.; and Cottam, H. B. Molecular basis for the immunostimulatory activity of guanine nucleoside analogs: activation of Toll-like receptor 7. *Proc. Natl. Acad. Sci. U.S.A* 2003, 100, 6646-6651.

10. Crozat, K. and Beutler, B. TLR7: A new sensor of viral infection. *Proc. Natl. Acad. Sci. U.S.A* 2004, 101, 6835-6836.
11. Diebold, S. S.; Kaisho, T.; Hemmi, H.; Akira, S.; and Reis e Sousa, C. Innate antiviral responses by means of TLR7-mediated recognition of single-stranded RNA. *Science* 2004, 303, 1529-1531.
12. Wierenga, W.; Skulnick, H. I.; Stringfellow, D. A.; Weed, S. D.; Renis, H. E.; and Eidson, E. E. 5-substituted 2-amino-6-phenyl-4(3H)-pyrimidinones. Antiviral- and interferon-inducing agents. *J. Med. Chem.* 1980, 23, 237-239.
13. Li, L. H.; Wallace, T. L.; Wierenga, W.; Skulnick, H. I.; and DeKoning, T. F. Antitumor activity of pyrimidinones, a class of small-molecule biological response modifiers. *J. Biol. Response Mod.* 1987, 6, 44-55.
14. Stringfellow, D. A. and Glasgow, L. A. Tilorone hydrochloride: an oral interferon-inducing agent. *Antimicrob. Agents Chemother.* 1972, 2, 73-78.
15. Stringfellow, D. A. Comparation interferon-inducing and antiviral properties of 2-amino-5-bromo-6-methyl-4-pyrimidinol (U-25,166), tilorone hydrochloride, and polyinosinic-polycytidylic acid. *Antimicrob. Agents Chemother.* 1977, 11, 984-992.
16. Hamilton, R. D.; Wynalda, M. A.; Fitzpatrick, F. A.; Teagarden, D. L.; Hamdy, A. H.; Snider, B. G.; Weed, S. D.; and Stringfellow, D. A. Comparison between circulating interferon and drug levels following administration of 2-amino-5-bromo-6-phenyl-4(3H)-pyrimidinone (ABPP) to different animal species. *J. Interferon Res.* 1982, 2, 317-327.
17. Gerster, J. F.; Lindstrom, K. J.; Miller, R. L.; Tomai, M. A.; Birmachu, W.; Bomersine, S. N.; Gibson, S. J.; lmbertson, L. M.; Jacobson, J. R.; Knafla, R. T.; Maye, P. V.; Nikolaides, N.; Oneyemi, F. Y.; Parkhurst, G. J.; Pecore, S. E.; Reiter, M. J.; Scribner, L. S.; Testerman, T. L.; Thompson, N. J.; Wagner, T. L.; Weeks, C. E.; Andre, J. D.; Lagain, D.; Bastard, Y.; and Lupu, M. Synthesis and structure-activity-relationships of 1H-imidazo[4,5-c]quinolines that induce interferon production. *J. Med. Chem.* 2005, 48, 3481-3491.
18. Miller, R. L.; Gerster, J. F.; Owens, M. L.; Slade, H. B.; and Tomai, M. A. Imiquimod applied topically: a novel immune response modifier and new class of drug. *Int. J. Immunopharmacol.* 1999, 21, 1-14.
19. Hemmi, H.; Kaisho, T.; Takeuchi, O.; Sato, S.; Sanjo, H.; Hoshino, K.; Horiuchi, T.; Tomizawa, H.; Takeda, K.; and Akira, S. Small anti-viral compounds activate immune cells via the TLR7 MyD88-dependent signaling pathway. *Nat. Immunol.* 2002, 3, 196-200.
20. Weterings, J. J.; Khan, S.; van der Heden van Noort G J; Melief, C. J.; Overkleeft, H. S.; van der Burg, S. H.; Ossendorp, F.; Van der Marel, G. A.; and Filippov, D. V. 2-Azidoalkoxy-7-hydro-8-oxoadenine derivatives as TLR7 agonists inducing dendritic cell maturation. *Bioorg. Med. Chem. Lett.* 2009, 19, 2249-2251.
21. Hirota, K.; Kazaoka, K.; Niimoto, I.; Kumihara, H.; Sajiki, H.; Isobe, Y.; Takaku, H.; To be, M.; Ogita, H.; Ogino, T.; Ichii, S.; Kurimoto, A.; and Kawakami, H. Discovery of 8-hydroxyadenines as a novel type of interferon inducer. *J. Med. Chem.* 2002, 45, 5419-5422.
22. Isobe, Y.; To be, M.; Ogita, H.; Kurimoto, A.; Ogino, T.; Kawakami, H.; Takaku, H.; Sajiki, H.; Hirota, K.; and Hayashi, H. Synthesis and structure-activity relationships of 2-substituted-8-hydroxyadenine derivatives as orally available interferon inducers without emetic side effects. *Bioorg. Med. Chem.* 2003, 11, 3641-3647.
23. Kurimoto, A.; Ogino, T.; Ichii, S.; Isobe, Y.; To be, M.; Ogita, H.; Takaku, H.; Sajiki, H.; Hirota, K.; and Kawakami, H. Synthesis and evaluation of 2-substituted 8-hydroxyadenines as potent interferon inducers with improved oral bioavailabilities. *Bioorg. Med. Chem.* 2004, 12, 1091-1099.
24. Shukla, N. M.; Kimbrell, M. R.; Malladi, S. S.; and David, S. A. Regioisomerism-dependent TLR7 agonism and antagonism in an imidazoquinoline. *Bioorg. Med. Chem. Lett.* 2009, 19, 2211-2214.
25. David, S. A.; Silverstein, R.; Amura, C. R.; Kielian, T.; and Morrison, D. C. Lipopolyamines: novel antiendotoxin compounds that reduce mortality in experimental sepsis caused by gram-negative bacteria. *Antimicrob. Agents Chemother.* 1999, 43, 912-919.
26. Miller, K. A.; Suresh Kumar, E. V. K.; Wood, S. J.; Cromer, J. R.; Datta, A.; and David, S. A. Lipopolysaccharide Sequestrants: Structural Correlates of Activity and Toxicity in Novel Acylhomospermines. *J. Med. Chem.* 2005, 48, 2589-2599.
27. Kawai, T. and Akira, S. Antiviral signaling through pattern recognition receptors. *J. Biochem.* 2007, 141, 137-145.
28. Warshakoon, H. J.; Hood, J. D.; Kimbrell, M. R.; Malladi, S.; Wu, W. Y.; Shukla, N. M.; Agnihotri, G.; Sil, D.; and David, S. A. Potential adjuvantic properties of innate immune stimuli. *Hum. Vaccin.* 2009, 5, 381-394.
29. Bachmann, M. F. and Jennings, G. T. Vaccine delivery: a matter of size, geometry, kinetics and molecular patterns. *Nat. Rev. Immunol.* 2010, 10, 787-796.
30. Zeng, W.; Ghosh, S.; Lau, Y. F.; Brown, L. E.; and Jackson, D. C. Highly immunogenic and totally synthetic lipopeptides as self-adjuvanting immunocontraceptive vaccines. *J. Immunol.* 2002, 169, 4905-4912.
31. Bettahi, I.; Zhang, X.; Afifi, R. E.; and BenMohamed, L. Protective immunity to genital herpes simplex virus type 1 and type 2 provided by self-adjuvanting lipopeptides that drive dendritic cell maturation and elicit a polarized Th1 immune response. *Viral Immunol.* 2006, 19, 220-236.
32. Abdel-Aal, A. B.; Batzloff, M. R.; Fujita, Y.; Barozzi, N.; Faria, A.; Simerska, P.; Moyle, P. M.; Good, M. F.; and Toth, I. Structure-activity relationship of a series of synthetic lipopeptide self-adjuvanting group a streptococcal vaccine candidates. *J. Med. Chem.* 2008, 51, 167-172.
33. Moyle, P. M. and Toth, I. Self-adjuvanting lipopeptide vaccines. *Curr. Med. Chem.* 2008, 15, 506-516.
34. Zeng, W.; Horrocks, K. J.; Robevska, G.; Wong, C. Y.; Azzopardi, K.; Tauschek, M.; Robins-Browne, R. M.; and Jackson, D. C. A modular approach to assembly of totally synthetic self-adjuvanting lipopeptide-based vaccines allows conformational epitope building. *J. Biol. Chem.* 2011.
35. Wilkinson, B. L.; Day, S.; Malins, L. R.; Apostolopoulos, V.; and Payne, R. J. Self-Adjuvanting Multicomponent Cancer Vaccine Candidates Combining Per-Glycosylated MUC1 Glycopeptides and the Toll-like Receptor 2 Agonist Pam(3) CysSer. *Angew. Chem. Int. Ed Engl.* 2011, 50, 1635-1639.
36. Zeng, W.; Ghosh, S.; Lau, Y. F.; Brown, L. E.; and Jackson, D. C. Highly immunogenic and totally synthetic lipopeptides as self-adjuvanting immunocontraceptive vaccines. *J. Immunol.* 2002, 169, 4905-4912.
37. Zeng, W.; Eriksson, E. M.; Lew, A.; and Jackson, D. C. Lipidation of intact proteins produces highly immunogenic vaccine candidates. *Mol. Immunol.* 2011, 48, 490-496.

38. Hill, B. G.; Reily, C.; Oh, J. Y.; Johnson, M. S.; and Landar, A. Methods for the determination and quantification of the reactive thiol proteome. *Free Radic. Biol. Med.* 2009, 47, 675-683.
39. Wenink, M. H.; Santegoets, K. C.; Broen, J. C.; van Bon, L.; Abdollahi-Roodsaz, S.; Popa, C.; Huijbens, R.; Remijn, T.; Lubberts, E.; van Riel, P. L.; van den Berg, W. B.; and Radstake, T. R. TLR2 promotes Th2/Th17 responses via TLR4 and TLR7/8 by abrogating the type I IFN amplification loop. *J. Immunol.* 2009, 183, 6960-6970.
40. Aliahmadi, E.; Gramlich, R.; Grutzkau, A.; Hitzler, M.; Kruger, M.; Baumgrass, R.; Schreiner, M.; Wittig, B.; Wanner, R.; and Peiser, M. TLR2-activated human langerhans cells promote Th17 polarization via IL-1 beta, TGF-beta and IL-23. *Eur. J. Immunol.* 2009, 39, 1221-1230.
41. Bracci, L.; La, S., V; Belardelli, F.; and Proietti, E. Type I interferons as vaccine adjuvants against infectious diseases and cancer. *Expert. Rev. Vaccines.* 2008, 7, 373-381.
42. Tovey, M. G.; Lallemand, C.; and Thyphronitis, G. Adjuvant activity of type I interferons. *Biol. Chem.* 2008, 389, 541-545.
43. Rajagopal, D.; Paturel, C.; Morel, Y.; Uematsu, S.; Akira, S.; and Diebold, S. S. Plasmacytoid dendritic cell-derived type I interferon is crucial for the adjuvant activity of Toll-like receptor δ agonists. *Blood.* 2010, 115, 1949-1957.
44. Berenson, L. S.; Ota, N.; and Murphy, K. M. Issues in T-helper 1 development—resolved and unresolved. *Immunol. Rev.* 2004, 202, 157-174.
45. Pulendran, B. Modulating TH1/TH2 responses with microbes, dendritic cells, and pathogen recognition receptors. *Immunol. Res.* 2004, 29, 187-196.
46. Gately, M. K. and Brunda, M. J. Interleukin-12: a pivotal regulator of cell-mediated immunity. *Cancer Treat. Res.* 1995, 80, 341-366.
47. Scott, P. and Trinchieri, G. IL-12 as an adjuvant for cell-mediated immunity. *Semin. Immunol.* 1997, 9, 285-291.
48. Eberl, M.; Beck, E.; Coulson, P. S.; Okamura, H.; Wilson, R. A.; and Mountford, A. P. IL-18 potentiates the adjuvant properties of IL-12 in the induction of a strong Th1 type immune response against a recombinant antigen. *Vaccine.* 2000, 18, 2002-2008.
49. Tough, D. F.; Zhang, X.; and Sprent, J. An IFN-gamma-dependent pathway controls stimulation of memory phenotype CD8+ T cell turnover in vivo by IL-12, IL-18, and IFN-gamma. *J. Immunol.* 2001, 166, 6007-6011.
50. Marshall, D. J.; Rudnick, K. A.; McCarthy, S. G.; Mateo, L. R.; Harris, M. C.; McCauley, C.; and Snyder, L. A. Interleukin-18 enhances Th1 immunity and tumor protection of a DNA vaccine. *Vaccine.* 2006, 24, 244-253.
51. Shukla, N. M.; Malladi, S. S.; Mutz, C. A.; Balakrishna, R.; and David, S. A. Structure-activity relationships in human toll-like receptor 7-active imidazoquinoline analogues. *J. Med. Chem.* 2010, 53, 4450-4465.
52. Wu, W.; Li, R.; Malladi, S. S.; Warshakoon, H. J.; Kimbrell, M. R.; Amolins, M. W.; Ukani, R.; Datta, A.; and David, S. A. Structure-activity relationships in toll-like receptor-2 agonistic diacylthioglycerol lipopeptides. *J. Med. Chem.* 2010, 53, 3198-3213.
53. David, S. A.; Smith, M. S.; Lopez, G.; Mukherjee, S.; Buch, S.; and Narayan, O. Selective transmission of R5-tropic HIV-1 from dendritic cells to resting CD4+ T cells. *AIDS Res. Human Retrovir.* 2001, 17, 59-68.
54. Jaini, R.; Kesaraju, P.; Johnson, J. M.; Altuntas, C. Z.; Jane-Wit, D.; and Tuohy, V. K. An autoimmune-mediated strategy for prophylactic breast cancer vaccination. *Nat. Med.* 2010, 16, 799-803.
55. Kaplan, C.; Valdez, J. C.; Chandrasekaran, R.; Eibel, H.; Mikecz, K.; Glant, T. T.; and Finnegan, A. Th1 and Th2 cytokines regulate proteoglycan-specific autoantibody isotypes and arthritis. *Arthritis Res.* 2002, 4, 54-58.
56. Pullen, G. R.; Fitzgerald, M. G.; and Hosking, C. S. Antibody avidity determination by ELISA using thiocyanate elution. *J. Immunol. Methods.* 1986, 86, 83-87.
57. Macdonald, R. A.; Hosking, C. S.; and Jones, C. L. The measurement of relative antibody affinity by ELISA using thiocyanate elution. *J. Immunol. Methods.* 1988, 106, 191-194.
58. Rappuoli, R. Conjugates and reverse vaccinology to eliminate bacterial meningitis. *Vaccine.* 2001, 19, 2319-2322.
59. Mawas, F.; Peyre, M.; Beignon, A. S.; Frost, L.; Del Giudice, G.; Rappuoli, R.; Muller, S.; Sesardic, D.; and Partidos, C. D. Successful induction of protective antibody responses against *Haemophilus influenzae* type b and diphtheria after transcutaneous immunization with the glycoconjugate polyribosyl ribitol phosphate-cross-reacting material 197 vaccine. *J. Infect. Dis.* 2004, 190, 1177-1182.
60. Broker, M.; Dull, P. M.; Rappuoli, R.; and Costantino, P. Chemistry of a new investigational quadrivalent meningococcal conjugate vaccine that is immunogenic at all ages. *Vaccine.* 2009, 27, 5574-5580.
61. Falugi, F.; Petracca, R.; Mariani, M.; Luzzi, E.; Mancianti, S.; Carinci, V.; Melli, M. L.; Finco, O.; Wack, A.; Di Tommaso, A.; De Magistris, M. T.; Costantino, P.; Del Giudice, G.; Abrignani, S.; Rappuoli, R.; and Grandi, G. Rationally designed strings of promiscuous CD4(+) T cell epitopes provide help to *Haemophilus influenzae* type b oligosaccharide: a model for new conjugate vaccines. *Eur. J. Immunol.* 2001, 31, 3816-3824.
62. Costantino, P.; Viti, S.; Podda, A.; Velmonte, M. A.; Nencioni, L.; and Rappuoli, R. Development and phase 1 clinical testing of a conjugate vaccine against meningococcus A and C. *Vaccine.* 1992, 10, 691-698.
63. Avci, F. Y. and Kasper, D. L. How bacterial carbohydrates influence the adaptive immune system. *Annu. Rev. Immunol.* 2010, 28:107-30., 107-130.
64. Kalka-Moll, W. M.; Tzianabos, A. O.; Bryant, P. W.; Niemeyer, M.; Ploegh, H. L.; and Kasper, D. L. Zwitterionic polysaccharides stimulate T cells by MHC class II-dependent interactions. *J. Immunol.* 2002, 169, 6149-6153.
65. Gallorini, S.; Berti, F.; Mancuso, G.; Cozzi, R.; Tortoli, M.; Volpini, G.; Telford, J. L.; Beninati, C.; Maione, D.; and Wack, A. Toll-like receptor 2 dependent immunogenicity of glycoconjugate vaccines containing chemically derived zwitterionic polysaccharides. *Proc. Natl. Acad. Sci. U.S.A.* 2009, 106, 17481-17486.
66. Gallorini, S.; Berti, F.; Parente, P.; Baronio, R.; Aprea, S.; D'Oro, U.; Pizza, M.; Telford, J. L.; and Wack, A. Introduction of zwitterionic motifs into bacterial polysaccharides generates TLR2 agonists able to activate APCs. *J. Immunol.* 2007, 179, 8208-8215.
67. Costantino, P.; Viti, S.; Podda, A.; Velmonte, M. A.; Nencioni, L.; and Rappuoli, R. Development and phase 1 clinical testing of a conjugate vaccine against meningococcus A and C. *Vaccine.* 1992, 10, 691-698.
68. Fiume, L. and Di Stefano, G. Lactosaminated human albumin, a hepatotropic carrier of drugs. *Eur. J. Pharm. Sci.* 2010, 40, 253-262.
69. Dosio, F.; Milla, P.; and Cattel, L. EC-145, a folate-targeted Vinca alkaloid conjugate for the potential treatment of folate receptor-expressing cancers. *Curr. Opin. Investig. Drugs* 2010, 11, 1424-1433.

70. Jaracz, S.; Chen, J.; Kuznetsova, L. V.; and Ojima, I. Recent advances in tumor-targeting anticancer drug conjugates. *Bioorg. Med. Chem.* 2005, 13, 5043-5054.
71. Lu, Y.; Sega, E.; Leamon, C. P.; and Low, P. S. Folate receptor-targeted immunotherapy of cancer: mechanism and therapeutic potential. *Adv. Drug Deliv. Rev.* 2004, 56, 1161-1176.
72. Botos, I.; Segal, D. M.; and Davies, D. R. The structural biology of Toll-like receptors. *Structure.* 2011, 19, 447-459.
73. Shukla, N. M.; Malladi, S. S.; Day, V.; and David, S. A. Preliminary evaluation of a 3H imidazoquinoline library as dual TLR7/TLR8 antagonists. *Bioorg. Med. Chem.* 2011, 19, 3801-3811.
74. Kimbrell, M. R.; Warshakoon, H.; Cromer, J. R.; Malladi, S.; Hood, J. D.; Balakrishna, R.; Scholdberg, T. A.; and David, S. A. Comparison of the immunostimulatory and proinflammatory activities of candidate Gram-positive endotoxins, lipoteichoic acid, peptidoglycan, and lipopeptides, in murine and human cells. *Immunol. Lett.* 2008, 118, 132-141.
75. Matsumoto, M.; Funami, K.; Oshiumi, H.; and Seya, T. Toll-like receptor 3: a link between toll-like receptor, interferon and viruses. *Microbiol. Immunol.* 2004, 48, 147-154.
76. Hoebe, K. and Beutler, B. LPS, dsRNA and the interferon bridge to adaptive immune responses: Trif, Tram, and other TIR adaptor proteins. *J. Endotoxin. Res.* 2004, 10, 130-136.
77. Sen, G. C. and Sarkar, S, N. Transcriptional signaling by double-stranded RNA: role of TLR3. *Cytokine Growth Factor Rev.* 2005, 16, 1-14.
78. Sioud, M. Innate sensing of self and non-self RNAs by Toll-like receptors. *Trends Mol. Med.* 2006, 12, 167-176.
79. Kawai, T. and Akira, S. Antiviral signaling through pattern recognition receptors. *J. Biochem.* 2007, 141, 137-145.
80. Uematsu, S, and Akira, S. Toll-like receptors and Type I interferons. *J. Biol. Chem.* 2007, 282, 15319-15323.
81. Kuznik, A.; Bencina, M.; Svajger, U.; Jeras, M.; Rozman, B.; and Jerala, R. Mechanism of endosomal TLR inhibition by antimalarial drugs and imidazoquinolines. *J. Immunol.* 2011, 186, 4794-4804.
82. Lee, J.; Chuang, T. H.; Redecke, V.; She, L.; Pitha, P. M.; Carson, D. A.; Raz, E.; and Cottam, H. B. Molecular basis for the immunostimulatory activity of guanine nucleoside analogs: activation of Toll-like receptor 7. *Proc. Natl. Acad. Sci. U.S.A.* 2003, 100, 6646-6651.
83. Gorden, K. B.; Gorski, K. S.; Gibson, S. J.; Kedl, R. M.; Kieper, W. C.; Qiu, X.; Tomai, M. A.; Alkan, S. S.; and Vasilakos, J. P. Synthetic TLR agonists reveal functional differences between human TLR7 and TLR8. *J. Immunol.* 2005, 174, 1259-1268.
84. Gorski, K. S.; Waller, E. L.; Bjornton-Severson, J.; Hanten, J. A.; Riter, C. L.; Kieper, W. C.; Gorden, K. B.; Miller, J. S.; Vasilakos, J. P.; Tomai, M. A.; and Alkan, S. S. Distinct indirect pathways govern human NK-cell activation by TLR-7 and TLR-8 agonists. *Int. Immunol.* 2006, 18, 1115-1126.
85. Agnihotri, G.; Crall, B. M.; Lewis, T. C.; Day, T. P.; Balakrishna, R.; Warshakoon, H. J.; Malladi, S. S.; and David, S. A. Structure-activity relationships in toll-like receptor 2-agonists leading to simplified monoacyl lipopeptides. *J. Med. Chem.* 2011, 54, 8148-8160.
86. Salunke, D. B.; Shukla, N. M.; Yoo, E.; Crall, B. M.; Balakrishna, R.; Malladi, S. S.; and David, S. A. Structure-Activity Relationships in Human Toll-like Receptor 2-Specific Monoacyl Lipopeptides. *J. Med. Chem.* 2012.

The invention claimed is:

1. An imidazoquinoline derived compound of Formula I or pharmaceutically acceptable salt thereof, wherein Formula I has the structure:

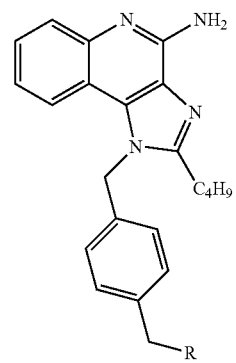

wherein, R is selected from the group consisting of: —NH ($R_5$) and isothiocyanate;

$R_5$ is selected from the group consisting of hydrogen, acetyl, —CO-tert-Bu (-Boc), —CO—$(CH_2)_x$—$R_6$, $C_1$-$C_{16}$ alkyl, —CO-4-(phenylboronic acid), —C(S)—NH—$(CH_2)_x$—NH—$(CH_2)_x$—NH—$(CH_2)_x$—$NH_2$,

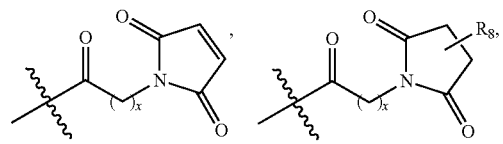

a reporter moiety, a tissue-specific moiety, a peptide antigen moiety, a protein antigen moiety, a polysaccharide antigen moiety, and a TLR2 agonist moiety;

$R_6$ is selected from the group consisting of hydrogen, alkyne, azido, carboxylic acid, and —CONH—$(CH_2)_x$—O—$(CH_2)_x$—O—$(CH_2)_x$—O—$(CH_2)_x$—$R_7$;

$R_7$ is selected from the group consisting of amino, isothiocyanate, and —NH—CO—$(CH_2)_x$—$CO_2H$;

$R_8$ is selected from a peptide antigen moiety or a protein antigen moiety; and x is any integer from 1 to 10.

2. The imidazoquinoline derived compound of claim 1, wherein the compound is chosen from the compound 1-(4-(Aminomethyl)benzyl)-2-butyl-1H-imidazo[4,5-c]quinolin-4-amine or pharmaceutically acceptable salts thereof. 3. The imidazoquinoline derived compound of claim 1, wherein the compound is chosen from: tert-butyl4-((4-amino-2-butyl-1H-imidazo[4,5-c]quinolin-1-yl)methyl)benzylcarbamate, 1-(4-(Aminomethyl)benzyl)-2-butyl-1H-imidazo[4,5-c]quinolin-4-amine, 2-Butyl-1-(4-(isothiocyanatomethyl)benzyl)-1H-imidazo[4,5-c]quinolin-4-amine, 1-(4-((4-amino-2-butyl-1H-imidazo[4,5-c]quinolin-1-yl)methyl)phenyl)-3,7,23-trioxo-12,15,18-trioxa-2,8,22-triazaheptacosan-27-oic acid, 5-(((4((4-amino-2-butyl-1H-imidazo[4,5-c]quinolin-1-yl)methyl)benzyl)amino)-5-oxopentanoic acid, $N^1$-(4-((4-amino-2-butyl-1H-imidazo[4,5-c]quinolin-1-yl)methyl)benzyl)-$N^5$-(3-(2-(2-(3-aminopropoxy)ethoxy)ethoxy)propyl)glutaramide (14), $N^1$-(4-((4-amino-2-butyl-1H-imidazo[4,5-c]quinolin-1-yl)methyl)benzyl)-$N^5$-(3-(2-(2-(3-isothiocyanatopropoxy)ethoxy)ethoxy)propyl)glutaramide, N-(4-((4-amino-2-butyl-1H-imidazo[4,5-c]quinolin-1-yl)methyl)benzyl)palmitamide, 2-butyl-1-(4-((hexadecylamino)methyl)benzyl)-1H-imidazo[4,5-c]quinolin-4-amine, N-(4-((4-amino-2-butyl-1H-imidazo[4,5-c]quinolin-1-yl)methyl)benzyl)-2-azidoacetamide, N-(4-((4-amino-2-butyl-1H-imidazo[4,5-c]quinolin-1-yl)methyl)benzyl)pent-4-ynamide, N-(4-((4-amino-2-butyl-1H-imidazo[4,5-c]quinolin-1-yl)methyl)benzyl)-3-(2,5-dioxo-2,5-dihydro-1H-pyrrol-1-yl)propanamide, (4(4-((4-amino-2-butyl-1H-imidazo[4,5-c]quinolin-1-yl)methyl)benzyl)carbamoyl)phenyl)boronic acid, 1-(4-((4-amino-2-butyl-1H-imidazo[4,5-c]quinolin-1-yl)methyl)benzyl)-3-(3-((4-((3-aminopropyl)amino)butyl)amino)propyl)thiourea, 2-(3-(4-((4-Amino-2-butyl-1H-imidazo[4,5-c]quinolin-1-yl)methyl)benzyl)thioureido)-6-(6-hydroxy-3-oxo-3H-xanthen-9-yl)benzoic acid, N-(9-(4-(3-(4-((4-amino-2-butyl-1H-imidazo[4,5-c]quinolin-1-yl)methyl)benzypthioureido)-2-carboxyphenyl)-6-(diethylamino)-3H-xanthen-3-ylidene)-N-ethylethanaminium, 5-(((4-(4,4-difluoro-5-(2-thienyl)-4-bora-3a,4a-diaza-s-indacene-3-yl)phenoxy)acetyl)amino) pentylamine, hydrochloride conjugate of 2-Butyl-1-(4-(isothiocyanatomethyl)benzyl)-1H-imidazo[4,5-c]quinolin-4-amine, Methyl 1-(4-((4-amino-2-butyl-1H-imidazo[4,5-c]quinolin-1-yl)methyl)phenyl)-6,9-dioxo-3-thioxo-2,4,7,10-tetraazadodecan-12-oate,

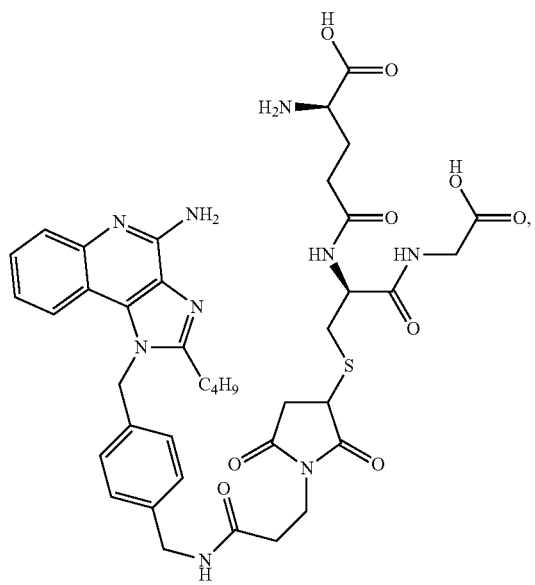

(2R)-methyl 2-amino-5-((2S)-3-(1-(3-(4-((4-amino-2-butyl-1H-imidazo[4,5-c]quinolin-1-yl)methyl)benzylamino)-3-oxopropyl)-2,5-dioxopyrrolidin-3-ylthio)-1-(2-methoxy-2-oxoethylamino)-1-oxopropan-2-ylamino)-5-oxopentanoate, compound 31, N-(4-((4-amino-2-butyl-1H-imidazo[4,5-c]quinolin-1-yl)methyl)benzyl)-N-((2R,3S,4R)-2,3,4,5,6-pentahydroxyhexyl)acetamide, 5-((4-((4-amino-2-butyl-1H-imidazo[4,5-c]quinolin-1-yl)methyl)benzyl) amino)-2-(4-(((2-amino-4-oxo-3,4-dihydropteridin-6-yl)methyl)amino)benzamido)-5-oxopentanoic acid, N-(4-((4-amino-2-butyl-1H-imidazo[4,5-c]quinolin-1-yl)methyl)benzyl)-5-((3aR, 4R,6aS)-2-oxohexahydro-1H-thieno[3,4-d]imidazol-4-yl) pentanamide, 4-(((4-((4-amino-2-butyl-1H-imidazo[4,5-c]quinolin-1-yl)methyl)benzypamino)methyl)-5-(hydroxymethyl)-2-methylpyridin-3-ol,

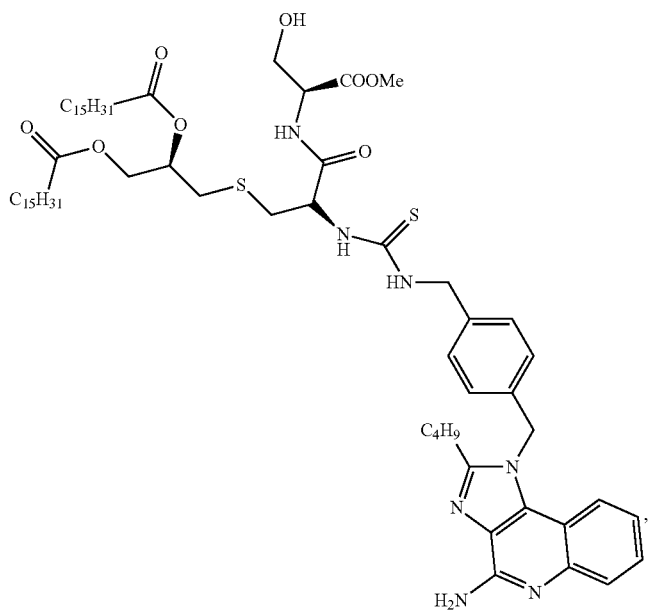

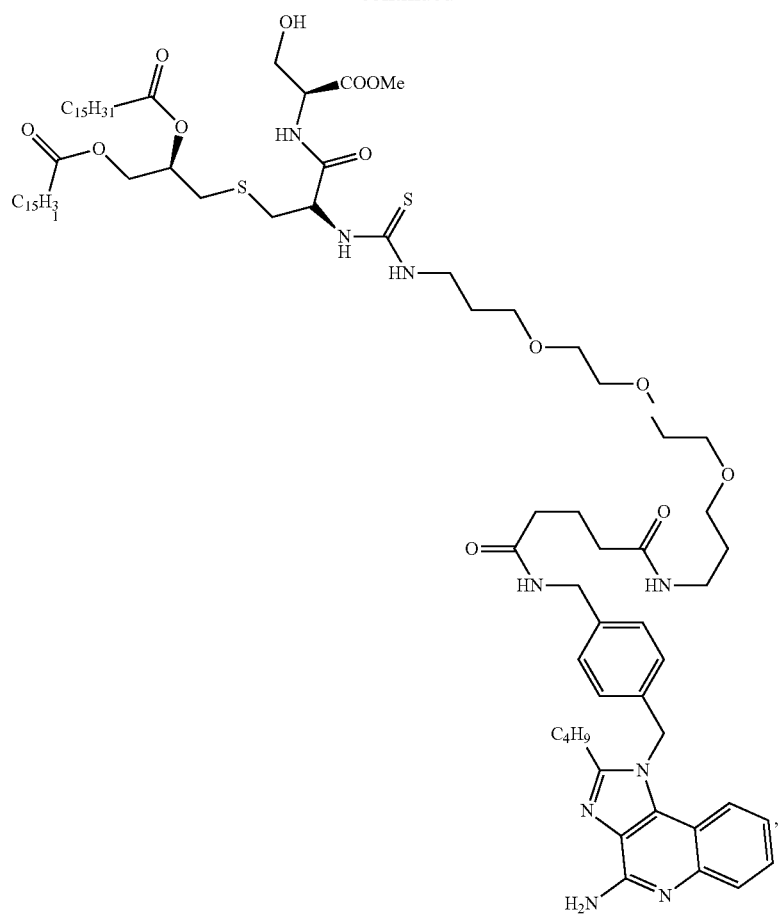
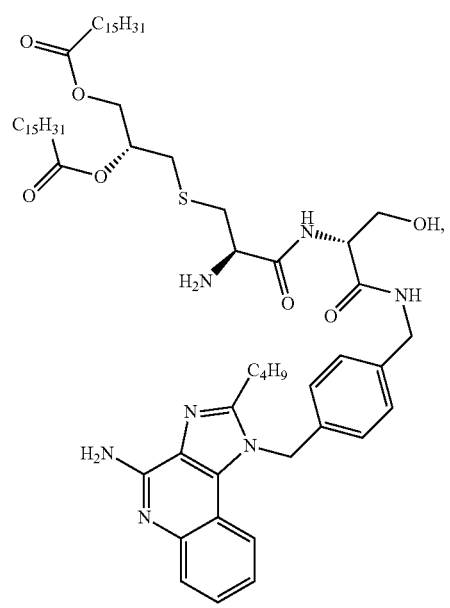

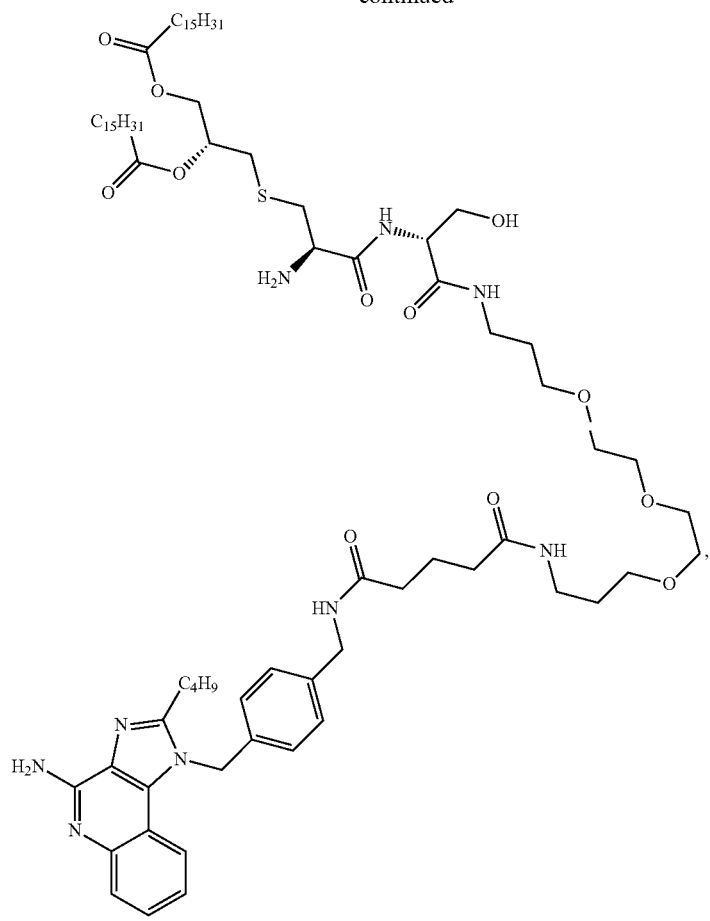
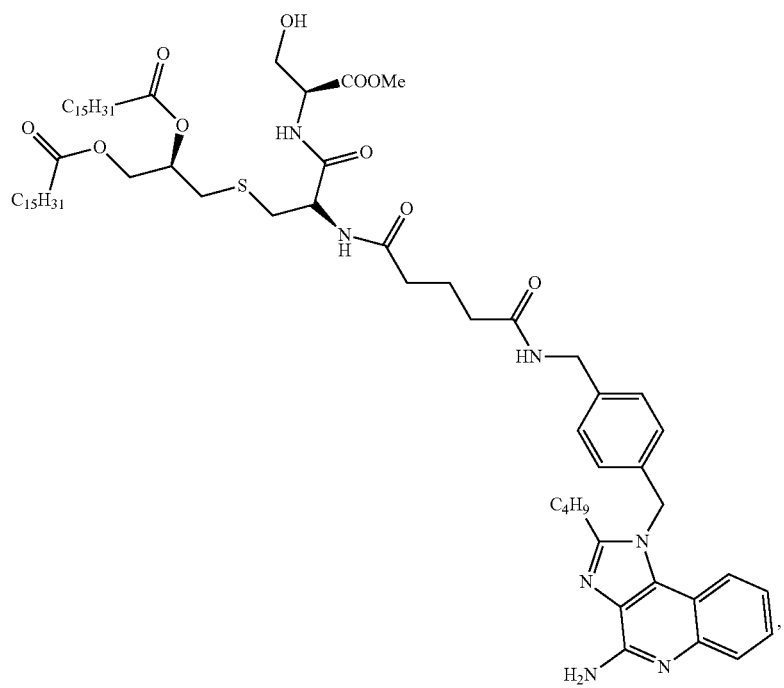

-continued

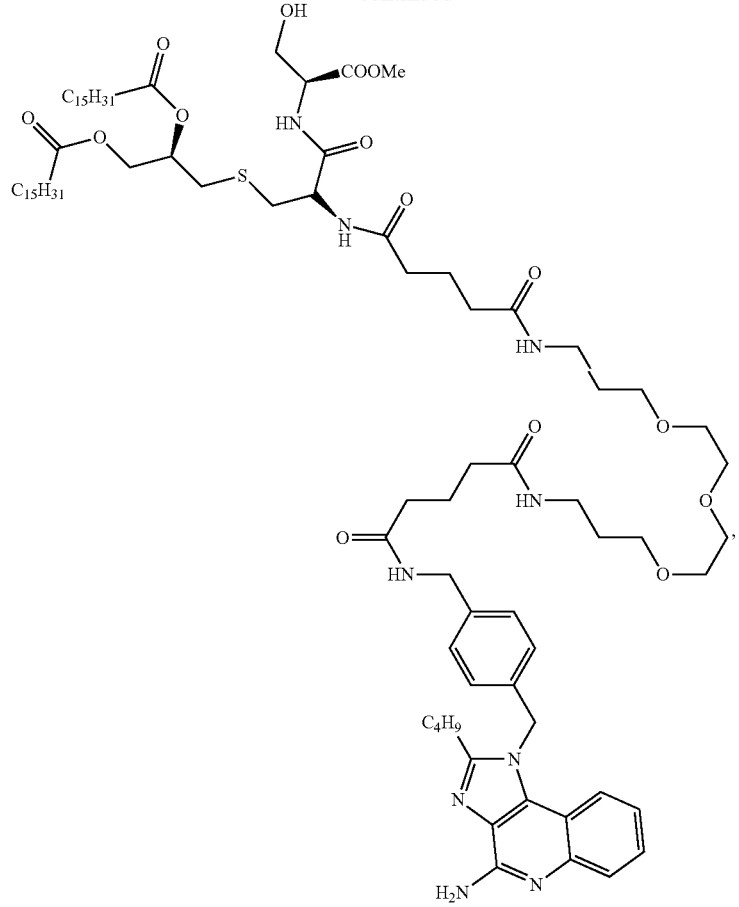

or pharmaceutically acceptable salts thereof.

4. The imidazoquinoline derived compound of claim 1, wherein the compound is capable of activating Toll-like receptor (TLR) 7.

5. The imidazoquinoline derived compound of claim 4, wherein the compound is chosen from tert-butyl 3-((4-amino-2-butyl-1H-imidazo[4,5-c]quinolin-1-yl)methyl)benzylcarbamate, tert-butyl 4-((4-amino-2-butyl-1H-imidazo[4,5-c]quinolin-1-yl)methyl)benzylcarbamate, 1-(3-(Aminomethyl)benzyl)-2-butyl-1H-imidazo[4,5-c]quinolin-4-amine, 1-(4-(Aminomethyl)benzyl)-2-butyl-1H-imidazo[4,5-c]quinolin-4-amine, 2-Butyl-1-(4-(isothiocyanatomethyl)benzyl)-1H-imidazo[4,5-c]quinolin-4-amine, 1-(4-((4-amino-2-butyl-1H-imidazo[4,5-c]quinolin-1-yl)methyl)phenyl)-3,7,23-trioxo-12,15,18-trioxa-2,8,22-triazaheptacosan-27-oic acid, 5-((4-((4-amino-2-butyl-1H-imidazo[4,5-c]quinolin-1-yl)methyl)benzyl)amino)-5-oxopentanoic acid, $N^1$-(4((4-amino-2-butyl-1H-imidazo[4,5-c]quinolin-1-yl)methyl)benzyl)-$N^5$-(3(2-(2-(3-aminopropoxy)ethoxy)ethoxy)propyl)glutaramide, $N^1$-(4((4-amino-2-butyl-1H-imidazo[4,5-c]quinolin-1-yl)methyl)benzyl)-$N^5$-(3-(2-(2-(3-isothiocyanatopropoxy)ethoxy)ethoxy)propyl)glutaramide, N-(4-((4-amino-2-butyl-1H-imidazo[4,5-c]quinolin-1-yl)methyl)benzyl)palmitamide, 2-butyl-1-(4-((hexadecylamino)methyl)benzyl)-1H-imidazo[4,5-c]quinolin-4-amine, N-(4-((4-amino-2-butyl-1H-imidazo[4,5-c]-quinolin-1-yl)methyl)benzyl)-2-azidoacetamide, N-(4-((4-amino-2-butyl-1H-imidazo[4,5-c]quinolin-1-yl)methyl)benzyl)pent-4-ynamide, N-(4-((4-amino-2-butyl-1H-imidazo[4,5- c]quinolin-1-yl)methyl) benzyl)-3-(2,5-dioxo-2,5-dihydro-1H-pyrrol-1-yl)propanamide, (4-((4-(((4-amino-2-butyl-1H-imidazo[4,5-c]quinolin-1-yl) methyl)benzyl)carbamoyl)phenyl)boronic acid, 1-(4-((4-amino-2-butyl-1H-imidazo[4,5-c]quinolin-1-yl)methyl) benzyl)-3-(3-((4-((3-aminopropyl)amino)butyl)amino) propyl)thiourea, 2-(3-(4-((4-Amino-2-butyl-1H-imidazo [4,5-c]quinolin-1-yl)methyl)benzyl)thioureido)-6-(6-hydroxy-3-oxo-3H-xanthen-9-yl)benzoic acid, N-(9-(4-(3-(4-((4-amino-2-butyl-1H-imidazo[4,5-c]quinolin-1-yl)methyl) benzyl)thioureido)-2-carboxyphenyl)-6-(diethylamino)-3H-xanthen-3-ylidene)-N-ethylethanaminium, 5-(((4-(4,4-difluoro-5-(2-thienyl)-4-bora-3a,4a-diaza-s-indacene-3-yl) phenoxy)acetyl)amino)pentylamine, hydrochloride conjugate of 2-Butyl-1-(4-(isothiocyanatomethyl)benzyl)-1H-imidazo[4,5-c]quinolin-4-amine, (2R)-methyl 2-amino-5-((2S)-3-(1-(3-(4-((4-amino-2-butyl-1H-imidazo[4,5-c] quinolin-1-yl)methyl)benzylamino)-3-oxopropyl)-2,5-dioxopyrrolidin-3-ylthio)-1-(2-methoxy-2-oxoethylamino)-1-oxopropan-2-ylamino)-5-oxopentanoate,

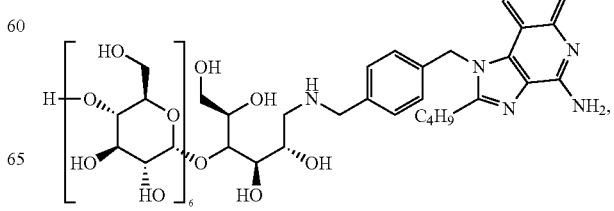

137

N-(4-((4-amino-2-butyl-1H-imidazo[4,5-c]quinolin-1-yl)methyl)benzyl)-N-((2R,3S,4R)-2,3,4,5,6-pentahydroxyhexyl)acetamide, 5-((4-((4-amino-2-butyl-1H-imidazo[4,5-c]quinolin-1-yl)methyl)benzyl) amino)-2-(4-(((2-amino-4-oxo-3,4-dihydropteridin-6-yl)methyl)amino)benzamido)-5-oxopentanoic acid, N-(4-((4-amino-2-butyl-1H-imidazo[4,

138

5-c]quinolin-1-yl)methyl)benzyl)-5-((3aR,4R,6aS)-2-oxohexahydro-1H-thieno[3,4-d]imidazol-4-yl)pentanamide, 4-(((4-((4-amino-2-butyl-1H-imidazo[4,5-c]quinolin-1-yl)methyl)benzyl)amino)methyl)-5-(hydroxymethyl)-2-methylpyridin-3-ol,

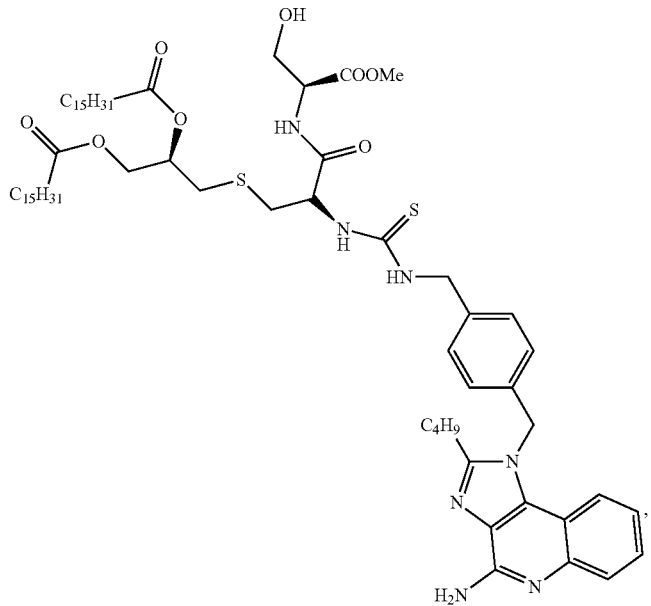

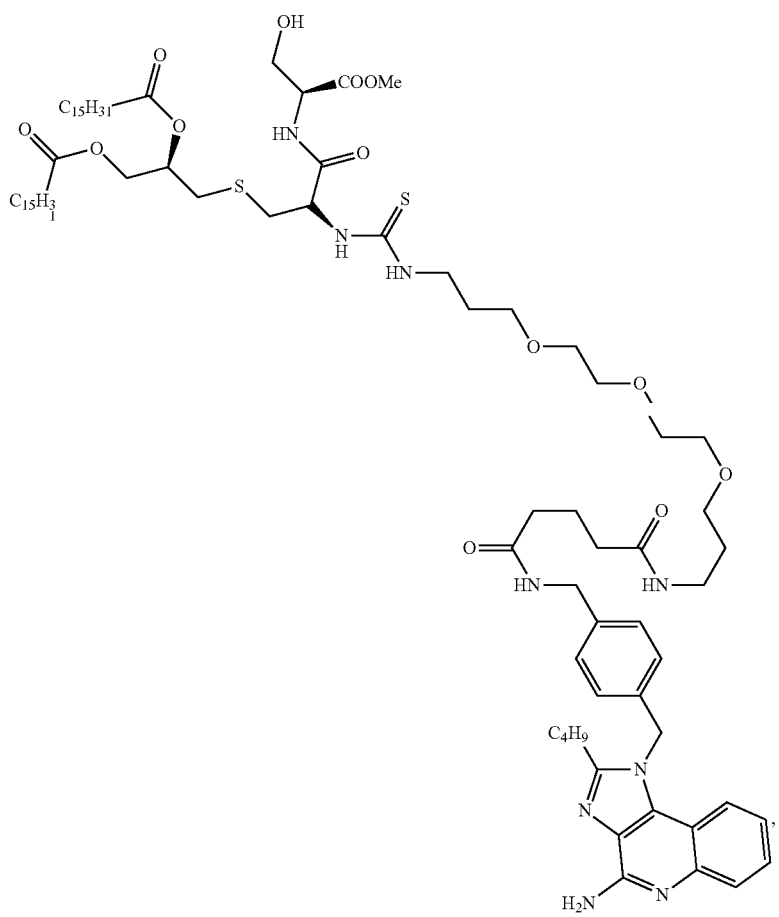

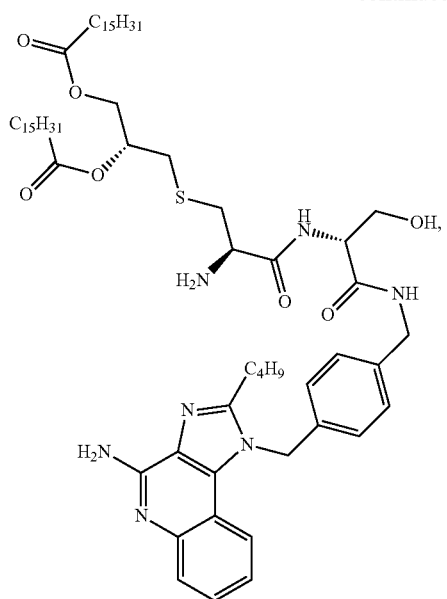
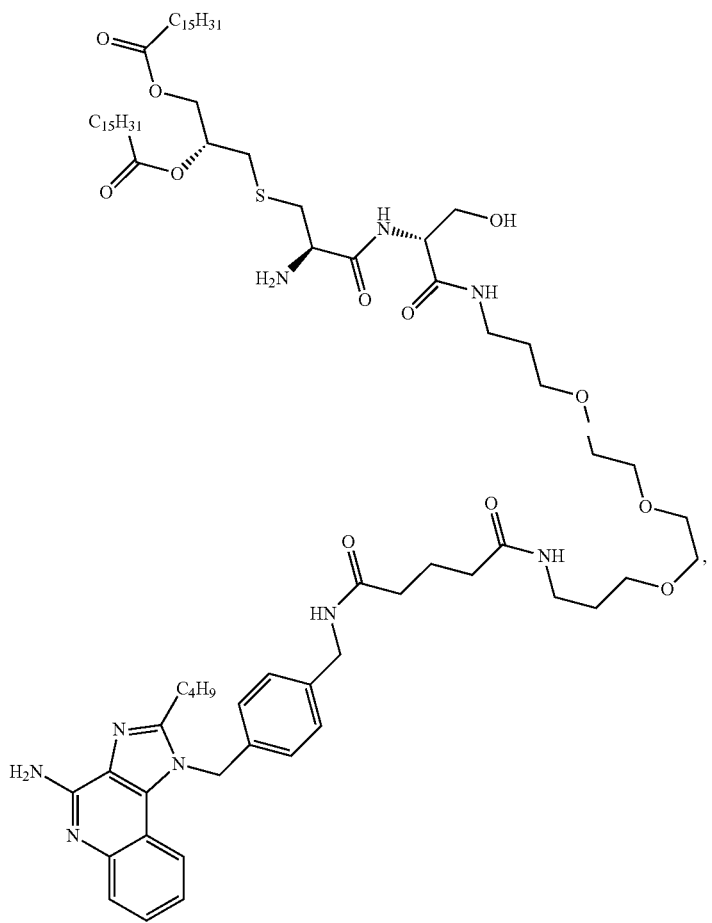

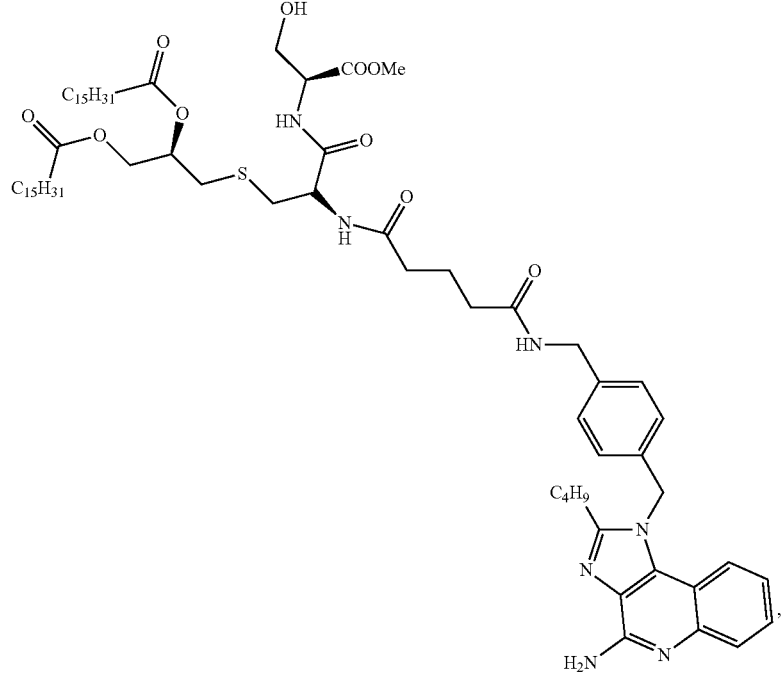
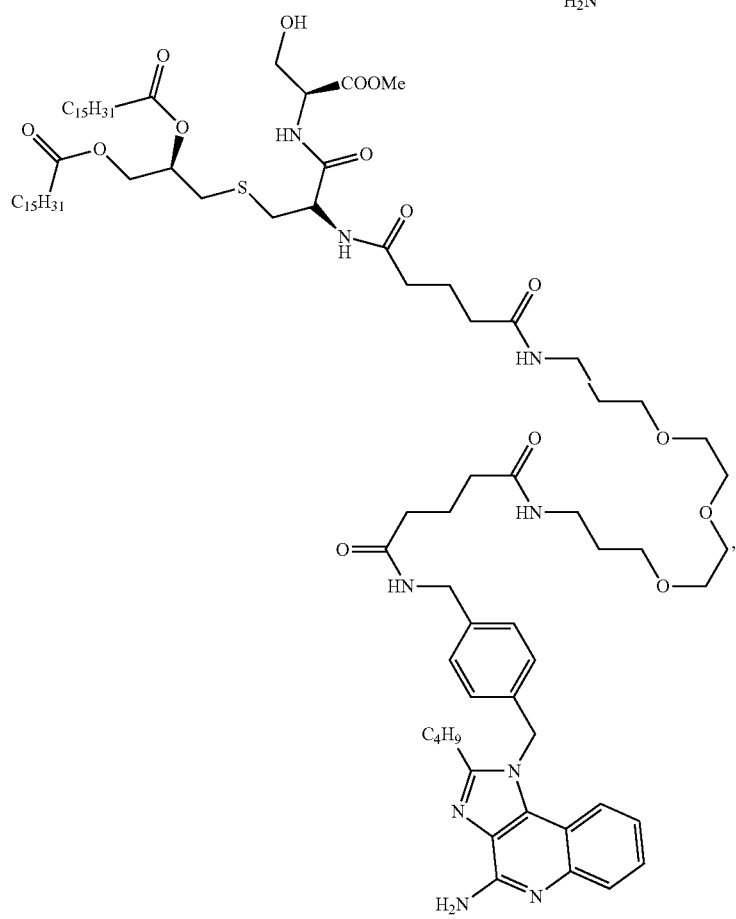
or pharmaceutically acceptable salts thereof.
6. The imidazoquinoline derived compound of claim 1, wherein the compound is capable of activating TLR7 and TLR8.
7. The imidazoquinoline derived compound of claim 6, wherein the compound is chosen from 1-(3-(Aminomethyl)benzyl)-2-butyl-1H-imidazo[4,5-c]quinolin-4-amine, 1-(4-(Aminomethyl)benzyl)-2-butyl-1H-imidazo[4,5-c]quinolin- 4-amine, N-(4-((4-amino-2-butyl-1H-imidazo[4,5-c]quinolin-1-yl)methyl)benzyl)pent-4-ynamide, 5-((4-((4-amino-2-butyl-1H-imidazo[4,5-c]quinolin-1-yl)methyl)benzyl) amino)-2-(4-(((2-amino-4-oxo-3,4-dihydropteridin-6-yl)methyl)amino)benzamido)-5-oxopentanoic acid, 4-(((4-((4-amino-2-butyl-1H-imidazo[4,5-c]quinolin-1-yl)methyl)benzyl)amino)methyl)-5-(hydroxymethyl)-2-methylpyridin-3-ol, or pharmaceutically acceptable salts thereof.

8. The imidazoquinoline derived compound of claim 1, wherein the compound of Formula I is chosen from an isothiocyanate derivative of Formula I and a maleimide derivative of Formula I.

9. The imidazoquinoline derived compound of claim 1, wherein $R_5$ comprises a reporter moiety comprising a reporter molecule chosen from a fluorescent molecule, an MRI agent, or a combination thereof.

10. The imidazoquinoline derived compound of claim 9, wherein the compound is chosen from compounds 2-(3-(4-((4-Amino-2-butyl-1H-imidazo [4,5-c]quinolin-1-yl)methyl)benzyl)thioureido)-6-(6-hydroxy-3-oxo-3H-xanthen-9-yl)benzoic acid, N-(9-(4-(3-(4-((4-amino-2-butyl-1H-imidazo[4,5-c]quinolin-1-yl)methyl)benzyl)thioureido)-2-carboxyphenyl)-6-(diethylamino)-3H-xanthen-3-ylidene)-N-ethylethanaminium, 5-(((4-(4,4-difluoro-5-(2-thienyl)-4-bora-3a,4a-diaza-s-indacene-3--yl)phenoxy)acetyl)amino)pentylamine, hydrochloride conjugate of 2-Butyl-1-(4-(isothiocyanatomethyl)benzyl)-1H-imidazo[4,5-c]quinolin-4-amine, or pharmaceutically acceptable salts thereof.

11. The imidazoquinoline derived compound of claim 9, wherein the reporter molecule is selected from the group consisting of: fluorescein, rhodamine B, bora-diazaindacene dye, 5-(((4-(4,4-difluoro-5-(2-thienyl)-4-bora-3a,4a-diaza-s-indacene-3-yl)phenoxy)acetyl)amino)pentylamine, hydrochloride, and biotin.

12. The imidazoquinoline derived compound of claim 1, wherein $R_5$ comprises an antigen moiety chosen from a peptide antigen moiety, a protein antigen moiety, or a polysaccharide antigen moiety, and wherein the imidazoquinoline derived compound is capable of activating TLR7.

13. The imidazoquinoline derived compound of claim 12, wherein the protein antigen moiety comprises α-lactalbumin.

14. The imidazoquinoline derived compound of claim 12, wherein the polysaccharide antigen moiety comprises maltoheptaose.

15. The imidazoquinoline derived compound of claim 1, wherein $R_5$ comprises a tissue-specific moiety including a tissue-specific agent.

16. The imidazoquinoline derived compound of claim 15, wherein the tissue-specific agent is chosen from galactose, folic acid, biotin, or pyridoxal.

17. The imidazoquinoline derived compound of claim 14, wherein the compound is chosen from compounds N-(4-((4-amino-2-butyl-1H-imidazo[4,5-c]quinolin-1-yl)methyl)benzyl)-N-((2R,3S,4R)-2,3,4,5,6-pentahydroxyhexyl)acetamide, 5-((4-((4-amino-2-butyl-1H-imidazo[4,5-c]quinolin-1-yl)methyl)benzyl) amino)-2-(4-(((2-amino-4-oxo-3,4-dihydropteridin-6-yl)methyl)amino)benzamido)-5-oxopentanoic acid, N-(4-((4-amino-2-butyl-1H-imidazo[4,5-c]quinolin-1-yl)methyl)benzyl)-5-((3aR,4R,6aS)-2-oxohexahydro-1H-thieno[3,4-d]imidazol-4-yl)pentanamide, 4-(((4-((4-amino-2-butyl-1H-imidazo[4,5-c]quinolin-1-yl)methyl)benzyl)amino)methyl)-5-(hydroxymethyl)-2-methylpyridin-3-ol, or pharmaceutically acceptable salts thereof.

18. The imidazoquinoline derived compound of claim 1, wherein $R_5$ comprises a TLR2 agonist moiety including a TLR2 agonist, and wherein the imidazoquinoline derived compound is capable of dual activation of TLR2 and TLR7.

19. The imidazoquinoline derived compound of claim 18, wherein the TLR2 agonist is a S[2,3-bis(palmitoyloxy)-(2RS)-propyl]-R-cysteinyl-S-serine (PAM(2)CS) compound.

20. The imidazoquinoline derived compound of claim 18, wherein the compound is chosen from compounds

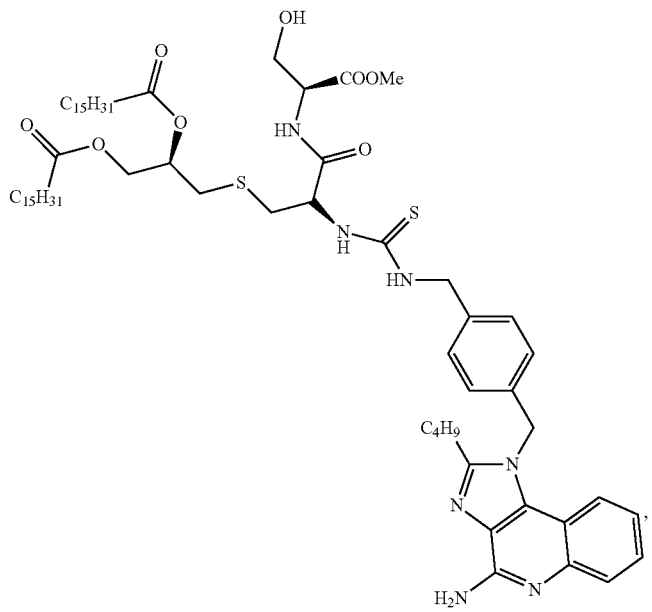

-continued
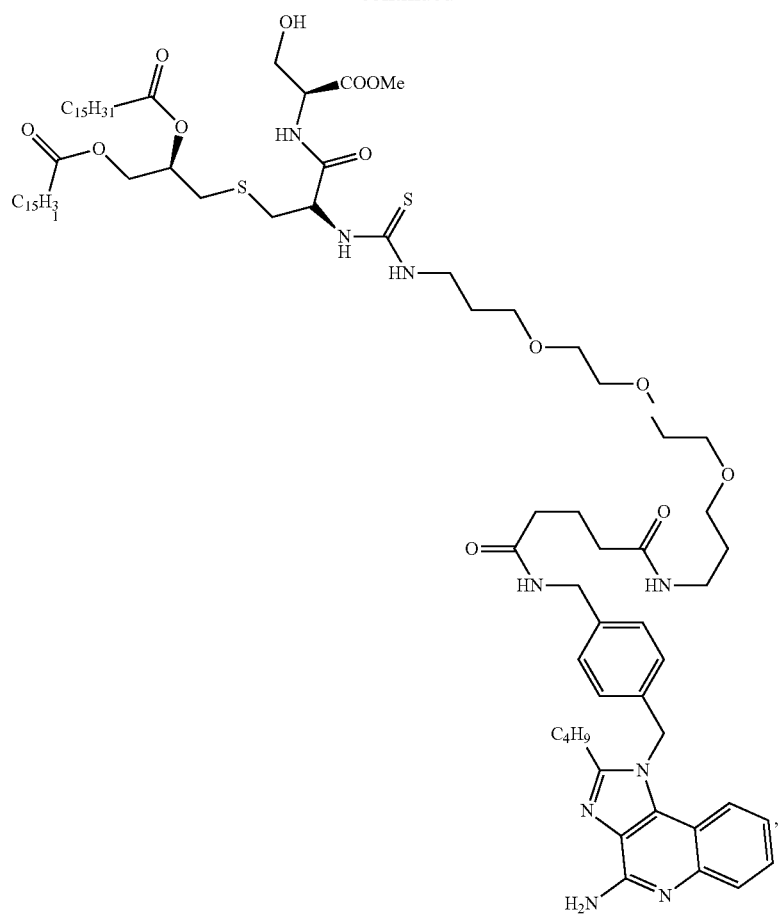
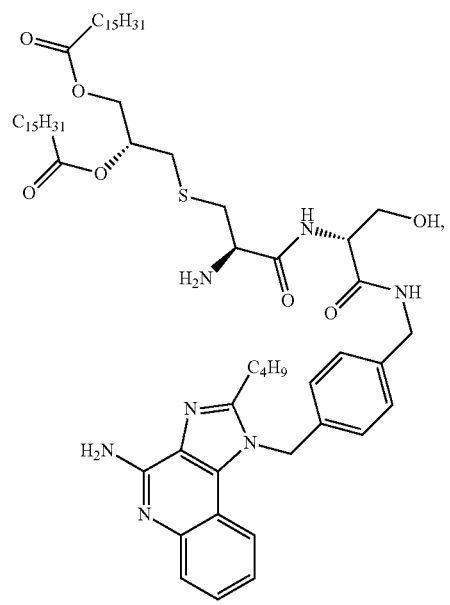

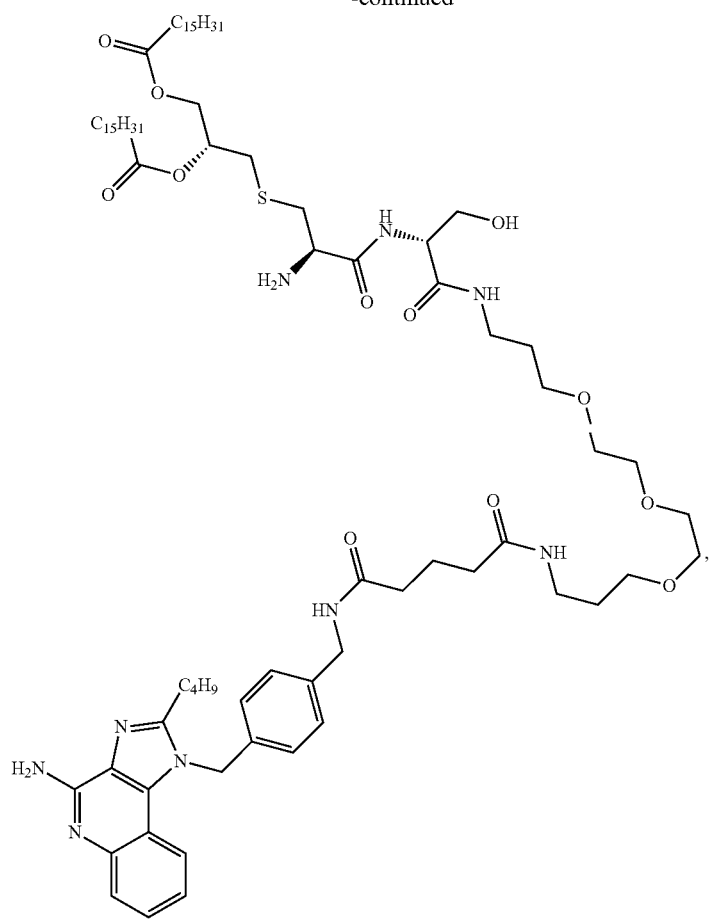
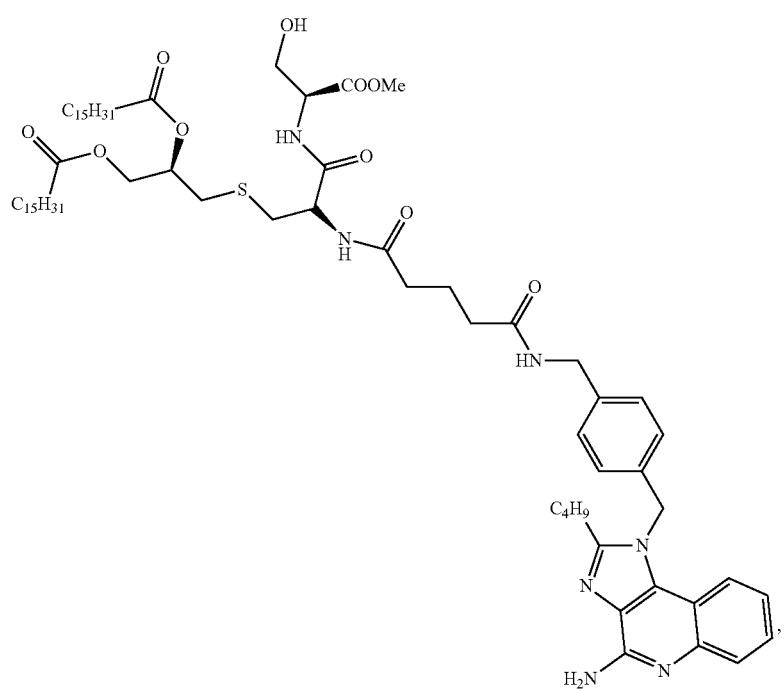

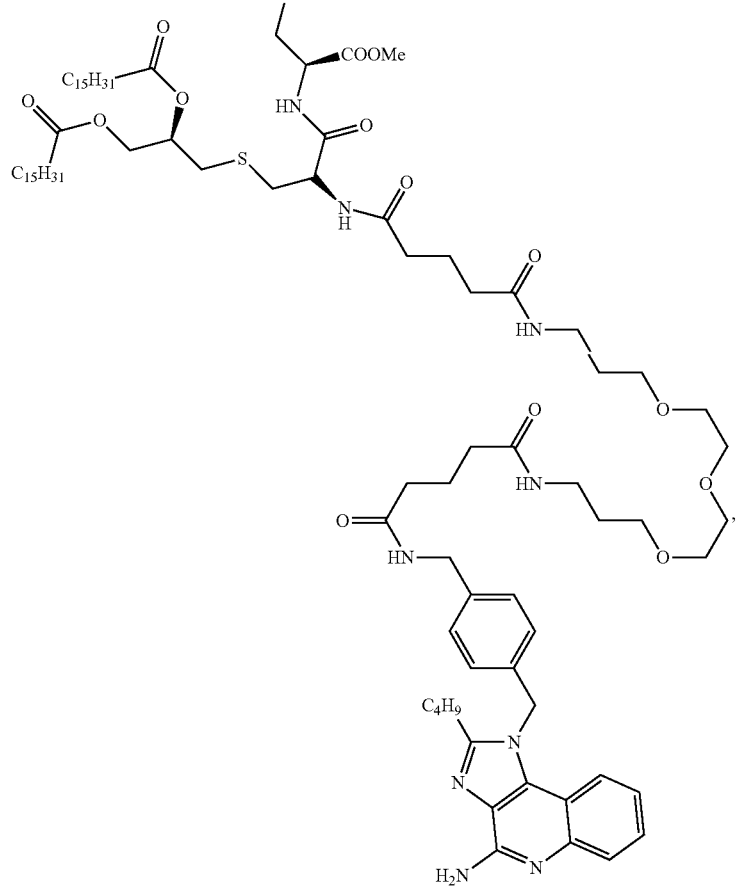

or pharmaceutically acceptable salts thereof.

21. An imidazoquinoline derived compound comprising a dimer or a dendrimer of a compound of Formula I, a compound of Formula II or pharmaceutically acceptable salts thereof, wherein Formula I

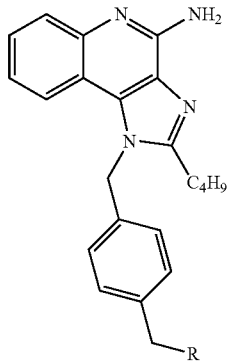

-continued

Formula II

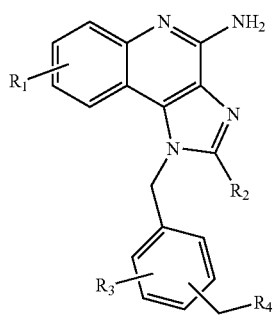

wherein, $R_1$ and $R_3$ are each independently selected from the group consisting of hydrogen, halogen, nitro, —$NH_2$, azido, hydroxyl, —$CF_3$, carboxylic acid and —$CO_2R_2$;

$R_2$ is a $C_2$-$C_5$ alkyl, and

R for Formula I and $R_4$ for Formula II are each independently selected from the group consisting of: —$NH(R_5)$ and isothiocyanate;

$R_5$ is selected from the group consisting of hydrogen, acetyl, —CO-tert-Bu (-Boc), —CO—$(CH_2)_x$—$R_6$, $C_1$-$C_{16}$ alkyl, —CO-4-(phenylboronic acid), —C(S)—NH—$(CH_2)_x$—NH—$(CH_2)_x$—NH—$(CH_2)_x$—$NH_2$,

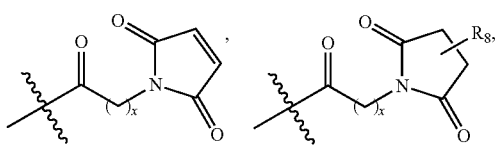

a reporter moiety, a tissue-specific moiety, a peptide antigen moiety, a protein antigen moiety, a polysaccharide antigen moiety, and a TLR2 agonist moiety;

$R_6$ is selected from the group consisting of hydrogen, alkyne, azido, carboxylic acid, and —CONH—$(CH_2)_x$—O—$(CH_2)_x$—O—$(CH_2)_x$—O—$(CH_2)_x$—$R_7$;

$R_7$ is selected from the group consisting of amino, isothiocyanate, and —NH—CO—$(CH_2)_x$—$CO_2H$;

$R_8$ is selected from a peptide antigen moiety or a protein antigen moiety; and x is any integer from 1 to 10.

22. The imidazoquinoline derived compound of claim 21, comprising a dendrimer of a compound of Formula I, wherein the compound of Formula I is the compound 1-(4-(Aminomethyl)benzyl)-2-butyl-1H-imidazo[4,5-c]quinolin-4-amine, and wherein the dendrimer is chosen from a trimer or a hexamer of the compound.

23. The imidazoquinoline derived dendrimer compound of claim 22, wherein the trimer of compound 7d comprises the compound 1,1',1"-(nitrilotris(ethane-2,1-diyl))tris(3-(4-((4-amino-2-butyl-1H-imidazo[4,5-c]quinolin-1-yl)methyl)benzyl)thiourea), or pharmaceutically acceptable salts thereof.

24. The imidazoquinoline derived dendrimer compound of claim 22, wherein the hexamer of compound 7d comprises the compound $N^1,N^1$-bis(2-(di(prop-2-yn-1-yl)amino)ethyl)-$N^2,N^2$-di(prop-2-yn-1-yl)ethane-1,2-diamine, or pharmaceutically acceptable salts thereof.

25. The imidazoquinoline derived compound of claim 21, wherein the compound is a dimer of a compound of Formula I chosen from the following compounds: $N^1,N^6$-bis(4-((4-amino-2-butyl-1H-imidazo[4,5-c]quinolin-1-yl)methyl)benzyl)adipamide, $N^1,N^6$-bis(4-((4-amino-2-butyl-1H-imidazo[4,5-c]quinolin-1-yl)methyl)benzyl)octanediamide, $N^1,N^{12}$-bis(4-((4-amino-2-butyl-1H-imidazo[4,5-c]quinolin-1-yl)methyl)benzyl)dodecane diamide, or pharmaceutically acceptable salts thereof.

26. The imidazoquinoline derived compound of claim 21, wherein the compound is a dimer of a compound of Formula II chosen from the following compounds: $N^1,N^6$-bis(4-amino-1-(4-(aminomethyl)benzyl)-2-butyl-1H-imidazo[4,5-c]quinolin-8-yl) adipamide, $N^1,N^6$-bis(4-amino-1-(4-(aminomethyl)benzyl)-2-butyl-1H-imidazo[4,5-c]quinolin-8-yl) octanediamide, $N^1,N^{12}$-bis(4-amino-1-(4-(aminomethyl)benzyl)-2-butyl-1H-imidazo[4,5-c]quinolin-8-yl) dodecanediamide, or pharmaceutically acceptable salts thereof.

27. The imidazoquinoline derived compound of claim 21, wherein the dimer or dendrimer compound is a Toll-like receptor (TLR) 7 agonist or a dual TLR7/TLR8 agonist.

28. The imidazoquinoline derived compound of claim 21, wherein the dimer or dendrimer compound is a TLR7 agonist chosen from the following compounds: 1,1',1"-(nitrilotris(ethane-2,1-diyl))tris(3-(4-((4-amino-2-butyl-1H-imidazo[4,5-c]quinolin-1-yl)methyl)benzyl)thiourea), $N^1,N^1$-bis(2-(di(prop-2-yn-1-yl)amino)ethyl)-$N^2,N^2$-di(prop-2-yn-1-yl)ethane-1,2-diamine, $N^1,N^6$-bis(4-((4-amino-2-butyl-1H-imidazo[4,5-c]quinolin-1-yl)methyl)benzyl)adipamide, $N^1,N^6$-bis(4-((4-amino-2-butyl-1H-imidazo[4,5-c]quinolin-1-yl)methyl)benzyl)octanediamide, $N^1,N^{12}$-bis(4-((4-amino-2-butyl-1H-imidazo[4,5-c]quinolin-1-yl)methyl)benzyl)dodecane diamide, $N^1,N^6$-bis(4-amino-1-(4-(aminomethyl)benzyl)-2-butyl-1H-imidazo[4,5-c]quinolin-8-yl) adipamide, $N^1,N^8$-bis(4-amino-1-(4-(aminomethyl)benzyl)-2-butyl-1H-imidazo[4,5-c]quinolin-8-yl) octanediamide, $N^1,N^{12}$-bis(4-amino-1-(4-(aminomethyl)benzyl)-2-butyl-1H-imidazo[4,5-c]quinolin-8-yl) dodecanediamide, or pharmaceutically acceptable salts thereof.

29. The imidazoquinoline derived compound of claim 21, wherein the dimer or dendrimer compound is a dual TLR7/TLR8 agonist chosen from compounds 1,1',1"-(nitrilotris(ethane-2,1-diyl))tris(3-(4-((4-amino-2-butyl-1H-imidazo[4,5-c]quinolin-1-yl)methyl)benzyl)thiourea), $N^1,N^{12}$-bis(4-((4-amino-2-butyl-1H-imidazo[4,5-c]quinolin-1-yl)methyl)benzyl)dodecane diamide, or pharmaceutically acceptable salts thereof.

30. An imidazoquinoline derived compound of Formula II or pharmaceutically acceptable salt thereof, wherein Formula II has the structure:

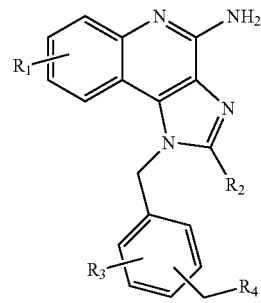

wherein, $R_1$ and $R_3$ are each independently selected from the group consisting of hydrogen, halogen, nitro, —$NH_2$, azido, hydroxyl, —$CF_3$, carboxylic acid, and —$CO_2R_2$;

$R_2$ is a $C_2$-$C_5$ alkyl, and $R_4$ selected from the group consisting of: —$NH(R_5)$ and isothiocyanate;

$R_5$ is selected from the group consisting of hydrogen, acetyl, —CO-tert-Bu (-Boc), —CO—$(CH_2)_x$—$R_6$, $C_1$-$C_{16}$ alkyl, —CO-4-, —C(S)—NH—$(CH_2)_x$—NH—$(CH_2)_x$—NH—$(CH_2)_x$—$NH_2$,

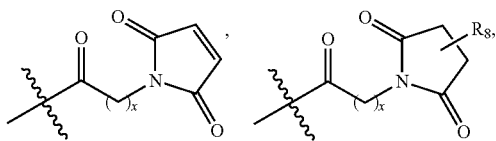

a reporter moiety, a tissue-specific moiety, a peptide antigen moiety, a protein antigen moiety, a polysaccharide antigen moiety, and a TLR2 agonist moiety;

$R_6$ is selected from the group consisting of hydrogen, alkyne, azido, carboxylic acid, and
—CONH—$(CH_2)_x$—O—$(CH_2)_x$—O—$(CH_2)_x$—O—$(CH_2)_x$—$R_7$;

$R_7$ is selected from the group consisting of amino, isothiocyanate, and —NH—CO—$(CH_2)_x$—$CO_2$H;

$R_8$ is selected from a peptide antigen moiety or a protein antigen moiety; and x is any integer from 1 to 10.

31. The imidazoquinoline derived compound of claim 30, wherein the compound is chosen from tert-butyl 3-((4-amino-2-butyl-1H-imidazo[4,5-c]quinolin-1-yl)methyl)benzylcarbamate, tert-butyl 4-((4-amino-2-butyl-1H-imidazo[4,5-c]quinolin-1-yl)methyl)benzylcarbamate, 1-(3-(Aminomethyl)benzyl)-2-butyl-1H-imidazo[4,5-c]quinolin-4-amine, 1-(4-(Aminomethyl)benzyl)-2-butyl-1H-imidazo[4,5-c]quinolin-4-amine, 2-Butyl-1-(4-(isothiocyanatomethyl)benzyl)-1H-imidazo[4,5-c]quinolin-4-amine, 1-(4-((4-amino-2-butyl-1H-imidazo[4,5-c]quinolin-1-yl)methyl)phenyl)-3,7,23-trioxo-12,15,18-trioxa-2,8,22-triazaheptacosan-27-oic acid, 5-((4-((4-amino-2-butyl-1H-imidazo[4,5-c]quinolin-1-yl)methyl)benzyl)amino)-5-oxopentanoic acid, $N^1$-(4-((4-amino-2-butyl-1H-imidazo[4,5-c]quinolin-1-yl)methyl)benzyl)-$N^5$-(3-(2-(2-(3-aminopropoxy)ethoxy)ethoxy)propyl)glutaramide, $N^1$-(4((4-amino-2-butyl-1H-imidazo[4,5-c]quinolin-1-yl)methyl)benzyl)-$N^5$-(3-(2-(2-(3-isothiocyanatopropoxy)ethoxy)ethoxy)propyl)glutaramide, N-(4-((4-amino-2-butyl-1H-imidazo[4,5-c]quinolin-1-yl)methyl)benzyl)palmitamide, 2-butyl-1-(4-((hexadecylamino)methyl)benzyl)-1H-imidazo[4,5-c]quinolin-4-amine, N-(4-((4-amino-2-butyl-1H-imidazo[4,5-c]quinolin-1-yl)methyl)benzyl)-2-azidoacetamide, N-(4-((4-amino-2-butyl-1H-imidazo[4,5-c]quinolin-1-yl)methyl)benzyl)pent-4-ynamide , N-(4-((4-amino-2-butyl-1H-imidazo[4,5-c]quinolin-1-yl)methyl) benzyl)-3-(2,5-dioxo-2,5-dihydro-1H-pyrrol-1-yl)propanamide, (4-((4-((4-amino-2-butyl-1H-imidazo[4,5-c]quinolin-1-yl)methyl) benzyl)carbamoyl)phenyl)boronic acid, 1-(4-((4-amino-2-butyl-1H-imidazo[4,5-c]quinolin-1-yl)methyl)benzyl)-3-(3-((4(3-aminopropyl)amino)butyl)amino)propyl)thiourea, 2-(3-(4-((4-Amino-2-butyl-1H-imidazo [4,5-c]quinolin-1-yl)methyl)benzyl)thioureido)-6-(6-hydroxy-3-oxo-3H-xanthen-9-yl)benzoic acid, N-(9-(4-(3-(4-((4-amino-2-butyl-1H-imidazo[4,5-c]quinolin-1-yl)methyl)benzyl)thioureido)-2-carboxyphenyl)-6-(diethylamino)-3H-xanthen-3-ylidene)-N-ethylethanaminium, 5-(((4-(4,4-difluoro-5-(2-thienyl)-4-bora-3a,4a-diaza-s-indacene-3-yl)phenoxy) acetyl)amino)pentylamine, hydrochloride conjugate of 2-Butyl-1-(4-(isothiocyanatomethyl)benzyl)-1H-imidazo[4,5-c]quinolin-4-amine, Methyl 1-(4-((4-amino-2-butyl-1H-imidazo[4,5-c]quinolin-1-yl)methyl)phenyl)-6,9-dioxo-3-thioxo-2,4,7,10-tetraazadodecan-12-oate,

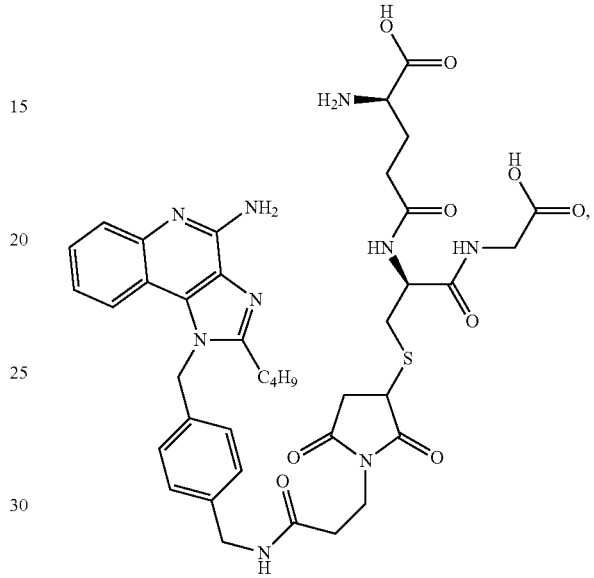

(2R)-methyl 2-amino-5-((2S)-3-(1-(3-(4-((4-amino-2-butyl-1H-imidazo[4,5-c]quinoli n-1-yl)methyl)benzylamino)-3-oxopropyl)-2,5-dioxopyrrolidin-3-ylthio)-1-(2-methoxy-2-oxoethylamino)-1-oxopropan-2-ylamino)-5-oxopentanoate,

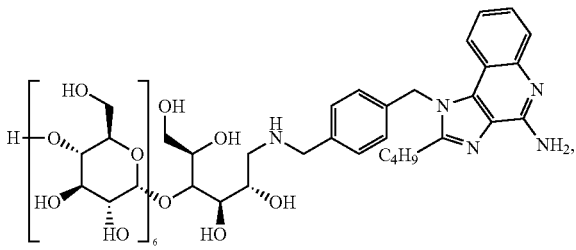

N-(4-((4-amino-2-butyl-1H-imidazo[4,5-c]quinolin-1-yl)methyl)benzyl)-N-((2R ,3S ,4R)-2,3,4,5,6-pentahydroxyhexyl)acetamide, 5-((4-((4-amino-2-butyl-1H-imidazo[4,5-c]quinolin-1-yl)methyl)benzyl) amino)-2-(4-(((2-amino-4-oxo-3,4-dihydropteridin-6-yl)methyl)amino)benzamido)-5-oxopentanoic acid, N-(4-((4-amino-2-butyl-1H-imidazo[4,5-c]quinolin-1-yl)methyl)benzyl)-5-((3aR,4R,6aS)-2-oxohexahydro-1H-thieno[3,4-d]imidazol-4-yl)pentanamide, 4-(((4-((4-amino-2-butyl-1H-imidazo[4,5-c]quinolin-1-yl)methyl)benzyl)amino)methyl)-5-(hydroxymethyl)-2-methylpyridin-3-ol 155
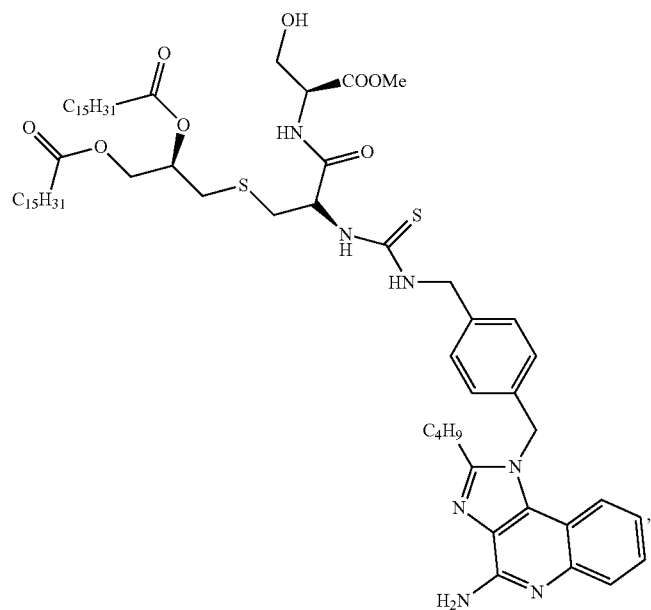
156
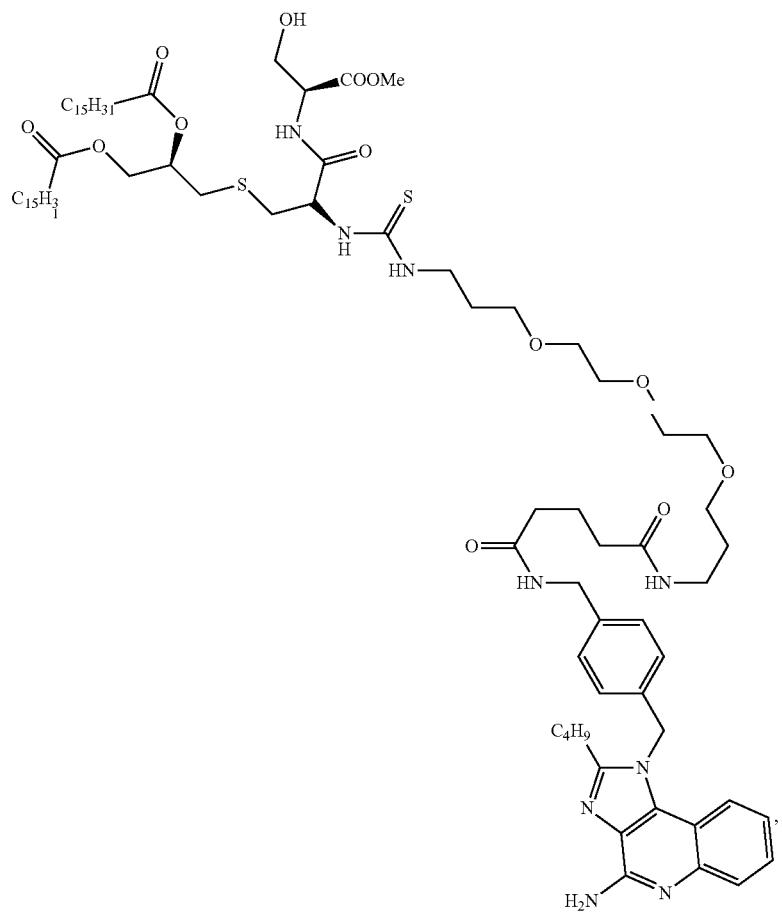

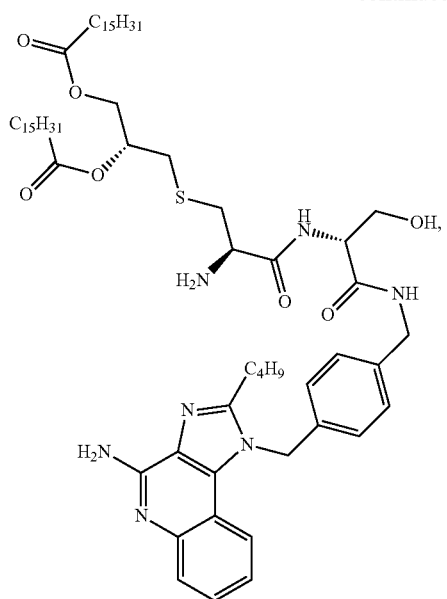
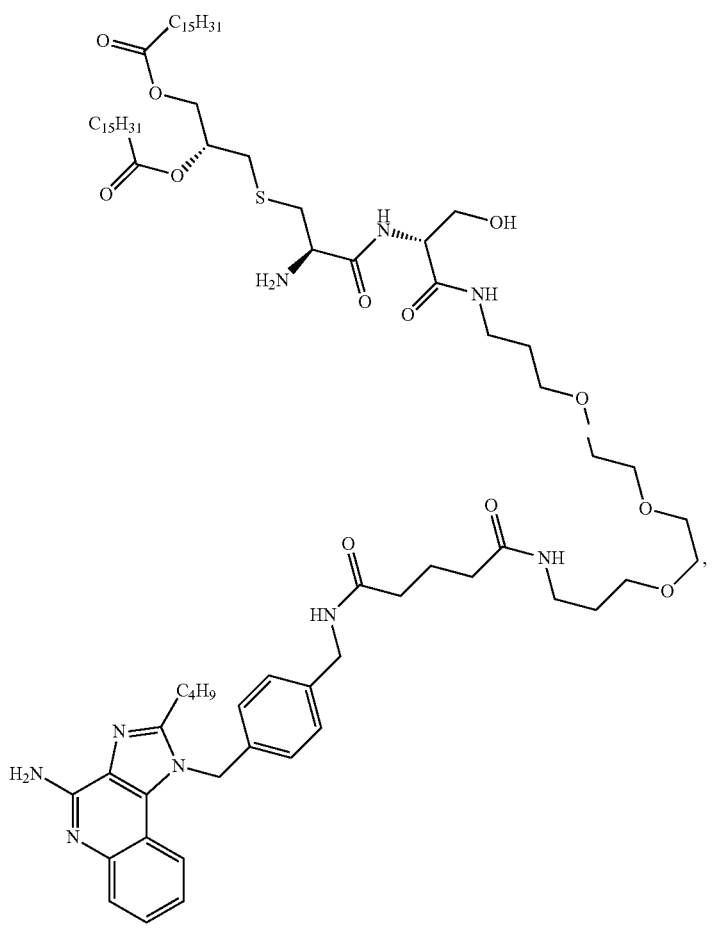

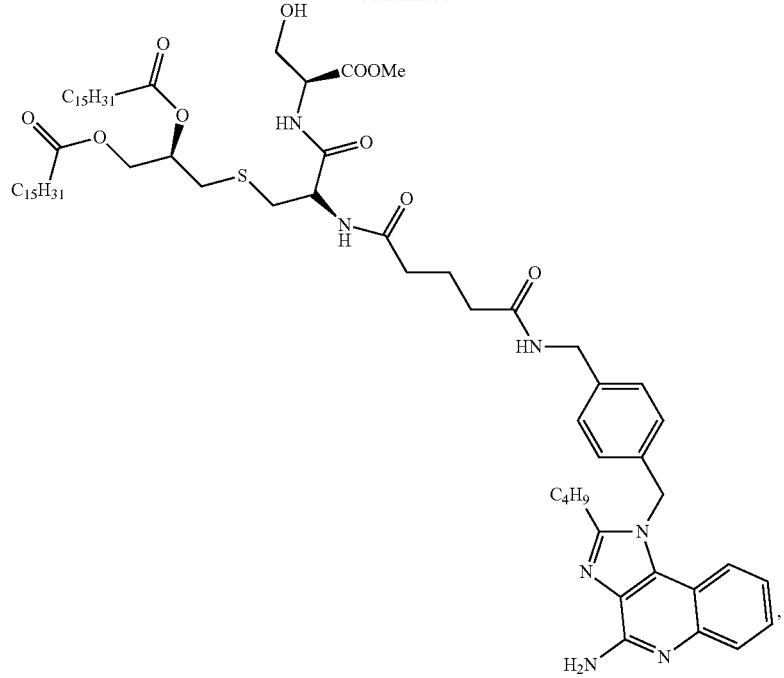

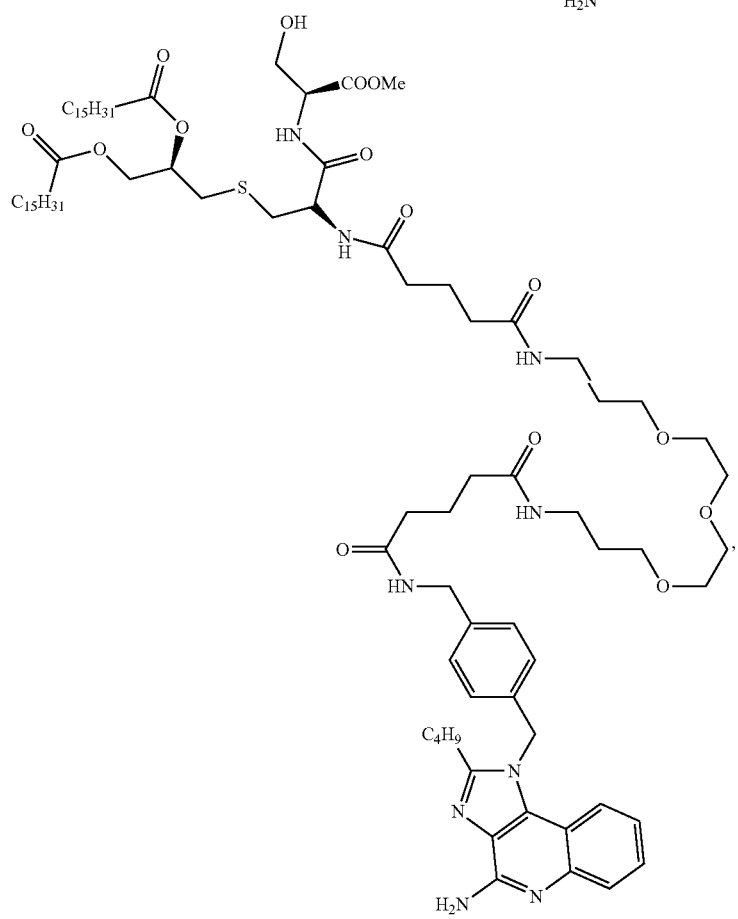

or pharmaceutically acceptable salts thereof.

32. The imidazoquinoline derived compound of claim 30, wherein the compound is capable of activating TLR7 or dual activation of TLR7 and TLR8.

33. A vaccine adjuvant comprising an imidazoquinoline derived compound of claim 1.

34. A self-adjuvanting vaccine comprising an imidazoquinoline derived compound of claim 1 coupled to an antigen.

35. The self-adjuvanting vaccine of claim 34, wherein the antigen is selected from a peptide antigen, a protein antigen, or a polysaccharide antigen.

36. A method of immunizing a host comprising:
   administering to the host an antigen, and
   administering to the host an adjuvant comprising an imidazoquinoline derived compound of claim 1 capable of activation of TLR7 or dual activation of TLR7 and TLR8, wherein the imidazoquinoline derived compound is administered with the antigen or is coupled to the antigen.

37. A probe comprising:
   a TLR7 ligand or a dual TLR7/TLR8 ligand comprising an imidazoquinoline derived compound of claim 1, and
   a reporter molecule capable of producing a detectable signal, coupled to the ligand.

38. A method of imaging activation of TLR 7, TLR 8, or both TLR7 and TLR8 comprising:
   contacting a sample comprising TLR7, TLR8 or both TLR7 and TLR8 with a probe of claim 37; and
   imaging the detectable signal produced by the reporter molecule.

39. A TLR7 antagonist comprising: an imidazoquinoline derived dimeric compound comprising a dimeric compound of Formula III, or pharmaceutically acceptable salts thereof, wherein

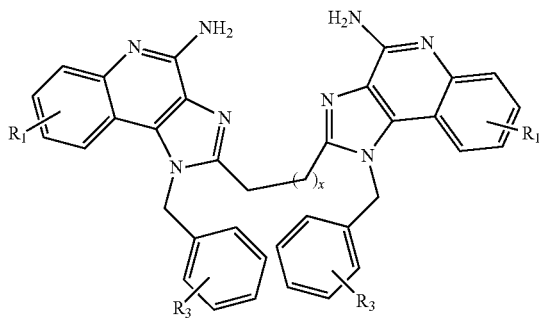

FORMULA III wherein $R_1$ is selected from the group consisting of hydrogen, halogen, nitro, —$NH_2$, azido, hydroxyl, and —$CF_3$, $R_3$ is selected from the group consisting of hydrogen and —$(CH_2)_x$—$NH_2$, and x is any integer form 1 to 10.

* * * * *